(12) United States Patent  
Capaldi et al.

(10) Patent No.: US 9,199,984 B2  
(45) Date of Patent: Dec. 1, 2015

(54) INHIBITION OF ENZYMES

(71) Applicant: CHIESI FARMACEUTICI S.p.A., Parma (IT)

(72) Inventors: Carmelida Capaldi, Parma (IT); Robert Andrew Heald, Harlow (GB); Nicholas Charles Ray, Harlow (GB); Jonathan Mark Sutton, Harlow (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 340 days.

(21) Appl. No.: 13/940,555

(22) Filed: Jul. 12, 2013

(65) Prior Publication Data

US 2014/0018345 A1   Jan. 16, 2014

(30) Foreign Application Priority Data

Jul. 12, 2012   (EP) .................................... 12176079  
Mar. 12, 2013   (EP) .................................... 13158756

(51) Int. Cl.
*C07D 401/02* (2006.01)
*C07D 401/10* (2006.01)
*C07D 401/14* (2006.01)
*A61K 31/4353* (2006.01)
*A61K 31/437* (2006.01)
*C07D 471/04* (2006.01)

(52) U.S. Cl.
CPC ..................................... *C07D 471/04* (2013.01)

(58) Field of Classification Search
CPC .... C07D 401/02; C07D 40/10; C07D 401/14; A61K 31/4353; A61K 31/437
USPC ............................ 546/118, 121; 514/300, 303
See application file for complete search history.

(56) References Cited

U.S. PATENT DOCUMENTS 8,338,604 B2 * 12/2012 Hynes et al. .................. 546/121  
2011/0082155 A1   4/2011 Murugan et al.

FOREIGN PATENT DOCUMENTS

WO   2009/061271   5/2009  
WO   2009/155389   12/2009

OTHER PUBLICATIONS

U.S. Appl. No. 14/571,755, filed Dec. 16, 2014, Alcaraz, et al.  
European Search Report in Application No. 12176079.7, issued Dec. 19, 2012.

* cited by examiner

*Primary Examiner* — Niloofar Rahmani  
(74) *Attorney, Agent, or Firm* — Oblon, McClelland, Maier & Neustadt, L.L.P.

(57) ABSTRACT

Compounds of formula (I):

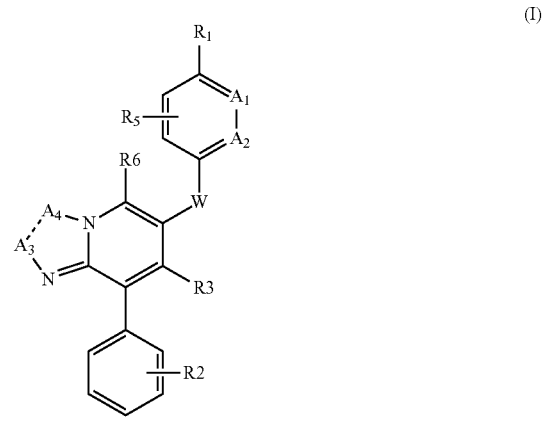

wherein $R_1$, $R_2$, $R_3$, $R_5$, $R_6$, $A_1$, $A_2$, $A_3$, $A_4$ assume meanings as defined in formula (I) are inhibitors of neutrophil elastase.

17 Claims, No Drawings

INHIBITION OF ENZYMES

CROSS REFERENCES TO RELATED APPLICATIONS

This application claims priority to European Patent Application No. 12176079.7, filed on Jul. 12, 2012, and European Patent Application No. 13158756.0, filed on Mar. 12, 2013, both of which are incorporated herein by reference in their entireties.

BACKGROUND OF THE INVENTION

1. Field of the Invention

This present invention relates to heterocyclic compounds, which are pyridine derivatives, and which have human neutrophil elastase inhibitory properties. The present invention also relates to the use of such compounds for the treatment of certain diseases and conditions.

2. Discussion of the Background

Human neutrophil elastase (FINE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (see Bieth, G. In *Regulation of Matrix accumulation*, Mecham, R. P. (Eds), Academic Press, NY, USA 1986, 217-306, which is incorporated herein by reference in its entirety). HNE has long been considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure, both small molecule inhibitors and protein inhibitors of HNE inhibit the inflammatory response and the development of emphysema (see Wright, J. L. et al. *Am. J. Respir. Crit. Care Med.* 2002, 166, 954-960; Churg, A. et al. *Am. J. Respir. Grit. Care Med.* 2003, 168, 199-207, which are incorporated herein by reference in their entireties). Thus, HNE may play a role both in matrix destruction and in amplifying inflammatory responses in chronic respiratory diseases where neutrophil influx is a characteristic feature. Indeed, HNE is believed to play a role in several pulmonary diseases, including chronic obstructive pulmonary disease (COPD), cystic fibrosis (CF), acute respiratory distress syndrome (ARDS), pulmonary emphysema, pneumonia, and lung fibrosis. It is also implicated in several cardiovascular diseases in which tissue remodeling is involved, for example, in heart failure and the generation of ischaemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (see Thompson, A. B.; Daughton, D.; et al. *Am. Rev. Respir. Dis.* 1989, 140, 1527-1537, which is incorporated herein by reference in its entirety). The major pathogenic determinant in COPD has long been considered to be the protease-anti-protease balance (also known as the 'elastase:anti-elastase hypothesis'), in which an imbalance of HNE and endogenous antiproteases such as α1-antitrypsin ($α_1$-AT), secretory leukocyte protease inhibitor (SLPI) and pre-elafin leads to the various inflammatory disorders of COPD. Individuals that have a genetic deficiency of the protease inhibitor α1-antitrypsin develop emphysema that increases in severity over time (see Laurrell, C. B.; Erikkson, S *Scand. J. Clin. Invest.* 1963 15, 132-140, which is incorporated herein by reference in its entirety). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Thus, there remains a need for compounds which exhibit human neutrophil elastase inhibitory properties.

SUMMARY OF THE INVENTION

Accordingly, it is one object of the present invention to provide novel compounds which exhibit human neutrophil elastase inhibitory properties.

It is another object of the present invention to provide novel pharmaceutical compositions which contain such a compound.

It is another object of the present invention to provide novel methods of treating and/or preventing certain diseases and conditions by administering such a compound.

These and other objects, which will become apparent during the following detailed description, have been achieved by the inventors' discovery of novel compounds of formula (I) described below, which are inhibitors of HNE, and are useful in the treatment of diseases or conditions in which FINE activity plays a part.

DETAILED DESCRIPTION OF THE PREFERRED EMBODIMENTS

Thus, in one embodiment, the invention provides compounds of formula (I):

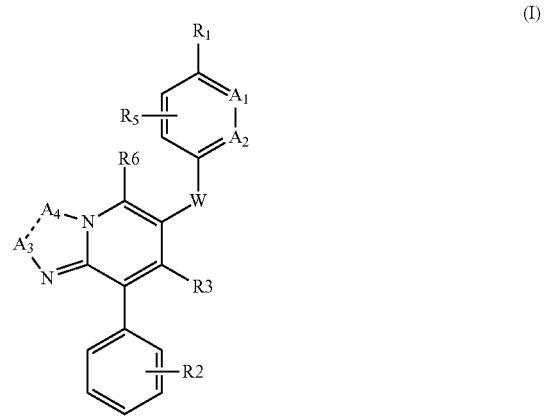

wherein $R_1$ is selected from halogen, —CN, —OH and a group $(C_1-C_4)$alkyl;

$R_2$ is selected from halogen, $(C_1-C_4)$alkyl, $(C_1-C_4)$haloalkyl, —CN, $(C_1-C_4)$alkoxy, $(C_1-C_4)$haloalkoxy, nitro, and a group —OH;

W is a"

(i) a 5,6-membered heteroarylene ring optionally substituted by one or two groups independently selected from halogen, —OH, $(C_1-C_4)$alkyl, $(C_1-C_4)$haloalkyl, —CN, $(C_1-C_4)$alkoxy, nitro, a group —$NHR_{18}$, a group —$COOR_{28}$, a group —$COR_{29}$, and a group —$CONHR_{19}$;

(ii) a $(C_5-C_6)$heterocycloalkylene ring partially unsaturated and optionally substituted by one or two groups independently selected from halogen, $(C_1-C_4)$alkyl, $(C_1-C_4)$haloalkyl, —CN, —OH, $(C_1-C_4)$alkoxy, nitro, carbonyl, a group —$NHR_{18}$, and a group —$CONHR_{19}$; or (iii) a phenylene group optionally substituted by one or two groups independently selected from halogen, $(C_1-C_4)$alkyl, $(C_1-C_4)$haloalkyl, —CN, nitro, a group —$NHR_{18}$, a group —$CONHR_{19}$, and a group —$OR_{20}$;

$R_{18}$ is hydrogen, $(C_1-C_4)$alkyl, a group —$SO_2R_{21}$ or a group $(C_1-C_4)$alkyl carbonyl;

$R_{21}$ is $(C_1-C_4)$alkyl;

$R_{19}$ is hydrogen or $(C_1-C_4)$alkyl;

$R_{20}$ is hydrogen, $(C_1-C_4)$alkyl or a group —$(C_1-C_4)$alkylene-$OR_{22}$;

$R_{22}$ is hydrogen or $(C_1-C_4)$alkyl;

$R_3$ is a group —$CH_2$—$R_{23}$;

$R_{23}$ is a group selected from hydrogen, $(C_1-C_4)$alkyl, $(C_1-C_4)$haloalkyl, —CN, $(C_1-C_4)$alkoxy and halogen;

$R_5$ is a group selected from hydrogen, $(C_1-C_4)$alkyl, $(C_1-C_4)$haloalkyl, —CN, $(C_1-C_4)$alkoxy and halogen;

$R_6$ is selected from hydrogen, halogen, $(C_1-C_4)$alkyl, and CN;

$A_1$ is a group —$CR_7$= or a group —N=;

$A_2$ is a group =$CR_8$— or a group =N—;

$R_7$ is selected from hydrogen, halogen, $(C_1-C_4)$alkyl, $(C_1-C_4)$haloalkyl and $(C_1-C_4)$alkoxy;

$R_8$ is selected from hydrogen, halogen, $(C_1-C_4)$alkyl, $(C_1-C_4)$haloalkyl, $(C_1-C_4)$alkoxy, a group —$S(C_1-C_4)$alkyl, and a group —$SO_2(C_1-C_4)$alkyl;

wherein $A_1$ and $A_2$ cannot be at the same time a group —N=;

$A_3$-$A_4$ is a moiety selected from a group —$CR_4$=N—, a group —$CR_4$=$CR_9$— and a group —$NR_{17}$—CO—;

$R_9$ is hydrogen or $(C_1-C_4)$alkyl;

$R_4$ is a group selected from hydrogen, $(C_1-C_4)$alkyl, —$NR_{10}R_{11}$, —$NHCOR_{12}$, —NHCOO—$R_{13}$, —NHCONR$_{27}$—$R_{14}$, $(C_1-C_4)$alkoxy, —NH$(CH_2)_n$—$SO_2(C_1-C_4)$alkyl, —$(NH)_q(CH_2)_n$—$(C_6H_6)$—$SO_2(C_1-C_4)$alkyl, —$NHSO_2(C_1-C_4)$alkyl and —$(NH)_r(CH_2)_n CONR_{15}R_{16}$;

$R_{17}$ is a group selected from hydrogen, $(C_1-C_4)$alkyl, —$(CH_2)_n$—$(C_6H_6)$—$SO_2(C_1-C_4)$alkyl, —$(CH_2)_n$—$SO_2(C_1-C_4)$alkyl and —$(CH_2)_n CONR_{15}R_{16}$;

n is zero or an integer ranging from 1 to 5;

q is zero or 1;

r is zero or 1;

$R_{10}$ is hydrogen, a group $(C_1-C_6)$alkyl, a group $(C_1-C_6)$hydroxyalkyl, a group $(C_1-C_4)$alkylene-NH—(C=NH)—$NH_2$, a group $(C_1-C_6)$alkyleneNR$_a$R$_b$, a group $(C_1-C_6)$alkyleneNR$_a$R$_d$, or a group $(C_1-C_6)$alkyleneN$^+$R$_a$R$_b$R$_c$;

$R_{11}$ is hydrogen, a group $(C_1-C_6)$alkyl, a group $(C_1-C_6)$hydroxyalkyl, a group $(C_1-C_4)$alkylene-NH—(C=NH)—$NH_2$, a group $(C_1-C_6)$alkyleneNR$_a$R$_b$ or a group $(C_1-C_6)$alkyleneN$^+$R$_a$R$_b$Rc;

or $R_{10}$ and $R_{11}$ together with the nitrogen atom they are linked to may form a $(C_5-C_7)$heterocycloalkyl;

$R_a$ and $R_b$ are at each occurrence independently hydrogen, $(C_1-C_4)$alkyl, which $(C_1-C_4)$alkyl may be optionally substituted by a group —$COOR_{30}$ or by a group $(C_5-C_7)$heterocycloalkyl, a group $(C_5-C_7)$heterocycloalkyl, a group $(C_1-C_6)$alkyleneNR$_e$R$_f$ or a group $(C_1-C_6)$alkyleneN$^+$R$_e$R$_f$R$_g$;

alternatively, $R_a$ and $R_b$, together with the nitrogen atom they are linked to may form a $(C_5-C_7)$heterocycloalkyl ring system optionally substituted by one or more groups $C_1-C_6$ alkyl and which $(C_5-C_7)$heterocycloalkyl optionally contains a group —S(O)— or —S(O)$_2$— or a further heteroatom which is oxygen, sulfur or nitrogen, said nitrogen atom optionally substituted by $(C_1-C_6)$alkyl;

or $R_a$ is as above defined and $R_b$ is linked to one carbon atom of the $(C_1-C_6)$alkylene portion of the group linked to the nitrogen to which they are connected to form a saturated $(C_5-C_6)$heterocycloalkyl ring;

$R_a$, $R_b$ and $R_c$ if simultaneously present are at each occurrence independently $(C_1-C_4)$alkyl, which $(C_1-C_4)$alkyl may be optionally substituted by a group —$COOR_{30}$ or by a group $(C_5-C_7)$heterocycloalkyl, a group $(C_5-C_7)$heterocycloalkyl, a group $(C_1-C_6)$alkyleneNR$_e$R$_f$ or a group $(C_1-C_6)$alkyleneN$^+$R$_e$R$_f$R$_g$; alternatively, $R_a$ and $R_b$ or $R_a$ and $R_c$, together with the nitrogen atom they are linked to may form a $(C_5-C_7)$heterocycloalkyl ring system optionally substituted by one or more groups $C_1-C_6$ alkyl or —$NHR_{24}$ and which $(C_5-C_7)$heterocycloalkyl ring optionally contains a group —S(O)— or —S(O)$_2$— or a further heteroatom which is oxygen, sulfur or nitrogen, said nitrogen atom optionally substituted by $(C_1-C_6)$ alkyl; or $R_a$ and $R_b$ are as above defined and $R_c$ is linked to one carbon atom of the $(C_1-C_6)$alkylene portion of the group linked to the nitrogen to which they are connected to form a saturated $(C_5-C_6)$heterocycloalkyl ring;

$R_d$ is $(C_5-C_7)$heterocycloalkyl;

$R_e$ and $R_f$ are at each occurrence independently hydrogen or $(C_1-C_4)$alkyl;

or $R_e$, $R_f$ and $R_g$ if simultaneously present are at each occurrence independently $(C_1-C_4)$alkyl;

$R_{12}$ is selected from —$(C_6H_6)$—$SO_2(C_1-C_4)$alkyl, $(C_1-C_6)$alkyl, $(C_1-C_4)$haloalkyl, $(C_5-C_7)$heterocycloalkyl, a group —$(CH_2)_n$—$S(O)_t(C_1-C_4)$alkyl, a group —$(CH_2)_n$—$S(O)_t(C_1-C_4)$alkylNR$_a$R$_b$, a group —$(CH_2)_n$—$S(O)_t(C_1-C_4)$alkylN$^+$R$_a$R$_b$R$_c$, a group $(C_1-C_4)$alkylene-NH—(C=NH)—$NH_2$, a group $(C_1-C_4)$alkylene-$CO_2H$, a group —$(C_1-C_4)$alkylene-$CO_2NR_{25}R_{26}$, a group —$(C_1-C_4)$alkylene-$CO_2NR_{25}(C_1-C_6)$alkyleneNR$_a$R$_b$, a group —$(C_1-C_4)$alkylene-$CO_2NR_{25}(C_1-C_6)$alkyleneN$^+$R$_a$R$_b$R$_c$, a group —$(C_1-C_6)$alkyleneNR$_a$R$_b$, a group —$(C_1-C_6)$alkyleneN$^+$R$_a$R$_b$R$_c$ and $(C_1-C_4)$alkyl$(C_5-C_7)$heterocycloalkyl, wherein such groups may be optionally substituted by one or two substituents selected from $(C_1-C_4)$alkyl, hydroxy, halogen, —$SO_2(C_1-C_4)$alkyl, amino or $(C_1-C_4)$alkylamino;

t may be zero, 1 or 2;

$R_{13}$ is selected in the group-$(C_6H_6)$—$SO_2$alkyl, $(C_1-C_6)$alkyl, $(C_1-C_4)$haloalkyl, $(C_5-C_7)$heterocycloalkyl, a group $(C_1-C_4)$alkylene-NH—(C=NH)—$NH_2$, $(C_1-C_6)$alkyleneNR$_a$R$_b$, —$(C_1-C_6)$alkyleneN$^+$R$_a$R$_b$R$_c$ and $(C_1-C_4)$alkylene$(C_5-C_7)$heterocycloalkyl, wherein such groups may be optionally substituted by one or two substituents selected from $(C_1-C_4)$alkyl, $(C_1-C_4)$alkoxy, hydroxy, halogen, —$SO_2(C_1-C_4)$alkyl, amino or $(C_1-C_4)$alkylamino;

$R_{14}$ is selected from $(C_1-C_4)$alkyl, —$(C_6H_6)$—$SO_2$alkyl, $(C_1-C_4)$haloalkyl, $(C_5-C_7)$heterocycloalkyl, a group $(C_1-C_4)$alkylene-NH—(C=NH)—$NH_2$, $(C_1-C_6)$alkyleneNR$_a$R$_b$, —$(C_1-C_6)$alkyleneN$^+$R$_a$R$_b$R$_c$ and $(C_1-C_4)$alkyl$(C_5-C_7)$heterocycloalkyl, wherein such groups may be optionally substituted by one or two substituents selected from $(C_1-C_4)$alkyl, hydroxy, halogen, —$SO_2(C_1-C_4)$alkyl, amino, $(C_1-C_4)$alkylcarbonyl and $(C_1-C_4)$alkylamino;

$R_{15}$ is hydrogen, a group $(C_1-C_6)$alkyl, a group $(C_1-C_4)$alkylene-NH—(C=NH)—$NH_2$, a group $(C_1-C_6)$alkyleneNR$_a$R$_b$, or a group —$(C_1-C_6)$alkyleneN$^+$R$_a$R$_b$R$_c$;

$R_{16}$ is hydrogen, a group $(C_1-C_6)$alkyl, a group $(C_1-C_4)$alkylene-NH—(C=NH)—NH$_2$, a group $(C_1-C_6)$alkyleneN-$R_aR_b$ or a group —$(C_1-C_6)$alkyleneN$^+R_aR_bR_c$;

or $R_{15}$ and $R_{16}$ together with the nitrogen atom they are linked to may form a $(C_5-C_7)$heterocycloalkyl;

$R_{24}$ is hydrogen or $(C_1-C_4)$alkyl;
$R_{25}$ is hydrogen or $(C_1-C_4)$alkyl;
$R_{26}$ is hydrogen or $(C_1-C_4)$alkyl;
$R_{27}$ is hydrogen or $(C_1-C_4)$alkyl;
$R_{28}$ is hydrogen or $(C_1-C_4)$alkyl;
$R_{29}$ is hydrogen or $(C_1-C_4)$alkyl;
$R_{30}$ is hydrogen or $(C_1-C_4)$alkyl;

wherein if one or more groups —$(C_1-C_6)$alkyleneN$^+R_aR_bR_c$, are present, they form quaternary salts with a pharmaceutically acceptable counter ion;

And wherein groups $R_{18}$, $R_{19}$, $R_{20}$, $R_{21}$, $R_{22}$, $R_{24}$, $R_{25}$, $R_{26}$, $R_{27}$, $R_{28}$, $R_{29}$, $R_{30}$, $R_a$, $R_b$, $R_c$, $R_d$, $R_e$, $R_f$, $R_g$, and n may assume the same or different meanings at each occurrence, if present in more than one group;

and pharmaceutically acceptable salts or solvate thereof.

The compounds of formula (I) above thereof may be prepared in the form of salts, particularly pharmaceutically acceptable salts, N-oxides, hydrates and solvates thereof. Any claim to a compound herein, or reference to "compounds of the invention", "compounds with which the invention is concerned", "compounds of formula (I)", and the like includes such compounds whether or not in salt, N-oxide, hydrate or solvate form.

The compounds of the present invention may be used in the treatment or prevention of diseases in which HNE is implicated, for example chronic obstructive pulmonary disease (COPD), chronic bronchitis, lung fibrosis, pneumonia, acute respiratory distress syndrome (ARDS), pulmonary emphysema, smoking-induced emphysema, bronchiectasis and cystic fibrosis.

Hence other aspects of the invention are (i) a pharmaceutical composition comprising a compound of the present invention and a pharmaceutically acceptable carrier or excipient; and (ii) the use of a compound of the invention for the manufacture of a medicament for the treatment or prevention of a disease or condition in which HNE is implicated.

Terminology.

The term "halogen atoms" as used herein includes fluorine, chlorine, bromine, and iodine, preferably chlorine.

As used herein, the term "$(C_1-C_x)$ alkyl" where x is an integer greater than 1, refers to straight-chained and branched alkyl groups wherein the number of constituent carbon atoms is in the range 1 to x. Particular alkyl groups are methyl, ethyl, n-propyl, isopropyl and t-butyl.

By analogy, the term "$(C_1-C_x)$alkylene", refers to a divalent $(C_1-C_x)$alkyl radical, wherein $(C_1-C_x)$alkyl is as above defined.

The term "$(C_1-C_x)$ alkoxy" where x is an integer greater than 1, refers to straight-chained and branched alkoxy groups wherein the number of constituent carbon atoms is in the range 1 to x. Particular alkyl groups are methoxyl, ethoxyl, n-propoxyl, isopropoxyl and t-butoxyl.

The expression "$(C_1-C_x)$haloalkyl" refers to the above defined "$(C_1-C_x)$alkyl" groups wherein one or more hydrogen atoms are replaced by one or more halogen atoms, which can be the same or different from each other. Examples of said $(C_1-C_6)$haloalkyl groups may thus include halogenated, poly-halogenated and fully halogenated alkyl groups wherein all of the hydrogen atoms are replaced by halogen atoms, e.g. trifluoromethyl or difluoro methyl groups.

The expressions "$(C_1-C_x)$haloalkoxy" refers to the above defined "$(C_1-C_x)$alkoxy" groups wherein one or more hydrogen atoms are replaced by one or more halogen atoms, which can be the same or different from each other. Examples of said $(C_1-C_6)$haloalkoxy groups may thus include halogenated, poly-halogenated and fully halogenated alkoxy groups wherein all of the hydrogen atoms are replaced by halogen atoms, e.g. trifluoromethoxy.

The expression "$(C_1-C_x)$hydroxyalkyl" refers to the above defined "$(C_1-C_x)$alkyl" groups wherein one or more hydrogen atoms are replaced by one or more groups —OH.

The expression "$(C_1-C_x)$alkylamino" refers to the above defined "$(C_1-C_x)$alkyl" groups wherein one or more hydrogen atoms are replaced by one or more groups —NH$_2$.

The term "$(C_3-C_y)$ cycloalkyl", where y is an integer greater than or equal to 3, refers to saturated cyclic hydrocarbon groups containing from 3 to y ring carbon atoms. Examples include cyclopropyl, cyclobutyl, cyclopentyl, cyclohexyl, and cycloheptyl.

The derived expression "$(C_3-C_y)$heterocycloalkyl" refers to saturated monocyclic $(C_3-C_y)$cycloalkyl groups, in which at least one ring carbon atom is replaced by a heteroatom (e.g. N, NH, S or O). Not limiting examples of $(C_3-C_y)$heterocycloalkyl are represented by: pyrrolidinyl, thiazolidinyl, piperazinyl, piperidinyl, morpholinyl, thiomorpholinyl, and azetidinyl.

By analogy, the term "$(C_3-C_y)$heterocycloalkylene", refers to a divalent $(C_3-C_y)$heterocycloalkyl radical, wherein $(C_3-C_y)$heterocycloalkyl is as above defined.

The expression "$(C_1-C_x)$alkylcarbonyl" refers to $(C_1-C_x)$alkylCO- groups wherein the group "$(C_1-C_x)$ alkyl" has the meaning above defined.

The expression "$(C_3-C_y)$cycloalkylcarbonyl" refers to $(C_3-C_y)$cycloalkylCO-groups wherein the group "$(C_3-C_y)$cycloalkyl" has the meaning above defined.

The term "$(C_2-C_6)$alkenyl" refers to straight or branched, conjugated or unconjugated, carbon chains with one or more double bonds, in cis or trans configuration, wherein the number atoms is in the range 2 to 6.

The term "$(C_5-C_z)$ cycloalkenyl", where z is an integer greater than or equal to 5, refers to cyclic hydrocarbon groups containing from 5 to z ring carbon atoms and one or more double bonds.

The term "$(C_2-C_6)$alkynyl" refers to straight or branched carbon chains with one or more triple bonds wherein the number atoms is in the range 2 to 6.

The term "$(C_3-C_y)$heterocycloalkyl$(C_1-C_x)$ alkyl" refers to the above "$(C_1-C_x)$alkyl" group wherein one or more hydrogen atoms are replaced by one or more "$(C_3-C_y)$heterocycloalkyl" groups.

The expression "ring system" refers to mono- or bicyclic ring systems which may be saturated, partially unsaturated or unsaturated, such as aryl, $(C_3-C_8)$ cycloalkyl, $(C_3-C_7)$ heterocycloalkyl or heteroaryl, having 5 to 11 ring atoms in which at least one ring atom is a heteroatom (e.g. N, S or O).

The expression "aryl" refers to mono or bi-cyclic ring systems which have 6 to 10 ring atoms, wherein at least one ring is aromatic.

The expression "heteroaryl" refers to mono or bi- cyclic ring systems with 5 to 11 ring atoms, in which at least one ring is aromatic and in which at least one ring atom is a heteroatom (e.g. N, NH, S or O).

Examples of suitable aryl or 5 or 6-membered heteroaryl monocyclic systems include, for instance, phenyl, thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolidinyl), furan (furanyl) radicals and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinolone (qinolinyl), isoquinoline (isoquinolinyl), indole (indolyl), isoindole (isoindolyl), benzothiophene (benzothiophenyl), dihydrobenzo dioxin, dihydrobenzo dioxepine, benzo oxazine radicals and the like.

The symbol "—$C_6H_6$—" indicates a divalent phenylene ring radical.

The term "salt" includes base addition and acid addition salts. The compounds of the invention which are acidic can form salts, including pharmaceutically acceptable salts, with bases such as alkali metal hydroxides, e.g., sodium and potassium hydroxides; alkaline earth metal hydroxides, e.g., calcium, barium and magnesium hydroxides; with organic bases, e.g., N-methyl-D-glucamine, choline tris(hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g., with hydrohalic acids such as hydrochloric or hydrobromic acids, sulphuric acid, nitric acid or phosphoric acid and the like, and with organic acids, e.g., with acetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds (I) which have a quaternary nitrogen can also form quaternary salts with a pharmaceutically acceptable counter-ion such as chloride, bromide, acetate, formate, p-toluenesulfonate, succinate, hemi-succinate, naphthalene-bis sulfonate, methanesulfonate, xinafoate, and the like.

Compounds of the present invention which contain one or more actual or potential stereogenic centres, because of the presence of asymmetric carbon atoms, can exist as a number of optical isomers (enantiomers, diastereoisomers and the like) with R or S stereochemistry at each stereogenic centre. The present invention includes all such optical isomers (enantiomers, diastereoisomers and the like) and mixtures thereof.

In one embodiment, the invention provides compounds of formula (I)':

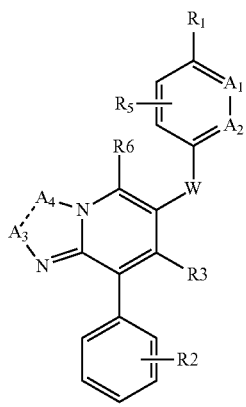

(I)

wherein $R_1$ is selected from halogen, —CN, —OH and a group $(C_1-C_4)$alkyl;

$R_2$ is selected from halogen, $(C_1-C_4)$alkyl, $(C_1-C_4)$haloalkyl, —CN, $(C_1-C_4)$alkoxy, $(C_1-C_4)$haloalkoxy, nitro, and a group —OH;

W is a:

(i) a 5,6-membered heteroarylene ring optionally substituted by one or two groups independently selected from halogen, —OH, $(C_1-C_4)$alkyl, $(C_1-C_4)$haloalkyl, —CN, $(C_1-C_4)$alkoxy, nitro, a group —$NHR_{18}$, and a group —$CONHR_{19}$;

(ii) a $(C_5-C_6)$heterocycloalkylene ring partially unsaturated and optionally substituted by one or two groups independently selected from halogen, $(C_1-C_4)$alkyl, $C_1-C_4$)haloalkyl, —CN, —OH, $(C_1-C_4)$alkoxy, nitro, carbonyl, a group —$NHR_{18}$, and a group —$CONHR_{19}$; or (iii) a phenylene group optionally substituted by one or two groups independently selected from halogen, $(C_1-C_4)$alkyl, $(C_1-C_4)$haloalkyl, —CN, nitro, a group —$NHR_{18}$, a group —$CONHR_{19}$, and a group —$OR_{20}$;

$R_{18}$ is hydrogen, $(C_1-C_4)$alkyl, a group —$SO_2R_{21}$;

$R_{21}$ is $(C_1-C_4)$alkyl;

$R_{19}$ is hydrogen or $(C_1-C_4)$alkyl;

$R_{20}$ is hydrogen, $(C_1-C_4)$alkyl or a group —$(C_1-C_4)$alkylene-$OR_{22}$;

$R_{22}$ is hydrogen or $(C_1-C_4)$alkyl;

$R_3$ is a group —$CH_2$—$R_{23}$;

$R_{23}$ is a group selected from hydrogen, $(C_1-C_4)$alkyl, $(C_1-C_4)$haloalkyl, —CN, $(C_1-C_4)$alkoxy and halogen;

$R_5$ is a group selected from hydrogen, $(C_1-C_4)$alkyl, $(C_1-C_4)$haloalkyl, —CN, $(C_1-C_4)$alkoxy and halogen;

$R_6$ is selected from hydrogen, halogen, $(C_1-C_4)$alkyl, and CN;

$A_1$ is a group —$CR_7$= or a group —N=;

$A_2$ is a group =$CR_8$— or a group =N—;

$R_7$ is selected from hydrogen, halogen, $(C_1-C_4)$alkyl, $(C_1-C_4)$haloalkyl and $(C_1-C_4)$alkoxy;

$R_8$ is selected from hydrogen, halogen, $(C_1-C_4)$alkyl, $(C_1-C_4)$haloalkyl, $(C_1-C_4)$alkoxy, a group —$S(C_1-C_4)$alkyl, and a group —$SO_2(C_1-C_4)$alkyl;

wherein $A_1$ and $A_2$ cannot be at the same time a group —N=;

$A_3$-$A_4$ is a moiety selected from a group —$CR_4$=N—, a group —$CR_4$=$CR_9$— and a group —$NR_{17}$—CO—;

$R_9$ is hydrogen or $(C_1-C_4)$alkyl;

$R_4$ is a group selected from hydrogen, $(C_1-C_4)$alkyl, —$NR_{10}R_{11}$, —$NHCOR_{12}$, —$NHCOO$—$R_{13}$, —$NH$—$CONH$—$R_{14}$, $(C_1-C_4)$alkoxy, —$NH(CH_2)_n$—$SO_2(C_1-C_4)$alkyl, —$(NH)_q(CH_2)_n$—$(C_6H_6)$—$SO_2(C_1-C_4)$alkyl, —$NHSO_2(C_1-C_4)$alkyl and —$(NH)_r(CH_2)_nCONR_{15}R_{16}$;

$R_{17}$ is a group selected from hydrogen, $(C_1-C_4)$alkyl, —$(CH_2)_n$—$(C_6H_6)$—$SO_2(C_1-C_4)$alkyl, —$(CH_2)_n$—$SO_2(C_1-C_4)$alkyl and —$(CH_2)_nCONR_{15}R_{16}$;

n is zero or an integer ranging from 1 to 5;

q is zero or 1;

r is zero or 1;

$R_{10}$ is hydrogen, a group $(C_1-C_6)$alkyl, a group $(C_1-C_6)$hydroxyalkyl, a group $(C_1-C_4)$alkylene-NH—(C=NH)—$NH_2$, a group $(C_1-C_6)$alkyleneNR$_a$R$_b$ or a group $(C_1-C_6)$alkyleneN$^+$R$_a$R$_b$R$_c$;

$R_{11}$ is hydrogen, a group $(C_1-C_6)$alkyl, a group $(C_1-C_6)$hydroxyalkyl, a group $(C_1-C_4)$alkylene-NH—(C=NH)—$NH_2$, a group $(C_1-C_6)$alkyleneNR$_a$R$_b$ or a group $(C_1-C_6)$alkyleneN$^+$R$_a$R$_b$Rc;

or $R_{10}$ and $R_{11}$ together with the nitrogen atom they are linked to may form a $(C_5-C_7)$heterocycloalkyl;

$R_a$ and $R_b$ are at each occurrence independently hydrogen or $(C_1-C_4)$alkyl; alternatively, $R_a$ and $R_b$, together with the nitrogen atom they are linked to may form a $(C_5-C_7)$heterocycloalkyl ring system optionally substituted by one or more groups $C_1-C_6$ alkyl and which $(C_5-C_7)$heterocycloalkyl optionally contains a group —S(O)— or —$S(O)_2$— or a further heteroatom which is oxygen, sulfur or nitrogen, said nitrogen atom optionally substituted by $(C_1-C_6)$alkyl;

or $R_a$ is as above defined and $R_b$ is linked to one carbon atom of the ($C_1$-$C_6$)alkylene portion of the group linked to the nitrogen to which they are connected to form a saturated ($C_5$-$C_6$)heterocycloalkyl ring;

$R_a$, $R_b$ and $R_c$ are at each occurrence independently ($C_1$-$C_4$)alkyl; alternatively, $R_a$ and $R_b$ or $R_a$ and $R_c$, together with the nitrogen atom they are linked to may form a ($C_5$-$C_7$) heterocycloalkyl ring system optionally substituted by one or more groups $C_1$-$C_6$ alkyl and which ($C_5$-$C_7$)heterocycloalkyl ring optionally contains a group —S(O)— or —S(O)$_2$— or a further heteroatom which is oxygen, sulfur or nitrogen, said nitrogen atom optionally substituted by ($C_1$-$C_6$) alkyl; or $R_a$ and $R_b$ are as above defined and $R_c$ is linked to one carbon atom of the ($C_1$-$C_6$)alkylene portion of the group linked to the nitrogen to which they are connected to form a saturated ($C_5$-$C_6$)heterocycloalkyl ring;

$R_{12}$ is selected from —($C_6H_6$)—$SO_2$($C_1$-$C_4$)alkyl, ($C_1$-$C_6$) alkyl, ($C_1$-$C_4$)haloalkyl, ($C_5$-$C_7$)heterocycloalkyl, a group —($CH_2$)$_n$—S(O)$_t$($C_1$-$C_4$)alkyl, a group ($C_1$-$C_4$)alkylene-NH—(C=NH)—$NH_2$, a group ($C_1$-$C_4$)alkylene-$CO_2$H, a group —($C_1$-$C_6$)alkyleneN$R_aR_b$, a group —($C_1$-$C_6$)alkyleneN$^+R_aR_bR_c$ and ($C_1$-$C_4$)alkyl($C_5$-$C_7$)heterocycloalkyl, wherein such groups may be optionally substituted by one or two substituents selected from ($C_1$-$C_4$)alkyl, hydroxy, halogen, —$SO_2$($C_1$-$C_4$)alkyl, amino or ($C_1$-$C_4$)alkylamino;

t may be zero, 1 or 2;

$R_{13}$ is selected in the group-($C_6H_6$)—$SO_2$alkyl, ($C_1$-$C_6$) alkyl, ($C_1$-$C_4$)haloalkyl, ($C_5$-$C_7$)heterocycloalkyl, a group ($C_1$-$C_4$)alkylene-NH—(C=NH)—$NH_2$, ($C_1$-$C_6$)alkyleneN$R_aR_b$, —($C_1$-$C_6$)alkyleneN$^+R_aR_bR_c$ and ($C_1$-$C_4$)alkylene ($C_5$-$C_7$)heterocycloalkyl, wherein such groups may be optionally substituted by one or two substituents selected from ($C_1$-$C_4$)alkyl, ($C_1$-$C_4$)alkoxy, hydroxy, halogen, —$SO_2$ ($C_1$-$C_4$)alkyl, amino or ($C_1$-$C_4$)alkylamino;

$R_{14}$ is selected from —($C_6H_6$)—$SO_2$alkyl, ($C_1$-$C_4$)haloalkyl, ($C_5$-$C_7$)heterocycloalkyl, a group ($C_1$-$C_4$)alkylene-NH—(C=NH)—$NH_2$, ($C_1$-$C_6$)alkyleneN$R_aR_b$, —($C_1$-$C_6$) alkyleneN$^+R_aR_bR_c$ and ($C_1$-$C_4$)alkyl($C_5$-$C_7$) heterocycloalkyl, wherein such groups may be optionally substituted by one or two substituents selected from ($C_1$-$C_4$) alkyl, hydroxy, halogen, —$SO_2$($C_1$-$C_4$)alkyl, amino, ($C_1$-$C_4$) alkylcarbonyl and ($C_1$-$C_4$)alkylamino;

$R_{15}$ is hydrogen, a group ($C_1$-$C_6$)alkyl, a group ($C_1$-$C_4$) alkylene-NH—(C=NH)—$NH_2$, a group ($C_1$-$C_6$)alkyleneN-$R_aR_b$, or a group —($C_1$-$C_6$)alkyleneN$^+R_aR_bR_c$;

$R_{16}$ is hydrogen, a group ($C_1$-$C_6$)alkyl, a group ($C_1$-$C_4$) alkylene-NH—(C=NH)—$NH_2$, a group ($C_1$-$C_6$)alkyleneN-$R_aR_b$ or a group —($C_1$-$C_6$)alkyleneN$^+R_aR_bR_c$;

or $R_{15}$ and $R_{16}$ together with the nitrogen atom they are linked to may form a ($C_5$-$C_7$)heterocycloalkyl;

wherein if one or more groups —($C_1$-$C_6$)alkyleneN$^+R_a$-$_bR_c$ are present, they form quaternary salts with a pharmaceutically acceptable counter ion;

and wherein groups $R_{18}$, $R_{19}$, $R_{20}$, $R_{21}$, $R_{22}$, $R_a$, $R_b$, $R_c$ and n may assume the same or different meanings at each occurrence, if present in more than one group;

and pharmaceutically acceptable salts or solvate thereof.

It is to be understood that all preferred groups or embodiments described herebelow and hereabove for compounds of formula (I) may be combined among each other and apply to compounds of formula (I)', (IA) and (IB) as well mutatis mutandis.

In a preferred embodiment, $R_1$ is —CN.

In a preferred embodiment, $R_2$ is ($C_1$-$C_4$)haloalkyl; in a further preferred embodiment, $R_2$ is 3-trifluoromethyl.

In a preferred embodiment, W is a 5,6-membered heteroaryl ring which is optionally substituted.

In a preferred embodiment, $R_3$ is a group —$CH_2$—$R_{23}$. In a further preferred embodiment, $R_3$ is a group —$CH_2$—$R_{23}$ and $R_{23}$ is hydrogen, for example $R_3$=methyl.

In a preferred embodiment, $R_5$ is hydrogen.

In a preferred embodiment, $R_6$ is hydrogen.

In a preferred embodiment, $A_1$ is a group —$CR_7$=. In a preferred embodiment, $R_7$ is hydrogen.

In a preferred embodiment, $A_2$ is a group —$CR_8$=. In a preferred embodiment, $R_8$ is hydrogen or group —$SO_2$($C_1$-$C_4$)alkyl.

In a preferred embodiment, $A_3$-$A_4$ is a moiety —$CR_4$=N—.

In a preferred embodiment, $R_4$ is a group selected from —$NR_{10}R_{11}$, —NHCO$R_{12}$, —NHCOO—$R_{13}$, —NHCONH—$R_{14}$, —NH($CH_2$)$_n$—$SO_2$($C_1$-$C_4$)alkyl, —(NH)$_q$ ($CH_2$)$_n$—($C_6H_6$)—$SO_2$($C_1$-$C_4$)alkyl, —$NHSO_2$($C_1$-$C_4$) alkyl and —(NH)$_r$($CH_2$)$_n$CON$R_{15}R_{16}$.

In a preferred embodiment, the invention provides compounds of formula (IA) and pharmaceutically acceptable salts thereof:

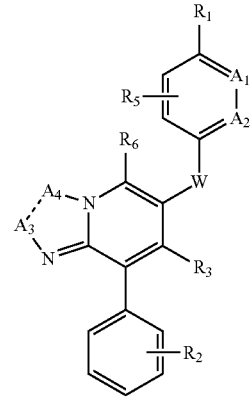

(IA)

wherein $A_3$-$A_4$ is a moiety —$CR_4$=N—, and $R_1$, $R_2$, $R_3$, $R_4$, $R_6$, $A_1$ and $A_2$ are as defined for compounds of formula (I).

In another preferred embodiment, the invention provides compounds of formula (IB) and pharmaceutically acceptable salts thereof:

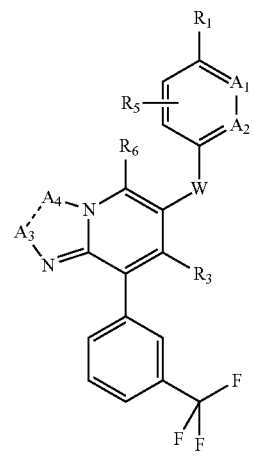

(IB)

wherein $R_2$ is 3-trifluoromethyl, and $R_1$, $R_3$, $R_4$, $R_6$, $A_3$-$A_4$, $A_1$ and $A_2$ are as defined for compounds of formula (I).

In a preferred embodiment, the compound of formula (I) is selected in the group consisting of:

4-{5-[2-Amino-7-methyl-8-(3-trifluoromethyl-phenyl)-[1,2,4]triazolo[1,5-a]pyridin-6-yl]-pyrazol-1-yl}-benzonitrile;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2,2,2-trifluoro-acetamide;

4-{5-[7-Methyl-8-(3-trifluoromethyl-phenyl)-[1,2,4]triazolo[1,5-a]pyridin-6-yl]-pyrazol-1-yl}-benzonitrile;

4-{5-[2,7-Dimethyl-8-(3-trifluoromethyl-phenyl)-[1,2,4]triazolo[1,5-a]pyridin-6-yl]-pyrazol-1-yl}-benzonitrile;

4-{5-[2,7-Dimethyl-8-(3-trifluoromethyl-phenyl)-imidazo[1,2-a]pyridin-6-yl]-pyrazol-1-yl}-benzonitrile;

4-{5-[7-Methyl-8-(3-trifluoromethyl-phenyl)-imidazo[1,2-a]pyridin-6-yl]-pyrazol-1-yl}-benzonitrile;

4-{5-[2-(4-Methanesulfonyl-phenylamino)-7-methyl-8-(3-trifluoromethyl-phenyl)-[1,2,4]triazolo[1,5-a]pyridin-6-yl]-pyrazol-1-yl}-benzonitrile;

4-{5-[2-(4-Methanesulfonyl-benzyl)-7-methyl-8-(3-trifluoromethyl-phenyl)-[1,2,4]triazolo[1,5-a]pyridin-6-yl]-pyrazol-1-yl}-benzonitrile;

4-{5-[7-Methyl-3-oxo-8-(3-trifluoromethyl-phenyl)-2,3-dihydro-[1,2,4]triazolo[4,3-a]pyridin-6-yl]-pyrazol-1-yl}-benzonitrile;

4-{5-[2-(4-Methanesulfonyl-benzyl)-7-methyl-3-oxo-8-(3-trifluoromethyl-phenyl)-2,3-dihydro-[1,2,4]triazolo[4,3-a]pyridin-6-yl]-pyrazol-1-yl}-benzonitrile;

2-[6-[2-(4-Cyano-phenyl)-2H-pyrazol-3-yl]-7-methyl-3-oxo-8-(3-trifluoromethyl-phenyl)-[1,2,4]triazolo[4,3-a]pyridin-2-yl]-N,N-dimethyl-acetamide;

2-[6-[2-(4-Cyano-phenyl)-2H-pyrazol-3-yl]-7-methyl-3-oxo-8-(3-trifluoromethyl-phenyl)-[1,2,4]triazolo[4,3-a]pyridin-2-yl]-N-methyl-acetamide;

4-{5-[2-(3-Methanesulfonyl-propyl)-7-methyl-3-oxo-8-(3-trifluoromethyl-phenyl)-2,3-dihydro-[1,2,4]triazolo[4,3-a]pyridin-6-yl]-pyrazol-1-yl}-benzonitrile;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-dimethylamino-acetamide;

{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-trimethyl-ammonium bromide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-dimethylamino-butyramide;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-propyl}-trimethyl-ammonium bromide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-(4-methyl-piperazin-1-yl)-acetamide;

4-{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-1,1-dimethyl-piperazin-1-ium iodide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-morpholin-4-yl-acetamide;

4-{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-1,1-dimethyl-piperazin-1-ium iodide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-morpholin-4-yl-acetamide;

N-[6-[1-(4-Cyano-phenyl)-1H-pyrazol-5-yl]-7-methyl-8-(3-trifluoromethyl-phenyl)-[1,2,4]triazolo[1,5-a]pyridin-2-yl]-2-(1,1-dioxothiomorpholin-4-yl)-acetamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-methanesulfonyl-benzamide;

4-{5-[2-(4-Methanesulfonyl-benzylamino)-7-methyl-8-(3-trifluoromethyl-phenyl)-[1,2,4]triazolo[1,5-a]pyridin-6-yl]-pyrazol-1-yl}-benzonitrile;

2-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N,N-dimethyl-acetamide;

1-{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-1,4-dimethyl-piperazin-1-ium chloride;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-acetamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-methanesulfonamide;

4-{5-[2-(3-Dimethylamino-propylamino)-7-methyl-8-(3-trifluoromethyl-phenyl)-[1,2,4]triazolo[1,5-a]pyridin-6-yl]-pyrazol-1-yl}-benzonitrile;

4-{5-[2-(2-Dimethylamino-ethylamino)-7-methyl-8-(3-trifluoromethyl-phenyl)-[1,2,4]triazolo[1,5-a]pyridin-6-yl]-pyrazol-1-yl}-benzonitrile;

4-{5-[2-(4-Dimethylamino-butylamino)-7-methyl-8-(3-trifluoromethyl-phenyl)-[1,2,4]triazolo[1,5-a]pyridin-6-yl]-pyrazol-1-yl}-benzonitrile;

4-{5-[2-Methoxy-7-methyl-8-(3-trifluoromethyl-phenyl)-[1,2,4]triazolo[1,5-a]pyridin-6-yl]-pyrazol-1-yl}-benzonitrile;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-propyl}-trimethyl-ammonium benzenesulfonate;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-ethyl}-trimethyl-ammonium benzenesulfonate;

{4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-butyl}-trimethyl-ammonium formate;

[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-carbamic acid ethyl ester;

[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-carbamic acid 2-methoxyethyl ester;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyloxy]-propyl}-trimethyl-ammonium formate;

(3-{3-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-ureido}-propyl)-trimethyl-ammonium formate;

N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-acetamide;

4-{5-[2-Amino-7-methyl-8-(3-trifluoromethyl-phenyl)-[1,2,4]triazolo[1,5-a]pyridin-6-yl]-pyrazol-1-yl}-3-methanesulfonyl-benzonitrile;

N-[6-[2-(4-Cyano-2-fluoro-phenyl)-2H-pyrazol-3-yl]-7-methyl-8-(3-trifluoromethyl-phenyl)-[1,2,4]triazolo[1,5-a]pyridin-2-yl]-acetamide;

N-[6-[2-(4-Cyano-phenyl)-4-methyl-2H-pyrazol-3-yl]-7-methyl-8-(3-trifluoromethyl-phenyl)-[1,2,4]triazolo[1,5-a]pyridin-2-yl]-acetamide;

N-[6-(4'-Cyano-biphenyl-2-yl)-7-methyl-8-(3-trifluoromethyl-phenyl)-[1,2,4]triazolo[1,5-a]pyridin-2-yl]-acetamide;

N-[6-[2-(4-Cyano-phenyl)-2H-pyrazol-3-yl]-7-methyl-8-(3-trifluoromethoxy-phenyl)-[1,2,4]triazolo[1,5-a]pyridin-2-yl]-acetamide;

N-[6-[2-(4-Cyano-phenyl)-2H-pyrazol-3-yl]-7-methyl-8-(3-trifluoromethyl-phenyl)[1,2,4]triazolo[1,5-a]pyridin-2-yl]-3-methanesulfinyl-propionamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-methanesulfonyl-propionamide;

4-{5-[2-(3-Methanesulfonyl-propylamino)-7-methyl-8-(3-trifluoromethyl-phenyl)-[1,2,4]triazolo[1,5-a]pyridin-6-yl]-pyrazol-1-yl}-benzonitrile;

4-{5-[2-(2-Hydroxy-ethylamino)-7-methyl-8-(3-trifluoromethyl-phenyl)-[1,2,4]triazolo[1,5-a]pyridin-6-yl]-pyrazol-1-yl}-benzonitrile;

4-{5-[2-(2-Hydroxy-propylamino)-7-methyl-8-(3-trifluoromethyl-phenyl)-[1,2,4]triazolo[1,5-a]pyridin-6-yl]-pyrazol-1-yl}-benzonitrile;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-piperidin-4-yl-urea;

(1-methyl-4-piperidyl)[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-urea;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-ethyl-urea;

4-{5-[2-(3-Hydroxy-propylamino)-7-methyl-8-(3-trifluoromethyl-phenyl)-[1,2,4]triazolo[1,5-a]pyridin-6-yl]-pyrazol-1-yl}-benzonitrile;

4-{5-[2-(4-Hydroxy-butylamino)-7-methyl-8-(3-trifluoromethyl-phenyl)-[1,2,4]triazolo[1,5-a]pyridin-6-yl]-pyrazol-1-yl}-benzonitrile;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-succinamic acid;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-methylamino-butyramide;

1-(1-Acetyl-piperidin-4-yl)-3-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-urea;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(1-methanesulfonyl-piperidin-4-yl)-urea;

4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N-methyl-butyramide;

4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N-(2-dimethylamino-ethyl)-N-methyl-butyramide;

4-{3-Amino-5-[2-amino-7-methyl-8-(3-trifluoromethyl-phenyl)-[1,2,4]triazolo[1,5-a]pyridin-6-yl]-[1,2,4]triazol-1-yl}-benzonitrile;

and pharmaceutically acceptable salts thereof.

In another preferred embodiment, the compound of formula (I) is selected in the group consisting of:

4-{5-[2-Amino-7-methyl-8-(3-trifluoromethyl-phenyl)-[1,2,4]triazolo[1,5-a]pyridin-6-yl]-pyrazol-1-yl}-benzonitrile;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2,2,2-trifluoro-acetamide;

4-{5-[7-Methyl-8-(3-trifluoromethyl-phenyl)-[1,2,4]triazolo[1,5-a]pyridin-6-yl]-pyrazol-1-yl}-benzonitrile;

4-{5-[2,7-Dimethyl-8-(3-trifluoromethyl-phenyl)-[1,2,4]triazolo[1,5-a]pyridin-6-yl]-pyrazol-1-yl}-benzonitrile;

4-{5-[2,7-Dimethyl-8-(3-trifluoromethyl-phenyl)-imidazo[1,2-a]pyridin-6-yl]-pyrazol-1-yl}-benzonitrile;

4-{5-[7-Methyl-8-(3-trifluoromethyl-phenyl)-imidazo[1,2-a]pyridin-6-yl]-pyrazol-1-yl}-benzonitrile;

4-{5-[2-(4-Methanesulfonyl-phenylamino)-7-methyl-8-(3-trifluoromethyl-phenyl)-[1,2,4]triazolo[1,5-a]pyridin-6-yl]-pyrazol-1-yl}-benzonitrile;

4-{5-[2-(4-Methanesulfonyl-benzyl)-7-methyl-8-(3-trifluoromethyl-phenyl)-[1,2,4]triazolo[1,5-a]pyridin-6-yl]-pyrazol-1-yl}-benzonitrile;

4-{5-[7-Methyl-3-oxo-8-(3-trifluoromethyl-phenyl)-2,3-dihydro-[1,2,4]triazolo[4,3-a]pyridin-6-yl]-pyrazol-1-yl}-benzonitrile;

4-{5-[2-(4-Methanesulfonyl-benzyl)-7-methyl-3-oxo-8-(3-trifluoromethyl-phenyl)-2,3-dihydro-[1,2,4]triazolo[4,3-a]pyridin-6-yl]-pyrazol-1-yl}-benzonitrile;

2-[6-[2-(4-Cyano-phenyl)-2H-pyrazol-3-yl]-7-methyl-3-oxo-8-(3-trifluoromethyl-phenyl)-[1,2,4]triazolo[4,3-a]pyridin-2-yl]-N,N-dimethyl-acetamide;

2-[6-[2-(4-Cyano-phenyl)-2H-pyrazol-3-yl]-7-methyl-3-oxo-8-(3-trifluoromethyl-phenyl)-[1,2,4]triazolo[4,3-a]pyridin-2-yl]-N-methyl-acetamide;

4-{5-[2-(3-Methanesulfonyl-propyl)-7-methyl-3-oxo-8-(3-trifluoromethyl-phenyl)-2,3-dihydro-[1,2,4]triazolo[4,3-a]pyridin-6-yl]-pyrazol-1-yl}-benzonitrile;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-dimethylamino-acetamide;

{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-trimethyl-ammonium bromide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-dimethylamino-butyramide;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-propyl}-trimethyl-ammonium bromide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-(4-methyl-piperazin-1-yl)-acetamide;

4-{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-1,1-dimethyl-piperazin-1-ium iodide;

N-[6-[2-(4-Cyano-phenyl)-2H-pyrazol-3-yl]-7-methyl-8-(3-trifluoromethyl phenyl)-[1,2,4]triazolo[1,5-a]pyridin-2-yl]-2-morpholin-4-yl-acetamide;

4-{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-1,1-dimethyl-piperazin-1-ium iodide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-morpholin-4-yl-acetamide;

N-[6-[1-(4-Cyano-phenyl)-1H-pyrazol-5-yl]-7-methyl-8-(3-trifluoromethyl-phenyl)-[1,2,4]triazolo[1,5-a]pyridin-2-yl]-2-(1,1-dioxothiomorpholin-4-yl)-acetamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-methanesulfonyl-benzamide;

4-{5-[2-(4-Methanesulfonyl-benzylamino)-7-methyl-8-(3-trifluoromethyl-phenyl)-[1,2,4]triazolo[1,5-a]pyridin-6-yl]-pyrazol-1-yl}-benzonitrile;

2-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N,N-dimethyl-acetamide;

1-{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-1,4-dimethyl-piperazin-1-ium chloride;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-acetamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-methanesulfonamide;

4-{5-[2-(3-Dimethylamino-propylamino)-7-methyl-8-(3-trifluoromethyl-phenyl)-[1,2,4]triazolo[1,5-a]pyridin-6-yl]-pyrazol-1-yl}-benzonitrile;

4-{5-[2-(2-Dimethylamino-ethylamino)-7-methyl-8-(3-trifluoromethyl-phenyl)-[1,2,4]triazolo[1,5-a]pyridin-6-yl]-pyrazol-1-yl}-benzonitrile;

4-{5-[2-(4-Dimethylamino-butylamino)-7-methyl-8-(3-trifluoromethyl-phenyl)-[1,2,4]triazolo[1,5-a]pyridin-6-yl]-pyrazol-1-yl}-benzonitrile;

4-{5-[2-Methoxy-7-methyl-8-(3-trifluoromethyl-phenyl)-[1,2,4]triazolo[1,5-a]pyridin-6-yl]-pyrazol-1-yl}-benzonitrile;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-propyl}-trimethyl-ammonium benzenesulfonate;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-ethyl}-trimethyl-ammonium benzenesulfonate;

{4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-butyl}-trimethyl-ammonium formate;

[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-carbamic acid ethyl ester;

[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-carbamic acid 2-methoxyethyl ester;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyloxy]-propyl}-trimethyl-ammonium formate;

(3-{3-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-ureido}-propyl)-trimethyl-ammonium formate;

N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-acetamide;

4-{5-[2-Amino-7-methyl-8-(3-trifluoromethyl-phenyl)-[1,2,4]triazolo[1,5-a]pyridin-6-yl]-pyrazol-1-yl}-3-methanesulfonyl-benzonitrile;

N-[6-[2-(4-Cyano-2-fluoro-phenyl)-2H-pyrazol-3-yl]-7-methyl-8-(3-trifluoromethyl-phenyl)-[1,2,4]triazolo[1,5-a]pyridin-2-yl]-acetamide;

N-[6-[2-(4-Cyano-phenyl)-4-methyl-2H-pyrazol-3-yl]-7-methyl-8-(3-trifluoromethyl-phenyl)-[1,2,4]triazolo[1,5-a]pyridin-2-yl]acetamide;

N-[6-(4'-Cyano-biphenyl-2-yl)-7-methyl-8-(3-trifluoromethyl-phenyl)-[1,2,4]triazolo[1,5-a]pyridin-2-yl]-acetamide;

N-[6-[2-(4-Cyano-phenyl)-2H-pyrazol-3-yl]-7-methyl-8-(3-trifluoromethoxy-phenyl)-[1,2,4]triazolo[1,5-a]pyridin-2-yl]-acetamide;

N-[6-[2-(4-Cyano-phenyl)-2H-pyrazol-3-yl]-7-methyl-8-(3-trifluoromethyl-phenyl)[1,2,4]triazolo[1,5-a]pyridin-2-yl]-3-methanesulfinyl-propionamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-methanesulfonyl-propionamide;

4-{5-[2-(3-Methanesulfonyl-propylamino)-7-methyl-8-(3-trifluoromethyl-phenyl)-[1,2,4]triazolo[1,5-a]pyridin-6-yl]-pyrazol-1-yl}-benzonitrile;

4-{5-[2-(2-Hydroxy-ethylamino)-7-methyl-8-(3-trifluoromethyl-phenyl)-[1,2,4]triazolo[1,5-a]pyridin-6-yl]-pyrazol-1-yl}-benzonitrile;

4-{5-[2-(2-Hydroxy-propylamino)-7-methyl-8-(3-trifluoromethyl-phenyl)-[1,2,4]triazolo[1,5-a]pyridin-6-yl]-pyrazol-1-yl}-benzonitrile;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-piperidin-4-yl-urea;

(1-methyl-4-piperidyl)[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-urea;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-ethyl-urea;

4-{5-[2-(3-Hydroxy-propylamino)-7-methyl-8-(3-trifluoromethyl-phenyl)-[1,2,4]triazolo[1,5-a]pyridin-6-yl]-pyrazol-1-yl}-benzonitrile;

4-{5-[2-(4-Hydroxy-butylamino)-7-methyl-8-(3-trifluoromethyl-phenyl)-[1,2,4]triazolo[1,5-a]pyridin-6-yl]-pyrazol-1-yl}-benzonitrile;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-succinamic acid;

N-[6-[2-(4-Cyano-phenyl)-2H-pyrazol-3-yl]-7-methyl-8-(3-trifluoromethyl-phenyl)-[1,2,4]-triazolo[1,5-a]pyridin-2-yl]-4-methylamino-butyramide;

1-(1-Acetyl-piperidin-4-yl)-3-[6-[2-(4-cyano-phenyl)-2H-pyrazol-3-yl]-7-methyl-8-(3-trifluoromethyl-phenyl)-[1,2,4]triazolo[1,5-a]pyridin-2-yl]urea;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(1-methanesulfonyl-piperidin-4-yl)-urea;

4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N-methyl-butyramide;

4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N-(2-dimethylamino-ethyl)-N-methyl-butyramide;

4-{3-Amino-5-[2-amino-7-methyl-8-(3-trifluoromethyl-phenyl)-[1,2,4]triazolo[1,5-a]pyridin-6-yl]-[1,2,4]triazol-1-yl}-benzonitrile;

1-[6-[2-(4-Cyano-phenyl)-2H-pyrazol-3-yl]-7-methyl-8-(3-trifluoromethyl-phenyl) [1,2,4]triazolo[1,5-a]pyridin-2-yl]-3-[3-(piperidin-4-ylamino)-propyl]-urea;

4-{5-[2-{3-[(Azetidin-3-ylmethyl)-amino]-propylamino}-7-methyl-8-(3-trifluoromethyl-phenyl)-[1,2,4]triazolo[1,5-a]pyridin-6-yl]-pyrazol-1-yl}-benzonitrile;

4-{5-[7-Methyl-2-[3-(piperidin-4-ylamino)-propylamino]-8-(3-trifluoromethyl-phenyl)-[1,2,4]triazolo[1,5-a]pyridin-6-yl]-pyrazol-1-yl}-benzonitrile;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-{3-[(3-dimethylamino-propyl)-methyl-amino]-propyl}-urea;

4-{5-[2-{3-[(3-Dimethylamino-propyl)-methyl-amino]-propylamino}-7-methyl-8-(3-trifluoromethyl-phenyl)-[1,2,4]triazolo[1,5-a]pyridin-6-yl]-pyrazol-1-yl}-benzonitrile;

4-{5-[7-Methyl-2-[3-(4-methylamino-piperidin-1-yl)-propylamino]-8-(3-trifluoromethyl-phenyl)-[1,2,4]triazolo[1,5-a]pyridin-6-yl]-pyrazol-1-yl}-benzonitrile;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-[2-(4-methylamino-piperidin-1-yl)-ethyl]-urea;

N-[6-[4-(4-Cyano-phenyl)-5-oxo-4,5-dihydro-1H-[1,2,4]triazol-3-yl]-7-methyl-8-(3-trifluoromethyl-phenyl)-[1,2,4]triazolo[1,5-a]pyridin-2-yl]-acetamide;

4-{5-[7-Methyl-2-[2-(piperidin-4-yl-amino)-ethylamino]-8-(3-trifluoromethyl-phenyl)-[1,2,4]triazolo[1,5-a]pyridin-6-yl]-pyrazol-1-yl}-benzonitrile;

4-{3-[2-Amino-7-methyl-8-(3-trifluoromethyl-phenyl)-[1,2,4]triazolo[1,5-a]pyridin-6-yl]-5-oxo-1,5-dihydro-[1,2,4]triazol-4-yl}-benzonitrile;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(R)-piperidin-3-yl-urea;

{3-[6-[2-(4-Cyano-phenyl)-5-methoxycarbonyl-2H-[1,2,4]triazol-3-yl]-7-methyl-8-(3-trifluoromethyl-phenyl)-[1,2,4]triazolo[1,5a]pyridin-2-ylcarbamoyl]-propyl}-trimethyl ammonium formate;

(3-{2-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-ylcarbamoyl]-ethanesulfonyl}-propyl)-trimethyl-ammonium formate;

N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-3-dimethylamino-propionamide;

N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-3-(3-dimethylamino-propane-1-sulfonyl)-propionamide;

3-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-1-(3-dimethylamino-propyl)-1-methyl-urea;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(S)-piperidin-3-yl-urea;

{3-[6-[5-Carboxy-2-(4-cyano-phenyl)-2H-[1,2,4]triazol-3-yl]-7-methyl-8-(3-trifluoromethyl-phenyl)-[1,2,4]triazolo[1,5-a]pyridin-2-ylcarbamoyl]-propyl}-trimethyl-ammonium formate;

{3-[6-[2-(4-Cyano-phenyl)-5-methoxycarbonyl-2H-[1,2,4]triazol-3-yl]-7-methyl-8-(3-trifluoromethyl-phenyl)-[1,2,4]triazolo[1,5-a]pyridin-2-ylcarbamoyl]-propyl}-trimethyl-ammonium bromide;

Carboxymethyl-(3-{3-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-ureido}-propyl)-dimethyl-ammonium formate;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(3-methylamino-propyl)-urea;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(3-dimethylamino-propyl)-urea;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-guanidino-propionamide;

{3-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-ylcarbamoyl]-propyl}-trimethyl-ammonium bromide;

N-[6-[1-(4-Cyano-phenyl)-1H-imidazol-2-yl]-7-methyl-8-(3-trifluoromethyl-phenyl)-[1,2,4]triazolo[1,5-a]pyridin-2-yl]acetamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-hydroxy-butyramide;

N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-4-dimethylamino-butyramide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-hydroxy-propionamide;

N-[6-[2-(5-Cyano-pyridin-2-yl)-2H-[1,2,4]triazol-3-yl]-7-methyl-8-(3-trifluoromethyl-phenyl)-[1,2,4]triazolo[1,5-a]pyridin-2-yl]-acetamide;

N-[6-[3-(4-Cyano-phenyl)-3H-imidazol-4-yl]-7-methyl-8-(3-trifluoromethyl-phenyl)-[1,2,4]triazolo[1,5-a]pyridin-2-yl]-acetamide;

N-[6-[5-Amino-2-(4-cyano-phenyl)-2H-[1,2,4]triazol-3-yl]-7-methyl-8-(3-trifluoromethyl-phenyl)-[1,2,4]triazolo[1,5-a]pyridin-2-yl]-acetamide;

5-[2-Acetylamino-7-methyl-8-(3-trifluoromethyl-phenyl)-[1,2,4]triazolo[1,5-a]pyridin-6-yl]-1-(4-cyano-phenyl)-1H-[1,2,4]triazole-3-carboxylic acid methyl ester;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-succinamide;

N-[6-[5-Acetylamino-2-(4-cyano-phenyl)-2H-[1,2,4]triazol-3-yl]-7-methyl-8-(3-trifluoromethyl-phenyl)-[1,2,4]triazolo[1,5-a]pyridin-2-yl]-acetamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-N'-(2-dimethylamino-ethyl)-N'-methylsuccinamide;

and pharmaceutically acceptable salts thereof.

The therapeutic utility of the present compounds is pertinent to any disease that is known to be at least partially mediated by the action of human neutrophil elastase. For example, the present compounds may be beneficial in the treatment of chronic obstructive pulmonary disease (COPD), cystic fibrosis (CF), acute respiratory distress syndrome (ARDS), pulmonary emphysema, pneumonia, Bronchiectasis and lung fibrosis.

The invention also concerns pharmaceutical formulations comprising, as an active ingredient, a compound of the invention. Other compounds may be combined with compounds of this invention for the prevention and treatment of inflammatory diseases of the lung. Thus the invention also concerns pharmaceutical compositions for preventing and treating inflammatory diseases of the lung comprising a therapeutically effective amount of a compound of the invention and one or more other therapeutic agents.

Suitable therapeutic agents for a combination therapy with compounds of the invention include: (1) a corticosteroid, for example fluticasone or budesonide; (2) a β2-adrenoreceptor agonist, for example salmeterol or formoterol; (3) a leukotriene modulator, for example montelukast or pranlukast; (4) anticholinergic agents, for example selective muscarinic-3 (M3) receptor antagonists such as tiotropium bromide; (5) phosphodiesterase-IV (PDE-IV) inhibitors, for example roflumilast or cilomilast; (6) an antitussive agent, such as codeine or dextromethorphan; and (7) a non-steroidal anti-inflammatory agent (NSAID), for example ibuprofen or ketoprofen.

The weight ratio of the first and second active ingredients may be varied and will depend upon the effective dose of each ingredient. Generally, an effective dose of each will be used.

The magnitude of prophylactic or therapeutic dose of a compound of the present invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

Another aspect of the invention provides pharmaceutical compositions which comprise a compound of the invention and a pharmaceutically acceptable carrier. The term "composition," as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the invention encompass any composition made by admixing a compound of the invention, additional active ingredient(s), and pharmaceutically acceptable excipients.

The pharmaceutical compositions of the invention comprise a compound of the present invention as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Any suitable route of administration may be employed for providing a mammal, especially a human, with an effective dosage of a compound of the present invention. In therapeutic use, the active compound may be administered by any convenient, suitable or effective route. Suitable routes of administration are known to those skilled in the art, and include oral, intravenous, rectal, parenteral, topical, ocular, nasal, buccal and pulmonary (by inhalation).

Compositions suitable for administration by inhalation are known, and may include carriers and/or diluents that are known for use in such compositions. The composition may contain 0.01 to 99% by weight of active compound. Preferably, a unit dose comprises the active compound in an amount of 1 μg to 10 mg.

The most suitable dosage level may be determined by any suitable method known to one skilled in the art. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease undergoing treatment.

For delivery by inhalation, the active compound is preferably in the form of microparticles. They may be prepared by a variety of techniques, including spray-drying, freeze-drying and micronization.

By way of example, a composition of the present invention may be prepared as a suspension for delivery from a nebulizer or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In a preferred embodiment, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

In the case of an aerosol-based formulation, a preferred composition is:

Compound of the invention 24 mg/canister
Lecithin, NF Liq. Conc. 1.2 mg/canister
Trichlorofluoromethane, NF 4.025 g/canister
Dichlorodifluoromethane, NF 12.15 g/canister.

Compounds of the present invention may be used in combination with other drugs that are used in the treatment/prevention/suppression or amelioration of the diseases or conditions for which present compounds are useful. Such other drugs may be administered, by a route and in an amount commonly used therefore, contemporaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the present invention include those that also contain one or more other active ingredients, in addition to a compound of the invention.

The agents of the invention may be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321, which is incorporated herein by reference in its entirety).

Methods of Synthesis.

The present invention further provides a process for the preparation of a compound of formula (I) or a pharmaceutically acceptable salt or quaternary salt thereof as defined above.

Compounds of the invention may be prepared according to routes illustrated below in Schemes 1-18. The skilled person may introduce, where appropriate, suitable variations to the conditions specifically described in the experimentals in order to adapt the synthetic routes to the provision of further compounds of the invention. Such variations may include, but are not limited to, use of appropriate starting materials to generate different compounds, changes in the solvent and temperature of reactions, replacements of reactives with analogous chemical role, introduction or removal of protection/deprotection stages of functional groups sensitive to reaction conditions and reagents. Also, introduction or removal of specific synthetic steps oriented to further functionalization of the chemical scaffold may be contemplated and is included within the scope of the present invention.

Processes, which can be used and are described and reported in Examples and Schemes, should not be viewed as limiting the scope of the synthetic methods available for the preparation of the compounds of the invention.

Compounds used as starting materials or intermediates may be commercially available, their preparation may be specifically described in the literature, or they may be prepared according to methods available in the literature and well known to the person skilled in the art. In some instances, procedures for the preparation of intermediates or starting materials may be also provided in the examples.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form. In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art [see, for a general reference, T. W. Green; Protective Groups in Organic Synthesis (Wiley, N.Y. 1981), which is incorporated herein by reference in its entirety].

Likewise, selective protection and deprotection of any of the said groups, for instance including carbonyl, hydroxyl or amino groups, may be accomplished according to very well-known methods commonly employed in organic synthetic chemistry.

Optional salification of the compounds of formula (I) may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

In the following Schemes, for compounds of formula (I) to (Iz), unless otherwise indicated, groups $A_1$, $A_2$, $A_3$, $A_4$, W, $R_1$ to $R_6$ have the same meanings as described for compounds of formula (I) above.

Scheme 1

(In)

(I)

Compounds of formula (I) where $A_3$-$A_4$ is —$CR_4$=N— or —$CR_4$=$CR_9$—, and $R_4$=—$NR_{10}R_{11}$, —$NHCOR_{12}$, —NH-COO—$R_{13}$, —$NR_{27}CONH$—$R_{14}$, —$NSO_2$alkyl or —(NH)r$(CH_2)CONR_{15}R_{16}$ may be prepared according to Scheme 1.

Compounds of formula (Ia), i.e. compounds of formula (I) where $A_3$-$A_4$ is —$CR_4$=N— or —$CR_4$=$CR_9$— and $R_4$=NHCOR$_{12}$ can be prepared from compounds of formula (In), i.e. compounds of formula (I) where $A_3$-$A_4$ is —CR$_4$=N— or —CR$_4$=CR$_9$— and R$_4$=NH$_2$, by methods such as acylation. Typical reaction conditions include the use of an acid chloride such as acetyl chloride in a solvent such as pyridine or THF with a base such as pyridine, triethylamine or DIPEA at a temperature of between RT and 120° C. Alternatively, compounds of formula (In) may be reacted with a carboxylic acid in the presence of HATU in a solvent such as DMF together with a base such as triethylamine at a temperature of between RT and 80° C.

Compounds of formula (Ib), i.e. compounds of formula (I) where A$_3$-A$_4$ is —CR$_4$=N— or —CR$_4$=CR$_9$— and R$_4$=NHCOO—R$_{13}$ or —NHCONR$_{27}$—R$_{14}$ may be prepared from compounds of formula (In) by reaction with an appropriately substituted chloroformate or isocyanate in a solvent such as pyridine or THF with a base such as pyridine, triethylamine or DIPEA at a temperature of between RT and 120° C.

Compounds of formula (Ib) as above defined, where R$_4$=—NHCONR$_{27}$—R$_{14}$ may also be prepared according to Scheme 1 via preparation of an intermediate tosyl urea wherein R$_4$=—NHCONR$_{27}$-Ts, followed by reaction with an amine of formula NH$_2$—R$_{14}$ (see WO2006/38116, which is incorporated herein by reference in its entirety, for a representative procedure). Typical reaction conditions consist of the reaction of a compound of formula (In) with tosyl isocyanate in a suitable solvent such as DMF at a temperature of from 0° C. to room temperature to give the intermediate tosyl urea. The transformation of R$_4$=—NHCONR$_{27}$-Ts to R$_4$=—NHCONR$_{27}$—R$_{14}$ may be achieved by heating a mixture of the intermediate tosyl urea solution with an appropriately substituted primary amine NH$_2$—R$_{14}$ at a temperature between 100 and 160° C. under microwave irradiation.

Compounds of formula (Ic), i.e. compounds of formula (I) where A$_3$-A$_4$ is —CR$_4$=N— or —CR$_4$=CR$_9$— and R$_4$=NR$_{10}$R$_{11}$ may be prepared from compounds of formula (In) using reductive ammination. Typical conditions include the use of an appropriately substituted benzaldehyde in the presence of titanium isopropoxide and triethylamine in a solvent such as DCM at temperatures of up to 65° C. followed by treatment with a reducing agent such as sodium borohydride in a solvent such as ethanol. Alternatively the transformation may be achieved by alkylation. Compounds of formula (In) can may be reacted with an appropriately substituted alkyl halide in the presence of a base such as caesium carbonate or potassium carbonate in a solvent such as DMF at RT.

Compounds of formula (Ic) as above defined may also be prepared according to Scheme 1 via preparation of the intermediate aryl halide (III), e.g. a compound corresponding to a compound of formula (Ic) wherein R$_4$=Cl. Typical reaction conditions consist of the reaction of a compound of formula (In) with t-butyl nitrite and copper (II) chloride in a solvent such as MeCN at 65° C. to give compounds of formula (III) as above defined. The transformation of R$_4$=C$_1$ to R$_4$=—NR$_{10}$R$_{11}$, or —NH(CH$_2$)$_n$—SO$_2$(C$_1$-C$_4$)alkyl, or —(NH)$_r$(CH$_2$)$_n$CONR$_{15}$R$_{16}$ wherein n=2-5" may be achieved by heating a mixture of an appropriately substituted primary amine in a solvent such as N-methylpyrrolidine with a base such as triethylamine at a temperature between 150 and 220° C. under microwave irradiation.

Compounds of formula (Id), i.e. compounds of formula (I) where A$_3$-A$_4$ is —CR$_4$=N— or —CR$_4$=CR$_9$— and R$_4$ is —NSO$_2$alkyl may be prepared from compounds of formula (In) using an appropriately substituted sulfonyl chloride such as methanesulfonyl chloride in a solvent such as pyridine at a temperature ranging from RT to 60° C.

Compounds of formula (Ie), i.e. compounds of formula (I) where A$_3$-A$_4$ is —CR$_4$=N— or —CR$_4$=CR$_9$— and R$_4$ is (C$_1$-C$_4$)alkoxy can be prepared from compounds of formula (III) by reaction with an alkoxide such as sodium methoxide in a solvent such as methanol at a temperature of from RT to 100° C. under microwave irradiation.

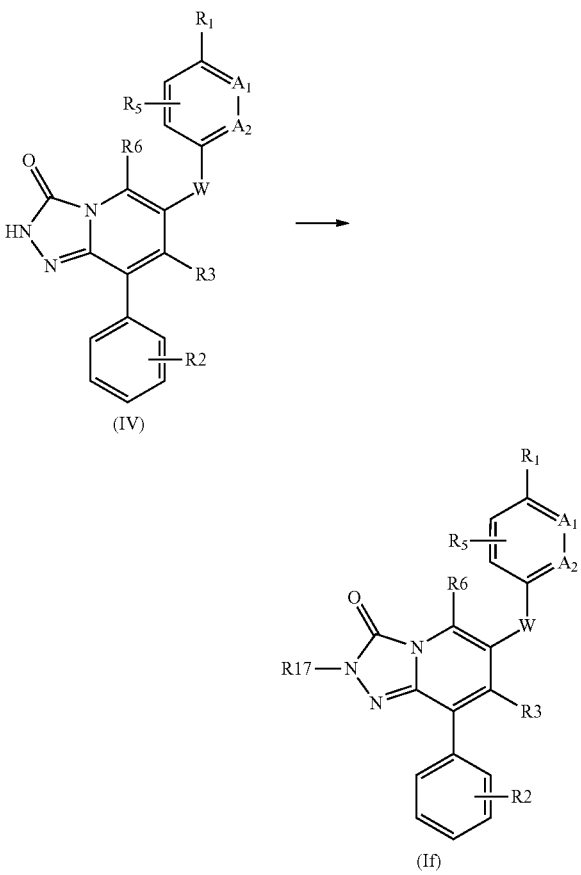

Compounds of formula (If), i.e. compounds of formula (I) where A$_3$-A$_4$ is —NR$_{17}$—CO—, can be prepared from compounds of formula (IV) according to Scheme 2. Typical reaction conditions include treatment with an appropriate alkylating agent such as 1-bromomethyl-4-methanesulfonylbenzene with a base such as caesium carbonate in a solvent such as DMF at ambient temperature.

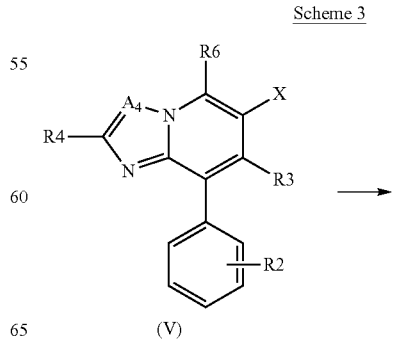

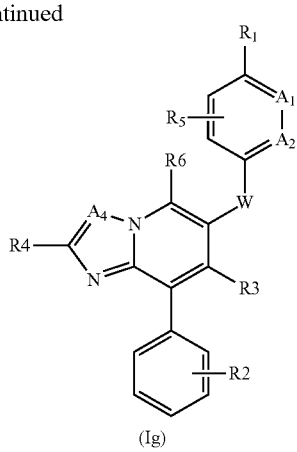

(Ig)

Compounds of formula (Ig), i.e. compounds of formula (I) where $A_3$-$A_4$ is —$CR_4$=N— or —$CR_4$=$CR_9$—, may be prepared from compounds of formula (V), wherein X is a suitable leaving group such as bromine, iodine or triflate, using known C—C and C—N cross-coupling methodologies described in the literature using a suitably functionalized linking group "W" such as aryl, heteroaryl, cycloalkyl or heterocycloalkyl boronic acid/boronate ester, stannane or zincate. Typical reaction conditions consist of the use of an organometallic reactant such as 4-(5-tributylstannanyl-pyrazol-1-yl)-benzonitrile and a palladium source such as bis(triphenylphosphine)palladium (II) dichloride and a solvent such as dioxane at a temperature of between 50° C. and reflux or higher temperatures using microwave irradiation.

Scheme 4

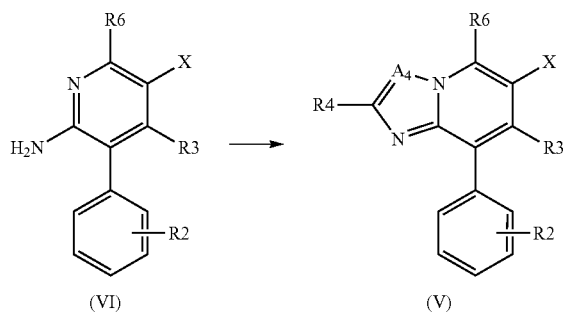

(VI) → (V)

Compounds of formula (Va), i.e. a compound of formula (V) as above defined wherein $R_4$=$NH_2$ and $A_4$=N may be prepared from compounds of formula (VI) according to Scheme 4 by reaction with a reagent such as ethoxycarbonyl isothiocyanate in a solvent such as dioxane at RT following treatment with hydroxylamine hydrochloride in a solvent such as ethanol or methanol together with a base such as diisopropylethylamine at elevated temperatures (≥60° C.).

Compounds of formula (Vb), i.e. a compound of formula (V) as above defined wherein where $R_4$=$NHCOCF_3$ and $A_4$=CH can be prepared from compounds of formula (VI) according to Scheme 4. Typical reaction conditions include treatment with p-toluenesulfonyl chloride in a solvent such as pyridine at a temperature of from RT to example 80° C. The intermediate p-toluenesulfonyl amide thus obtained may be treated with a base such as sodium hydride in a solvent such as DMF and then reacted with 2-iodoacetamide and an acylating agent, such as trifluoroacetic anhydride, in a solvent such as DCM at reflux.

Compounds of formula (Vc), i.e. a compound of formula (V) as above defined wherein where $R_4$ is methyl or hydrogen can be prepared from compounds of formula (VI), according to Scheme 4. Typical conditions consist of treatment of (VI) with chloropropanone or chloroacetaldehyde, as appropriate, in a solvent such as ethanol or MeCN at reflux for a time period of up to 2 days to give compounds of formula (Vc). Alternatively, compounds of formula (VI) can be treated with dimethylformamide dimethyl acetal or dimethylacetamide dimethylacetal, as appropriate, in a solvent such as DMF or IPA at a temperature of up to 130° C. followed by reaction with a reagent such as hydroxylamine hydrochloride or hydroxylamine-O-sulfonic acid in a solvent such as ethanol or methanol and pyridine at temperatures ranging from 0° C. to 50° C. to give compounds of formula (Vc).

Scheme 5

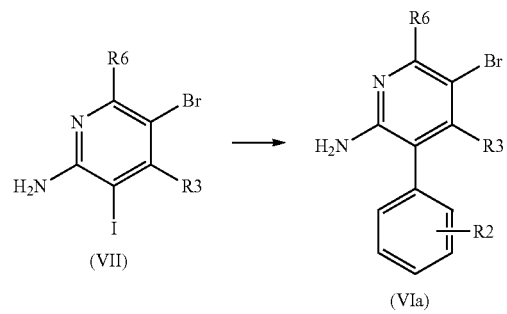

(VII) → (VIa)

Compounds of formula (VIa), i.e. a compound of formula (VI) as above defined wherein X is bromine, may be obtained from compounds of formula (VII) according to Scheme 5 by using known metal-catalysed C—C cross-coupling methodologies or other methods described in the literature using coupling partners such as aryl boronic acids. Typical reaction conditions consist of the use of an organometallic reactant such as 3-(trifluoromethyl)benzene boronic acid and a palladium source such as 1,1'-bis(diphenylphosphino)ferrocene-palladium (II) dichloride dichloromethane together with a base such as aqueous sodium carbonate and solvents such as toluene and ethanol at reflux temperatures. Compounds of formula (VII) may be prepared using other methods described in the literature.

Scheme 6

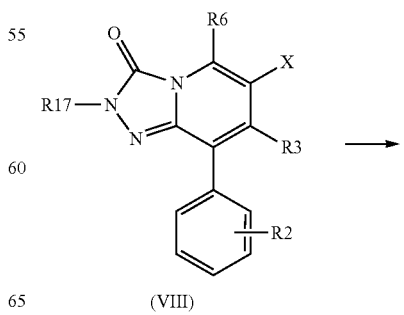

(VIII)

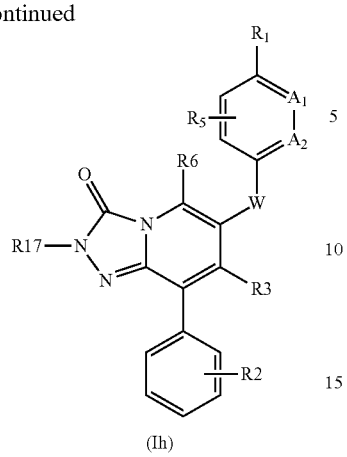

(Ih)

Compounds of formula (Ih), i.e. a compound of formula (I) wherein $A_3$-$A_4$ is —$NR_{17}CO$—, may be obtained from compounds of formula (VIII) according to Scheme 6 using the methods described for the transformation of compounds of formula (V) to compounds of formula (Ig) in Scheme 3.

Scheme 7

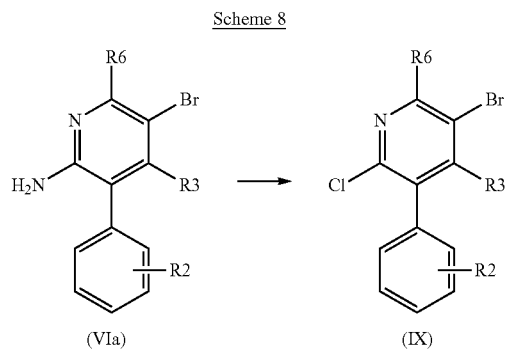

(IX) → (VIIIa)

Compounds of formula (VIIIa), i.e. a compound of formula (VIII) as above defined wherein X is bromine, can be obtained from compounds of formula (IX) according to Scheme 7 by reaction with hydrazine hydrate in a solvent such as dioxane at a temperature up to 100° C. followed by reaction with an acylating agent such as carbonyl diimidazole in a solvent such as THF.

Scheme 8

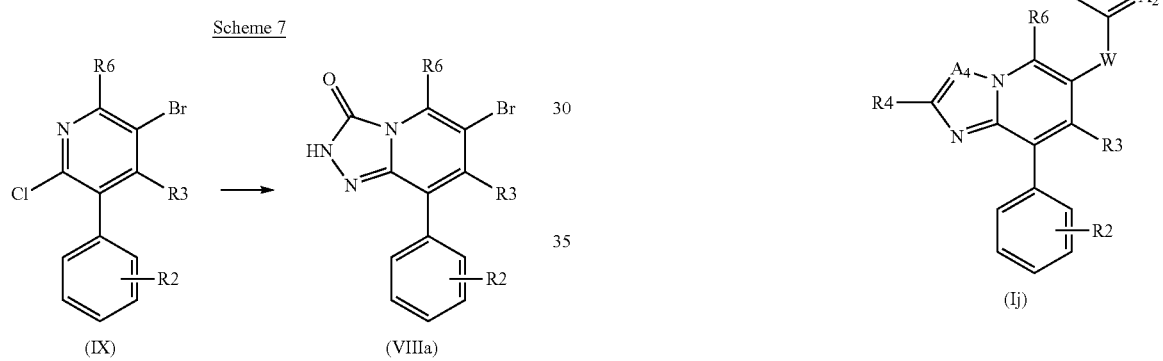

(VIa) (IX)

Compounds of formula (IX) can be prepared from compounds of formula (VIa) by typical reaction conditions consisting of the use of a diazotising agent such as t-butyl nitrite in a solvent such MeCN at temperatures of from RT up to 70° C. and quenching with a chloride source such as aqueous hydrogen chloride solution.

Scheme 9

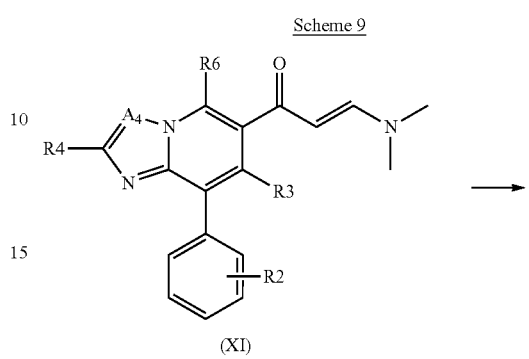

(XI)

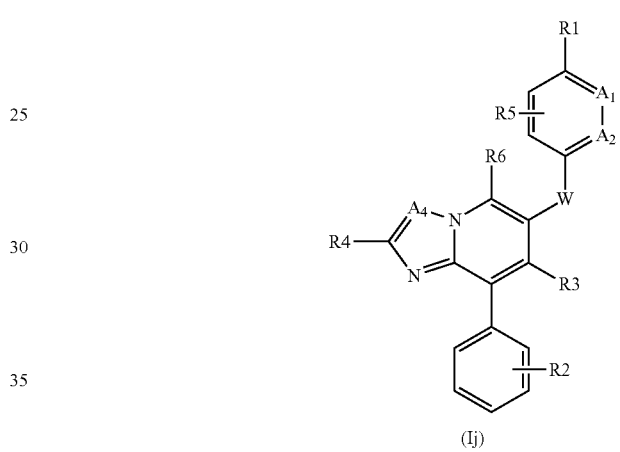

(Ij)

Compounds of formula (Ij), i.e. a compound of formula (I) wherein $A_3$-$A_4$ is —$CR_4$=N— or —$CR_4$=$CR_9$— and where linker "W" is a 1,5-disubstitiuted pyrazole may be prepared from compounds of formula (XI), wherein $A_3$-$A_4$ is —$CR_4$=N— or —$CR_4$=$CR_9$—, according to Scheme 9. Compounds of formula (XI) may be reacted with an appropriately substituted hydrazine. Typical conditions involve heating a compound of formula (XI) with an aryl/heteroaryl hydrazine under acidic conditions, such as HCl or acetic acid, in a high boiling alcohol solvent such as n-butanol.

Scheme 10

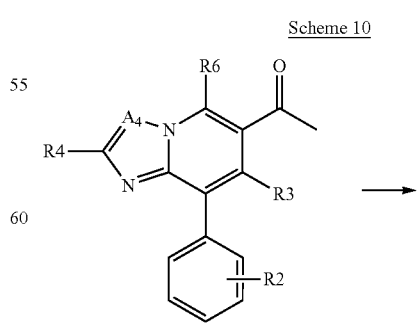

(XII)

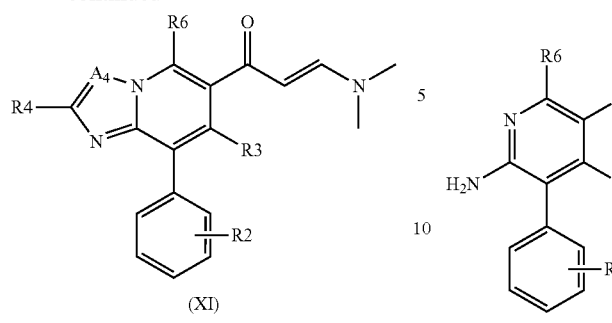

(XI)

Compounds of formula (XI) as above defined may be prepared from compounds of formula (XII), wherein $A_3$-$A_4$ is —$CR_4$=N— or —$CR_4$=$CR_9$—, by reaction with dimethyl formamide dimethyl acetal under reflux conditions in a high boiling solvent such as toluene.

Scheme 11

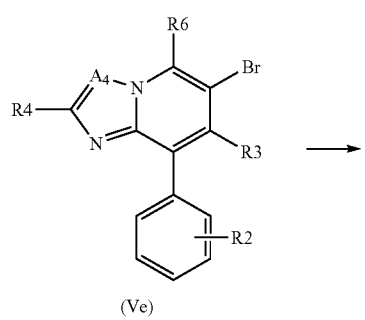

(Ve)

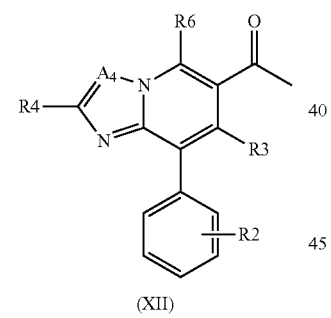

(XII)

Compounds of formula (XII) may be obtained from compounds of formula (Ve), i.e. a compound of formula (V) as above defined wherein $A_3$-$A_4$ is —$CR_4$=N— or —$CR_4$=$CR_9$ and X is bromine, according to Scheme 11 using C—C cross coupling methodologies described in the literature. Typical reaction conditions involve the use of an organometallic reagent such as tributyl(1-ethoxyvinyl) tin and a palladium source such as bis(triphenylphosphine)palladium (II) dichloride in a solvent such as DMF at a temperature of between 50° C. and reflux or higher temperatures using microwave irradiation, followed by hydrolysis of the intermediate enol ether with an aqueous acid such as HCl. Alternatively, the intermediate enol may be obtained from compounds of formula (Ve) using a Heck reaction with 1-vinyloxy-butane. Typical reaction conditions involve the use of palladium source such as palladium (II) acetate in a solvent such as MeCN at a temperature of between 50° C. and reflux.

Scheme 12

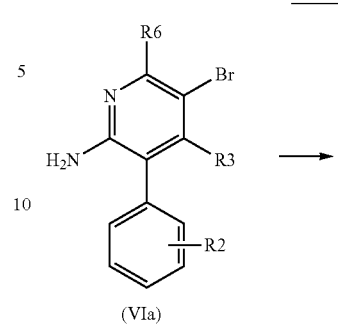

(VIa)

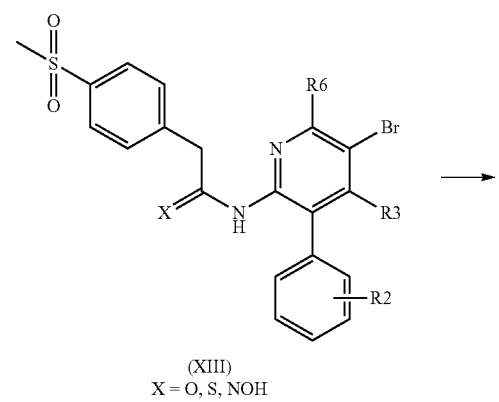

(XIII)
X = O, S, NOH

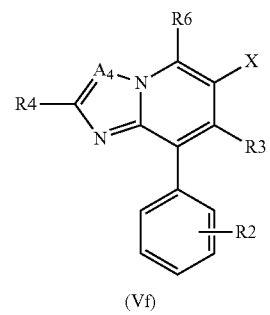

(Vf)

Compounds of formula (Vf), i.e. a compound of formula (V) wherein $A_3$-$A_4$ is —$CR_4$=N— or —$CR_4$=$CR_9$, X is bromine and $R_4$=$CH_2PhSO_2Me$ may be prepared from compounds of formula (VIa) as above defined according to Scheme 12. Typical reaction conditions consist of the reaction of (VIa) with 4-(methylsulfonyl)phenylacetic acid chloride in a solvent such as DCM at a temperature of between 0° C. and RT to give compounds of formula (XIIIa) where X=O. Compounds of formula (XIIIa) where X=O can be transformed to the corresponding thioamide compounds of formula (XIIIb) where X=S by use the of a thiolating agent such as Lawesson's reagent in a solvent such as toluene at reflux. Compounds of formula (XIIIc) where X=NOH can be prepared from compounds of formula (XIIIb) by treatment with hydroxylamine hydrochloride and a base such as triethylamine in a solvent such as ethanol at RT. Compounds of formula (Vf) can be can obtained from compounds of formula (XIIIc) by suspension in a solvent such as toluene, together with a base such as pyridine, and treatment with p-toluenesulfonyl chloride at a temperature ranging from 0° C. to RT.

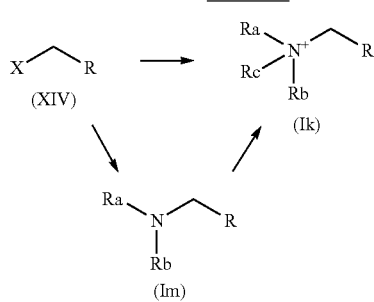

Scheme 13

Compounds of formula (Im) or (Ik), i.e. compounds of formula (I) which incorporate a group $(C_1-C_6)$alkyleneN-$R_aR_b$ or a group $(C_1-C_6)$alkyleneN$^+R_aR_bRc$ respectively as substituents, may be prepared according to Scheme 13.

Compounds of formula (Ik) can be obtained directly by alkylation reaction of an appropriate tertiary amine $R_aR_bR_c$, N, such as trimethylamine or dimethylpiperazine, with compounds of formula (XIV), wherein X is an appropriate leaving group (X=Cl, Br, I, tosylate etc.) and group —CH$_2$R represents the portion of a compound of formula (Ik) remaining out of its substitution by a group $(C_1-C_4)$alkyleneN$^+R_aR_bR_c$. Typical conditions could involve heating a tertiary amine in a solvent such as ethanol or THF at elevated temperatures of between 60° C. and 150° C., using microwave irradiation.

Alternatively, the transformation of compounds of formula (XIV) to compounds of formula (Ik) may be achieved via the tertiary amine (Im) formation, where Ra and Rb≠H. Tertiary amine compounds of formula (Im) may be prepared from compounds of formula (XIV) by reaction with a secondary amine $R_aR_b$NH. Typical reaction conditions include the use of a base such as caesium carbonate or potassium carbonate in a solvent such as DMF at RT. The conversion of compounds of formula (Im), where $R_a$ and $R_b$≠ H, to compounds of formula (Ik) can be obtained using methylating agents such as methyl bromide, methyl iodide or methyl benzenesulfonate. Typical reaction conditions consist of the use of a solvent such as MeCN or acetone at a temperature of between RT to 60° C. under conventional or microwave heating.

Furthermore, primary and secondary amine compounds of formula (Im) may also be prepared from compounds of formula (XIV) by reaction with ammonia or a suitable primary amine RaNH$_2$, respectively to give a primary amine or secondary amine.

The following compounds shown in Schemes 14-17 may also be prepared by those skilled in the art.

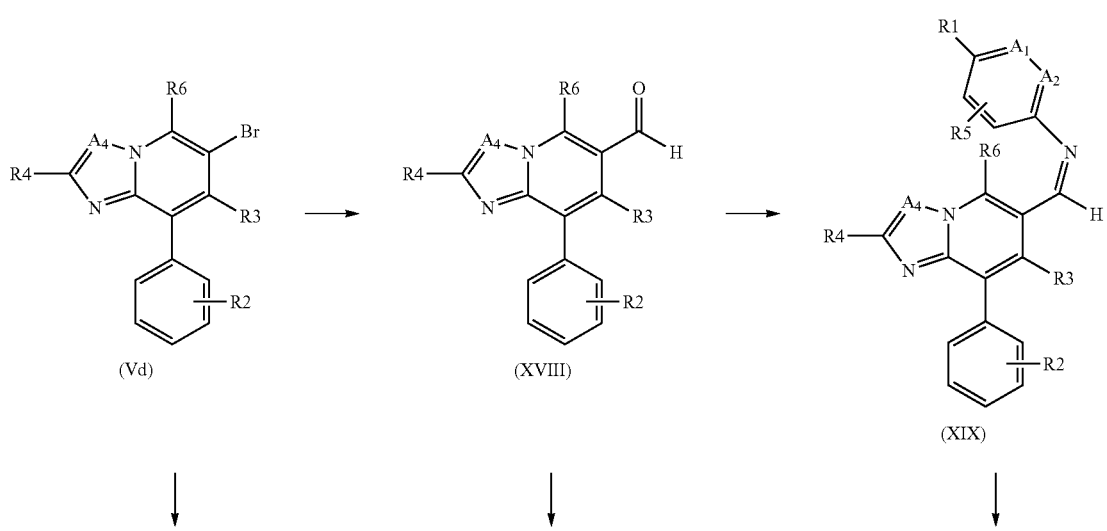

Scheme 14

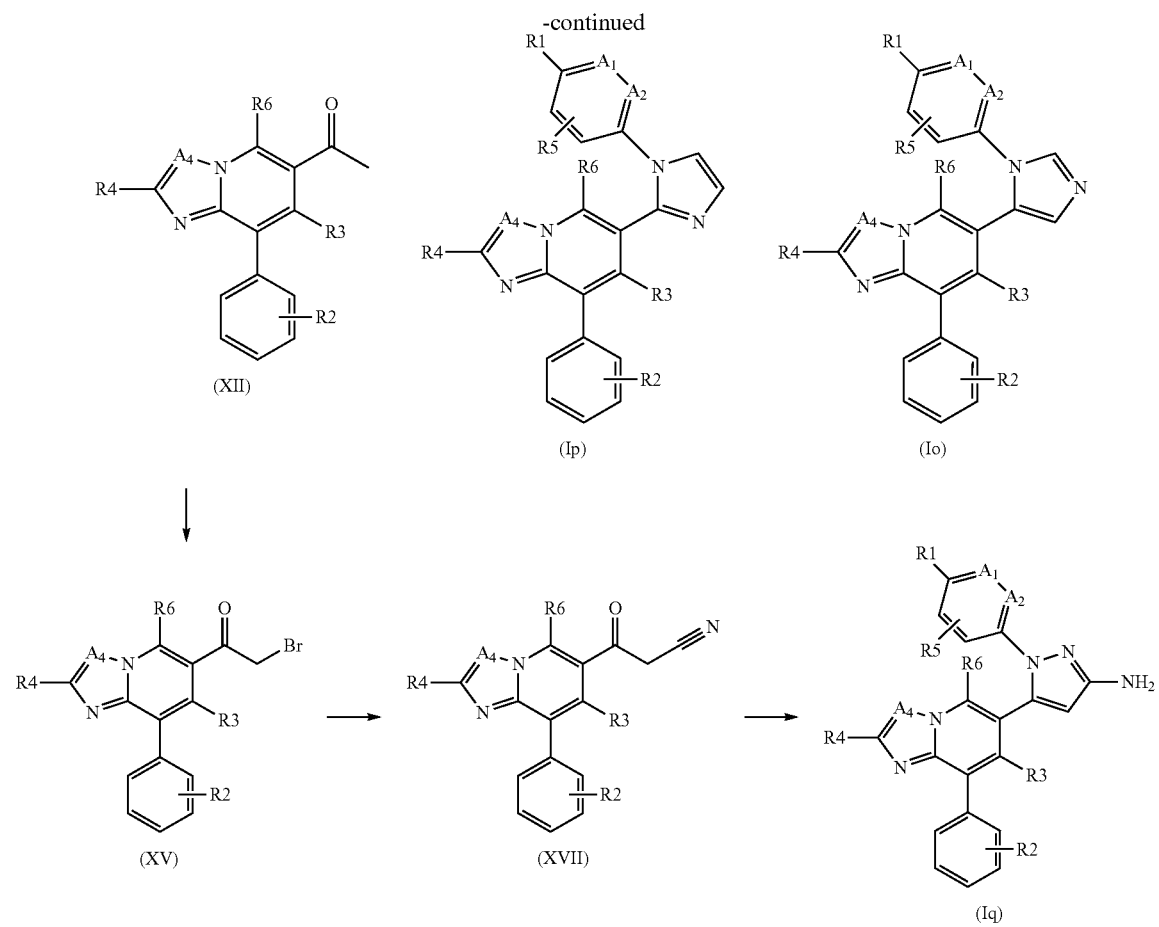

Compounds of formula (Iq), (Io) and (Ip), i.e. compounds of formula (I) as above represented wherein $A_3$-$A_4$ is —$CR_4$=N— or —$CR_4$=$CR_9$ and $R_4$ is an $NH_2$ or an $NHCOR_{12}$ group, may be prepared according to Scheme 14. Compounds of formula (Io) can also be prepared according to Scheme 4. Compounds of formula (XV), wherein $A_3$-$A_4$ is —$CR_4$=N— or —$CR_4$=$CR_9$ and $R_4$ is an $NH_2$ or an $NHCOR_{12}$ group, can be prepared from compounds of formula (XII), wherein $A_3$-$A_4$ is —$CR_4$=N— or —$CR_4$=$CR_9$ and $R_4$ is an $NH_2$ or an $NHCOR_{12}$ group, by treatment with a suitable brominating agent such as N-bromosuccinimide (NBS) or bromine. Typical conditions involve stirring (XII) with NBS, in a suitable solvent such as THF at ambient temperature. Compounds of formula (XVII), wherein $A_3$-$A_4$ is —$CR_4$=N— or —$CR_4$=$CR_9$ and $R_4$ is an $NH_2$ or an $NHCOR_{12}$ group, can be formed from compounds of formula (XV) by nucleophilic displacement of bromide with cyanide. Typical conditions involve stirring compound (XV) with a metal cyanide such as sodium or potassium cyanide in a suitable solvent such as water or DMF at ambient temperature. Compounds of formula (Iq) can be prepared from compounds of formula (XVII). Typical conditions involve stirring (XVII) with the desired aryl hydrazine in a high boiling solvent such as n-butanol at reflux temperatures.

Compounds of formula (XVIII), wherein $A_3$-$A_4$ is —$CR_4$=N— or —$CR_4$=$CR_9$ and $R_4$ is an $NH_2$ or an $NHCOR_{12}$ group, can be prepared from compounds of formula (Vd), i.e. a compound of formula (V) as above defined wherein $A_3$-$A_4$ is —$CR_4$=N— or —$CR_4$=$CR_9$ and $R_4$ is an $NH_2$ or an $NHCOR_{12}$ group, by palladium catalysed carbonylation. Typical conditions involve heating the aryl bromide with sodium formate and carbon monoxide gas (at atmospheric pressure or pressures up to 150 psi) in the presence of a palladium catalyst such as $Pd_2(PPh_3)_2Cl_2$ in a high boiling solvent such as DMF at temperatures of between 100° C. and 150° C. Compounds of formula (XIX), wherein $A_3$-$A_4$ is —$CR_4$=N— or —$CR_4$=$CR_9$ and $R_4$ is an $NH_2$ or an $NHCOR_{12}$ group, can be prepared from compounds of formula (XVIII); typical conditions involve stirring compound (XVIII) with the desired aniline, for example p-cyanoaniline, in the presence of a strong acid such as p-toluenesulfonic acid in a high boiling solvent such as toluene under conditions which azeotropically remove water such as in a Dean-Stark apparatus. Compounds of formula (Io) can be prepared from compounds of formula (XIX) by reaction with tosylmethylisocyanide (TOSMIC), (see EP1424329, which is incorporated herein by reference in its entirety, for a representative procedure). Typical reaction conditions involve stirring in a solvent such as dimethoxyethane at ambient temperature.

Compounds of formula (Ip) can be prepared from compounds of formula (XVIII). Typical conditions involve stirring the desired aniline, for example p-cyanoaniline, with glyoxal in a suitable solvent such as methanol at ambient temperature, followed by addition of compound (XVIII) and ammonium chloride and stirring at reflux in the presence of a strong acid such as phosphoric acid, (see WO2008/54584, which is incorporated herein by reference in its entirety, for a representative procedure).

Scheme 15
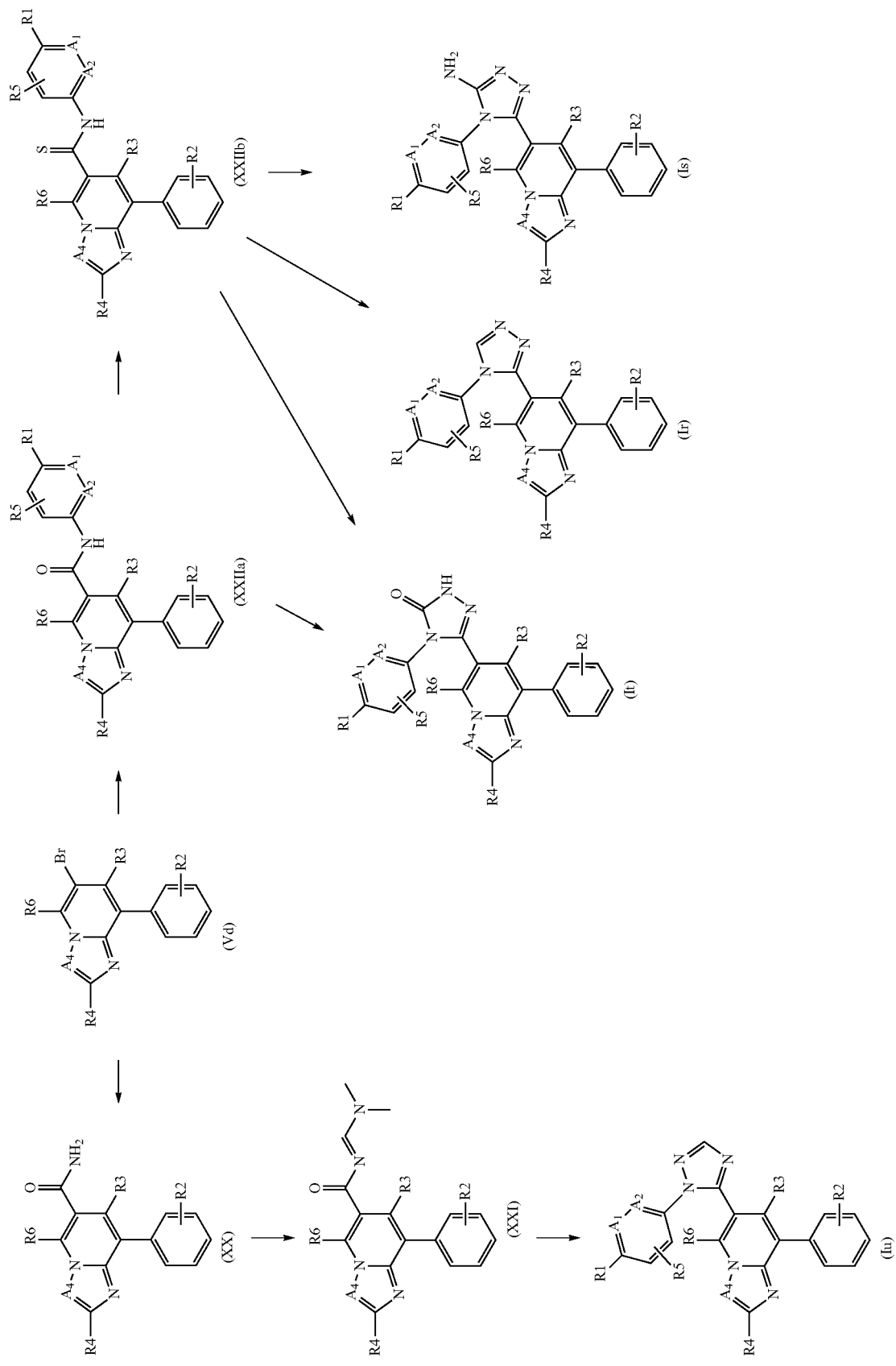

Compounds of formula (Iu), (Ir), (Is), and (It), i.e. compounds of formula (I) as above represented wherein $A_3$-$A_4$ is —$CR_4$=N— or —$CR_4$=$CR_9$ and $R_4$ is an $NH_2$ or an $NHCOR_{12}$ group, may be synthesized from compounds of formula (Vd) as above defined according to Scheme 15. Compounds of formula (XX), wherein $A_3$-$A_4$ is —$CR_4$=N— or —$CR_4$=$CR_9$ and $R_4$ is an $NH_2$ or an $NHCOR_{12}$ group, can be prepared from compounds of formula (Vd) by palladium catalysed carbonylation. Typical conditions involve microwave heating of a mixture of (XX) and hydroxylamine hydrochloride in the presence of a suitable metal carbonyl such as molybdenum hexacarbonyl, a suitable palladium catalyst/ligand system such as trans-bis(acetato)bis[o-(di-o-tolylphosphino)benzyl]dipalladium(II)/tri-tert-butyl phosphine (Herrmann-Beller Catalyst) and a suitable base such as DBU, in a suitable solvent such as dioxane, at temperatures of between 120° C. and 150° C. Compounds of formula (XXI), wherein $A_3$-$A_4$ is —$CR_4$=N— or —$CR_4$=$CR_9$ and $R_4$ is an $NH_2$ or an $NHCOR_{12}$ group can be prepared from compounds of formula (XX) by reaction with a one carbon electrophile such as dimethylformamide dimethylacetal (DMF-DMA). Typical conditions involve heating (XX) with DMF-DMA in a suitable solvent such as THF at temperatures of between 80-100° C. using microwave irradiation. Compounds of formula (Iu) can be prepared from compounds of formula (XXI) by heating with suitable aryl hydrazine such as p-cyanophenylhydrazine in a suitable solvent such as acetic acid at temperatures of between 80-100° C. using microwave irradiation, (see U.S. Pat. No. 4,259,504, which is incorporated herein by reference in its entirety, for a representative procedure).

Compounds of formula (XXIIa), wherein $A_3$-$A_4$ is —$CR_4$=N— or —$CR_4$=$CR_9$ and $R_4$ is an $NH_2$ or an $NHCOR_{12}$ group, can be prepared from compounds of formula (Vd) by palladium catalyzed carbonylation. Typical conditions involve microwave heating of a mixture of (Vd) and a suitable aniline such as p-cyanoaniline in the presence of a suitable metal carbonyl such as molybdenum hexacarbonyl, a suitable palladium catalyst/ligand system such as trans-bis(acetato)bis[o-(di-o-tolylphosphino)benzyl]dipalladium (II)/tri-tert-butyl phosphine and a suitable base such as DBU, in a suitable solvent such as dioxane, at temperatures of between 120° C. and 150° C. Compounds of formula (XXIIb), wherein $A_3$-$A_4$ is —$CR_4$=N— or —$CR_4$=$CR_9$ and $R_4$ is an $NH_2$ or an $NHCOR_{12}$ group mabe prepared from compounds of formula (XXIIa), followed by treatment with Lawesson's reagent in a suitable solvent such as THF at temperatures of between 80-100° C. Alternatively compounds of formula (XXIIb) may be prepared from compounds of formula (Vd) by treatment with a suitable organolithium reagent such as n-butyllithium in a suitable solvent such as THF, at temperatures of between −78° C. and 0° C. and the resultant anion treated with a suitable isothiocyanate such as p-cyanophenyl isothiocyanate at temperatures of between −78° C. and 0° C. Compounds of formula (Ir) can be prepared from compounds of formula (XXIIb) by reaction with a suitably substituted hydrazine. Typical conditions involve heating (XXIIb) with formic hydrazide in a suitable solvent such as DMF at reflux temperature (150-160° C.), (see J. Med. Chem. 2006, 49 (14), 4044, which is incorporated herein by reference in its entirety, for a representative procedure). Compounds of formula (Is) can be prepared from compounds of formula (XXIIb) by reaction with hydrazine hydrate in a suitable solvent such as ethanol, at temperatures of between 50-70° C., followed by cyclisation with cyanogen bromide in a suitable solvent such as methanol at ambient temperature, (see Biorg. Med. Chem. Letters 1998, 8 (22), 3153, which is incorporated herein by reference in its entirety, for a representative procedure). Compounds of formula (It) can be prepared from compounds of formula (XXIIb) by reaction with a suitably substituted hydrazine. Typical conditions involve heating (XXIIb) with methyl hydrazinocarboxylate in the presence of a mercury (II) chloride and suitable base such as pyridine, in a suitable solvent such as dioxane at reflux temperature, (see US2008/125587, which is incorporated herein by reference in its entirety, for a representative procedure). Alternatively compounds of formula (It) may be prepared from compounds of formula (XXIIa) by treatment with a suitable chlorinating agent such as thionyl chloride at temperatures of between room temperature and reflux. The resultant imidate may be converted into compounds of formula (It) by treatment with a suitable hydrazide such as hydrazinecarboxylic acid ethyl ester, followed by cyclisation with a suitable base such as sodium methoxide.

Scheme 16

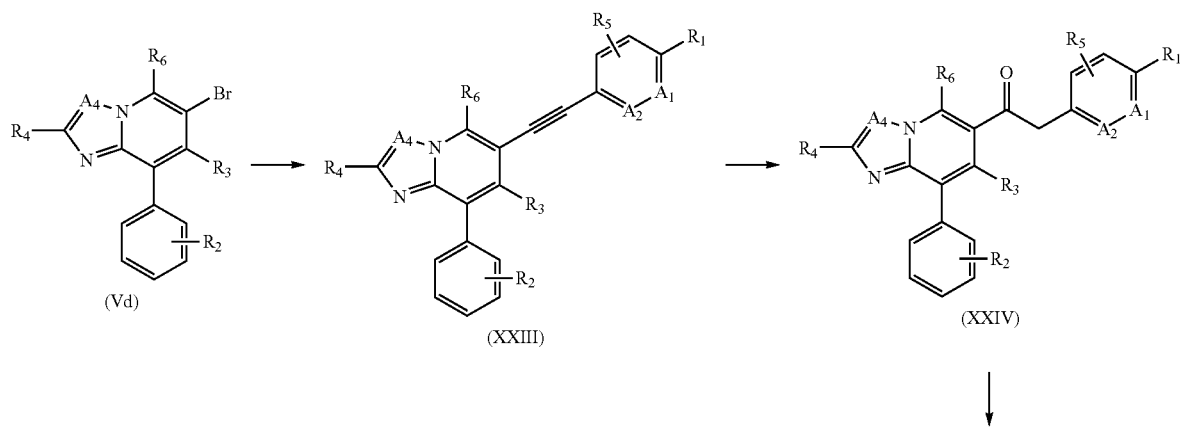

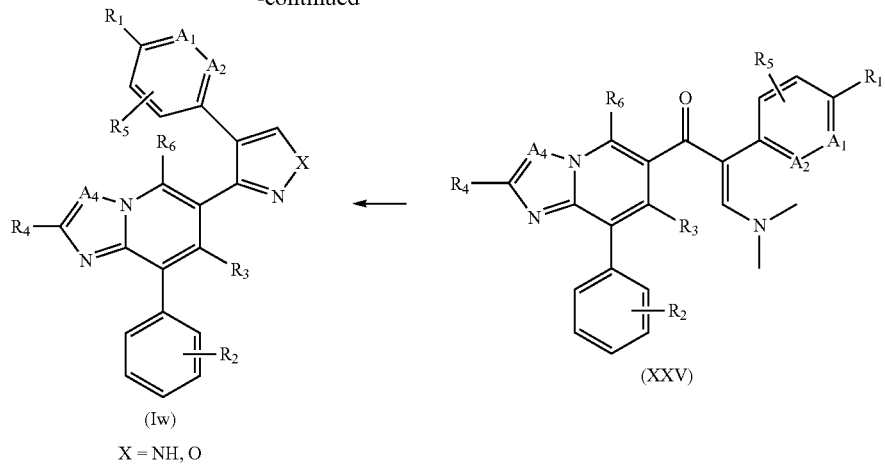

(Iw)
X = NH, O (XXV)

Compounds of formula (Iw), i.e. compounds of formula (I) as above represented wherein $A_3$-$A_4$ is —$CR_4$=N— or —$CR_4$=$CR_9$ and $R_4$ is an $NH_2$ or an $NHCOR_{12}$ group, may be prepared from compounds of formula (Vd) according to Scheme 16. Compounds of formula (XXIII), wherein $A_3$-$A_4$ is —$CR_4$=N— or —$CR_4$=$CR_9$ and $R_4$ is an $NH_2$ or an $NHCOR_{12}$ group, can be prepared from compounds of formula (Vd) by Sonogashira coupling. Typical reaction conditions involve stirring (Vd) with a suitably substituted alkyne such as p-cyanophenyl acetylene in the presence of copper(I) iodide and a suitable base such as triethylamine in a suitable solvent such as THF at temperatures of ambient up to 60° C. Compounds of formula (XXIV), wherein $A_3$-$A_4$ is —$CR_4$=N— or —$CR_4$=$CR_9$ and $R_4$ is an $NH_2$ or an $NHCOR_{12}$ group, can be prepared from compounds of formula (XXIII) by hydrolysis. Typical conditions involve heating (XXIII) in a suitable solvent such as formic acid using microwave irradiation at temperatures of between 100-120° C. Compounds of formula (XXV), wherein $A_3$-$A_4$ is —$CR_4$=N— or —$CR_4$=$CR_9$ and $R_4$ is an $NH_2$ or an $NHCOR_{12}$ group, can be synthesized from compounds of formula (XXIV) by treatment with a one carbon electrophile such as dimethylformamide dimethylacetal (DMF-DMA). Typical conditions involve heating (XXIV) with DMF-DMA in a suitable solvent such as THF at temperatures of between 80-100° C. using microwave irradiation. Compounds of formula (Iw) can be prepared from compounds of formula (XXV) by treatment with hydroxylamine (where X=O) or hydrazine (where X=NH). Typical conditions involve heating (XXV) with the relevant nucleophile in a suitable solvent such as ethanol at temperatures of between 80-100° C. using microwave irradiation, (For X=O, see Eur. J. Med. Chem. 2010, 45 (11), 4887; for X=NH see WO2009/137538, which are incorporated herein by reference in their entireties, for representative procedures).

Scheme 17

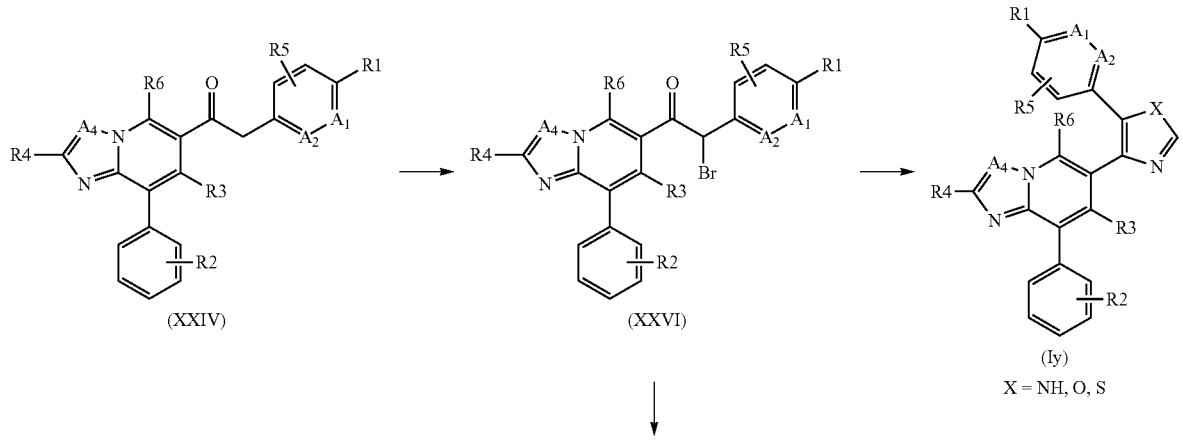

(XXIV) → (XXVI) → (Iy)
X = NH, O, S

-continued

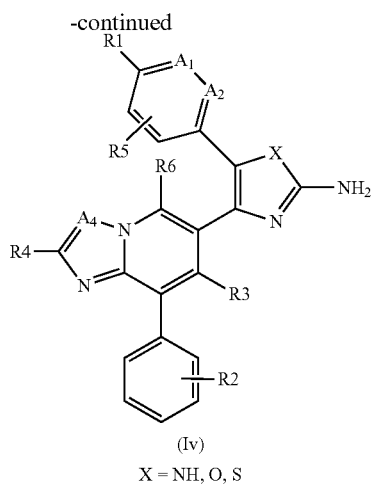

(Iv)

X = NH, O, S

Compounds of formula (Iy) and (Iv), i.e. compounds of formula (I) as above represented wherein $A_3$-$A_4$ is —$CR_4$=N— or —$CR_4$=$CR_9$ and $R_4$ is an $NH_2$ or an $NHCOR_{12}$ group, can be prepared from compounds of formula (XXIV) as above defined according to Scheme 17. Compounds of formula (XXVI), wherein $A_3$-$A_4$ is —$CR_4$=N— or —$CR_4$=$CR_9$ and $R_4$ is an $NH_2$ or an $NHCOR_{12}$ group, can be prepared from compounds of formula (XXIV) by treatment with a suitable brominating agent such as N-bromosuccinimide (NBS) or bromine. Typical conditions involve stirring (XXIV) with bromine in the presence of acetic acid in a suitable solvent such as THF at ambient temperature. Compounds of formula (Iy), where X=NH, can be prepared from (XXVI) by treatment with formamide. Typical conditions involve stirring (XXVI) with formamide in a suitable solvent such as water at reflux temperatures. Compounds of formula (Iy), where X=O, can be prepared from (XXVI) by treatment with formic acid. Typical conditions involve heating (XXVI) with formic acid in the presence of ammonium formate at reflux temperature. Compounds of formula (Iy), where X=S, can be prepared from (XXVI) by treatment with phosphorus pentasulfide ($P_2S_5$) and formamide. Typical conditions involve heating (XXVI) with $P_2S_5$ and formamide in a suitable solvent such as toluene at reflux temperature, (for X=O, see J. Med. Chem. 2005, 48 (6), 1849; for X=NH, see U.S. Pat. No. 4,576,958; for X=S, see U.S. Pat. No. 4,451,471, which are incorporated herein by reference in their entireties, for representative procedures).

Compounds of formula (Iv), where X=NH, can be prepared from (XXVI) by treatment with N-acyl guanidine. Typical conditions involve stirring (XXVI) with N-acylguanidine in a suitable solvent such as DMF at ambient temperature, followed by deacetylation of the resulting product with a strong acid, typically sulphuric acid in a suitable solvent, typically methanol/water, at reflux temperatures. Compounds of formula (Iv), where X=O, can be prepared from (XXVI) by treatment with urea. Typical conditions involve stirring (XXVI) with urea in a suitable solvent such as DMF at reflux temperatures. Compounds of formula (Iv), where X=S, can be prepared from (XXVI) by treatment with thiourea. Typical conditions involve stirring of (XXVI) with thiourea in a suitable solvent such as ethanol heating to 100-120° C. using microwave irradiation, (for X=O, see Chemissche Berichte 1959, 1944; for X=NH, see J. Med. Chem. 2011, 54 (3), 472; for X=S, see Tet. Letters 2006, 5171, which are incorporated herein by reference in their entireties, for representative procedures).

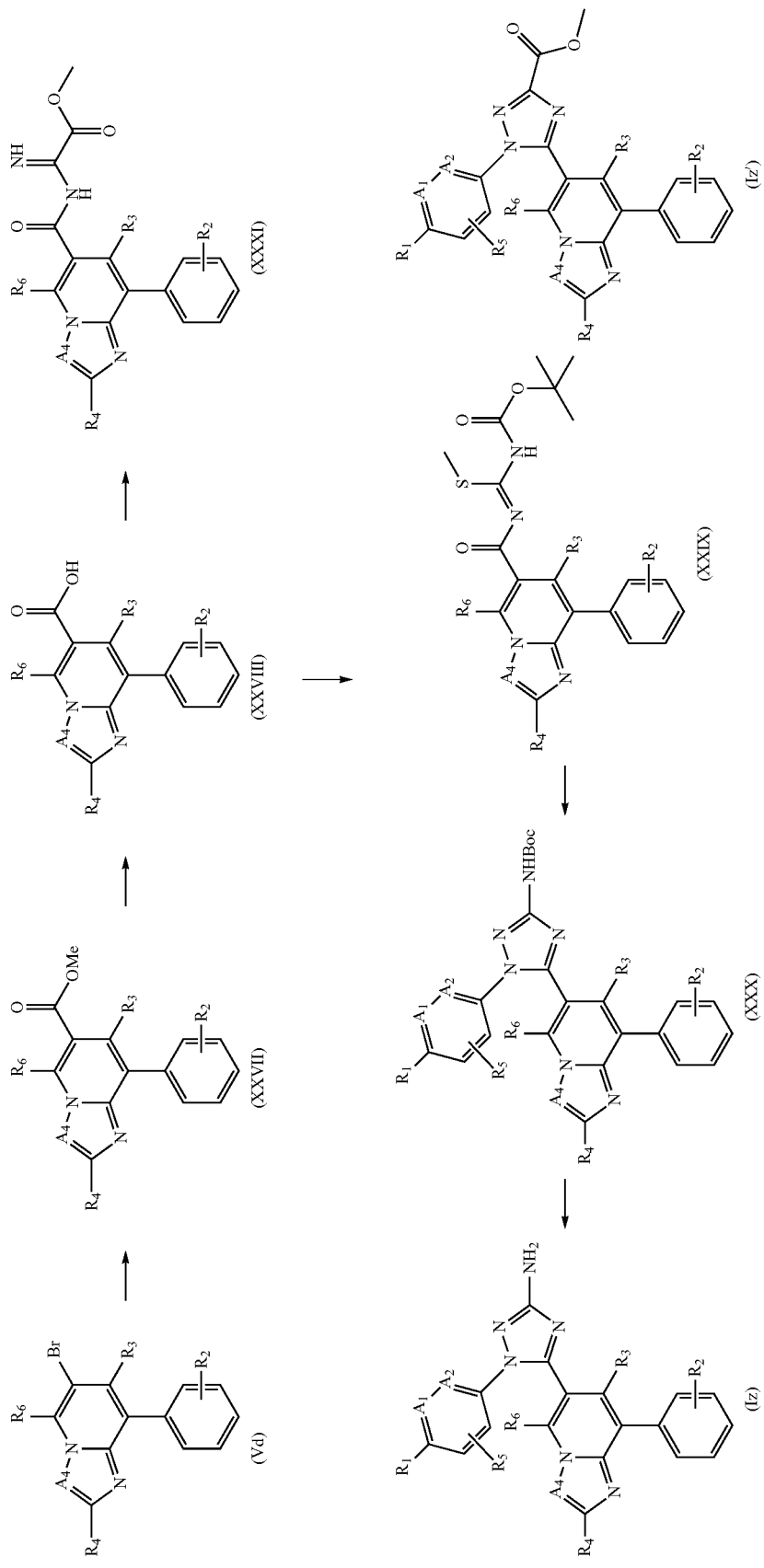

Compounds of formula (Iz), i.e. compounds of formula (I) as above represented wherein $A_3$-$A_4$ is —$CR_4$=N— or —$CR_4$=$CR_9$ and $R_4$ is an $NH_2$ or an $NHCOR_{12}$ group, may be synthesized from compounds of formula (Vd) according to Scheme 18. Compounds of formula (XXVII), wherein $A_3$-$A_4$ is —$CR_4$=N— or —$CR_4$=$CR_9$ and $R_4$ is an $NH_2$ or an $NHCOR_{12}$ group, can be prepared from compounds of formula (Vd) by palladium catalysed carbonylation. Typical conditions involve microwave heating of (Vd) in the presence of a suitable metal carbonyl such as molybdenum hexacarbonyl, a suitable palladium catalyst/ligand system such as trans-bis(acetato)bis[o-(di-o-tolylphosphino)benzyl]dipalladium (II)/tri-tert-butylphosphine (Herrmann-Beller Catalyst) and a suitable base such as DBU, in a suitable solvent such as MeCN/methanol, at temperatures of between 120° C. and 150° C. Compounds of formula (XXVIII), wherein $A_3$-$A_4$ is —$CR_4$=N— or —$CR_4$=$CR_9$ and $R_4$ is an $NH_2$ or an $NHCOR_{12}$ group, can be prepared from compounds of formula (XXVII) by hydrolysis, for example with lithium hydroxide in solvents such as THF and water. Compounds of formula (XXIX), wherein $A_3$-$A_4$ is —$CR_4$=N— or —$CR_4$=$CR_9$ and $R_4$ is an $NH_2$ or an $NHCOR_{12}$ group, may be synthesized from compounds of formula (XXVIII) by amide formation using an appropriately substituted thiourea and a coupling agent such as HATU in a solvent such as THF together with a base such as triethylamine at a temperature of between RT and 80° C. Compounds of formula (XXX), wherein $A_3$-$A_4$ is —$CR_4$=N— or —$CR_4$=$CR_9$ and $R_4$ is an $NH_2$ or an $NHCOR_{12}$ group, can be prepared from compounds of formula (XXIX) by reaction with a suitably substituted hydrazine. Typical conditions involve heating (XXIX) with the aryl hydrazine in the presence of a suitable base, such as DIPEA, in a suitable solvent such as DMF at 80° C. Compounds of formula (Iz) can be prepared from compounds of formula (XXX) by acetylation using acetyl chloride in a solvent such as THF with a base, such as triethylamine followed by deprotection using an acid such as TFA in a solvent such as DCM at room temperature or by deprotection of (XXX) directly without the acetylation step.

Compounds of formula (Iz'), i.e. compounds of formula (I) as above represented wherein $A_3$-$A_4$ is —$CR_4$=N— or —$CR_4$=$CR_9$ and $R_4$ is an $NH_2$ or an $NHCOR_{12}$ group, may also be synthesised from compounds of formula (Vd) according to Scheme 18. Compounds of formula (XXXI) can be prepared from compounds of formula (XXVIII) by reaction with a suitably substituted amidine such as amino-iminoacetic acid methyl ester. Typical conditions involve treatment of (XXVIII) with the amidine in the presence of a suitable coupling agent such as HATU, using a base, such as DIPEA, in a suitable solvent such as DMF room temperature. Compounds of formula (Iz') can be prepared from compounds of formula (XXXI) by reaction with a suitably substituted aryl-hydrazine, such as 4-hydrazino-benzonitrile in a solvent such as acetic acid at temperature of between RT and reflux.

Finally, compounds of formula (Iq), (Io), (Ip), (Iu), (Ir), (Is), (It), (Iw), (Iv), (Iy), (Iz) and (Iz') where $R_4$=$NH_2$, can be prepared from corresponding compounds of formula (Iq), (Io), (Ip), (Iu), (Ir), (Is), (It), (Iw), (Iv), (Iy), (Iz) and (Iz') where $R_4$=an acyl group (or other suitable protecting group) by hydrolysis under suitable acid or base conditions. Typical basic conditions involve stirring compounds of formula (Iq), (Io), (Ip), (Iu), (Ir), (Is), (It), (Iw), (Iv), (Iy), (Iz) and (Iz') where $R_4$=acetyl, in a suitable solvent such as methanol with a base such as potassium carbonate at ambient temperature. Further elaboration of compounds of formula (Iq), (Io), (Ip), (Iu), (Ir), (Is), (It), (Iw), (Iv), (Iy), (Iz) and (Iz') where $R_4$=$NH_2$, to compounds where $R_4$=—$NR_{10}R_{11}$, —NH—$COR_{12}$, —NHCOO—$R_{13}$, —NHCONH—$R_{14}$, —$NSO_2$alkyl and —$(NH)_r(CH_2)CONR_{15}R_{16}$ may be achieved according to Scheme 1. Elaboration of these compounds, bearing a suitable leaving group (X=Cl, Br, I, tosylate etc.), to amino or quaternary amino compounds can be obtained according to Scheme 13.

According to appropriate adaptation of the Synthetic Schemes/methods or Experimental procedures herein reported, which would be known to the persons skilled in the art, the following compounds may be prepared:

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-[3-(piperidin-4-ylamino)-propyl]-urea;

4-{5-[2-{3-[(Azetidin-3-ylmethyl)-amino]-propylamino}-7-methyl-8-(3-trifluoromethyl-phenyl)-[1,2,4]triazolo[1,5-a]pyridin-6-yl]-pyrazol-1-yl}-benzonitrile;

4-{5-[7-Methyl-2-[3-(piperidin-4-ylamino)-propylamino]-8-(3-trifluoromethyl-phenyl)-[1,2,4]triazolo[1,5-a]pyridin-6-yl]-pyrazol-1-yl}-benzonitrile;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-{3-[(3-dimethylamino-propyl)-methyl-amino]-propyl}-urea;

4-{5-[2-{3-[(3-Dimethylamino-propyl)-methyl-amino]-propylamino}-7-methyl-8-(3-trifluoromethyl-phenyl)-[1,2,4]triazolo[1,5-a]pyridin-6-yl]-pyrazol-1-yl}-benzonitrile;

4-{5-[7-Methyl-2-[3-(4-methylamino-piperidin-1-yl)-propylamino]-8-(3-trifluoromethyl-phenyl)-[1,2,4]triazolo[1,5-a]pyridin-6-yl]-pyrazol-1-yl}-benzonitrile;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-[2-(4-methylamino-piperidin-1-yl)-ethyl]-urea;

N-[6-[4-(4-Cyano-phenyl)-5-oxo-4,5-dihydro-1H-[1,2,4]triazol-3-yl]-7-methyl-8-(3-trifluoromethyl-phenyl)-[1,2,4]triazolo[1,5-a]pyridin-2-yl]-acetamide;

4-{5-[7-Methyl-2-[2-(piperidin-4-yl-amino)-ethylamino]-8-(3-trifluoromethyl-phenyl)-[1,2,4]triazolo[1,5-a]pyridin-6-yl]-pyrazol-1-yl}-benzonitrile;

4-{3-[2-Amino-7-methyl-8-(3-trifluoromethyl-phenyl)-[1,2,4]triazolo[1,5-a]pyridin-6-yl]-5-oxo-1,5-dihydro-[1,2,4]triazol-4-yl}-benzonitrile;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(R)-piperidin-3-yl-urea;

{3-[6-[2-(4-Cyano-phenyl)-5-methoxycarbonyl-2H-[1,2,4]triazol-3-yl]-7-methyl-8-(3-trifluoromethyl-phenyl)-[1,2,4]triazolo[1,5a]pyridin-2-ylcarbamoyl]-propyl}-trimethyl ammonium formate;

(3-{2-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-ylcarbamoyl]-ethanesulfonyl}-propyl)-trimethyl-ammonium formate;

N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-3-dimethylamino-propionamide;

N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-3-(3-dimethylamino-propane-1-sulfonyl)-propionamide;

3-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-1-(3-dimethylamino-propyl)-1-methyl-urea;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(S)-piperidin-3-yl-urea;

{3-[6-[5-Carboxy-2-(4-cyano-phenyl)-2H-[1,2,4]triazol-3-yl]-7-methyl-8-(3-trifluoromethyl-phenyl)-[1,2,4]triazolo[1,5-a]pyridin-2-ylcarbamoyl]-propyl}-trimethyl-ammonium formate;

{3-[6-[2-(4-Cyano-phenyl)-5-methoxycarbonyl-2H-[1,2,4]triazol-3-yl]-7-methyl-8-(3-trifluoromethyl-phenyl)-[1,2,4]triazolo[1,5-a]pyridin-2-ylcarbamoyl]-propyl}-trimethyl-ammonium bromide;

Carboxymethyl-(3-{3-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-ureido}-propyl)-dimethyl-ammonium formate;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(3-methylamino-propyl)-urea;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(3-dimethylamino-propyl)-urea;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-guanidino-propionamide;

{3-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-ylcarbamoyl]-propyl}-trimethyl-ammonium bromide;

N-[6-[1-(4-Cyano-phenyl)-1H-imidazol-2-yl]-7-methyl-8-(3-trifluoromethyl-phenyl)-[1,2,4]triazolo[1,5-a]pyridin-2-yl]-acetamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-hydroxy-butyramide;

N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-4-dimethylamino-butyramide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-hydroxy-propionamide;

N-[6-[2-(5-Cyano-pyridin-2-yl)-2H-[1,2,4]triazol-3-yl]-7-methyl-8-(3-trifluoromethyl-phenyl)-[1,2,4]triazolo[1,5-a]pyridin-2-yl]-acetamide;

N-[6-[3-(4-Cyano-phenyl)-3H-imidazol-4-yl]-7-methyl-8-(3-trifluoromethyl-phenyl)-[1,2,4]triazolo[1,5-a]pyridin-2-yl]-acetamide;

N-[6-[5-Amino-2-(4-cyano-phenyl)-2H-[1,2,4]triazol-3-yl]-7-methyl-8-(3-trifluoromethyl-phenyl)-[1,2,4]triazolo[1,5-a]pyridin-2-yl]-acetamide;

5-[2-Acetylamino-7-methyl-8-(3-trifluoromethyl-phenyl)-[1,2,4]triazolo[1,5-a]pyridin-6-yl]-1-(4-cyano-phenyl)-1H-[1,2,4]triazole-3-carboxylic acid methyl ester;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-succinamide;

N-[6-[5-Acetylamino-2-(4-cyano-phenyl)-2H-[1,2,4]triazol-3-yl]-7-methyl-8-(3-trifluoromethyl-phenyl)-[1,2,4]triazolo[1,5-a]pyridin-2-yl]-acetamide; and N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-N'-(2-dimethylamino-ethyl)-N'-methylsuccinamide.

Other features of the invention will become apparent in the course of the following descriptions of exemplary embodiments which are given for illustration of the invention and are not intended to be limiting thereof.

EXAMPLES

General Experimental Details

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane. The following abbreviations have been used: br=broad signal, s=singlet, d=doublet, dd=double doublet, t=triplet, td=triplet of doublets, q=quartet, m=multiplet. NMR analysis of compounds purified by HPLC showed various amounts of formic acid equivalents (not described).

Purification by chromatography refers to purification using the CombiFlash® Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 μm and nominal 60Å porosity. For alternative purification, where an Isolute® SCX-2 cartridge was used, 'Isolute® SCX-2 cartridge' refers to a pre-packed polypropylene column containing a non-end-capped propylsulphonic acid functionalised silica strong cation exchange sorbent. Similarly, where products were purified by 'Isolute® PE-AX cartridge, this refers to a pre-packed polypropylene column containing a silica-based sorbent with a chemically bonded quaternary ammonium functional group.

Where thin layer chromatography (TLC) has been used, it refers to silica gel TLC using plates, typically 3×6 cm silica gel on aluminium foil plates with a fluorescent indicator (254 nm), (e.g. Fluka 60778). All solvents and commercial reagents were used as received.

Compounds purified by preparative HPLC were purified using a $C_{18}$-reverse-phase column (100×22.5 mm i.d Genesis column with 7 μm particle size or 250×21.2 mm i.d. Gemini column with 5 μm particle size), or a Phenyl-cHexyl column (250×21.2 mm i.d. Gemini column with 5 μm particle size), UV detection at 220, 230 or 254 nm, flow 10-20 mL/min, eluting with gradients from 95-5 to 5-95% water/acetonitrile or water/MeOH containing 0.1% TFA or 0.1% formic acid. Fractions containing the required product (identified by TLC and/or LCMS analysis) were pooled, the organic fraction removed by evaporation, and the remaining aqueous fraction lyophilised, to give the final product. Reactions were not carried out under an inert atmosphere unless specified.

Microwave experiments were carried out using a Biotage Initiator 60™ which uses a single-mode resonator and dynamic field tuning. Temperature from 40-250° C. can be achieved, and pressures of up to 30 bar can be reached.

Compound names were generated using the Autonom 2000 feature in MDL ISIS™/Draw 2.5 SP2 software.

Analytical LC-MS Conditions

Method 1

| | |
|---|---|
| Instrumentation | HP1100 (binary pump/PDA detector) + Platform LC Mass Spectrometer |
| Column | Phenomenex Luna $C_{18}$ 3 μm, 30 × 4.6 mm |
| Mobile Phase A | 0.1% aqueous formic acid |
| Mobile Phase B | 0.1% formic acid in MeCN |
| Flow | 2.0 mL/min |

-continued

| Gradient Program | Time (mins) | % A | % B |
|---|---|---|---|
| | 0.0 | 95 | 05 |
| | 0.5 | 95 | 05 |
| | 4.5 | 05 | 95 |
| | 5.5 | 05 | 95 |
| | 6.0 | 95 | 05 |

| | |
|---|---|
| Sample | 20 μL injection (Open Access) |
| Detectors | UV, diode array 190-450 nm |
| | MS, mass 160-1000 (or 100-800, or 160-1300) in ES+ & ES− (200 μL/min split to MS) |
| | Sedex 85 evaporative light scattering detector |

Method 2

| | |
|---|---|
| Instrumentation | HP1050 (quaternary pump/PDA detector) + Platform II Mass Spectrometer |
| Column | Phenomenex Luna $C_{18}$ 3 μm, 30 × 4.6 mm |
| Mobile Phase A | 0.1% aqueous formic acid |
| Mobile Phase B | 0.1% formic acid in MeCN |
| Flow | 2.0 mL/min |

| Gradient Program | Time (mins) | % A | % B |
|---|---|---|---|
| | 0.0 | 95 | 05 |
| | 0.3 | 95 | 05 |
| | 4.3 | 05 | 95 |
| | 5.3 | 05 | 95 |
| | 5.8 | 95 | 05 |
| | 6.0 | 95 | 05 |

| | |
|---|---|
| Sample | 20 μL injection (Open Access) |
| Detectors | UV, diode array 190-450 nm |
| | MS, mass 160-1000 (or 100-800, or 160-1300) in ES+ & ES− (200 μL/min split to MS) |
| | Sedex. 85 evaporative light scattering detector |

Method 3

| | |
|---|---|
| Instrumentation | Acquity UPLC (binary pump/PDA detector) + ZQ Mass Spectrometer |
| Column | ACQUITY UPLC BEH $C_{18}$ 1.7 μm, 100 × 2.1 mm, maintained at 40° C. |
| Mobile Phase A | 0.1% aqueous formic acid |
| Mobile Phase B | 0.1% formic acid in MeCN |
| Flow | 0.4 mL/min |

| Gradient Program | Time (mins) | % A | % B |
|---|---|---|---|
| | 0.0 | 95 | 05 |
| | 0.4 | 95 | 05 |
| | 6.0 | 05 | 95 |
| | 6.8 | 05 | 95 |
| | 7.0 | 95 | 05 |
| | 8.0 | 95 | 05 |

| | |
|---|---|
| Sample | 2 μL injection of a 0.5 mg/mL solution in an appropriate solvent at 20° C. |
| Detectors | UV, diode array 200-500 nm |
| | MS, mass 100-800 (or -1500) in ES+ & ES− (no split to MS) |
| Data Analysis | Peak area percentage (APCT) with an integration threshold of 0.2% (relative) |

Method 4

| | |
|---|---|
| Instrumentation | Acquity UPLC (binary pump/PDA detector) + ZQ Mass Spectrometer |
| Column | ACQUITY UPLC HSS T3 1.8 μm, 100 × 2.1 mm, maintained at 40° C. |
| Mobile Phase A | 0.1% aqueous formic acid |
| Mobile Phase B | 0.1% formic acid in MeCN |
| Flow | 0.4 mL/min |

| Gradient Program | Time (mins) | % A | % B |
|---|---|---|---|
| | 0.0 | 95 | 05 |
| | 0.4 | 95 | 05 |
| | 6.0 | 05 | 95 |
| | 6.8 | 05 | 95 |
| | 7.0 | 95 | 05 |
| | 8.0 | 95 | 05 |

| | |
|---|---|
| Sample | 2 μL injection of a 0.5 mg/mL solution in an appropriate solvent at 20° C. |
| Detectors | UV, diode array 200-500 nm |
| | MS, mass 100-800 (or -1500) in ES+ & ES− (no split to MS) |
| Data Analysis | Peak area percentage (APCT) with an integration threshold of 0.2% (relative) |

Method 5

| | |
|---|---|
| Instrumentation | Waters (1525 binary pump/PDA detector) + Waters ZMD Mass Spectrometer |
| Column | Phenomenex Luna C18(2) 3μ, 30 × 4.6 mm |
| Mobile Phase A | 0.1% aqueous formic acid |
| Mobile Phase B | 0.1% formic acid in acetonitrile |
| Flow | 2.0 ml/min |

| Gradient Program | Time (mins) | % A | % B |
|---|---|---|---|
| | 0.0 | 95 | 05 |
| | 0.5 | 95 | 05 |
| | 4.5 | 05 | 95 |
| | 5.5 | 05 | 95 |
| | 6.0 | 95 | 05 |

| | |
|---|---|
| Sample | 20 μl injection (Open Access) |
| Detectors | UV, diode array 190-450 nm |
| | MS, mass 160-1000 (or 100-800, or 160-1300) in ES+ & ES− (200 μl/min split to MS) |
| | Sedex 65 evaporative light scattering detector |

Abbreviations
aq Aqueous
app Apparent
bs (NMR) Broad singlet
° C. Centigrade
$CDCl_3$ Deuterated chloroform
DCM Dichloromethane/Methylene Chloride
d (NMR) Doublet
dd (NMR) Doublet of doublets
DAD Diode Array Detection (LCMS)
DIPEA Diisopropylethylamine
DMF N,N-Dimethylformamide
DMSO Dimethylsulfoxide
DMSO-$d_6$ Deuterated dimethylsulfoxide
Et Ethyl
EtOAc Ethyl acetate
EtOH Ethanol
Ex Example
g Gram
NMR Nuclear magnetic resonance
  HATU    O-(7-azabenzotriazol-1-yl)-N,N,N',N'-tetramethyluroniumhexafluorophosphate
HCl Hydrochloric Acid
HPLC High Pressure Liquid Chromatography
hr Hour(s)
hz Hertz
IMS Industrial Methylated Spirit (3-5% methanol in ethanol)
Int Intermediate
IPA Isopropyl alcohol
iPr Isopropyl
$K_2CO_3$ Potassium Carbonate Lawesson's reagent 2,4-bis(4-Methoxyphenyl)-1,3,2,4-dithiadiphosphetane-2,4-disulfide LC-MS Liquid Chromatography Mass Spectrometry
m (NMR) Multiplet
M Molarity (concentration)
MeBr Bromomethane
MeCN Acetonitrile
MeOH Methanol
mg milligram
MgSO$_4$ Magnesium Sulfate
MHz Megahertz
Min(s) Minute(s)
mmol Millimoles
mol Moles
N Normal (concentration)
Na$_2$SO$_4$ Sodium Sulphate
NaOMe Sodium Methoxide
NH$_3$ Ammonia
NMP N-Methyl2-pyrrolidone
Pr n-Propyl
q (NMR) Quartet
qn(NMR) Quintet
Rf Retention factor (TLC)
RT Room (ambient) temperature
Rt Retention time (LCMS or HPLC)
s(NMR) Singlet
SCX-2 strong cationic exchange resin
t(NMR) Triplet
TFA Trifluoroacetic acid
THF Tetrahydrofuran
TLC Thin layer chromatography
δ Chemical shift value in parts per million relative to tetramethylsilane.

Detailed synthetic pathways and procedures for specific examples are outlined in Examples 1-61. Examples 62-97 were prepared according to procedures described above and their $^1$H NMR and LCMS data are reported.

In the procedures that follow, after each starting material, reference to a compound number is sometimes provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Example 1

4-{5-[2-Amino-7-methyl-8-(3-trifluoromethyl-phenyl)-[1,2,4]triazolo[1,5-a]pyridin-6-yl]-pyrazol-1-yl}-benzonitrile

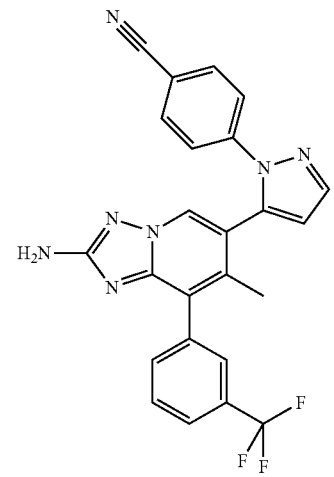 [SMILES: Cc1c(-c2ccnn2-c2ccc(C#N)cc2)cn2nc(N)nc2c1-c1cccc(C(F)(F)F)c1]

Step 1. 5-Bromo-4-methyl-3-(3-trifluoromethyl-phenyl)-pyridin-2-ylamine (Intermediate 1)

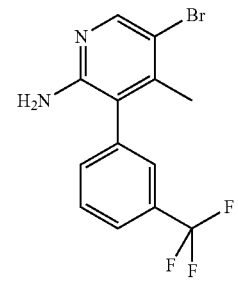 [SMILES: Cc1c(Br)cnc(N)c1-c1cccc(C(F)(F)F)c1]

5-Bromo-3-iodo-4-methyl-pyridin-2-ylamine (20.0 g, 63.9 mmol) and 3-(trifluoromethyl)benzene boronic acid (12.73 g, 67.0 mmol) were mixed with sodium carbonate (2 M, 160 mL, 320 mmol), toluene (570 mL) and IMS (190 mL) and degassed. 1,1'-bis(diphenylphosphino)ferrocenepalladium (II) dichloride dichloromethane (3.13 g, 36.83 mmol) was added and the reaction mixture was degassed again before heating to reflux for 2 hrs. A second reaction was carried on 1.08 times the scale. The two batches were combined and the solvent was removed in vacuo and the resulting mixture was partitioned between DCM and water. The organic phase was separated and was washed with water, dried (Na$_2$SO$_4$) and concentrated in vacuo. The resultant residue was purified by flash chromatography through a pad of silica, eluting with a gradient of 5-30% EtOAc in cyclohexane to give the title compound as a beige solid (34.6 g).

LC-MS (Method 1): Rt=3.30 min, m/z=331/333 [M+H]$^+$

Step 2. 6-Bromo-7-methyl-8-(3-trifluoromethyl-phenyl)-[1,2,4]triazolo[1,5-a]pyridin-2-ylamine (Intermediate 2)

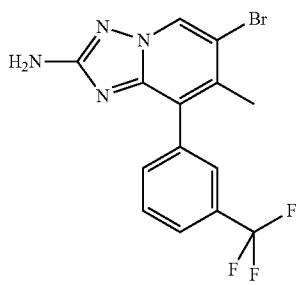 [SMILES: Cc1c(Br)cn2nc(N)nc2c1-c1cccc(C(F)(F)F)c1]

5-Bromo-4-methyl-3-(3-trifluoromethyl-phenyl)-pyridin-2-ylamine (Int. 1, 12.0 g, 36.25 mmol) was stirred in dioxane (250 mL) at RT and ethoxycarbonyl isothiocyanate (4.27 mL, 36.25 mmol) was added dropwise. The reaction mixture was stirred for 18 hrs, then the solvent was evaporated in vacuo. The resultant residue was dissolved in MeOH/IMS (1:1, 460 mL) and hydroxylamine hydrochloride (12.58 g, 181 mmol) was added and the reaction mixture was heated to 60° C. DIPEA (18.6 mL, 109 mmol) was added, and the reaction mixture was heated for a further 4.5 rs before allowing to cool. The resultant precipitate was collected by filtration, washed with MeOH and dried to afford the title compound as a white solid (11.49 g).

LC-MS (Method 2): Rt=3.45 min, m/z=371/373 [M+H]$^+$

Step 3.
4-(5-Tributylstannanyl-pyrazol-1-yl)-benzonitrile (Intermediate 3)

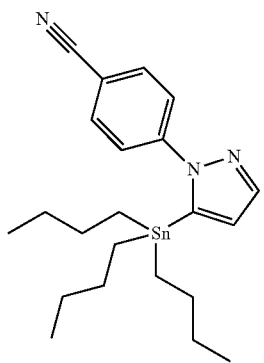 [SMILES: CCC[CH2][Sn]([CH2]CCC)([CH2]CCC)[c]1ccnn1-c1ccc(C#N)cc1]

Hexyl lithium (2.3 M in hexanes) (16.96 mL, 39.01 mmol) was added to a stirred solution of 2,2,6,6-tetramethyl-piperidine (6.85 mL, 40.63 mmol) in dry THF (15 mL) at −30° C. and the resulting suspension was stirred for 20 minutes. The suspension was allowed to warm to 10° C. to aid dissolution and was added, via cannula, to a solution of 4-pyrazol-1-yl-benzonitrile (5.50 g, 32.51 mmol, prepared according to *Bioorganic & Medicinal Chemistry Letters*, 2006, 16(11), 2955-2959, which is incorporated herein by reference in its entirety) in THF (85 mL) at −78° C., keeping the internal reaction temperature<-50° C. The resulting reaction mixture was stirred at −75° C. for 4 hrs and tributyl tin(IV) chloride (9.08 mL, 33.49 mmol) was added keeping the internal reaction temperature<-60° C. during addition. The reaction mixture was stirred at −60° C. for 1.5 rsh then allowed to warm to RT. The resulting solution was quenched by addition of EtOAc (100 mL) and then washed with water (2×50 mL) followed by saturated brine (50 mL). The organic extract was dried (Na$_2$SO$_4$), filtered and concentrated in vacuo. The resultant residue was purified by flash chromatography, eluting with a gradient of 0-5% EtOAc in pentane to give the title compound as an amber oil that solidified on standing (10.11 g).

LC-MS (Method 1): Rt=5.36 min, m/z=459 [M+H]$^+$

Step 4. 4-{5-[2-Amino-7-methyl-8-(3-trifluoromethyl-phenyl)-[1,2,4]triazolo[1,5-a]pyridin-6-yl]-pyrazol-1-yl}-benzonitrile (Example 1)

6-Bromo-7-methyl-8-(3-trifluoromethyl-phenyl)-[1,2,4]triazolo[1,5-a]pyridin-2-ylamine (Int. 2, 100 mg, 0.27 mmol) and 4-(5-tributylstannanyl-pyrazol-1-yl)-benzonitrile (Int. 3, 115 mg, 0.25 mmol) were dissolved in THF (5 mL) and degassed then bis(triphenylphosphine)palladium (II) dichloride (18 mg, 0.025 mmol) was added. The reaction mixture was stirred at reflux temperature for 21 hrs then allowed to cool before washing with cesium fluoride (saturated aqueous solution) and extracting with EtOAc (2×30 mL). The combined organic extracts were filtered and the filtrate was concentrated in vacuo. The resultant residue was subjected to preparative C$_{18}$ HPLC, eluting with a gradient 40-90% MeCN in water (+0.1% formic acid) to afford 51 mg of an impure title compound (containing 25% starting material) which was dissolved in THF (3 mL) with 4-(5-tributylstannanyl-pyrazol-1-yl)-benzonitrile (Int. 3, 4.72 g, 0.103 mmol) and degassed before addition of bis(triphenylphosphine)palladium (II) dichloride (10 mg, 0.014 mmol). The reaction mixture was heated at 75° C. for 6.5 h then purified using an SCX-2 cartridge (loading in MeOH/eluting with 2 N NH$_3$ in MeOH). The resultant residue was taken up in MeOH (5 mL) and treated with 3-mercaptopropylethyl sulfide silica (PhosphonicS SPM 32, 0.5 eq by weight) and stirred at 50° C. for 1 hr then filtered and evaporated. The resultant residue was dissolved in DCM then filtered and evaporated in vacuo before further purification by preparative C$_{18}$ HPLC, eluting with a gradient 40-90% MeCN in water (+0.1% formic acid) to give the title compound as a white solid (25 mg).

LC-MS (Method 3): Rt=4.63 min, m/z=460.0 [M+H]$^+$ $^1$H NMR (400 MHz, DMSO-d$_6$) δ 8.67 (1H, s), 7.95 (1H, d J=1.8 Hz), 7.92-7.87 (2H, m), 7.77 (1H, d J=7.6 Hz), 7.72

(1H, t J=8 Hz), 7.66 (1H, s), 7.63 (1H, d J=7.6 Hz), 7.59-7.54 (2H, m), 6.76 (1H, d J=1.8 Hz), 6.14 (2H, s), 1.69 (3H, s).

Example 2

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2,2,2-trifluoro-acetamide

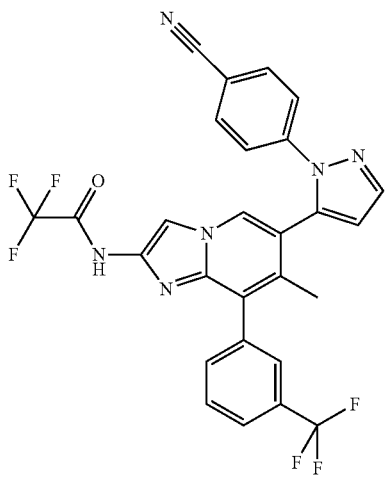 [SMILES: Cc1c(-c2ccnn2-c2ccc(C#N)cc2)cn2cc(NC(=O)C(F)(F)F)nc2c1-c1cccc(C(F)(F)F)c1]

Step 1. N-[5-Bromo-4-methyl-3-(3-trifluoromethyl-phenyl)-pyridin-2-yl]-4-methyl-benzenesulfonamide (Intermediate 4)

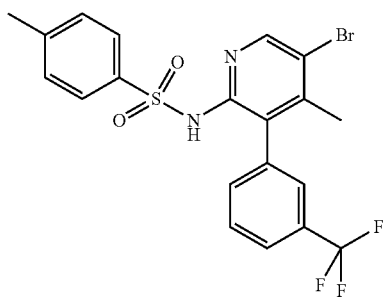 [SMILES: Cc1ccc(S(=O)(=O)Nc2ncc(Br)c(C)c2-c2cccc(C(F)(F)F)c2)cc1]

To a solution of 5-bromo-4-methyl-3-(3-trifluoromethyl-phenyl)-pyridin-2-ylamine (Int. 1, 1.91 g, 5.77 mmol) in pyridine (25 mL) was added p-toluenesulfonyl chloride (1.75 g, 9.18 mmol) and then the reaction mixture was heated at 80° C. for 23 hrs. The solvent was removed by evaporation in vacuo and then the residue was purified by flash chromatography, eluting with a gradient of 0-30% EtOAc in cyclohexane, to give the title compound as an off-white solid (2.41 g).

LC-MS (Method 2): Rt=3.65 min, m/z=485/487 [M]+

Step 2. N-[6-Bromo-7-methyl-8-(3-trifluoromethyl-phenyl)-imidazo[1,2-a]pyridin-2-yl]-2,2,2-trifluoro-acetamide (Intermediate 5)

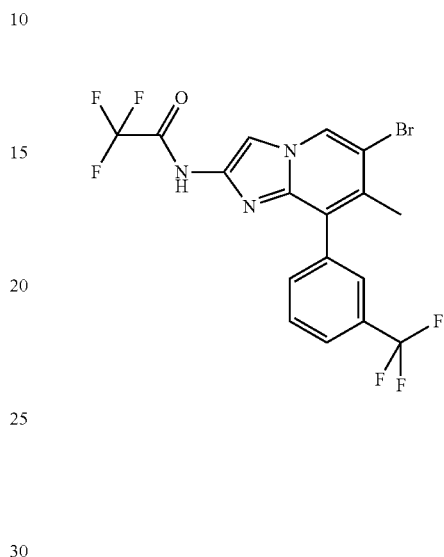

To a solution of N-[5-bromo-4-methyl-3-(3-trifluoromethyl-phenyl)-pyridin-2-yl]-4-methyl-benzenesulfonamide (Int. 4, 800 mg, 1.65 mmol) in DMF (10 mL), sodium hydride (79 mg, 1.98 mmol) was added. The reaction mixture was stirred at RT for 30 mins before the addition of 2-iodoacetamide (366 mg, 1.98 mmol). The reaction mixture was stirred at RT for 2 hrs then at 60° C. for 21 h before being partitioned between EtOAc (20 mL) and water (20 mL). The aqueous phase was extracted with EtOAc (3×20 mL) and the combined organic extracts were dried (Na₂SO₄), filtered and concentrated in vacuo. The resultant residue was taken up in DCM (15 mL) and treated with trifluoroacetic anhydride (15 mL) then the mixture was heated at reflux for 1.5 hrs. The reaction mixture was evaporated in vacuo and then partitioned between DCM and water. The organic phase was separated and concentrated in vacuo. The residue was triturated with MeOH to give a yellow precipitate that was collected by filtration to afford the title compound (118 mg).

LC-MS (Method 1): Rt=3.61 min, m/z=465.8/468 [M]+

Step 3. N-[6-[2-(4-Cyano-phenyl)-2H-pyrazol-3-yl]-7-methyl-8-(3-trifluoromethyl-phenyl)-imidazo[1,2-a]pyridin-2-yl]-2,2,2-trifluoro-acetamide (Example 2)

The title compound was prepared from N-[6-bromo-7-methyl-8-(3-trifluoromethyl-phenyl)-imidazo[1,2-a]pyridin-2-yl]-2,2,2-trifluoro-acetamide (Int. 5, 35 mg, 0.075 mmol) and 4-(5-tributylstannanyl-pyrazol-1-yl)-benzonitrile (Int. 3, 52 mg, 0.113 mmol) using a similar method to that used in Example 1 (Step 4), (6 mg).

LC-MS (Method 3): Rt=4.70 min, m/z=555.0 [M+H]+

¹H NMR (400 MHz, DMSO-d₆) δ 8.50 (1H, s), 7.99 (1H, d J=1.7 Hz), 7.91-7.86 (2H, m), 7.83 (1H, d J=7.7 Hz), 7.79-7.72 (1H, m), 7.71-7.63 (3H, m), 7.61-7.56 (2H, m), 6.81 (1H, s), 1.65 (3H, s).

Example 3

4-{5-[7-Methyl-8-(3-trifluoromethyl-phenyl)-[1,2,4]triazolo[1,5-a]pyridin-6-yl]-pyrazol-1-yl}-benzonitrile

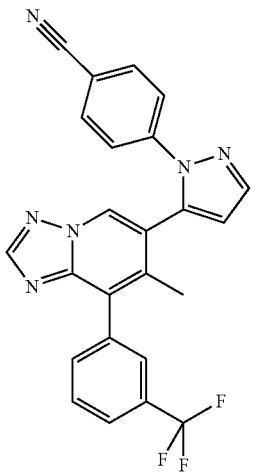 [SMILES: Cc1c(-c2ccnn2-c2ccc(C#N)cc2)cn2ncnc2c1-c1cccc(C(F)(F)F)c1]

Step 1. 6-Bromo-7-methyl-8-(3-trifluoromethyl-phenyl)-[1,2,4]triazolo[1,5-a]pyridine (Intermediate 6)

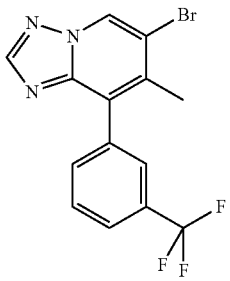 [SMILES: Cc1c(Br)cn2ncnc2c1-c1cccc(C(F)(F)F)c1]

A suspension of 5-bromo-4-methyl-3-(3-trifluoromethyl-phenyl)-pyridin-2-ylamine (Int. 1, 1.0 g, 3.02 mmol) in IPA (3 mL) was treated with dimethylformamide dimethyl acetal (522 μL, 3.93 mmol) then heated at reflux for 3 hrs. The reaction mixture was cooled to 50° C. and hydroxylamine hydrochloride (273 mg, 3.93 mmol) was added. The reaction mixture was stirred at 50° C. for 1.5 hrs then allowed to cool and the resultant precipitate was collected by filtration, washing with IMS. The solid thus obtained was dissolved in THF (10 mL) and cooled to 0° C. before dropwise addition of trifluoroacetic anhydride (481 μL, 3.46 mmol), keeping the internal temperature below 10° C. Once addition was complete the reaction mixture was stirred at room temperature for 18 hrs. Sodium hydrogen carbonate (5% solution, 25 mL) was added and the mixture was extracted with EtOAc (2×25 mL). The combined organic extracts were washed with 5% sodium hydrogen carbonate solution (15 mL), then dried (Na₂SO₄), filtered and concentrated in vacuo to give the title compound as a white solid (1.05 g).

LC-MS (Method 2): Rt=3.74 min, m/z=355.9 [M]⁺

Step 2. 4-{5-[7-Methyl-8-(3-trifluoromethyl-phenyl)-[1,2,4]triazolo[1,5-a]pyridin-6-yl]-pyrazol-1-yl}-benzonitrile (Example 3)

The title compound was prepared from 6-bromo-7-methyl-8-(3-trifluoromethyl-phenyl)-[1,2,4]triazolo[1,5-a]pyridine (Int. 6, 100 mg, 0.281 mmol) and 4-(5-tributylstannanyl-pyrazol-1-yl)-benzonitrile (Int. 3, 193 mg, 0.421 mmol) using a similar method to that used in Example 1 (Step 4) (91 mg).

LC-MS (Method 3): Rt=4.94 min, m/z=444.9 [M+H]⁺

1H NMR (400 MHz, DMSO-d₆) δ 9.15 (1H, s), 8.49 (1H, s), 8.00 (1H, d J=1.9 Hz), 7.91-7.86 (2H, m), 7.84 (1H, d J=8 Hz), 7.78-7.73 (2H, m), 7.70 (1H, d J=8 Hz), 7.62-7.57 (2H, m), 6.84 (1H, d J=1.8 Hz), 1.80 (3H, s).

Example 4

4-{5-[2,7-Dimethyl-8-(3-trifluoromethyl-phenyl)-[1,2,4]triazolo[1,5-a]pyridin-6-yl]-pyrazol-1-yl}-benzonitrile

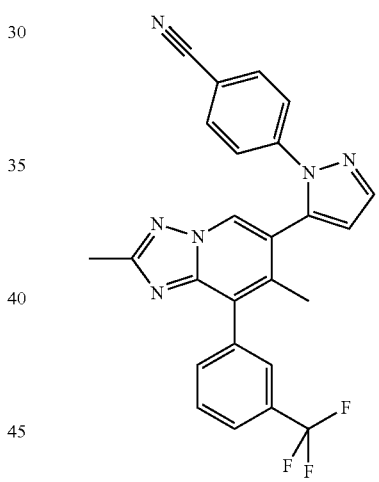

Step 1. 6-Bromo-2,7-dimethyl-8-(3-trifluoromethyl-phenyl)-[1,2,4]triazolo[1,5-a]pyridine (Intermediate 7)

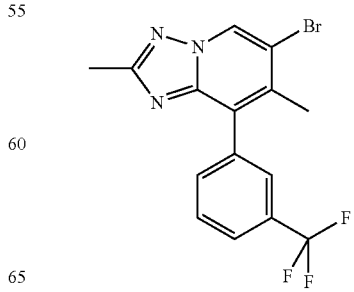

To a stirred solution of 5-bromo-4-methyl-3-(3-trifluoromethyl-phenyl)-pyridin-2-ylamine (Int. 1, 1.0 g, 3.02 mmol) in DMF (5 mL) was added dimethylacetamide dimethyl acetal (1.33 mL, 9.06 mmol) and the reaction mixture was heated at 130° C. for 3 hrs. The reaction mixture was cooled then concentrated in vacuo. The resultant residue was dissolved in MeOH (10 mL) and pyridine (486 µL, 6.04 mmol) was added before the mixture was cooled to 0° C. and hydroxylamine-O-sulfonic acid (512 mg, 4.53 mmol) was added. The reaction mixture was allowed to warm to RT and stirred at this temperature for 20 hrs. The resultant precipitate was collected by filtration, then washed with MeOH to afford the title compound as a grey solid (323 mg).

LC-MS (Method 1): Rt=3.92 min, m/z=370/372 [M]⁺

Step 2. 4-{5-[2,7-Dimethyl-8-(3-trifluoromethyl-phenyl)-[1,2,4]triazolo[1,5-a]pyridin-6-yl]-pyrazol-1-yl}-benzonitrile (Example 4)

The title compound was prepared from 6-bromo-2,7-dimethyl-8-(3-trifluoromethyl-phenyl)-[1,2,4]triazolo[1,5-a]pyridine (Int. 7, 100 mg, 0.27 mmol) and 4-(5-tributylstannanyl-pyrazol-1-yl)-benzonitrile (Int. 3, 186 mg, 0.405 mmol) using a similar method to that used in Example 1 (Step 4) (91 mg).

LC-MS (Method 3): Rt=5.03 min, m/z=458.9 [M+H]⁺

1H NMR (400 MHz, DMSO-d₆) δ 9.00 (1H, s), 7.99 (1H, d J=1.8 Hz), 7.91-7.86 (2H, m), 7.83 (1H, d J=7.9 Hz), 7.76 (1H, d t=7.8 Hz), 7.70 (1H, s), 7.67 (1H, d J=7.8 Hz), 7.60-7.55 (2H, m), 6.82 (1H, d J=1.8 Hz), 2.42 (3H, s), 1.77 (3H, s).

Example 5

4-{5-[2,7-Dimethyl-8-(3-trifluoromethyl-phenyl)-imidazo[1,2-a]pyridin-6-yl]-pyrazol-1-yl}-benzonitrile

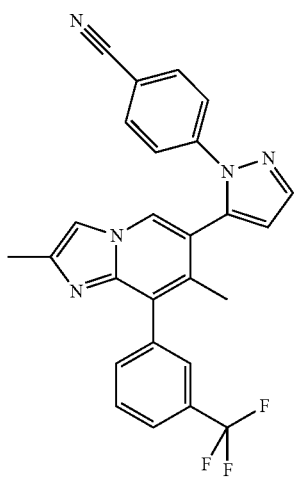 [SMILES: Cc1cn2cc(-c3ccnn3-c3ccc(C#N)cc3)c(C)c(-c3cccc(C(F)(F)F)c3)c2n1]

Step 1. 6-Bromo-2,7-dimethyl-8-(3-trifluoromethyl-phenyl)-imidazo[1,2-a]pyridine (Intermediate 8)

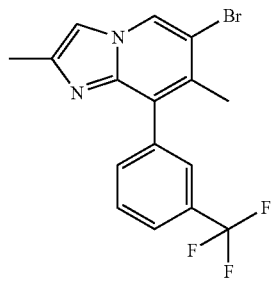 [SMILES: Cc1cn2cc(Br)c(C)c(-c3cccc(C(F)(F)F)c3)c2n1]

5-Bromo-4-methyl-3-(3-trifluoromethyl-phenyl)-pyridin-2-ylamine (Int. 1, 500 mg, 1.51 mmol) and 1-chloropropan-2-one (144 µL, 1.81 mmol) were heated at reflux in IMS (3 mL) for 18 hrs then a further quantity of 1-chloropropan-2-one (144 µL) was added. Heating was continued for 24 hrs then the solvent was evaporated in vacuo and the residue was purified by flash chromatography eluting with a gradient of 0-50% EtOAc in cyclohexane then 0-10% (2N NH₃ in MeOH) in DCM to give the title compound as a cream solid (455 mg).

LC-MS (Method 2): Rt=2.31 and 2.36 min, m/z=368.9, 370.9 [M+H]⁺

Step 2. 4-{5-[2,7-Dimethyl-8-(3-trifluoromethyl-phenyl)-imidazo[1,2-a]pyridin-6-yl]-pyrazol-1-yl}-benzonitrile (Example 5)

The title compound was prepared from 6-bromo-2,7-dimethyl-8-(3-trifluoromethyl-phenyl)-imidazo[1,2-a]pyridine (Int. 8, 50 mg, 0.136 mmol) and 4-(5-tributylstannanyl-pyrazol-1-yl)-benzonitrile (Int. 3, 125 mg, 0.270 mmol) using a similar method to that used in Example 1 (Step 4) (61 mg).

LC-MS (Method 3): Rt=3.68 min, m/z=458 [M+H]⁺

¹H NMR (400 MHz, DMSO) δ 8.61 (1H, s), 7.96 (1H, d J=1.8 Hz), 7.92-7.87 (2H, m), 7.79 (1H, d J=8 Hz), 7.73 (1H, t J=8 Hz), 7.69 (1H, d J=0.8 Hz), 7.63 (2H, d J=6.5 Hz), 7.58-7.54 (2H, m), 6.76 (1H, d J=1.8 Hz), 2.26 (3H, s), 1.64 (3H, s).

Example 6

4-{5-[7-Methyl-8-(3-trifluoromethyl-phenyl)-imidazo[1,2-a]pyridin-6-yl]-pyrazol-1-yl}-benzonitrile

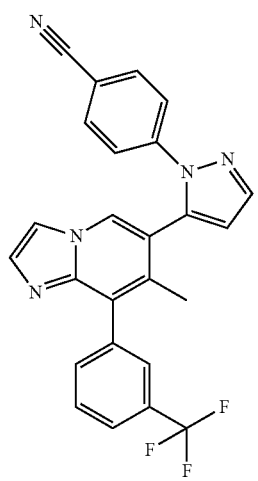 [SMILES: Cc1c(-c2ccnn2-c2ccc(C#N)cc2)cn2ccnc2c1-c1cccc(C(F)(F)F)c1]

Step 1. 6-Bromo-7-methyl-8-(3-trifluoromethyl-phenyl)-imidazo[1,2-a]pyridine (Intermediate 9)

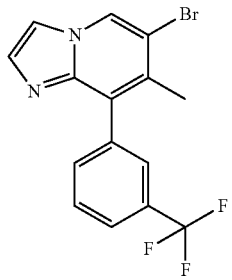 [SMILES: Cc1c(Br)cn2ccnc2c1-c1cccc(C(F)(F)F)c1]

The title compound was prepared from 5-bromo-4-methyl-3-(3-trifluoromethyl-phenyl)-pyridin-2-ylamine (Int. 1, 237 mg, 0.716 mmol), using a similar method to that used in Example 5 (Step 1) and replacing 1-chloropropan-2-one with 2-chloroacetaldehyde (185 μL, 1.43 mmol) (233 mg).
LC-MS (Method 2): Rt=2.34 min, m/z=354.9 $[M]^+$

Step 2. 4-{5-[7-Methyl-8-(3-trifluoromethyl-phenyl)-imidazo[1,2-a]pyridin-6-yl]-pyrazol-1-yl}-benzonitrile (Example 6)

The title compound was prepared from 6-bromo-7-methyl-8-(3-trifluoromethyl-phenyl)-imidazo[1,2-a]pyridine (Int. 9, 30 mg, 0.085 mmol) and 4-(5-tributylstannanyl-pyrazol-1-yl)-benzonitrile (Int. 3, 62 mg, 0.135 mmol) using a similar method to that used in Example 1 (Step 4) (28 mg).
LC-MS (Method 3): Rt=3.56 min, m/z=443.9 $[M+H]^+$
1H NMR (400 MHz, DMSO-$d_6$) δ 8.72 (1H, s), 7.98 (1H, d J=1.8 Hz), 7.96 (1H, d J=1.3 Hz), 7.93-7.88 (2H, m), 7.79 (1H, d J=7.9 Hz), 7.73 (1H, t J=7.8 Hz), 7.68 (1H, s), 7.64 (1H, d J=7.8 Hz), 7.61-7.57 (2H, m), 7.54 (1H, d J=1.3 Hz), 6.78 (1H, d J=1.8 Hz), 1.68 (3H, s).

Example 7

4-{5-[2-(4-Methanesulfonyl-phenylamino)-7-methyl-8-(3-trifluoromethyl-phenyl)-[1,2,4]triazolo[1,5-a]pyridin-6-yl]-pyrazol-1-yl}-benzonitrile

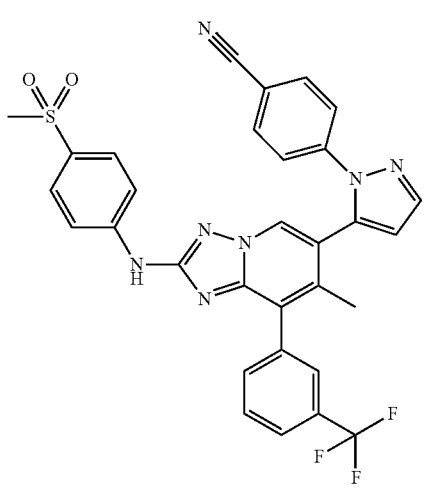 [SMILES: Cc1c(-c2ccnn2-c2ccc(C#N)cc2)cn2nc(Nc3ccc(S(C)(=O)=O)cc3)nc2c1-c1cccc(C(F)(F)F)c1]

A mixture of 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 20 mg, 0.0435 mmol), 4-bromophenyl methylsulfone (20 mg, 0.087 mmol), tris(dibenzylideneacetone)-dipalladium (0) (8 mg, 0.0087 mmol), 2,2'-bis(diphenylphosphino)-1,1'binapthalene (16 mg, 0.026 mmol) and sodium tert-butoxide (10 mg, 0.109 mmol) in THF (0.5 mL) was degassed then heated at 130° C. using microwave irradiation for 1 hr. The volatiles were removed in vacuo and the resulting residue was then purified by flash chromatography eluting with a gradient 0-10% (2N $NH_3$ in MeOH) in DCM and then by preparative HPLC, eluting with a gradient of 40-90% MeCN in water (+0.1% formic acid) to give the title compound as a white solid (10 mg).

LC-MS (Method 3): Rt=5.22 min, m/z=614.1 $[M+H]^+$ $^1$H NMR (400 MHz, DMSO-$d_6$) δ 10.36 (1H, s), 9.02 (1H, s), 7.99 (1H, d J=1.8 Hz), 7.92-7.87 (2H, m), 7.85-7.74 (7H, m), 7.70 (1H, d J=7.2 Hz), 7.64-7.59 (2H, m), 6.82 (1H, d J=1.8 Hz), 3.13 (3H, s), 1.76 (3H, s).

Example 8

4-{5-[2-(4-Methanesulfonyl-benzyl)-7-methyl-8-(3-trifluoromethyl-phenyl)-[1,2,4]triazolo[1,5-a]pyridin-6-yl]-pyrazol-1-yl}-benzonitrile

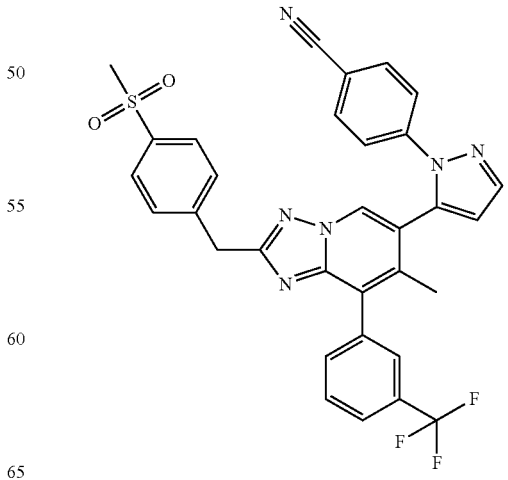

Step 1. N-[5-Bromo-4-methyl-3-(3-trifluoromethyl-phenyl)-pyridin-2-yl]-2-(4-methanesulfonyl-phenyl)-acetamide (Intermediate 10)

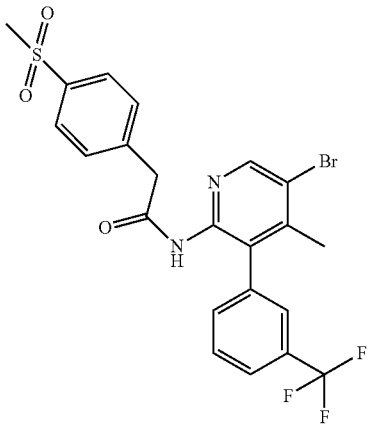 [SMILES: Cc1c(Br)cnc(NC(=O)Cc2ccc(S(C)(=O)=O)cc2)c1-c1cccc(C(F)(F)F)c1]

To a suspension of 4-(methylsulfonyl)phenylacetic acid (388 mg, 1.8 mmol) in dry DCM (5 mL) was added oxalyl chloride (320 μL, 3.6 mmol) followed by DMF (2 drops). The reaction mixture was stirred at RT for 3 hrs then the solvent was removed in vacuo. The resultant residue was taken up in DCM (2 mL) and added dropwise to a stirring solution of 5-bromo-4-methyl-3-(3-trifluoromethyl-phenyl)-pyridin-2-ylamine (Int. 1, 500 mg, 1.51 mmol) and triethylamine (420 μL, 36.02 mmol) in DCM (2 mL) at 0-5° C. The reaction mixture was stirred at 0-5° C. for 3 hrs then gradually warmed to RT over 5 hrs. The reaction mixture was partitioned between saturated sodium hydrogen carbonate solution and DCM. The organic phase was concentrated in vacuo and purified by flash chromatography eluting with a gradient of 0-100% EtOAc in cyclohexane to give the title compound as an orange glass (308 mg).

LC-MS (Method 2): Rt=3.43 min, m/z=526.9, 528.9 [M+H]$^+$

Step 2. N-[5-Bromo-4-methyl-3-(3-trifluoromethyl-phenyl)-pyridin-2-yl]-2-(4-methanesulfonyl-phenyl)-thioacetamide (Intermediate 11)

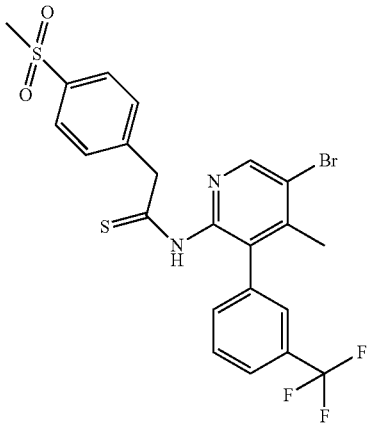 [SMILES: Cc1c(Br)cnc(NC(=S)Cc2ccc(S(C)(=O)=O)cc2)c1-c1cccc(C(F)(F)F)c1]

To a suspension of N-[5-bromo-4-methyl-3-(3-trifluoromethyl-phenyl)-pyridin-2-yl]-2-(4-methanesulfonyl-phenyl)-acetamide (Int. 10, 305 mg, 0.579 mmol) in toluene (15 mL) was added Lawesson's reagent (234 mg, 0.579 mmol) and the reaction mixture was heated at 110° C. for 24 hrs. A further amount of Lawesson's reagent (351 mg) was added and heating was continued for 2.5 hrs before a final addition of Lawesson's reagent (234 mg) was made. The reaction mixture was heated for 19 hrs then cooled, concentrated in vacuo and the resultant residue purified by flash chromatography eluting with a gradient of 0-50% ethyl acetate in cyclohexane to give the title compound as an orange glass (191 mg).

LC-MS (Method 2): Rt=3.73 min, m/z=542.9 [M]$^+$

Step 3. N-[5-Bromo-4-methyl-3-(3-trifluoromethyl-phenyl)-pyridin-2-yl]-N'-hydroxy-2-(4-methane-sulfonyl-phenyl)-acetamidine (Intermediate 12)

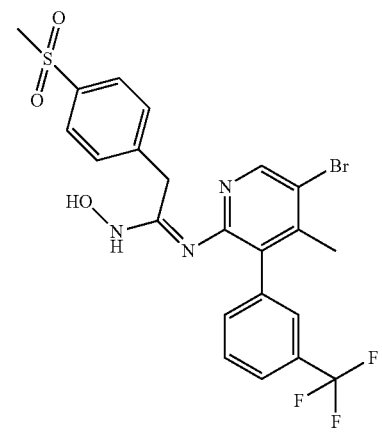 [SMILES: Cc1c(Br)cnc(/N=C(\Cc2ccc(S(C)(=O)=O)cc2)NO)c1-c1cccc(C(F)(F)F)c1]

To a solution of N-[5-bromo-4-methyl-3-(3-trifluoromethyl-phenyl)-pyridin-2-yl]-2-(4-methanesulfonyl-phenyl)-thioacetamide (Int. 11, 190 mg, 0.35 mmol) in IMS (3 mL) was added triethylamine (63 μL, 0.45 mmol) followed by hydroxylamine hydrochloride (29 mg, 0.42 mmol). After stirring at room temperature for 30 mins, water (10 mL) was added and the resultant orange solid was collected by filtration then dried at 50° C. under vacuum to give the title compound (165 mg).

LC-MS (Method 1): Rt=3.92 min, m/z=541.9 [M]$^+$

Step 4. 6-Bromo-2-(4-methanesulfonyl-benzyl)-7-methyl-8-(3-trifluoromethyl-phenyl)-[1,2,4]triazolo[1,5-a]pyridine (Intermediate 13)

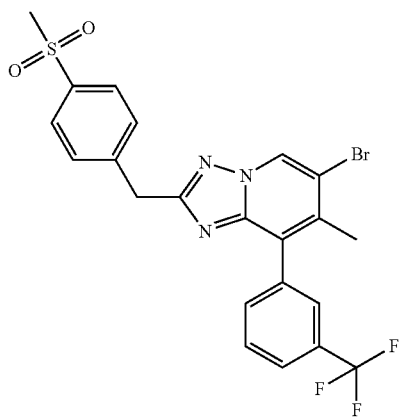 [SMILES: Cc1c(Br)cn2nc(Cc3ccc(S(C)(=O)=O)cc3)nc2c1-c1cccc(C(F)(F)F)c1]

A suspension of N-[5-bromo-4-methyl-3-(3-trifluoromethyl-phenyl)-pyridin-2-yl]-N'-hydroxy-2-(4-methanesulfonyl-phenyl)-acetamidine (Int. 12, 165 mg, 0.304 mmol) in toluene (6 mL) and pyridine (98 µL, 1.218 mmol) was cooled to 0° C. and p-toluenesulfonyl chloride (232 mg, 1.218 mmol) was added. The reaction mixture was stirred at 0° C. for 25 mins then at RT for 6 days. Sodium hydrogen carbonate (saturated solution, 30 mL) was added and the mixture was extracted with DCM (2×30 mL). The organic phase was concentrated and the resultant residue purified by flash chromatography eluting with a gradient of 0-100% EtOAc in cyclohexane to give the title compound as a yellow solid (164 mg).
LC-MS (Method 1): Rt=4.03 min, m/z=523.9 [M]⁺

Step 5. 4-{5-[2-(4-Methanesulfonyl-benzyl)-7-methyl-8-(3-trifluoromethyl-phenyl)-[1,2,4]triazolo[1,5-a]pyridin-6-yl]-pyrazol-1-yl}-benzonitrile (Example 8)

The title compound was prepared from 6-bromo-2-(4-methanesulfonyl-benzyl)-7-methyl-8-(3-trifluoromethyl-phenyl)-[1,2,4]triazolo[1,5-a]pyridine (Int. 13, 50 mg, 0.095 mmol) and 4-(5-tributylstannanyl-pyrazol-1-yl)-benzonitrile (Int. 3, 100 mg, 0.218 mmol) using a similar method to that used in Example 1 (Step 4) (29 mg).

LC-MS (Method 3): Rt=5.12 min, m/z=613.0 [M+H]⁺
¹H NMR (400 MHz, CDCl₃) δ 8.53 (1H, s), 7.92-7.85 (3H, m), 7.72 (1H, d J=8 Hz), 7.68-7.58 (6H, m), 7.53-7.47 (3H, m), 6.58 (1H, d J=1.9 Hz), 4.33 (2H, s), 3.03 (3H, s), 1.83 (3H, s).

Example 9

4-{5-[7-Methyl-3-oxo-8-(3-trifluoromethyl-phenyl)-2,3-dihydro-[1,2,4]triazolo[4,3-a]pyridin-6-yl]-pyrazol-1-yl}-benzonitrile

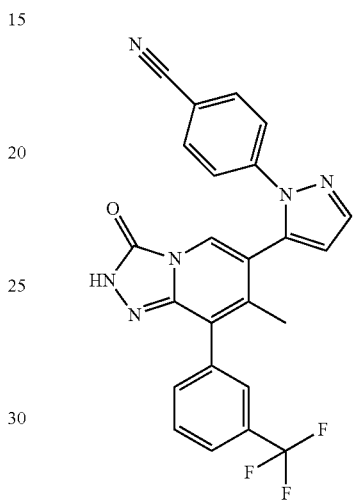

Step 1. 5-Bromo-2-chloro-4-methyl-3-(3-trifluoromethyl-phenyl)-pyridine (Intermediate 14)

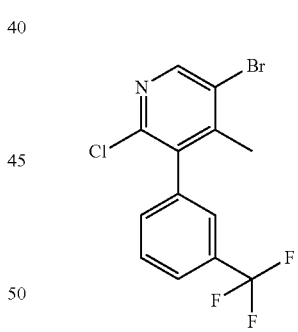

To a suspension of copper (II) chloride (421 mg, 3.92 mmol) and t-butyl nitrite (466 µL, 3.92 mmol) in dry MeCN (12 mL) at 70° C. was added 5-bromo-4-methyl-3-(3-trifluoromethyl-phenyl)-pyridin-2-ylamine (Int. 1, 864 mg, 2.61 mmol) dropwise as a solution in MeCN (3 mL) over 5 mins. The reaction mixture was stirred at 70° C. for 3.5 hrs then poured onto 5 N aqueous HCl (20 mL). The reaction mixture was extracted with EtOAc (4×20 mL) then the combined organic extracts were dried (Na₂SO₄), filtered and evaporated in vacuo. The resultant residue was purified by flash chromatography, eluting with a gradient of 0-100% EtOAc in cyclohexane to give the title compound as an orange solid (184 mg).

LC-MS (Method 1): Rt=4.40 min, m/z=350 [M]⁺

Step 2. 6-Bromo-7-methyl-8-(3-trifluoromethyl-phenyl)-2H-[1,2,4]triazolo[4,3-a]pyridin-3-one (Intermediate 15)

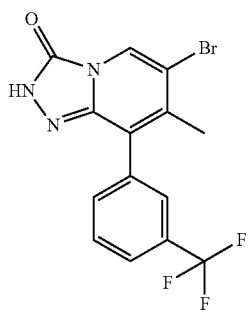 [SMILES: Cc1c(Br)cn2c(=O)[nH]nc2c1-c1cccc(C(F)(F)F)c1]

A solution of 5-bromo-2-chloro-4-methyl-3-(3-trifluoromethyl-phenyl)-pyridine (Int. 14, 176 mg, 0.503 mmol) and hydrazine hydrate (2.5 mL, 52 mmol) in dioxane (5 mL) was heated at 90° C. for 7 hrs. A further quantity of hydrazine hydrate (2.5 mL) was added and the reaction mixture heated at 90° C. for 18 hrs and then at 100° C. for 5 days. The reaction mixture was cooled then poured into water (15 mL) and extracted with EtOAc (3×15 mL). The combined organic extracts were dried (Na$_2$SO$_4$), filtered and evaporated in vacuo to afford a yellow solid. The solid was dissolved in THF (2 mL) and then N,N'-carbonyldiimidazole (375 mg, 2.31 mmol) was added and the reaction mixture stirred at RT for 22 hrs before being concentrated in vacuo. The resultant residue was purified by flash chromatography, eluting with a gradient of 0-100% EtOAc in cyclohexane to give the title compound as a tan solid (184 mg).

LC-MS (Method 2): Rt=3.12 min, m/z=371.9 [M]$^+$

Step 3. 4-{5-[7-Methyl-3-oxo-8-(3-trifluoromethyl-phenyl)-2,3-dihydro-[1,2,4]triazolo[4,3-a]pyridin-6-yl]-pyrazol-1-yl}-benzonitrile (Example 9)

The title compound was prepared from 6-bromo-7-methyl-8-(3-trifluoromethyl-phenyl)-2H-[1,2,4]triazolo[4,3-a]pyridin-3-one (Int. 15, 140 mg, 0.38 mmol) and 4-45-tributylstannanyl-pyrazol-1-yl)-benzonitrile (Int. 3, 310 mg, 0.68 mmol) using a similar method to that used in Example 1 (Step 4) (2 mg).

LC-MS (Method 3): Rt=4.63 min, m/z=460.9 [M+H]$^+$ $^1$H NMR (400 MHz, DMSO-d$_6$) δ 12.53 (1H, br s), 7.95 (1H, d J=1.7 Hz), 7.94-7.92 (2H, m), 7.92-7.90 (1H, m), 7.80 (1H, d J=7.9 Hz), 7.73 (1H, d J=7.9 Hz), 7.71-7.69 (1H, m), 7.69-7.65 (2H, m), 7.61 (1H, d J=7.5 Hz), 6.76 (1H, d J=1.8 Hz), 1.55 (3H, s).

Example 10

4-{5-[2-(4-Methanesulfonyl-benzyl)-7-methyl-3-oxo-8-(3-trifluoromethyl-phenyl)-2,3-dihydro-[1,2,4]triazolo[4,3-a]pyridin-6-yl]-pyrazol-1-yl}-benzonitrile

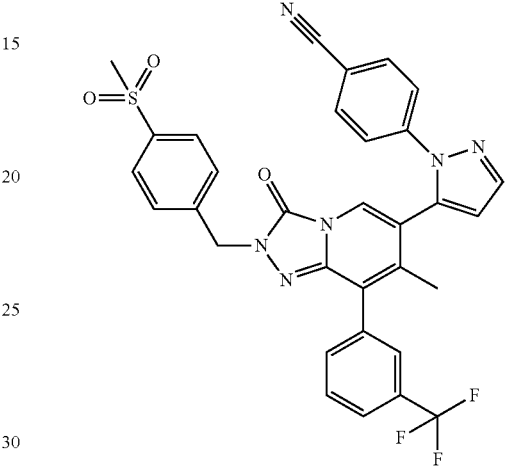

Step 1. 6-Bromo-2-(4-methanesulfonyl-benzyl)-7-methyl-8-(3-trifluoromethyl-phenyl)-2H-[1,2,4]triazolo[4,3-a]pyridin-3-one (Intermediate 16)

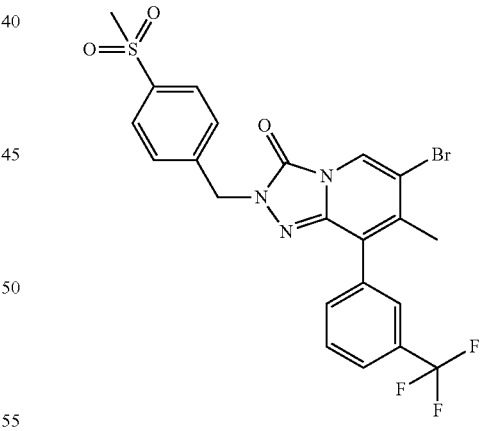

To a solution of 6-bromo-7-methyl-8-(3-trifluoromethyl-phenyl)-2H-[1,2,4]triazolo[4,3-a]pyridin-3-one (Int. 15, 55 mg, 0.148 mmol) in DMF (3 mL) was added cesium carbonate (58 mg, 0.177 mmol) followed by 4-(methylsulfonyl)benzyl bromide (40 mg, 0.163 mmol) and the mixture was stirred at RT for 20 hrs. Further amounts of cesium carbonate (25 mg) and 4-(methylsulfonyl)benzyl bromide (20 mg) were added and stirring was continued for 2 hrs. Water was added and the mixture was extracted with EtOAc (2×25 mL). The combined organic extracts were washed with brine then dried (Na$_2$SO$_4$), filtered and evaporated in vacuo. The resultant residue was purified by flash chromatography, eluting with a gradient of 0-100% EtOAc in cyclohexane to give the title compound as a yellow solid (49 mg).

LC-MS (Method 1): Rt=3.87 min, m/z=539.9 [M]+

Step 2. 4-{5-[2-(4-Methanesulfonyl-benzyl)-7-methyl-3-oxo-8-(3-trifluoromethyl-phenyl)-2,3-dihydro-[1,2,4]triazolo[4,3-a]pyridin-6-yl]-pyrazol-1-yl}-benzonitrile (Example 10).

The title compound was prepared from 6-bromo-2-(4-methanesulfonyl-benzyl)-7-methyl-8-(3-trifluoromethyl-phenyl)-2H-[1,2,4]triazolo[4,3-a]pyridin-3-one (Int. 16, 45 mg, 0.083 mmol) and 4-(5-tributylstannanyl-pyrazol-1-yl)-benzonitrile (Int. 3, 69 mg, 0.15 mmol) by a similar method to that used in Example 1 (Step 4) (24 mg).

LC-MS (Method 3): Rt=5.01 min, m/z=629.0 [M+H]+
¹H NMR (400 MHz, DMSO-d₆) δ 8.06 (1H, s), 7.95 (1H, d J=1.8 Hz), 7.94-7.87 (4H, m), 7.79 (1H, d J=7.9 Hz), 7.74-7.68 (3H, m), 7.61 (2H, d J=8.4 Hz), 7.54 (2H, d J=8.4 Hz), 6.76 (1H, d J=1.8 Hz), 5.23 (2H, s), 3.19 (3H, s), 1.53 (3H, s).

Example 11

2-[6-[2-(4-Cyano-phenyl)-2H-pyrazol-3-yl]-7-methyl-3-oxo-8-(3-trifluoromethyl-phenyl)-[1,2,4]triazolo[4,3-a]pyridin-2-yl]-N,N-dimethyl-acetamide To a solution of 4-{5-[7-methyl-3-oxo-8-(3-trifluoromethyl-phenyl)-2,3-dihydro-[1,2,4]triazolo[4,3-a]pyridin-6-yl]-pyrazol-1-yl}-benzonitrile (Ex. 9, 55 mg. 0.12 mmol) in DMF (3 mL) was added cesium carbonate (58 mg, 0.18 mmol) followed by 2-chloro-N,N-dimethylacetamide (19 μL, 0.18 mmol). The reaction mixture was stirred at RT for 18 hrs then water was added and the reaction mixture was extracted with EtOAc (2×20 mL). The combined organic extracts were dried (Na₂SO₄), filtered and evaporated in vacuo. The resultant residue was purified by preparative HPLC, eluting with a gradient of 20-70% MeCN in water (+0.1% formic acid) to give the title compound as a yellow solid (22 mg).

LC-MS (Method 3): Rt=4.69 min, m/z=546.0 [M+H]+
¹H NMR (400 MHz, DMSO-d₆) δ 8.03 (1H, s), 7.98-7.93 (3H, m), 7.81 (1H, d J=8.0 Hz), 7.74 (1H, d J=7.8 Hz), 7.73-7.68 (2H, m), 7.65-7.59 (2H, m), 6.77 (1H, d J=1.8 Hz), 4.84 (2H, s), 3.00 (3H, s), 2.81 (3H, s), 1.56 (3H, s).

Example 12

2-[6-[2-(4-Cyano-phenyl)-2H-pyrazol-3-yl]-7-methyl-3-oxo-8-(3-trifluoromethyl-phenyl)-[1,2,4]triazolo[4,3-a]pyridin-2-yl]-N-methyl-acetamide

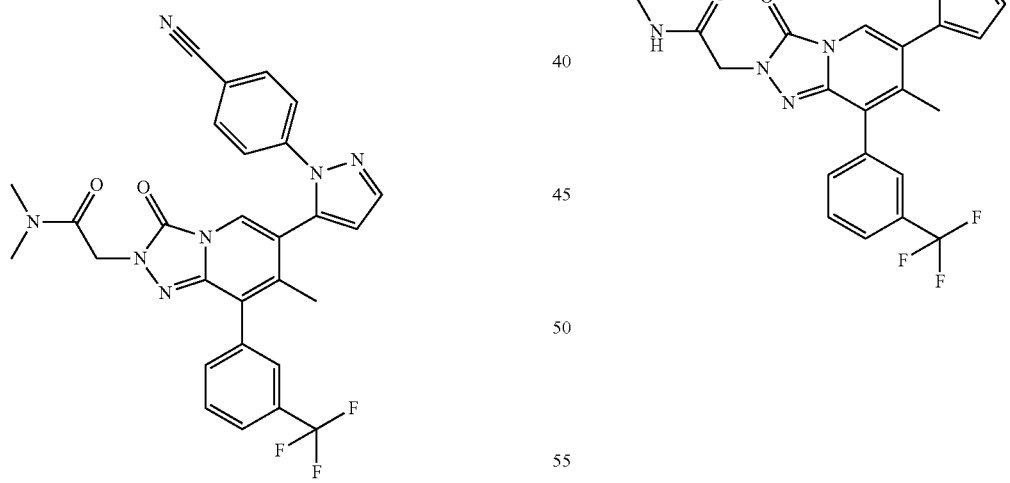

The title compound was prepared from 4-{5-[7-methyl-3-oxo-8-(3-trifluoromethyl-phenyl)-2,3-dihydro-[1,2,4]triazolo[4,3-a]pyridin-6-yl]-pyrazol-1-yl}-benzonitrile (Ex. 9, 55 mg. 0.12 mmol) and 2-chloro-N-methylacetamide (19 μL, 0.18 mmol), using a similar method to that used in Example 11 (25 mg).

LC-MS (Method 3): Rt=4.50 min, m/z=531.9 [M+H]+
¹H NMR (400 MHz, DMSO) δ 8.04 (1H, s), 7.97-7.91 (4H, m), 7.81 (1H, d J=8.0 Hz), 7.74 (1H, d J=7.9 Hz), 7.72-7.68

(2H, m), 7.66-7.60 (2H, m), 6.76 (1H, d J=1.8 Hz), 4.47 (2H, s), 2.59 (3H, d J=4.5 Hz), 1.57 (3H, s).

Example 13

4-{5-[2-(3-Methanesulfonyl-propyl)-7-methyl-3-oxo-8-(3-trifluoromethyl-phenyl)-2,3-dihydro-[1,2,4]triazolo[4,3-a]pyridin-6-yl]-pyrazol-1-yl}-benzonitrile

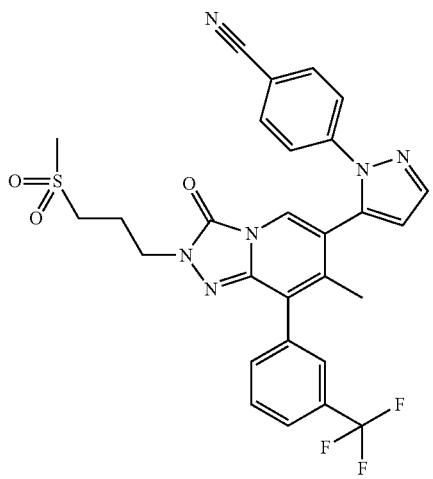 [SMILES: Cc1c(-c2ccnn2-c2ccc(C#N)cc2)cn2c(=O)n(CCCS(C)(=O)=O)nc2c1-c1cccc(C(F)(F)F)c1]

The title compound was prepared from 4-{5-[7-methyl-3-oxo-8-(3-trifluoromethyl-phenyl)-2,3-dihydro-[1,2,4]triazolo[4,3-a]pyridin-6-yl]-pyrazol-1-yl}-benzonitrile (Ex. 9, 70 mg. 0.152 mmol) and 1-bromo-3-methanesulfonyl-propane (53 mg, 0.264 mmol) using a similar method to that employed for Example 11 (27 mg).

LC-MS (Method 3): Rt=4.71 min, m/z=580.9 [M+H]$^+$ $^1$H NMR (400 MHz, DMSO-d$_6$) δ 8.01 (1H, s), 7.96-7.89 (3H, m), 7.81 (1H, d J=7.8 Hz), 7.74 (1H, d J=7.8 Hz), 7.72-7.65 (3H, m), 7.62 (1H, d J=7.6 Hz), 6.74 (1H, d J=1.8 Hz), 3.99 (2H, t J=6.7 Hz), 3.21-3.14 (2H, m), 2.94 (3H, s), 2.13-2.01 (2H, m), 1.54 (3H, s).

Example 14

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-dimethylamino-acetamide

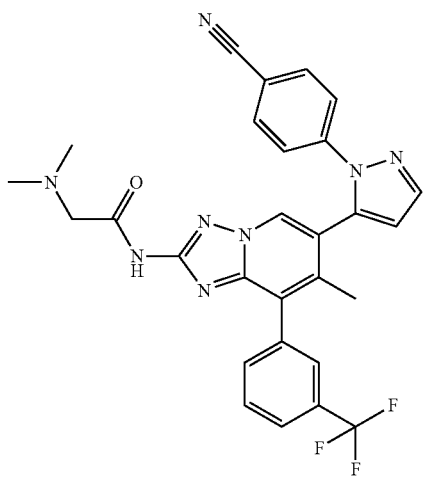 [SMILES: Cc1c(-c2ccnn2-c2ccc(C#N)cc2)cn2nc(NC(=O)CN(C)C)nc2c1-c1cccc(C(F)(F)F)c1]

4-{5-[2-Amino-7-methyl-8-(3-trifluoromethyl-phenyl)-[1,2,4]triazolo[1,5-a]pyridin-6-yl]-pyrazol-1-yl}-benzonitrile (Ex. 1, 459 mg, 1 mmol), N,N-dimethylglycine (206 mg, 2 mmol), and triethylamine (0.278 mL, 2 mmol) were stirred in dry DMF (5 mL) and then HATU (760 mg, 2 mmol) was added portionwise. The reaction mixture was heated at 70° C. for 40 mins then a further quantity of HATU (760 mg, 2 mmol) was added and the mixture heated at 80° C. for 1 hr. The reaction mixture was allowed to cool and then partitioned between EtOAc and water. The organic layer was washed with water followed by brine, and then dried (Na$_2$SO$_4$), filtered and concentrated in vacuo. The resultant residue was treated with DCM, the suspension filtered and the filtrate purified by flash chromatography with a gradient of 0-10% MeOH in DCM to afford the title compound as a white solid (88 mg).

LC-MS (Method 3): Rt=3.62 min, m/z=545.1 [M+H]$^+$

1H NMR (400 MHz, CDCl$_3$) δ 9.95 (1H, s), 8.60 (1H, s), 7.88 (1H, d J=1.8 Hz), 7.74 (1H, d J=7.8 Hz), 7.69-7.63 (3H, m), 7.61 (1H, s), 7.53 (1H, d J=7.6 Hz), 7.50-7.45 (2H, m), 6.59 (1H, d J=1.8 Hz), 3.16 (2H, s), 2.35 (6H, s), 1.85 (3H, s)

Example 15

{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-trimethyl-ammonium bromide

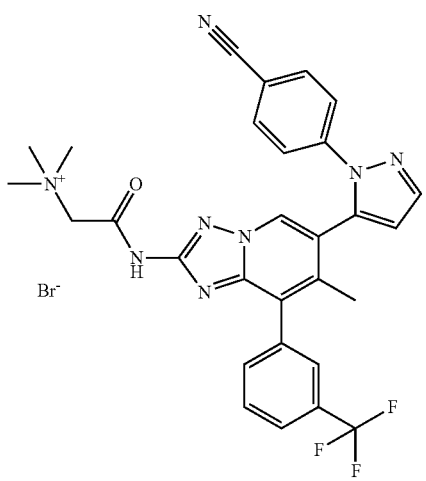 [SMILES: Cc1c(-c2ccnn2-c2ccc(C#N)cc2)cn2nc(NC(=O)C[N+](C)(C)C)nc2c1-c1cccc(C(F)(F)F)c1 ; [Br-]]

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-dimethylamino-acetamide (Ex. 14, 10 mg, 0.018 mmol) was stirred in MeCN (0.5 mL) and a solution of MeBr (ca. 30% in MeCN, 0.01 mL) added, followed after 15 mins by a further MeBr solution (0.05 mL). The reaction mixture was stirred for 18 hrs before being concentrated in vacuo to give title compound as an off-white solid (11 mg).

LC-MS (Method 3): Rt=3.65 min, m/z=559.1 [M]+

1H NMR (400 MHz, CDCl₃) δ 8.52 (1H, s), 7.86 (1H, d J=1.8), 7.70-7.55 (6H, m), 7.48 (2H, d J=8.6 Hz), 6.58 (1H, d J=1.6 Hz), 5.24 (2H, s), 3.42 (9H, s), 1.86 (3H, s)

Example 16

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-dimethylamino-butyramide

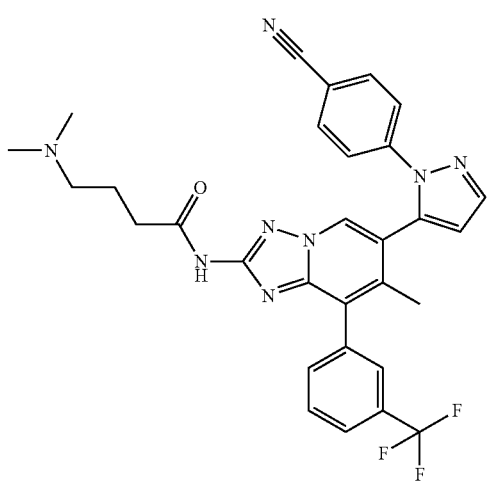 [SMILES: Cc1c(-c2ccnn2-c2ccc(C#N)cc2)cn2nc(NC(=O)CCCN(C)C)nc2c1-c1cccc(C(F)(F)F)c1]

The title compound was prepared from 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 150 mg, 0.33 mmol) and 4-dimethylamino-butyric acid (107 mg, 0.64 mmol) using a similar method to that employed for Example 14 (38 mg).

LC-MS (Method 3): Rt=3.65 min, m/z=573.1 [M+H]+

¹H NMR (400 MHz, CDCl₃) δ 11.93 (1H, br s), 8.57 (1H, s), 7.87 (1H, d J=1.7 Hz), 7.74 (1H, s), 7.70 (1H, d J=8.0 Hz), 7.67-7.62 (2H, m), 7.60 (1H, d J=8.0 Hz), 7.51-7.45 (3H, m), 6.58 (1H, d J=1.7 Hz), 2.62 (2H, s), 2.53 (2H, t J=6.5 Hz), 2.32 (6H, s), 1.95-1.85 (5H, m).

Example 17

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-propyl}-trimethyl-ammonium bromide

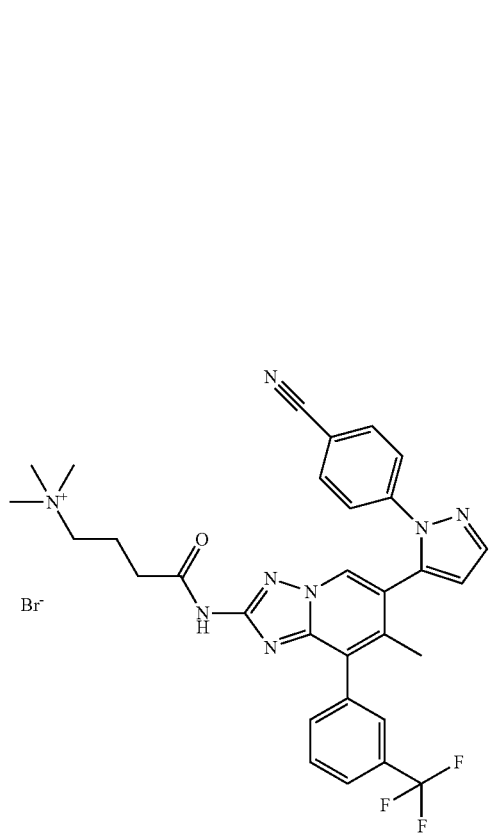 [SMILES: Cc1c(-c2ccnn2-c2ccc(C#N)cc2)cn2nc(NC(=O)CCC[N+](C)(C)C)nc2c1-c1cccc(C(F)(F)F)c1 ; [Br-]]

The title compound was prepared from N-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-4-dimethylamino-butyramide (Ex. 16, 25 mg, 0.044 mmol) and MeBr (ca. 30% in EtOH, 0.15 mL) using a similar method to that employed for Example 15 (30 mg).

LC-MS (Method 3): Rt=3.67 min, m/z=587.1 [M]$^+$ $^1$H NMR (400 MHz, CDCl$_3$) δ 9.61 (1H, br s), 8.52 (1H, s), 7.87 (1H, d J=1.8 Hz), 7.71-7.58 (5H, m), 7.57-7.47 (3H, m), 6.60 (1H, d J=1.8 Hz), 3.38-3.78 (2H, m), 3.34 (9H, s), 2.79 (2H, br s), 2.22-2.09 (2H, m), 1.86 (3H, s).

Example 18

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-(4-methyl-piperazin-1-yl)-acetamide

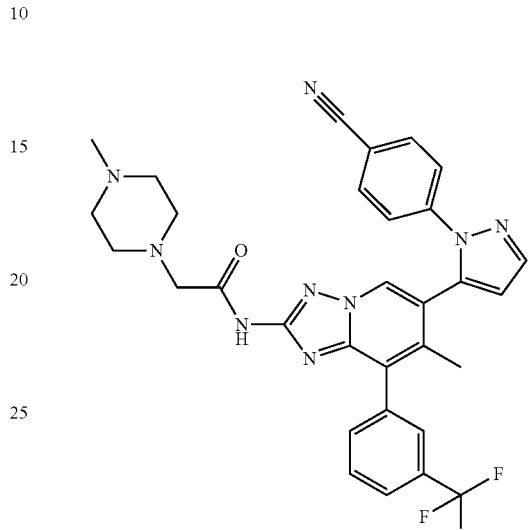

Step 1. 2-Chloro-N-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-acetamide (Intermediate 17)

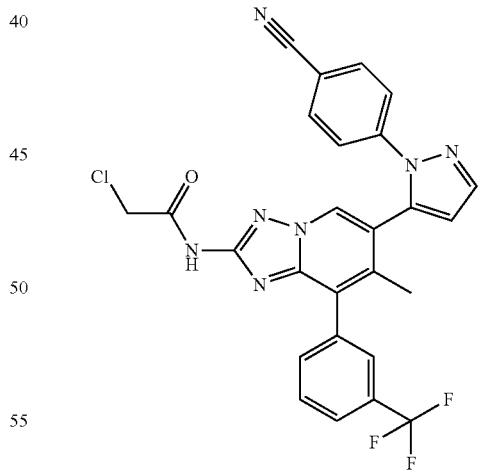

4-{5-[2-Amino-7-methyl-8-(3-trifluoromethyl-phenyl)-[1,2,4]triazolo[1,5-a]pyridin-6-yl]-pyrazol-1-yl}-benzonitrile (Ex. 1, 400 mg, 0.87 mmol) was stirred in dry THF (5 mL) and DIPEA (0.3 mL, 1.765 mmol) was added followed by the dropwise addition of chloroacetyl chloride (104 μL, 1.258 mmol). After 45 mins, a further quantity (69 μL) of chloroacetyl chloride was added and stirring was continued for 18 hrs. The reaction mixture was partitioned between EtOAc and water, the organic layer washed with saturated brine and then dried (Na$_2$SO$_4$) and concentrated in vacuo. The resultant residue was purified by flash chromatography eluting with 65% EtOAc in cyclohexane to give title compound (334 mg).

LC-MS (Method 1): Rt=3.77 min, m/z=536 [M+H]$^+$

Step 2. N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-(4-methyl-piperazin-1-yl)-acetamide (Example 18)

2-Chloro-N-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-acetamide (Int. 17, 150 mg, 0.28 mmol) was stirred in dry DMF (3 mL), then K$_2$CO$_3$ (83 mg, 0.60 mmol) and 1-methylpiperazine (56 mg, 0.56 mmol) were added. Stirring was continued for 2 hrs at RT then the reaction mixture was partitioned between EtOAc and water. The organic layer was washed with water followed by saturated brine, then dried (Na$_2$SO$_4$) and concentrated in vacuo. The resultant residue was purified by flash chromatography eluting with a gradient of 2-5% MeOH in DCM followed by 10% (2M NH$_3$ in MeOH) in DCM to give the title compound as a white solid (128 mg).

LC-MS (Method 3): Rt=3.60 min, m/z=600.1 [M+H]$^+$ $^1$H NMR (400 MHz, CDCl$_3$) δ 9.72 (1H, s), 8.60 (1H, s), 7.88 (1H, d J=1.7 Hz), 7.75 (1H, d J=7.8 Hz), 7.70-7.61 (4H, m), 7.54 (1H, d J=7.7 Hz), 7.50-7.45 (2H, m), 6.59 (1H, d J=1.8 Hz), 3.22 (2H, s), 2.64 (4H, br s), 2.49 (4H, br s), 2.31 (3H, s), 1.86 (3H, s).

Example 19

4-{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-1,1-dimethyl-piperazin-1-ium iodide

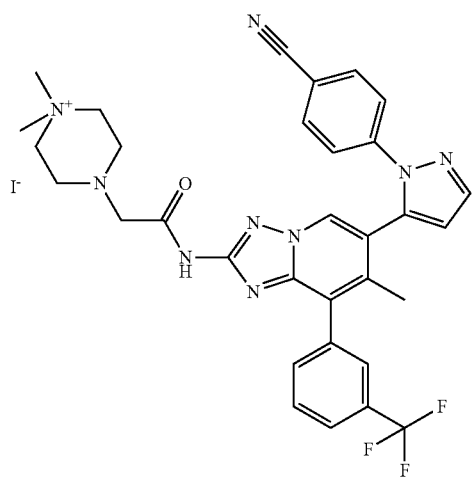 [SMILES: [I-] ; Cc1c(-c2ccnn2-c2ccc(C#N)cc2)cn2nc(NC(=O)CN3CC[N+](C)(C)CC3)nc2c1-c1cccc(C(F)(F)F)c1]

The title compound was prepared from N-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-2-(4-methyl-piperazin-1-yl)-acetamide (Ex. 18, 130 mg, 0.22 mmol) and MeI (27 μL, 0.880 mmol.) using a similar method to that employed for Example 15 (105 mg).

LC-MS (Method 3): Rt=3.56 min, m/z=614.2 [M]$^+$ $^1$H NMR (400 MHz, CDCl$_3$) δ 10.75 (1H, s), 9.01 (1H, s), 8.00 (1H, d J=1.8 Hz), 7.91-7.86 (2H, m), 7.83 (1H, d J=7.8 Hz), 7.77 (1H, d J=7.8 Hz), 7.75-7.71 (1H, m), 7.68 (1H, d J=7.5 Hz), 7.60-7.56 (2H, m), 6.82 (1H, d J=1.8 Hz), 3.46-3.35 (6H, m), 3.10 (6H, s), 2.94-2.85 (4H, m), 1.79 (3H, s).

Example 20

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-morpholin-4-yl-acetamide

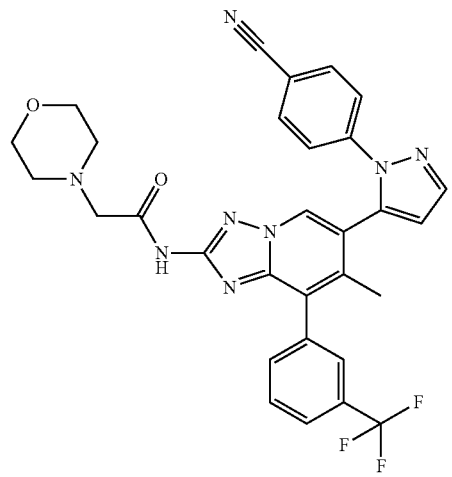 [SMILES: Cc1c(-c2ccnn2-c2ccc(C#N)cc2)cn2nc(NC(=O)CN3CCOCC3)nc2c1-c1cccc(C(F)(F)F)c1]

The title compound was prepared from 2-chloro-N-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-acetamide (Int. 17, 80 mg, 0.149 mmol) and morpholine (26 mg, 0.299 mmol) using a similar method to that employed for Example 18, Step 2 (50 mg).

LC-MS (Method 3): Rt=3.73 min, m/z=587.1 [M+H]$^+$ $^1$H NMR (400 MHz, CDCl$_3$) δ 9.66 (1H, s), 8.60 (1H, s), 7.88 (1H, d J=1.9 Hz), 7.75 (1H, d J=7.9 Hz), 7.68 (1H, d J=7.7 Hz), 7.67-7.60 (3H, m), 7.53 (1H, d J=7.9 Hz), 7.49-7.44 (2H, m), 6.60 (1H, d J=1.8 Hz), 3.75 (4H, t J=4.7 Hz), 3.22 (2H, s), 2.61 (4H, t J=4.6 Hz), 1.86 (3H, s).

Example 21

N-[6-[1-(4-Cyano-phenyl)-1H-pyrazol-5-yl]-7-methyl-8-(3-trifluoromethyl-phenyl)-[1,2,4]triazolo[1,5-a]pyridin-2-yl]-2-(1,1-dioxothiomorpholin-4-yl)-acetamide

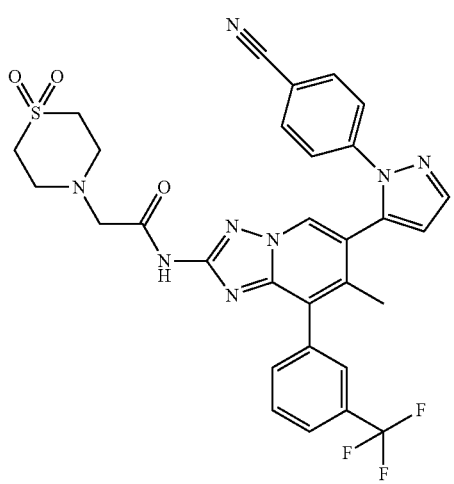 [SMILES: Cc1c(-c2ccnn2-c2ccc(C#N)cc2)cn2nc(NC(=O)CN3CCS(=O)(=O)CC3)nc2c1-c1cccc(C(F)(F)F)c1]

The title compound was prepared from 2-chloro-N-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-acetamide (Int. 17, 50 mg, 0.0934 mmol) and thiomorpholine 1,1-dioxide (20 mg, 0.148 mmol) using a similar method to that employed for Example 18, Step 2 (10 mg).

LC-MS (Method 3): Rt=4.52 min, m/z=635.1 [M+H]$^+$ $^1$H NMR (400 MHz, CDCl$_3$) δ 9.44 (1H, s), 8.59 (1H, s), 7.89 (1H, d J=1.8 Hz), 7.76 (1H, d J=7.9), 7.69 (1H, d J=7.9), 7.67-7.63 (2H, m), 7.61 (1H, s), 7.52 (1H, d J=7.4), 7.49-7.44 (2H, m), 7.60 (1H, d J=1.8 Hz), 3.42 (2H, s), 3.22-3.06 (8H, m), 1.88 (3H, s).

Example 22

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-methanesulfonyl-benzamide

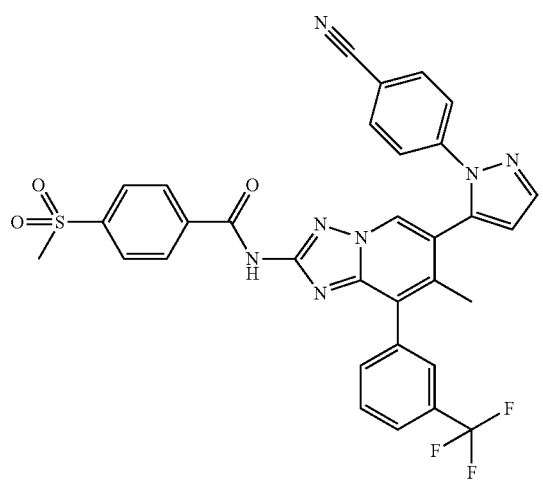 [SMILES: Cc1c(-c2ccnn2-c2ccc(C#N)cc2)cn2nc(NC(=O)c3ccc(S(C)(=O)=O)cc3)nc2c1-c1cccc(C(F)(F)F)c1]

The title compound was prepared from 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 100 mg, 0.218 mmol) and 4-(methylsulfonyl)benzoic acid (56.7 mg, 0.283 mmol) using a similar method to that employed for Example 14 (3%).

LC-MS (Method 3): Rt=4.84 min, m/z=642.1 [M+H]$^+$ $^1$H NMR (400 MHz, CDCl$_3$) δ 8.95 (1H, s), 8.64 (1H, s), 8.12-8.04 (4H, m), 7.90 (1H, s), 7.74 (1H, d=8 Hz), 7.69-7.62 (4H, m), 7.49 (3H, d J=8.5 Hz), 6.64 (1H, s), 3.09 (3H, s), 1.90 (3H, s).

Example 23

4-{5-[2-(4-Methanesulfonyl-benzylamino)-7-methyl-8-(3-trifluoromethyl-phenyl)-[1,2,4]triazolo[1,5-a]pyridin-6-yl]-pyrazol-1-yl}-benzonitrile

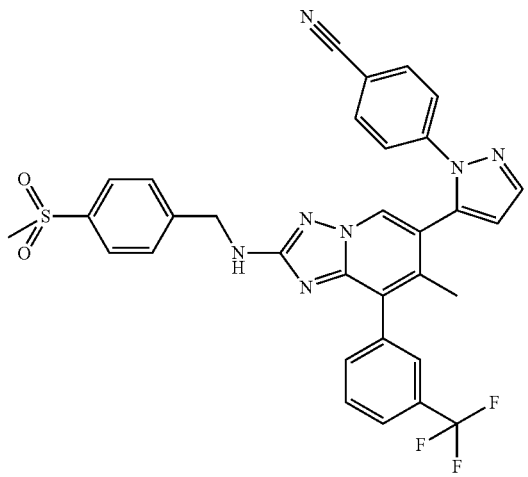 [SMILES: Cc1c(-c2ccnn2-c2ccc(C#N)cc2)cn2nc(NCc3ccc(S(C)(=O)=O)cc3)nc2c1-c1cccc(C(F)(F)F)c1]

6-Bromo-7-methyl-8-(3-trifluoromethyl-phenyl)-[1,2,4]triazolo[1,5-a]pyridin-2-ylamine (Int. 2, 120 mg, 0.323 mmol) and 4-(methylsulfonyl)benzaldehyde (118 mg, 0.64 mmol) were stirred in dry DCM (3 mL) then triethylamine ((0.097 mL, 0.70 mmol) was added. To the suspension was added titanium (IV) isopropoxide (182 mg, 0.64 mmol) and the mixture was stirred under argon for 65 hrs. The solvent was evaporated in vacuo and IMS (3 mL) was added, followed by sodium borohydride (25 mg, 0.66 mmol). After stirring for 3.5 hrs a further quantity of sodium borohydride (15 mg) was added and after another 1.5 hrs a further amount of sodium borohydride (10 mg) was added and the mixture stirred for a further 1 hr. Water and DCM were added and the mixture was filtered to collect a solid precipitate which was combined with the concentrated DCM extract to give 93 mg of the intermediate [6-bromo-7-methyl-8-(3-trifluoromethyl-phenyl)-[1,2,4]triazolo[1,5-a]pyridin-2-yl]-(4-methanesulfonyl-benzyl)-amine. The title compound was prepared from the crude intermediate thus obtained (150 mg) and 4-(5-tributylstannanyl-pyrazol-1-yl)-benzonitrile (Int. 3, 204 mg, 0.445 mmol) using a similar method to that used in Example 1 (Step 4) (55 mg).

LC-MS (Method 3): Rt=5.06 min, m/z=628.1 [M+H]$^+$

¹H NMR (400 MHz, CDCl₃) δ 8.31 (1H, s), 7.90 (2H, d J=8.0 Hz), 7.85 (1H, d J=1.8 Hz), 7.71-7.63 (3H, m), 7.62-7.55 (4H, m), 7.53-7.45 (3H, m), 6.55 (1H, d J=1.8 Hz), 5.09 (1H, t J=6.5 Hz), 4.67 (2H, d J=6.5 Hz), 3.04 (3H, s), 1.77 (3H, s).

Example 24

2-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N,N-dimethyl-acetamide

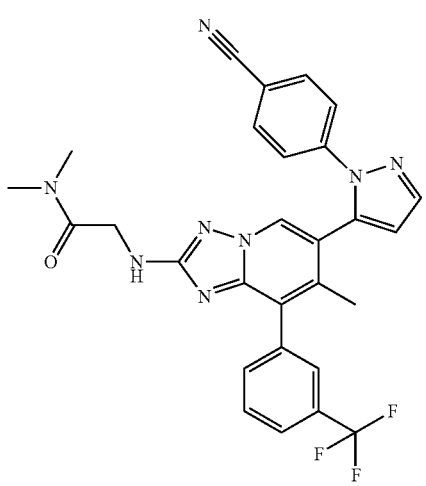 [SMILES: Cc1c(-c2ccnn2-c2ccc(C#N)cc2)cn2nc(NCC(=O)N(C)C)nc2c1-c1cccc(C(F)(F)F)c1]

The title compound was prepared from 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 100 mg, 0.218 mmol) and 2-chloro-N,N-dimethylacetamide (40 mg, 0.332 mmol) using a similar method to that used in Example 11 (6 mg).

LC-MS (Method 3): Rt=4.73 min, m/z=545.1 [M+H]⁺

¹H NMR (400 MHz, DMSO-d₆) δ 8.74 (1H, s), 7.96 (1H, d J=1.8 Hz), 7.93-7.88 (2H, m), 7.79 (1H, d J=7.8 Hz), 7.76-7.68 (2H, m), 7.64 (1H, d J=7.6 Hz), 7.59-7.55 (2H, m), 6.75 (1H, d J=1.8 Hz), 6.58 (1H, t J=5.9 Hz), 4.00 (2H, d J=6.0 Hz), 2.96 (3H, s), 2.82 (3H, s), 1.71 (3H, s).

Example 25

1-{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-1,4-dimethyl-piperazin-1-ium chloride

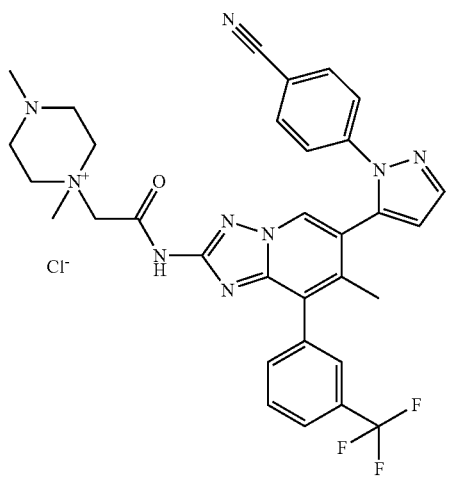 [SMILES: Cc1c(-c2ccnn2-c2ccc(C#N)cc2)cn2nc(NC(=O)C[N+]3(C)CCN(C)CC3)nc2c1-c1cccc(C(F)(F)F)c1 ; [Cl-]]

The title compound was prepared from 2-chloro-N-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-acetamide (Int. 17, 80 mg, 0.149 mmol) and 1,4-dimethyl-piperazine (34 mg, 0.298 mmol) using a similar method to that employed for Example 18 (step 2) (38 mg).

LC-MS (Method 3): Rt=3.39 min, m/z=614.1 [M]⁺

¹H NMR (400 MHz, CDCl₃) δ 8.71 (1H, s), 8.50 (1H, s), 7.87 (1H, d J=1.8 Hz), 7.72-7.55 (6H, m), 7.49-7.43 (2H, m), 6.60 (1H, d J=1.8 Hz), 3.65 (3H, s), 4.03 (2H, s), 3.43 (4H, s), 2.88-2.78 (2H, m), 2.75-2.65 (2H, m), 2.38 (3H, s), 1.88 (3H, s).

Example 26

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-acetamide

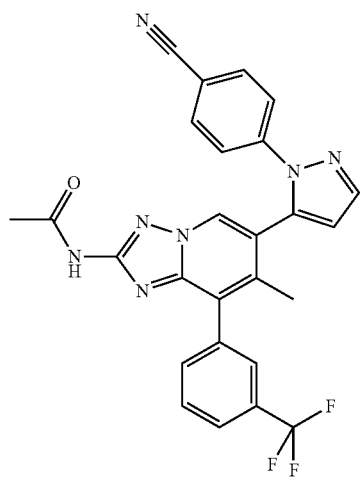 [SMILES: CC(=O)Nc1nc2c(-c3cccc(C(F)(F)F)c3)c(C)c(-c3ccnn3-c3ccc(C#N)cc3)cn2n1]

Step 1. N-[6-Bromo-7-methyl-8-(3-trifluoromethyl-phenyl)-[1,2,4]triazolo[1,5-a]pyridin-2-yl]-acetamide (Intermediate 18)

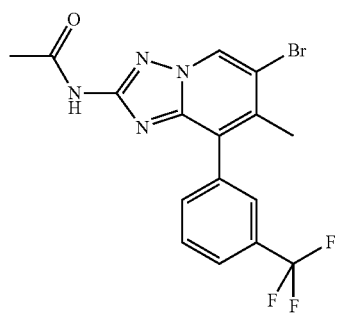 [SMILES: CC(=O)Nc1nc2c(-c3cccc(C(F)(F)F)c3)c(C)c(Br)cn2n1]

The title compound was prepared from 6-bromo-7-methyl-8-(3-trifluoromethyl-phenyl)-[1,2,4]triazolo[1,5-a]pyridin-2-ylamine (Int. 2, 6.7 g, 18.06 mmol) and acetyl chloride (2.83 mL, 39.7 mmol) using a similar method to that employed for Intermediate 17 (5.65 g).

LC-MS (Method 2): Rt=3.32 min, m/z=414 [M+H]$^+$

Step 2. N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-acetamide (Example 26)

The title compound was prepared from the N-[6-bromo-7-methyl-8-(3-trifluoromethyl-phenyl)-[1,2,4]triazolo[1,5-a]pyridin-2-yl]-acetamide (Int. 18, 65 mg, 0.157 mmol) and 4-(5-tributylstannanyl-pyrazol-1-yl)-benzonitrile (Int. 3, 79 mg, 0.173 mmol) using a similar method to that used in Example 1 (Step 4) (26 mg).

LC-MS (Method 3): Rt=4.57 min, m/z=502.0 [M+H]$^+$ $^1$H NMR (400 MHz, CDCl$_3$) δ 10.88 (1H, s), 9.01 (1H, s), 7.99 (1H, d J=1.7 Hz), 7.91-7.86 (2H, m), 7.82 (1H, d J=8.2 Hz), 7.76 (1H, d J=7.7 Hz), 7.73 (1H, s), 7.67 (1H, d J=7.7 Hz), 7.61-7.56 (2H, m), 6.81 (1H, s), 2.07 (3H, s), 1.76 (3H, s).

Example 27

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-methanesulfonamide

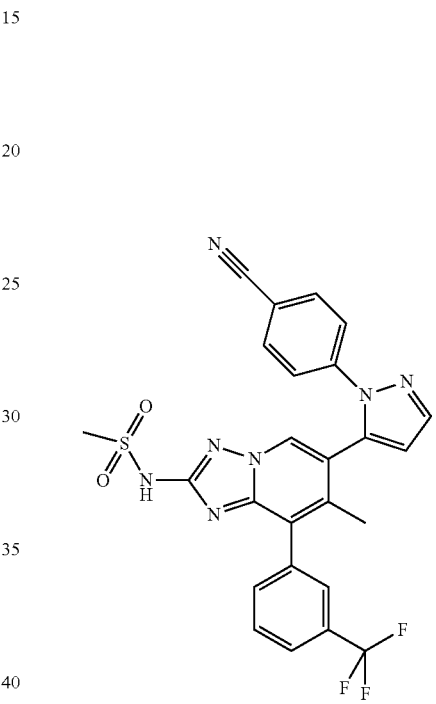

4-{5-[2-Amino-7-methyl-8-(3-trifluoromethyl-phenyl)-[1,2,4]triazolo[1,5-a]pyridin-6-yl]-pyrazol-1-yl}-benzonitrile (Ex. 1, 150 mg, 0.326 mmol) was dissolved in pyridine (4 mL) and methanesulfonyl chloride (50 μL, 0.652 mmol) was added. The reaction mixture was stirred at RT for 18 hrs then at 60° C. for 3 hrs. A further quantity of methanesulfonyl chloride (50 μL) was added and the mixture was heated at 60° C. overnight. The reaction mixture was allowed to cool then water was added and the mixture was extracted with EtOAc. The organic extract was washed with 1 M HCl followed by water and then saturated brine, before being dried (Na$_2$SO$_4$), filtered and concentrated in vacuo. The resultant residue was purified by flash chromatography eluting with a gradient of 0-50% EtOAc in cyclohexane to give the title compound as a tan solid (85 mg).

LC-MS (Method 3) Rt=4.83 mins, m/z=537.9 [M+H]$^+$ $^1$H NMR (400 MHz, CDCl$_3$) δ 11.39 (1H, s), 9.03 (1H, s), 7.99 (1H, d J=1.8 Hz), 7.92-7.86 (2H, m), 7.84-7.79 (1H, m), 7.75 (2H, t J=7.8 Hz), 7.70-7.66 (1H, m), 7.62-7.57 (2H, m), 6.80 (1H, d J=1.8 Hz), 3.30 (3H, s), 1.76 (3H, s).

Example 28

4-{5-[2-(3-Dimethylamino-propylamino)-7-methyl-8-(3-trifluoromethyl-phenyl)-[1,2,4]triazolo[1,5-a]pyridin-6-yl]-pyrazol-1-yl}-benzonitrile

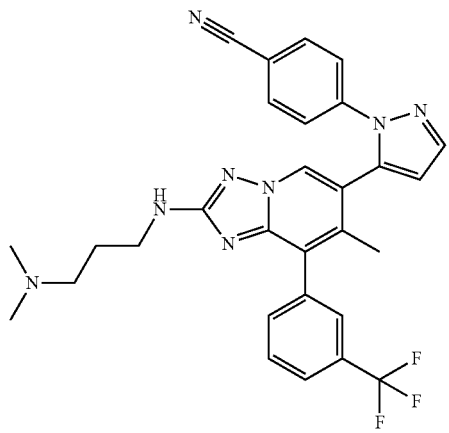 [SMILES: Cc1c(-c2ccnn2-c2ccc(C#N)cc2)cn2nc(NCCCN(C)C)nc2c1-c1cccc(C(F)(F)F)c1]

Step 1. 4-{5-[2-Chloro-7-methyl-8-(3-trifluoromethyl-phenyl)-[1,2,4]triazolo[1,5-a]pyridin-6-yl]-pyrazol-1-yl}-benzonitrile (Intermediate 19)

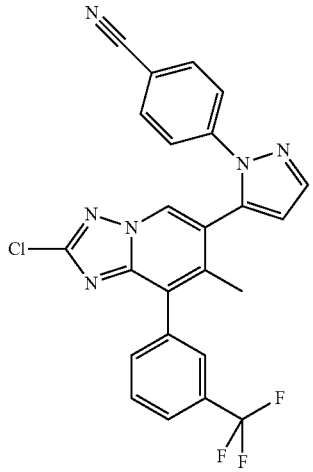 [SMILES: Cc1c(-c2ccnn2-c2ccc(C#N)cc2)cn2nc(Cl)nc2c1-c1cccc(C(F)(F)F)c1]

The title compound was prepared from 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 100 mg, 0.22 mmol) using a similar method to that used for Intermediate 14 (73 mg).

LC-MS (Method 3): Rt=5.46 min, m/z=478.9 [M+H]+

$^1$H NMR (400 MHz, CDCl$_3$) δ 8.53 (1H, s), 7.89 (1H, d J=1.7 Hz), 7.72 (1H, app d J=7.9 Hz), 7.70-7.62 (3H, m), 7.58 (1H, s), 7.55-7.48 (3H, m), 6.63 (1H, d J=1.7 Hz), 1.87 (3H, s).

Step 2. 4-{5-[2-(3-Dimethylamino-propylamino)-7-methyl-8-(3-trifluoromethyl-phenyl)-[1,2,4]triazolo[1,5-a]pyridin-6-yl]-pyrazol-1-yl}-benzonitrile (Example 28)

To a solution of 4-{5-[2-chloro-7-methyl-8-(3-trifluoromethyl-phenyl)-[1,2,4]triazolo[1,5-a]pyridin-6-yl]-pyrazol-1-yl}-benzonitrile (Int. 19, 68 mg, 0.14 mmol) in NMP (2.5 mL) was added N,N-dimethyl-propane-1,3-diamine (54 µL, 0.43 mmol) followed by triethylamine (39 µL, 0.28 mmol). The reaction mixture was heated to 220° C. for 5 hrs using microwave irradiation. The cooled reaction mixture was concentrated in vacuo then loaded onto a SCX-2 cartridge (2 g) in MeOH. After washing with DCM/MeOH, the crude product was eluted with 2 M NH$_3$ in MeOH and following concentration in vacuo gave a brown oil (53 mg). The oil thus obtained was purified using preparative TLC (20×20 cm×1 mm) eluting with 20% MeOH in DCM to give the title compound as a pale yellow oil, which solidified on standing (14 mg).

LC-MS (Method 3): Rt=3.72 min, m/z=545.1 [M+H]+

$^1$H NMR (400 MHz, CDCl$_3$) δ 8.32 (1H, s), 7.85 (1H, d J=1.7 Hz), 7.71-7.58 (5H, m), 7.54-7.48 (3H, m), 6.57 (1H, d J=1.8 Hz), 5.25 (1H br s), 3.46 (2H, m), 2.52 (2H, t J=6.9 Hz), 2.31 (6H, s), 1.86 (2H, qn J=6.9 Hz), 1.77 (3H, s).

Example 29

4-{5-[2-(2-Dimethylamino-ethylamino)-7-methyl-8-(3-trifluoromethyl-phenyl)-[1,2,4]triazolo[1,5-a]pyridin-6-yl]-pyrazol-1-yl}-benzonitrile

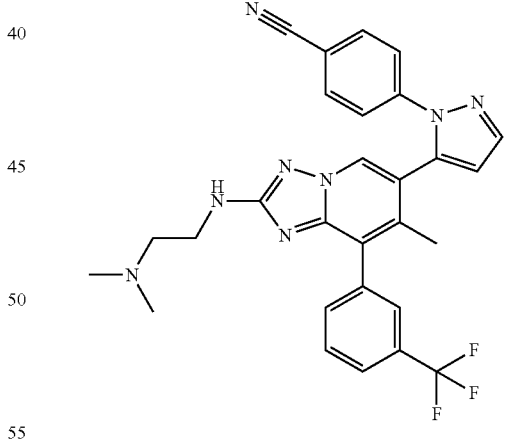

The title compound was prepared from 4-{5-[2-chloro-7-methyl-8-(3-trifluoromethyl-phenyl)-[1,2,4]triazolo[1,5-a]pyridin-6-yl]-pyrazol-1-yl}-benzonitrile (Int. 19, 92 mg, 0.19 mmol) and N,N-dimethyl-ethane-1,2-diamine (1.5 mL) using a similar method to that used in Example 28 (61 mg).

LC-MS (Method 3): Rt=3.69 min, m/z=531.1 [M+H]+

$^1$H NMR (400 MHz, CDCl$_3$) δ 8.32 (1H, s), 7.85 (1H, d J=1.8 Hz), 7.70-7.58 (5H, m), 7.54-7.48 (3H, m), 6.56 (1H, d

J=1.8 Hz), 5.25 (1H app t J=5.2 Hz), 3.40 (2H, q J=5.9 Hz), 2.53 (2H, t J=5.9 Hz), 2.24 (6H, s), 1.77 (3H, s).

Example 30

4-{5-[2-(4-Dimethylamino-butylamino)-7-methyl-8-(3-trifluoromethyl-phenyl)-[1,2,4]triazolo[1,5-a]pyridin-6-yl]-pyrazol-1-yl}-benzonitrile

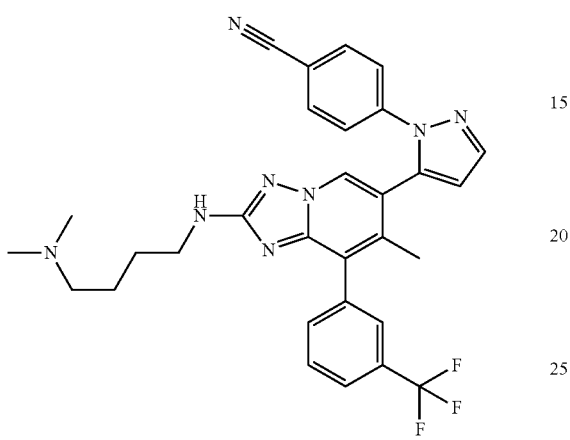

The title compound was prepared from 4-{5-[2-chloro-7-methyl-8-(3-trifluoromethyl-phenyl)-[1,2,4]triazolo[1,5-a]pyridin-6-yl]-pyrazol-1-yl}-benzonitrile (Int. 19, 93 mg, 0.19 mmol) and N,N-dimethyl-butane-1,4-diamine (1.0 mL) using a similar method to that used in Example 28 (47 mg).

LC-MS (Method 3): Rt=3.78 min, m/z=559.1 [M+H]$^+$ $^1$H NMR (400 MHz, CDCl$_3$) δ 8.32 (1H, s), 7.85 (1H, d J=1.8 Hz), 7.70-7.58 (5H, m), 7.54-7.48 (3H, m), 6.56 (1H, app d J=1.8 Hz), 4.89 (1H, br s), 3.37 (2H, t J=6.5 Hz), 2.32 (2H, t J=7.2 Hz), 2.23 (6H, s), 1.76 (3H, s), 1.67 (2H, app qn J=7.2 Hz), 1.58 (2H, app qn J=7.5 Hz).

Example 31

4-{5-[2-Methoxy-7-methyl-8-(3-trifluoromethyl-phenyl)-[1,2,4]triazolo[1,5-a]pyridin-6-yl]-pyrazol-1-yl}-benzonitrile

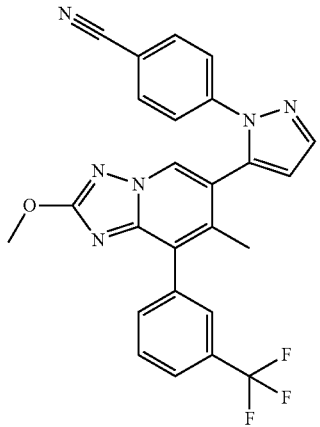 [SMILES: COc1nc2c(-c3cccc(C(F)(F)F)c3)c(C)c(-c3ccnn3-c3ccc(C#N)cc3)cn2n1]

A cloudy solution of 4-{5-[2-chloro-7-methyl-8-(3-trifluoromethyl-phenyl)-[1,2,4]triazolo[1,5-a]pyridin-6-yl]-pyrazol-1-yl}-benzonitrile (Int. 19, 22 mg, 0.046 mmol) and NaOMe (25% Wt, 0.75 mL, 3.3 mmol) in MeOH (0.75 mL) was heated at 100° C. for 30 mins using microwave irradiation. The cooled reaction mixture was evaporated in vacuo preparative TLC (20×20 cm×1 mm) eluting with 50% EtOAc in cyclohexane to give the title compound as a white solid (6 mg).

LC-MS (Method 3): Rt=5.25 min, m/z=474.9 [M+H]$^+$ $^1$H NMR (400 MHz, CDCl$_3$) δ 8.40 (1H, s), 7.88 (1H, d J=1.8 Hz), 7.72-7.63 (3H, m), 7.62-7.59 (2H, m), 7.54-7.48 (3H, m), 6.80 (1H, app d J=1.8 Hz), 4.08 (3H, s), 1.84 (3H, s).

Example 32

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-propyl}-trimethyl-ammonium benzenesulfonate

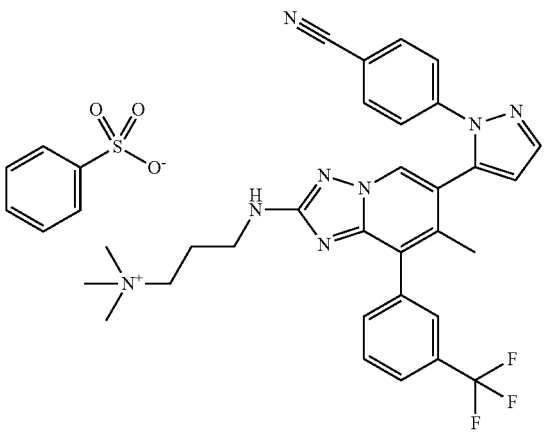 [SMILES: O=S(=O)([O-])c1ccccc1 ; Cc1c(-c2ccnn2-c2ccc(C#N)cc2)cn2nc(NCCC[N+](C)(C)C)nc2c1-c1cccc(C(F)(F)F)c1]

To a solution of 4-{5-[2-(3-dimethylamino-propylamino)-7-methyl-8-(3-trifluoromethyl-phenyl)-[1,2,4]triazolo[1,5-a]pyridin-6-yl]-pyrazol-1-yl}-benzonitrile (Ex. 28, 55 mg, 0.10 mmol) in acetone (0.44 mL) was added methylbenzenesulfonate (15 μL, 0.11 mmol) at ambient temperature. The reaction mixture was heated 55° C. for 1.5 hrs. The cooled reaction mixture was concentrated in vacuo to give a clear colorless oil. The oil thus obtained was triturated in diethyl ether and the resultant solid taken up in minimal EtOAc and Et$_2$O added until a white solid formed. The precipitate was collected by filtration, washed with Et$_2$O and dried in vacuo to yield the title compound as a white solid (64 mg).

LC-MS (Method 3): Rt=3.71 min, m/z=559.0 [M]$^+$ $^1$H NMR (400 MHz, CDCl$_3$) δ 8.32 (1H, s), 7.86-7.83 (3H, m), 7.68-7.63 (3H, m), 7.62-7.56 (2H, m), 7.53-7.47 (3H, m), 7.29-7.24 (3H obs m), 6.56 (1H, d J=1.7 Hz), 5.72 (1H, t J=6.0 Hz), 3.62 (2H, m), 3.42 (2H, q J=6.1 Hz), 3.20 (9H, s), 2.12 (2H, m), 1.75 (3H, s).

Example 33

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-ethyl}-trimethyl-ammonium benzenesulfonate The title compound was prepared from 4-{5-[2-(3-dimethylamino-ethylamino)-7-methyl-8-(3-trifluoromethyl-phenyl)-[1,2,4]triazolo[1,5-a]pyridin-6-yl]-pyrazol-1-yl}-benzonitrile (Ex. 29, 50 mg, 0.094 mmol) using a similar method to that used in Example 32 (51 mg).

LC-MS (Method 3): Rt=3.70 min, m/z=545.0 [M]$^+$ $^1$H NMR (400 MHz, CD$_3$OD) δ 8.57 (1H, s), 7.91 (1H, d J=1.8 Hz), 7.85-7.66 (7H, m), 7.62-7.55 (3H, m), 7.44-7.37 (3H, m), 6.74 (1H, d J=1.8 Hz), 3.80 (2H, app t J=6.2 Hz), 3.58 (2H, t J=6.2 Hz), 3.18 (9H, s), 1.83 (3H, s).

Example 34

{4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-butyl}-trimethyl-ammonium formate

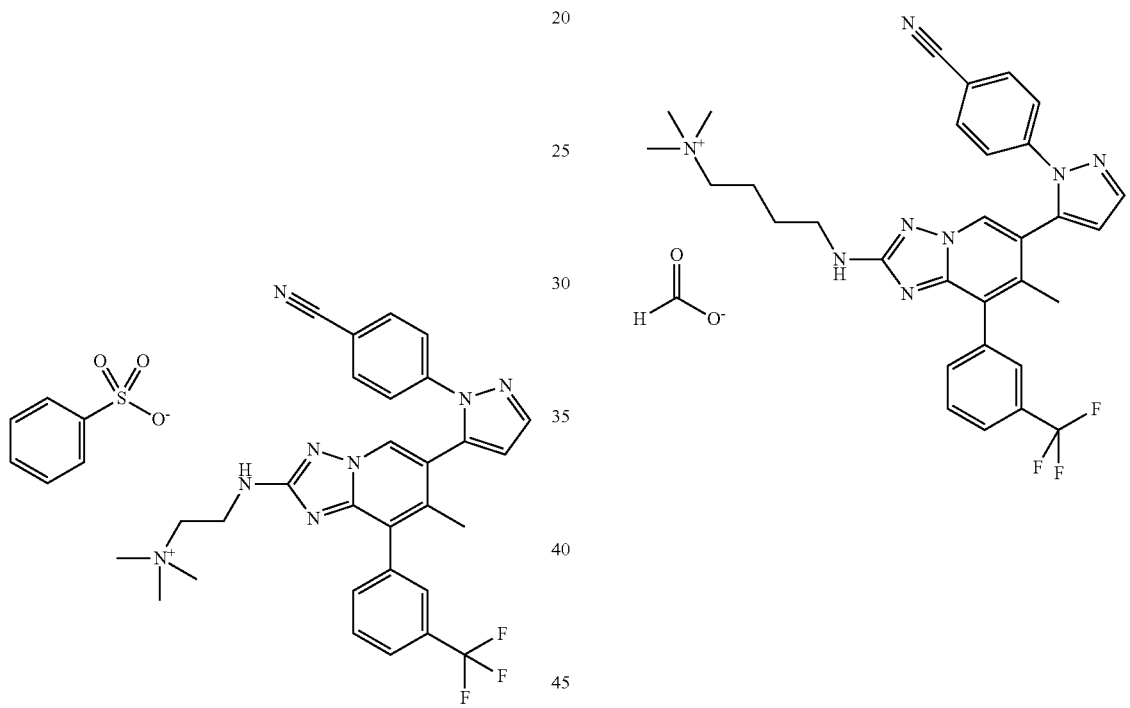

To a solution of 4-{5-[2-(4-dimethylamino-butylamino)-7-methyl-8-(3-trifluoromethyl-phenyl)-[1,2,4]triazolo[1,5-a]pyridin-6-yl]-pyrazol-1-yl}-benzonitrile (Ex. 30, 44 mg, 0.079 mmol) in acetone (0.4 mL) was added methylbenzenesulfonate (12 μL, 0.087 mmol) at ambient temperature. The reaction mixture was heated at 55° C. under N$_2$ for 2.5 hrs. A further quantity of methylbenzenesulfonate (3.2 μL) was added and the mixture was heated at 55° C. for 1 hr. Once cooled the volatiles were evaporated in vacuo and the residue azeotroped with diethyl ether. The resultant residue was subjected to preparative C$_{18}$ HPLC, eluting with a gradient of 20-70% MeCN in water (+0.1% formic acid) to give the title compound as a white solid (10 mg).

LC-MS (Method 3): Rt=3.79 min, m/z=573.1 [M]$^+$

1H NMR (400 MHz, DMSO-d$_6$) δ 8.70 (1H, s), 8.46 (1H, br s), 7.97 (1H, d J=1.8 Hz), 7.92-7.88 (2H, m), 7.79 (1H, d J=8.1 Hz), 7.75-7.67 (2H, m), 7.64 (1H, d J=7.7 Hz), 7.59-7.55 (2H, m), 6.85 (1H, t J=6.0 Hz), 6.76 (1H, d J=1.8 Hz), 3.32-3.25 (2H, m), 3.21 (2H, q J=6.5 Hz), 3.02 (9H, s), 1.80-1.67 (5H, m), 1.59-1.48 (2H, m).

Example 35

[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-carbamic acid ethyl ester

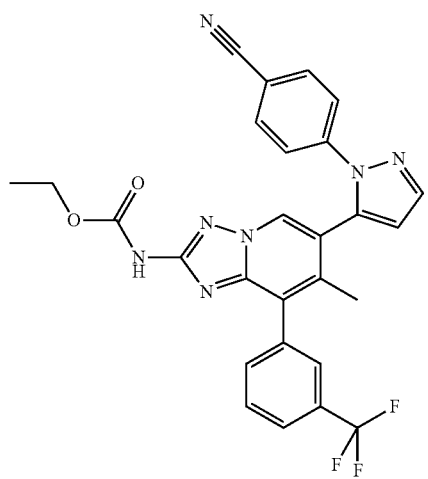 [SMILES: CCOC(=O)Nc1nc2c(-c3cccc(C(F)(F)F)c3)c(C)c(-c3ccnn3-c3ccc(C#N)cc3)cn2n1]

A solution of 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 100 mg, 0.218 mmol) and ethyl chloroformate (104 µL, 1.089 mmol) in pyridine (2.5 mL) was heated at 120° C. for 20 mins using microwave irradiation. The reaction mixture was azeotroped with toluene in vacuo. The resultant residue was subjected to preparative C18 HPLC, eluting with a gradient of 40-80% MeCN in water (+0.1% formic acid) to give the title compound as a white solid (24 mg).

LC-MS (Method 3): Rt=4.99 min, m/z=532.0 [M+H]$^+$ $^1$H NMR (400 MHz, DMSO-d$_6$) δ 10.52 (1H, s), 9.00 (1H, s), 7.98 (1H, d J=1.8 Hz), 7.91-7.86 (2H, m), 7.81 (1H, d J=8.0 Hz), 7.75 (1H, t J=7.8 Hz), 7.72 (1H, s), 7.67 (1H, d J=7.6 Hz), 7.61-7.56 (2H, m), 6.81 (1H, d J=1.8 Hz), 4.10 (2H, q J=7.2 Hz), 1.74 (3H, s), 1.20 (3H, t J=6.8 Hz).

Example 36

[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-carbamic acid 2-methoxyethyl ester

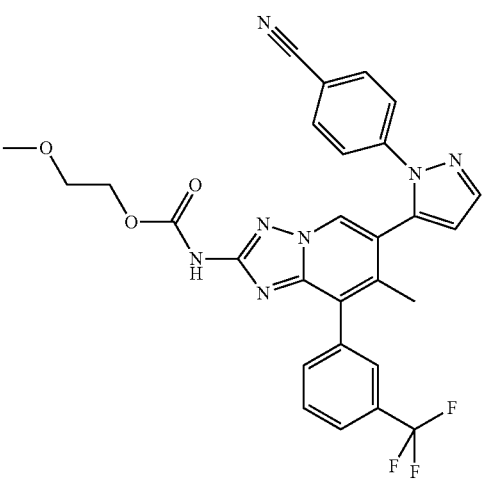 [SMILES: COCCOC(=O)Nc1nc2c(-c3cccc(C(F)(F)F)c3)c(C)c(-c3ccnn3-c3ccc(C#N)cc3)cn2n1]

The title compound was prepared from 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 100 mg, 0.218 mmol) using a similar method to that used in Example 35 (15%).

LC-MS (Method 3): Rt=4.80 min, m/z=562.0 [M+H]$^+$ $^1$H NMR (400 MHz, DMSO-d$_6$) δ 10.56 (1H, s), 8.94 (1H, s), 7.93 (1H, d J=1.8 Hz), 7.86-7.81 (2H, m), 7.76 (1H, d J=7.9 Hz), 7.70 (1H, t J=7.8 Hz), 7.63 (1H, s), 7.62 (1H, d J=7.7 Hz), 7.56-7.50 (2H, m), 6.75 (1H, d J=1.8 Hz), 4.14 (2H, m), 3.48 (2H, m), 3.21 (3H, s), 1.69 (3H, s).

Example 37

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyloxy]-propyl}-trimethyl-ammonium formate

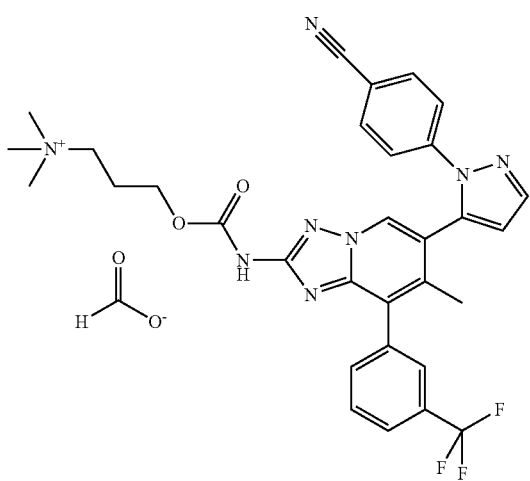

Step 1. [6-[2-(4-Cyano-phenyl)-2H-pyrazol-3-yl]-7-methyl-8-(3-trifluoromethyl-phenyl)-[1,2,4]triazolo[1,5-a]pyridin-2-yl]-carbamic acid 3-chloro-propyl ester (Intermediate 20)

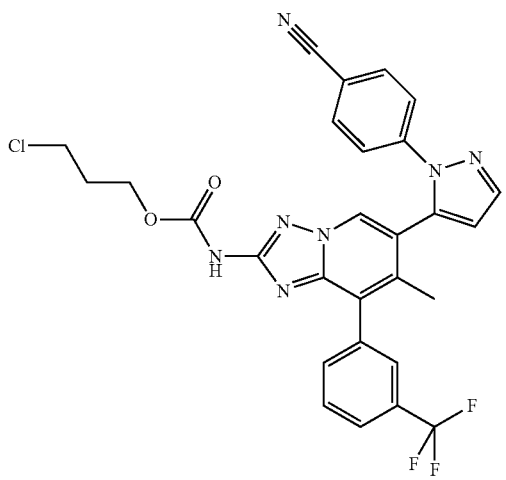 [SMILES: Cc1c(-c2ccnn2-c2ccc(C#N)cc2)cn2nc(NC(=O)OCCCCl)nc2c1-c1cccc(C(F)(F)F)c1]

3-Chloropropyl chloroformate (133 µL, 1.089 mmol) was added to a mixture of 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 100 mg, 0.218 mmol) and pyridine (107 µL, 1.308 mmol) in THF (3 mL) and the mixture was stirred rapidly for 20 mins at RT then heated at 60° C. 20 mins using microwave irradiation. The reaction mixture was concentrated in vacuo to give the title compound (125 mg of impure product contains chloroformate).

LC-MS (Method 2): Rt=3.90 mins, m/z=580 [M+H]$^+$

Step 2. {3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyloxy]-propyl}-trimethyl-ammonium chloride (Example 37)

A solution of [6-[2-(4-cyano-phenyl)-2H-pyrazol-3-yl]-7-methyl-8-(3-trifluoromethyl-phenyl)-[1,2,4]triazolo[1,5-a]pyridin-2-yl]-carbamic acid 3-chloro-propyl ester (Int. 20, 125 mg, 0.218 mmol) in MeCN (3.5 mL) was treated with trimethylamine solution in EtOH (4.2M, 1.5 mL) and heated for 1 hr at 100° C. using microwave irradiation. A further amount of trimethylamine in EtOH was added (1 mL) and the heating continued at 100° C. for 20 mins. The reaction mixture was concentrated in vacuo then azeotroped with toluene in vacuo. The resultant residue was subjected to preparative $C_{18}$ HPLC chromatography, eluting with a gradient of 10-70% MeCN in water+0.1% formic acid) to give the title compound as a white solid (20 mg).

LC-MS (Method 3) Rt=3.71 mins, m/z=603.1 [M]$^+$ $^1$H NMR (400 MHz, DMSO) δ 10.69 (1H, s), 8.99 (1H, s), 8.45 (1.4H, s), 7.99 (1H, d J=1.8 Hz), 7.91-7.86 (2H, m), 7.82 (1H, d J=7.7 Hz), 7.78-7.71 (2H, m), 7.67 (1H, d J=7.7 Hz), 7.61-7.56 (2H, m), 6.81 (1H, d J=1.8 Hz), 4.14 (2H, t d=6.3 Hz), 3.61-3.30 (2H, m (under water peak)), 3.06 (9H, s), 2.13-2.00 (2H, m), 1.78 (3H, s).

Example 38

(3-{3-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-ureido}-propyl)-trimethyl-ammonium formate

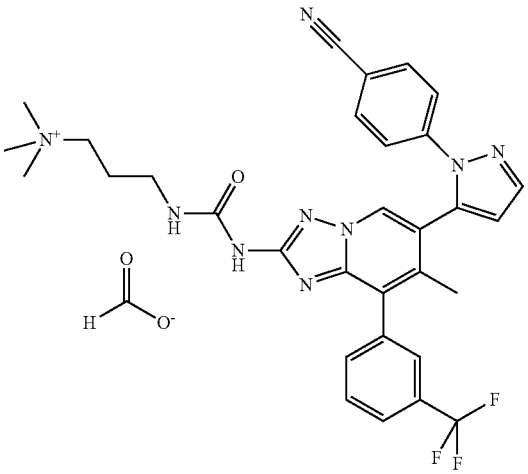

Step 1. 1-(3-Chloro-propyl)-3-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-urea (Intermediate 21)

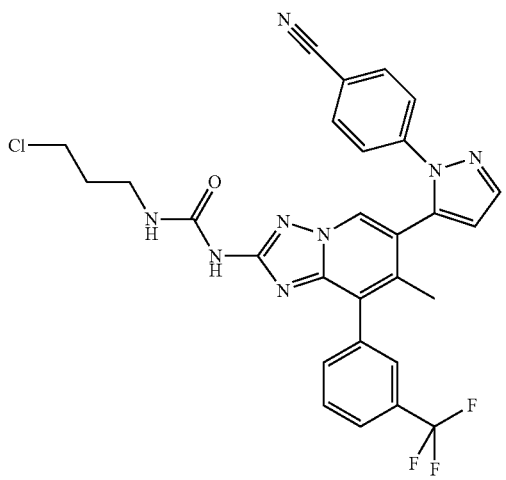 [SMILES: Cc1c(-c2ccnn2-c2ccc(C#N)cc2)cn2nc(NC(=O)NCCCCl)nc2c1-c1cccc(C(F)(F)F)c1]

A solution of 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 100 mg, 0.218 mmol) and 3-chloropropyl isocyanate (111 µL, 1.089 mmol) in THF (2.5 mL) was heated at 120° C. for 3 hr using microwave irradiation. The reaction mixture was concentrated in vacuo then subjected to flash chromatography eluting with a gradient of 25-100% EtOAc in cyclohexane to give the title compound (125 mg).

LC-MS (Method 1) Rt=4.01 mins, m/z=579 [M+H]$^+$

Step 2. (3-{3-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-ureido}-propyl)-trimethyl-ammonium formate (Example 38)

A solution of 1-(3-chloro-propyl)-3-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-urea (Int. 21, 125 mg, 0.216 mmol) in MeCN (5 mL) was treated with trimethylamine solution in EtOH (4.2 M, 0.5 mL, 2.16 mmol) and heated for 20 mins at 100° C. using microwave irradiation.

Further trimethylamine/EtOH solution was added (0.5 mL) and heating continued at 120° C. for 1 hr. The reaction mixture was concentrated in vacuo then azeotroped with toluene and dried in vacuo. The resultant residue was subjected to preparative $C_{18}$ HPLC, eluting with a gradient of 10-60% MeCN in water (+0.1% formic acid) to give the title compound as a white solid (24 mg).

LC-MS (Method 4): Rt=3.67 mins, m/z=602.1 [M]$^+$ $^1$H NMR (400 MHz, DMSO-d$_6$) δ 10.14 (1H, s), 8.93 (1H, s), 8.41 (1.6H, s), 8.04 (1H, t J=5.5 Hz), 8.00 (1H, d J=1.8 Hz), 7.91-7.86 (2H, m), 7.84 (1H, d J=8.1 Hz), 7.79-7.74 (2H, m), 7.70 (1H, d J=7.7 Hz), 7.61-7.55 (2H, m), 6.81 (1H, d J=1.8 Hz), 3.33-3.25 (2H, m), 3.24-3.16 (2H, m), 3.03 (9H, s), 1.91-1.82 (2H, m), 1.80 (3H, s).

Example 39

N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-acetamide

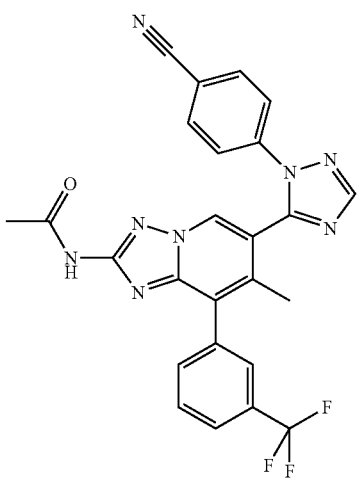 [SMILES: CC(=O)Nc1nc2c(-c3cccc(C(F)(F)F)c3)c(C)c(-c3ncnn3-c3ccc(C#N)cc3)cn2n1]

Step 1. 2-Acetylamino-7-methyl-8-(3-trifluoromethyl-phenyl)-[1,2,4]triazolo[1,5-a]pyridine-6-carboxylic acid amide (Intermediate 22)

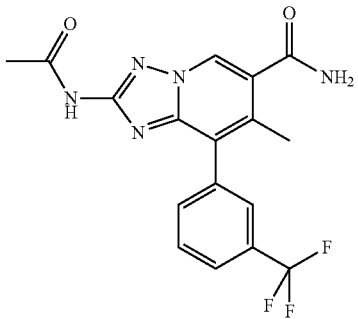 [SMILES: CC(=O)Nc1nc2c(-c3cccc(C(F)(F)F)c3)c(C)c(C(N)=O)cn2n1]

A mixture of N-[6-bromo-7-methyl-8-(3-trifluoromethyl-phenyl)-[1,2,4]triazolo[1,5-a]pyridin-2-yl]-acetamide (Int. 18, 330 mg, 0.80 mmol), hydroxylamine hydrochloride (112 mg, 1.60 mmol), trans-bis(acetato)bis[o-(di-o-tolylphosphino)benzyl]dipalladium(II) (38 mg, 0.04 mmol), tri-tert-butylphosphonium tetrafluoroborate, (22 mg, 0.08 mmol), 1,8-diazabicyclo[5.4.0]undec-7-ene (0.12 mL, 0.80 mmol), N,N-diisopropylethylamine, (0.28 mL, 1.60 mmol) and molybdenum hexacarbonyl (106 mg, 0.40 mmol) in dioxane (2 mL) was heated at 150° C. for 20 minutes using microwave irradiation. The reaction mixture was cooled and filtered through Celite®. The solvent was concentrated in vacuo and the residue purified by chromatography eluting with a gradient of 0-100% cyclohexane in EtOAc and then with 10% MeOH in EtOAc to afford the title compound as a beige foam (105 mg).

LC-MS (Method 1): Rt=2.63 min, m/z=378.1 [M+H]$^+$

Step 2. N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-acetamide (Example 39)

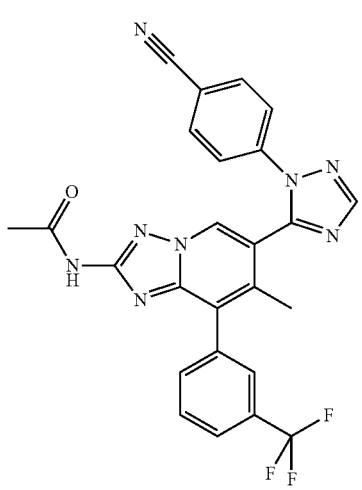 [SMILES: CC(=O)Nc1nc2c(-c3cccc(C(F)(F)F)c3)c(C)c(-c3ncnn3-c3ccc(C#N)cc3)cn2n1]

To a solution of 2-acetylamino-7-methyl-8-(3-trifluoromethyl-phenyl)-[1,2,4]triazolo[1,5-a]pyridine-6-carboxylic acid amide (Int. 22, 100 mg, 0.27 mmol) in THF (2 mL) was added N,N-dimethylformamide dimethyl acetal, (53 µL, 0.40 mmol) and the reaction mixture was heated at 100° C. for 10 mins using microwave irradiation. The solvent was removed in vacuo to afford crude 2-acetylamino-7-methyl-8-(3-trifluoromethyl-phenyl)-[1,2,4]triazolo[1,5-a]pyridine-6-carboxylic acid 1-dimethylamino-meth-(E)-ylideneamide intermediate. To a solution of the material thus obtained in acetic acid (2 mL) was added 4-hydrazino-benzonitrile hydrochloride (43 mg, 0.25 mmol). The mixture was heated at 90° C. for 15 minutes using microwave irradiation. The solvent was removed in vacuo and the residue azeotroped with toluene (2×5 mL). The resultant residue was purified by flash chromatography eluting with a gradient of 0-100% cyclohexane in EtOAc and then with 10% MeOH in EtOAc followed by preparative $C_{18}$ HPLC, eluting with a gradient of 10-90% MeCN in water (+0.1% formic acid) to afford the title compound as a white solid (15 mg).

LC-MS (Method 3): Rt=4.24 min, m/z=502.9 [M+H]$^+$ $^1$H NMR (400 MHz, DMSO-d$_6$) δ 10.92 (1H, bs), 9.07 (1H, s), 8.51 (1H, s), 7.96 (2H, dt), 7.81-7.86 (2H, m), 7.75-7.78 (2H, m), 7.67 (2H, dt), 2.06 (3H, s), 1.97 (3H, s)

Example 40

4-{5-[2-Amino-7-methyl-8-(3-trifluoromethyl-phenyl)-[1,2,4]triazolo[1,5-a]pyridin-6-yl]pyrazol-1-yl}-3-methanesulfonyl-benzonitrile

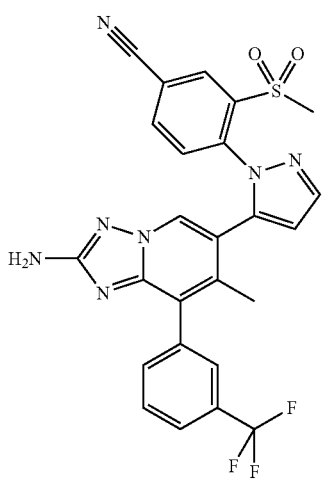 [SMILES: Cc1c(-c2ccnn2-c2ccc(C#N)cc2S(C)(=O)=O)cn2nc(N)nc2c1-c1cccc(C(F)(F)F)c1]

Step 1. 4-Hydrazino-3-methanesulfonyl-benzonitrile (Intermediate 23)

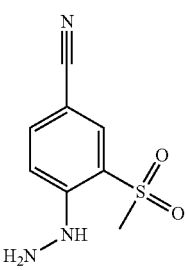

A suspension of 4-fluoro-3-(methylsulfonyl)benzonitrile (1.96 g, 9.83 mmol) in IMS (30 mL) was treated with hydrazine monohydrate (1.19 mL, 24.8 mmol) and then heated at reflux for 1 hr. The reaction mixture was cooled then filtered and the solid residue was collected and dried in vacuo to afford the title compound as a cream solid (1.64 g).

LC-MS (Method 2): Rt=1.92 min, m/z=212 [M+H]$^+$

Step 2. N-[6-Acetyl-7-methyl-8-(3-trifluoromethyl-phenyl)-[1,2,4]triazolo[1,5-a]pyridin-2-yl]-acetamide (Intermediate 24)

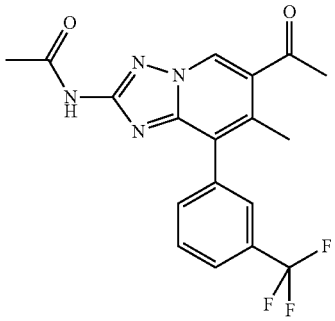 [SMILES: CC(=O)Nc1nc2c(-c3cccc(C(F)(F)F)c3)c(C)c(C(C)=O)cn2n1]

N-[6-Bromo-7-methyl-8-(3-trifluoromethyl-phenyl)-[1,2,4]triazolo[1,5-a]pyridin-2-yl]-acetamide (Int. 18, 1.07 g, 2.59 mmol), bis(triphenylphosphine)palladium (II) dichloride (91 mg, 0.13 mmol) and tributyl(1-ethoxyvinyl) tin were suspended in dry DMF (8 mL) and degassed with argon. The reaction mixture was heated at 120° C. for 20 min using microwave irradiation. 1 M HCl (10 mL) was added and the reaction mixture was stirred for 1 hr before being partitioned between EtOAc (100 mL) and water (100 mL). The organic layer was washed with saturated brine, then dried ($Na_2SO_4$) and concentrated in vacuo to give a yellow solid. The solid was triturated with EtOAc and the solid collected by filtration, washing with EtOAc, to give the title compound as a cream solid (680 mg).

LC-MS (Method 1): Rt=3.16 min, m/z=377.2 [M+H]$^+$

Step 3. N-[6-(3-Dimethylamino-acryloyl)-7-methyl-8-(3-trifluoromethyl-phenyl)-[1,2,4]triazolo[1,5-a]pyridin-2-yl]-acetamide (Intermediate 25)

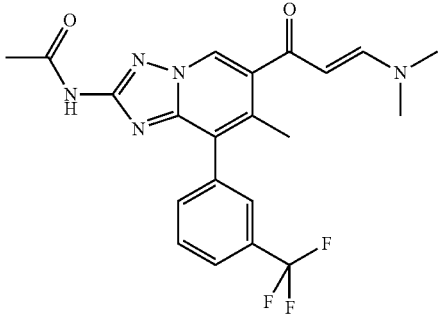 [SMILES: CC(=O)Nc1nc2c(-c3cccc(C(F)(F)F)c3)c(C)c(C(=O)/C=C/N(C)C)cn2n1]

A suspension of N-[6-acetyl-7-methyl-8-(3-trifluoromethyl-phenyl)-[1,2,4]triazolo[1,5-a]pyridin-2-yl]-acetamide (Int. 24, 732 mg, 1.947 mmol) and dimethylformamide dimethylacetal (4 mL) in toluene (10 mL) was heated at 100° C. for 2 hrs. The reaction mixture was cooled then EtOAc (50 mL) was added and the resultant precipitate was collected by filtration to afford the title compound as a white solid (508 mg).

LC-MS (Method 1): Rt=2.82 min, m/z=432 [M+H]$^+$

Step 4. 4-{5-[2-Amino-7-methyl-8-(3-trifluoromethyl-phenyl)-[1,2,4]triazolo[1,5-a]pyridin-6-yl]-pyrazol-1-yl}-3-methanesulfonyl-benzonitrile (Example 40)

N-[6-(3-Dimethylamino-acryloyl)-7-methyl-8-(3-trifluoromethyl-phenyl)-[1,2,4]triazolo[1,5-a]pyridin-2-yl]-acetamide (Int. 25, 247 mg, 0.573 mmol) and 4-hydrazino-3-methanesulfonyl-benzonitrile (Int. 22, 181 mg, 0.86 mmol) were heated at 100° C. in a mixture of n-butanol (10 mL) and conc. HCl (0.3 mL) for 1.5 h. EtOAc was added and the mixture was concentrated in vacuo. The resultant residue was purified by preparative $C_{18}$ HPLC, eluting with a gradient of 40-90% MeCN in water (+0.1% formic acid) to give the title compound as a yellow solid (10 mg).

LC-MS (Method 3): Rt=4.44 min, m/z=538.0 [M+H]$^+$ $^1$H NMR (400 MHz, DMSO) δ 8.51 (1H, d J=1.8 Hz), 8.29 (1H, s), 8.21 (1H, dd J=8.0, 1.8 Hz), 8.00 (1H, d, 2.0 Hz), 7.79 (1H, d J=8.0 Hz), 7.76-7.70 (2H, m), 7.68 (1H, d J=7.7 Hz), 7.56 (1H, d J=8.0 Hz), 6.84 (1H, d J=1.8 Hz), 6.10 (2H, s), 3.64 (3H, s), 2.07 (3H, s).

Example 41

N-[6-[2-(4-Cyano-2-fluoro-phenyl)-2H-pyrazol-3-yl]-7-methyl-8-(3-trifluoromethyl-phenyl)-[1,2,4]triazolo[1,5-a]pyridin-2-yl]-acetamide

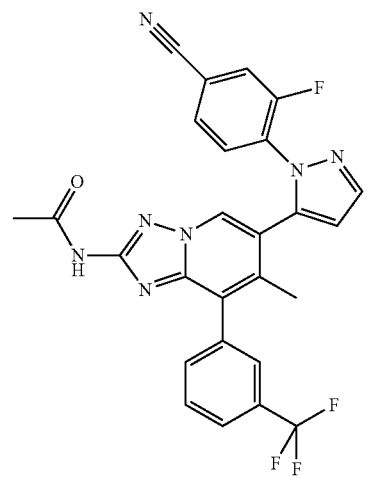 [SMILES: CC(=O)Nc1nc2c(-c3cccc(C(F)(F)F)c3)c(C)c(-c3ccnn3-c3ccc(C#N)cc3F)cn2n1]

The title compound was prepared from N-[6-(3-dimethylamino-acryloyl)-7-methyl-8-(3-trifluoromethyl-phenyl)-[1,2,4]triazolo[1,5-a]pyridin-2-yl]-acetamide (Int. 25, 85 mg, 0.197 mmol) and 3-fluoro-4-hydrazino-benzonitrile (45 mg, 0.298 mmol) using similar methods to those employed in Example 40, Step 4 and Example 26, Step 1 (22 mg).

LC-MS (Method 3): Rt=4.53 min, m/z=519.9 [M+H]$^+$

1H NMR (400 MHz, DMSO) 10.86 (1H, s), 8.89 (1H, s), 8.02-8.00 (2H, m), 7.88-7.80 (3H, m), 7.77 (1H, d J=7.8 Hz), 7.74 (1H, s), 7.69 (1H, d J=7.8 Hz), 6.86 (1H, d J=1.9 Hz), 2.04 (3H, s), 1.97 (3H, s).

Example 42

N-[6-[2-(4-Cyano-phenyl)-4-methyl-2H-pyrazol-3-yl]-7-methyl-8-(3-trifluoromethyl-phenyl)-[1,2,4]triazolo[1,5-a]pyridin-2-yl]-acetamide

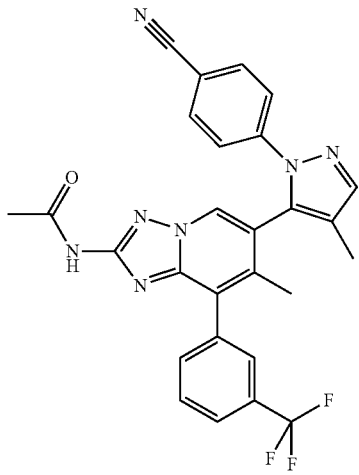 [SMILES: CC(=O)Nc1nc2c(-c3cccc(C(F)(F)F)c3)c(C)c(-c3c(C)cnn3-c3ccc(C#N)cc3)cn2n1]

Step 1. N-[7-Methyl-6-propionyl-8-(3-trifluoromethyl-phenyl)-[1,2,4]triazolo[1,5-a]pyridin-2-yl]acetamide (Intermediate 26)

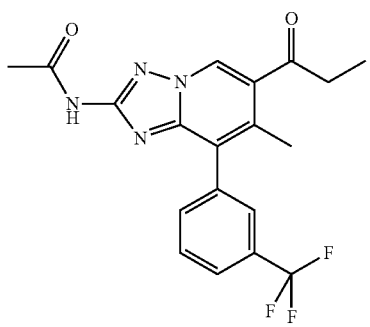 [SMILES: CCC(=O)c1cn2nc(NC(C)=O)nc2c(-c2cccc(C(F)(F)F)c2)c1C]

A mixture of N-[6-bromo-7-methyl-8-(3-trifluoromethyl-phenyl)-[1,2,4]triazolo[1,5-a]pyridin-2-yl]-acetamide (Int. 18, 0.5 g, 1.21 mmol) was combined with ethyl-1-propenyl ether (125 mg, 1.45 mmol), triethylamine (202 μL, 1.45 mmol), palladium (II) acetate (3 mg, 0.012 mmol), tri-O-tolylphosphine (15 mg, 0.048 mmol) in DMF (7 mL) was degassed and then heated at 130° C. for 5 hrs. Further amounts of palladium (II) acetate (3 mg) and ethyl-1-propenyl ether (125 mg) were added and heating was continued for 5 days. 1 M HCl (5 mL) was added and the mixture was stirred vigorously for 40 mins. The mixture was partitioned between EtOAc (100 mL) and water (100 mL) and the organic layer was washed with saturated brine, then dried (Na$_2$SO$_4$) and concentrated in vacuo. The resultant residue was purified by chromatography, eluting with a gradient of 0-10% MeOH in DCM followed by trituration with DCM and ether. The resultant precipitate was collected by filtration and dried to afford the title compound as a white solid (11%)

LC-MS (Method 1): Rt=3.37 min, m/z=391 [M+H]$^+$

Step 2. N-[6-[2-(4-Cyano-phenyl)-4-methyl-2H-pyrazol-3-yl]-7-methyl-8-(3-trifluoromethyl-phenyl)-[1,2,4]triazolo[1,5-a]pyridin-2-yl]-acetamide (Example 42)

The title compound was prepared from N-[7-methyl-6-propionyl-8-(3-trifluoromethyl-phenyl)-[1,2,4]triazolo[1,5-a]pyridin-2-yl]-acetamide (Int. 26, 11 mg, 0.023 mmol) and 4-hydrazino-benzonitrile (7 μL, 0.051 mmol) using similar methods to those employed in Example 40, Steps 3 and 4. During step 4 the acetyl group was lost, which was re-introduced by reaction with acetyl chloride using a similar method to that used for Intermediate 18 to give the title compound as a cream solid (3 mg).

LC-MS (Method 3): Rt=4.77 min, m/z=515.9 [M+H]$^+$

1H NMR (400 MHz, DMSO) δ 10.89 (1H, s), 9.05 (1H, s), 7.89-7.83 (3H, m), 7.81 (111, d J=7.7 Hz), 7.77-7.72 (2H, m), 7.69 (1H, d J=7.7 Hz), 7.56-7.51 (2H, m), 2.07 (3H, s), 2.03 (3H, s), 1.69 (3H, s).

Example 43

N-[6-(4'-Cyano-biphenyl-2-yl)-7-methyl-8-(3-trifluoromethyl-phenyl-[1,2,4]triazolo[1,5-a]pyridin-2-yl]-acetamide

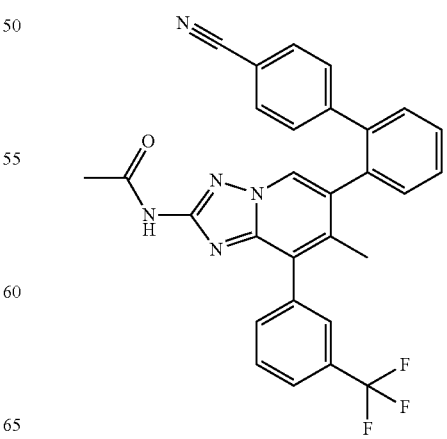

Step 1. 2'-(4,4,5,5-Tetramethyl-[1,3,2]dioxaborolan-2-yl)-biphenyl-4-carbonitrile (Intermediate 27)

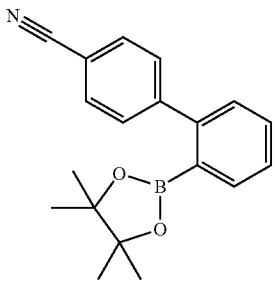 [SMILES: CC1(C)OB(c2ccccc2-c2ccc(C#N)cc2)OC1(C)C]

A mixture of 2'-bromo-biphenyl-4-carbonitrile (prepared according to *Tetrahedron* 2002, 58, 5779-5787, which is incorporated herein by reference in its entirety) (250 mg, 0.969 mmol), bis(pinacalatodiboron) (296 mg, 1.162 mmol) and potassium acetate (332 mg, 3.391 mmol) in dioxane (5 mL) was degassed under argon, then Pd(dppf)Cl$_2$.DCM (40 mg, 0.049 mmol) was added and the degassing repeated. The resulting mixture was heated at 120° C. for 1 hr using microwave irradiation. The reaction mixture was concentrated in vacuo and partitioned between water and DCM and the organic extract was washed with saturated brine, dried (Na$_2$SO$_4$), filtered and concentrated in vacuo. The resultant residue was purified by flash chromatography eluting with a gradient of 0-50% EtOAc in cyclohexane to give the title compound as clear oil (120 mg).

LC-MS (Method 1): Rt=4.25 min, m/z=306 [M+H]$^+$

Step 2. N-[6-(4'-Cyano-biphenyl-2-yl)-7-methyl-8-(3-trifluoromethyl-phenyl)-[1,2,4]triazolo[1,5-a]pyridin-2-yl]-acetamide (Example 43)

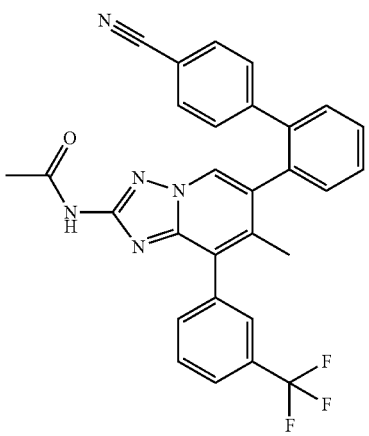 [SMILES: CC(=O)Nc1nc2c(-c3cccc(C(F)(F)F)c3)c(C)c(-c3ccccc3-c3ccc(C#N)cc3)cn2n1]

A mixture 6-bromo-7-methyl-8-(3-trifluoromethyl-phenyl)-[1,2,4]triazolo[1,5-a]pyridin-2-ylamine (Int. 2, 121 mg, 0.328 mmol), 2'-(4,4,5,5-tetramethyl-[1,3,2]dioxaborolan-2-yl)-biphenyl-4-carbonitrile (Int. 27, 120 mg, 0.393 mmol) and 2 M Na$_2$CO$_3$ (0.5 mL) in toluene was degassed under argon. Pd(PPh$_3$)$_4$ was added and the degassing repeated, before the reaction mixture was heated at 120° C. for 30 mins using microwave irradiation. Further Pd(PPh$_3$)$_4$ (10 mg) was added and the heating continued for 30 minutes. The reaction mixture was concentrated in vacuo and partitioned between water and DCM and the organic extract was washed with saturated brine, dried (Na$_2$SO$_4$), filtered and concentrated in vacuo. The intermediate T-[2-amino-7-methyl-8-(3-trifluoromethyl-phenyl)-[1,2,4]triazolo[1,5-a]pyridin-6-yl]-biphenyl-4-carbonitrile was obtained after purification by flash chromatography, eluting with a gradient of 0-6% MeOH in DCM to give a white solid (20 mg). The title compound was obtained using a similar method to that employed in Intermediate 18 (4 mg).

LC-MS (Method 3): Rt=5.22 min, m/z=512.9 [M+H]$^+$ $^1$H NMR (400 MHz, DMSO-d$_6$) δ 10.74 (1H, br. s), 8.69 (1H, s), 7.76-7.64 (4H, m), 7.61-7.47 (6H, m), 7.39 (2H, m), 2.00 (3H, s), 1.66 (3H, s).

Example 44

N-[6-[2-(4-Cyano-phenyl)-2H-pyrazol-3-yl]-7-methyl-8-(3-trifluoromethoxy-phenyl)-[1,2,4]triazolo[1,5-a]pyridin-2-yl]-acetamide

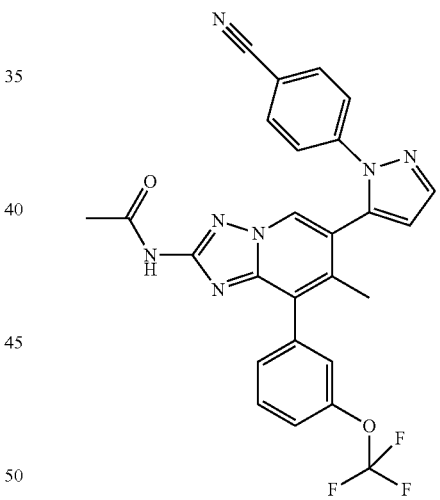

The title compound was prepared from 5-bromo-3-iodo-4-methyl-pyridin-2-ylamine and 3-trifluoromethoxy-phenyl-boronic acid using similar methods to those employed in Example 1, Steps 1, 2 and 4, followed by Intermediate 18.

LC-MS (Method 3): Rt=4.69 min, m/z=517.9 [M+H]$^+$

1H NMR (400 MHz, DMSO) δ 10.89 (1H, s), 9.01 (1H, s), 7.98 (1H, d J=1.8 Hz), 7.91-7.86 (2H, m) 7.64 (1H, t J=8.0

Hz), 7.61-7.55 (2H, m), 7.47-7.39 (2H, m), 7.35 (1H, s), 6.81 (1H, d J=1.8 Hz), 2.07 (3H, s), 1.74 (3H, s).

Examples 45 and 46

N-[6-[2-(4-Cyano-phenyl)-2H-pyrazol-3-yl]-7-methyl-8-(3-trifluoromethyl-phenyl)[1,2,4]triazolo[1,5-a]pyridin-2-yl]-3-methanesulfinyl-propionamide (Example 45) and N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-methanesulfonyl-propionamide (Example 46)

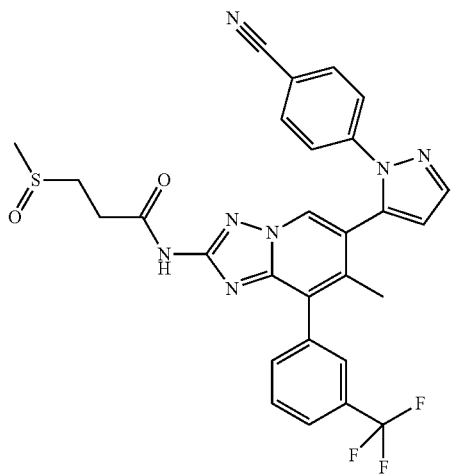

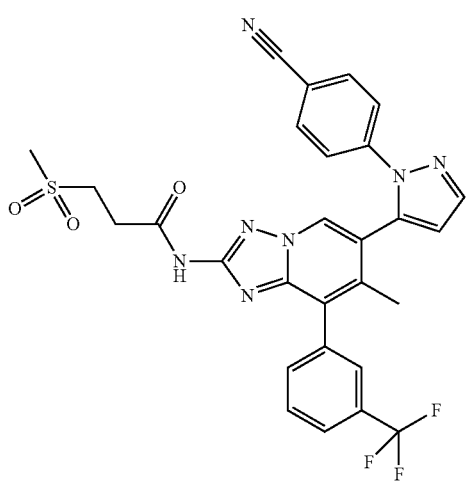

Step 1. N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-methylsulfanyl-propionamide (Intermediate 28)

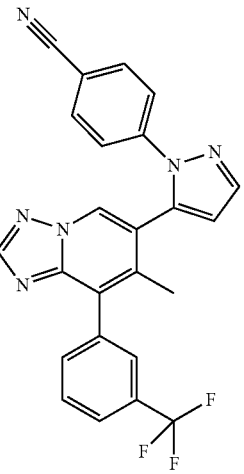

The title compound was prepared from 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 100 mg, 0.218 mmol) and 3-methylsulfanyl-propionic acid (45 µL, 0.436 mmol) by a similar method to that employed in Example 16 (130 mg).
LC-MS (Method 2): Rt=3.75 min, m/z=562 [M+1-1]$^+$ Step 2. N-[6-[2-(4-Cyano-phenyl)-2H-pyrazol-3-yl]-7-methyl-8-(3-trifluoromethyl-phenyl)[1,2,4]triazolo[1,5-a]pyridin-2-yl]-3-methanesulfinyl-propionamide (Example 45) and N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-methanesulfonyl-propionamide (Example 46)

To a stirred solution of N-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-3-methylsulfanyl-propionamide (Int. 28, 127 mg, 0.113 mmol) in DCM (5 mL) at 0° C. was added 3-chloroperbenzoic acid (29 mg, 0.17 mmol) and the reaction mixture was stirred for 2 hrs. A further quantity of 3-chloroperbenzoic acid (30 mg) was added and stirring was continued at RT for 16 hrs then a further quantity of 3-chloroperbenzoic acid (60 mg) was added and stirring was continued at RT for 22 hrs. The reaction mixture was partitioned between 1N NaOH (10 mL) and DCM and the organic phase was dried (Na$_2$SO$_4$), filtered and concentrated in vacuo. The resultant residue was purified by flash chromatography, eluting with a gradient 0-3% MeOH in DCM and then by preparative C$_{18}$ HPLC, eluting with a gradient of 40-98% MeCN in water (+0.1% formic acid) to give the title compounds as white solids.
Example 45 (9 mg); LC-MS (Method 3): Rt=4.24 min, m/z=578 [M+H]$^+$
1H NMR (400 MHz, DMSO) δ 11.09 (1H, s), 9.03 (1H, s), 8.00 (1H, d J=1.8 Hz), 7.91-7.86 (2H, m), 7.82 (1H, d J=8.0 Hz), 7.78-7.72 (2H, m), 7.68 (1H, d J=7.6 Hz), 7.61-7.56 (2H, m), 6.81 (1H, d J=1.8 Hz), 3.13-3.01 (2H, m), 2.92-2.72 (2H, m), 2.53 (3H, s), 1.78 (3H, s).

Example 46 (12 mg); LC-MS (Method 3): Rt=4.50 min, m/z=594 [M+H]⁺

1H NMR (400 MHz, DMSO) δ 11.13 (1H, s), 9.03 (1H, s), 7.99 (1H, d J=1.9 Hz), 7.91-7.86 (2H, m), 7.82 (1H, d J=7.8 Hz), 7.78-7.72 (2H, m), 7.68 (1H, d J=7.6 Hz), 7.61-7.56 (2H, m), 6.81 (1H, d J=1.7 Hz), 3.40 (2H, t J=7.4 Hz), 2.99 (3H, s), 2.86 (2H, br s), 1.77 (3H, s).

Example 47

4-{5-[2-(3-Methanesulfonyl-propylamino)-7-methyl-8-(3-trifluoromethyl-phenyl)-[1,2,4]triazolo[1,5-a]pyridin-6-yl]-pyrazol-1-yl}-benzonitrile

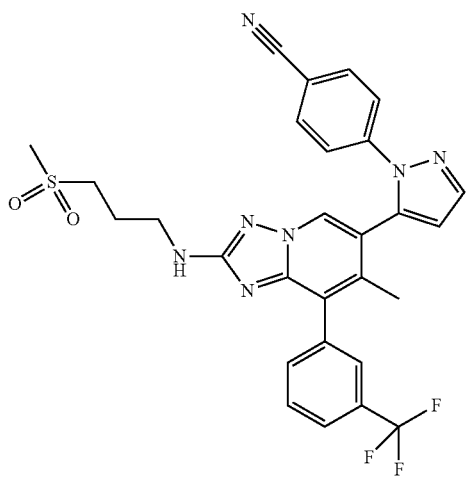 [SMILES: Cc1c(-c2ccnn2-c2ccc(C#N)cc2)cn2nc(NCCCS(C)(=O)=O)nc2c1-c1cccc(C(F)(F)F)c1]

Step 1. 6-Bromo-2-chloro-7-methyl-8-(3-trifluoromethyl-phenyl)-[1,2,4]triazolo[1,5-a]pyridine (Intermediate 29)

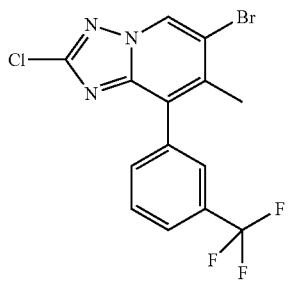 [SMILES: Cc1c(Br)cn2nc(Cl)nc2c1-c1cccc(C(F)(F)F)c1]

The title compound was prepared from 6-bromo-7-methyl-8-(3-trifluoromethyl-phenyl)-[1,2,4]triazolo[1,5-a]pyridin-2-ylamine (Int. 2, 356 mg, 0.959 mmol) using a similar method to that employed in Intermediate 14 (130 mg).

LC-MS (Method 5): Rt=4.20 min, m/z=389.9/391.9 [M]⁺

Step 2. [6-Bromo-7-methyl-8-(3-trifluoromethyl-phenyl)-[1,2,4]triazolo[1,5-a]pyridin-2-yl]-(3-methylsulfanyl-propyl)-amine (Intermediate 30)

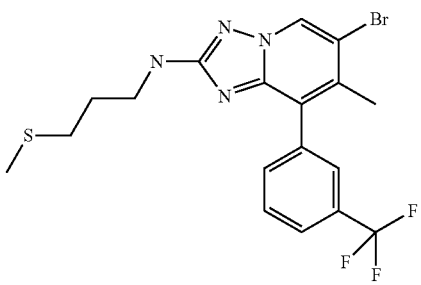 [SMILES: CSCCCNc1nc2c(-c3cccc(C(F)(F)F)c3)c(C)c(Br)cn2n1]

To a suspension of 6-bromo-2-chloro-7-methyl-8-(3-trifluoromethyl-phenyl)-[1,2,4]triazolo[1,5-a]pyridine (Int. 29, 125 mg, 0.32 mmol) in IMS (5 mL) was added 3-methylsulfanyl-propylamine (215 µL, 1.92 mmol) and the reaction mixture was heated under microwave irradiation at 155° C. for 2 hrs. After this time more 3-methylsulfanyl-propylamine (490 µL) was added and heating continued for 3 hrs then a further portion of 3-methylsulfanyl-propylamine (490 µL) was added and heating continued for 7 hrs. The resultant residue was loaded onto an SCX-2 cartridge and eluted with MeOH and then further purified by flash chromatography, eluting with a gradient of 0-50% EtOAc in cyclohexane to give the title compound as a colourless glass (57 mg).

LC-MS (Method 2): Rt=4.32 min, m/z=459/461 [M]⁺

Step 3. 4-{5-[7-Methyl-2-(3-methylsulfanyl-propylamino)-8-(3-trifluoromethyl-phenyl)-[1,2,4]triazolo[1,5-a]pyridin-6-yl]-pyrazol-1-yl}-benzonitrile (Intermediate 31)

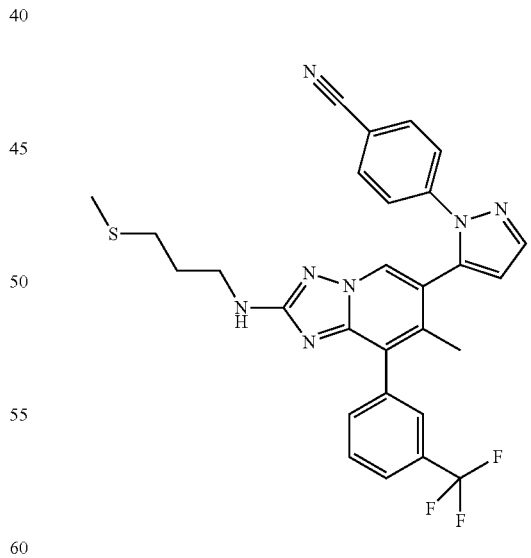

The title compound was prepared from [6-bromo-7-methyl-8-(3-trifluoromethyl-phenyl)-[1,2,4]triazolo[1,5-a]pyridin-2-yl]-(3-methyl sulfanyl-propyl)-amine (Int. 30, 55 mg, 0.120 mmol) using a similar method to that employed in Example 1, step 4 (37 mg).

LC-MS (Method 2): Rt=4.13 min, m/z=548 [M+H]⁺

Step 4. 4-{5-[2-(3-Methanesulfonyl-propylamino)-7-methyl-8-(3-trifluoromethyl-phenyl)-[1,2,4]triazolo[1,5-a]pyridin-6-yl]-pyrazol-1-yl}-benzonitrile

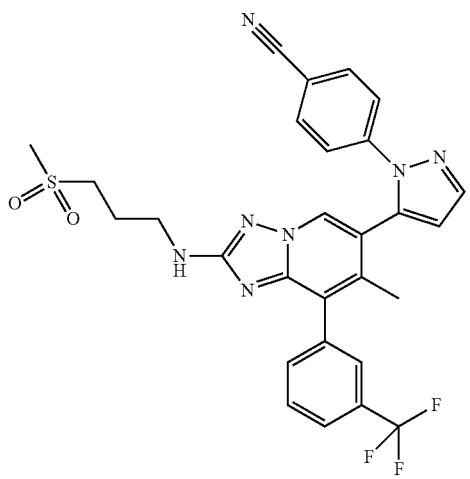 [SMILES: Cc1c(-c2ccnn2-c2ccc(C#N)cc2)cn2nc(NCCCS(C)(=O)=O)nc2c1-c1cccc(C(F)(F)F)c1]

The title compound was prepared from 4-{5-[7-methyl-2-(3-methylsulfanyl-propylamino)-8-(3-trifluoromethyl-phenyl)-[1,2,4]triazolo[1,5-a]pyridin-6-yl]-pyrazol-1-yl}-benzonitrile (Int. 31, 55 mg, 0.120 mmol) using a similar method to that employed in Example 46 (13 mg).

LC-MS (Method 3): Rt=4.72 min, m/z=580 [M+H]$^+$

1H NMR (400 MHz, DMSO) δ 8.74 (1H, s), 7.96 (1H, d J=1.7 Hz), 7.92-7.87 (2H, m), 7.78 (1H, d J=8.0 Hz), 7.72 (1H, t J=7.5 Hz), 7.68 (1H, s), 7.64 (1H, d J=7.7 Hz), 7.60-7.55 (2H, m), 6.89 (1H, t J=6.0 Hz), 6.76 (1H, d J=1.7 Hz), 3.33-3.22 (2H, m, obs.), 3.19-3.08 (2H, m), 2.94 (3H, s), 2.00-1.89 (2H, m), 1.70 (3H, s).

Example 48

4-{5-[2-(2-Hydroxy-ethylamino)-7-methyl-8-(3-trifluoromethyl-phenyl)-[1,2,4]triazolo[1,5-a]pyridin-6-yl]-pyrazol-1-yl}-benzonitrile

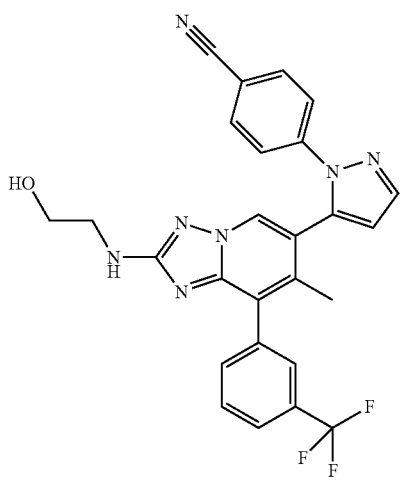 [SMILES: Cc1c(-c2ccnn2-c2ccc(C#N)cc2)cn2nc(NCCO)nc2c1-c1cccc(C(F)(F)F)c1]

4-{5-[2-Chloro-7-methyl-8-(3-trifluoromethyl-phenyl)-[1,2,4]triazolo[1,5-a]pyridin-6-yl]-pyrazol-1-yl}-benzonitrile (Int. 19, 50 mg, 0.104 mmol) in ethanolamine (1.5 mL) was heated under microwave irradiation at 150° C. for 30 mins. The reaction mixture was partitioned between water and DCM and the organic phase was dried (Na$_2$SO$_4$), filtered and concentrated in vacuo. The resultant residue was triturated in MeCN and then purified by preparative C$_{18}$ HPLC, eluting with a gradient of 20-90% MeCN in water (+0.1% formic acid) to give the title compound as a white solid (8 mg).

LC-MS (Method 2): Rt=4.55 min, m/z=504 [M+H]$^+$

1H NMR (400 MHz, DMSO) δ 8.72 (1H, s), 7.95 (1H, d J=1.7 Hz), 7.92-7.87 (2H, m), 7.78 (1H, d J=8.0 Hz), 7.71 (1H t J=7.4 Hz), 7.68 (1H, s), 7.63 (1H, d J=7.6 Hz), 7.60-7.55 (2H, m), 6.76 (1H, d J=1.7 Hz), 6.63 (1H, t J=6.0 Hz), 4.59 (1H, t J=5.5 Hz), 3.53-3.46 (2H, m), 3.27-3.19 (2H, m), 1.70 (3H, s).

Example 49

4-{5-[2-(2-Hydroxy-propylamino)-7-methyl-8-(3-trifluoromethyl-phenyl)-[1,2,4]triazolo[1,5-a]pyridin-6-yl]-pyrazol-1-yl}-benzonitrile

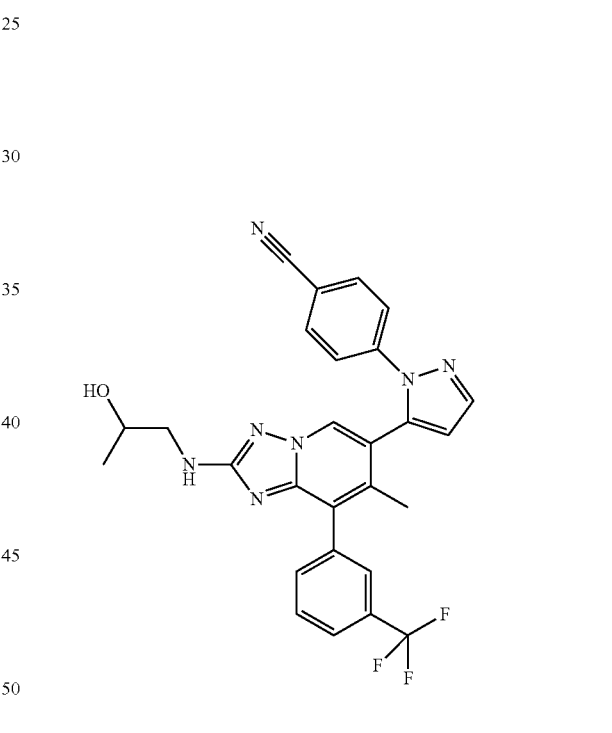

The title compound was prepared from 4-{5-[2-chloro-7-methyl-8-(3-trifluoromethyl-phenyl)-[1,2,4]triazolo[1,5-a]pyridin-6-yl]-pyrazol-1-yl}-benzonitrile (Int. 19 60 mg, 0.105 mmol) and 1-amino-propan-2-ol using a similar method to that employed in Example 48 (16 mg).

LC-MS (Method 2): Rt=4.72 min, m/z=518 [M+H]$^+$

1H NMR (400 MHz, DMSO) δ 8.72 (1H, s), 7.96 (1H, d J=2.0 Hz), 7.92-7.87 (2H, m), 7.78 (1H, d J=7.8 Hz), 7.72 (1H, t J=7.7 Hz), 7.78 (1H, s), 7.63 (1H, d J=7.7 Hz), 7.60-7.55 (2H, m), 6.76 (1H, d J=1.8 Hz), 6.62 (1H, d J=6.1 Hz), 4.59 (1H, d J=4.7 Hz), 3.82-3.71 (1H, m), 3.18-3.00 (2H, m), 1.70 (3H, s), 1.05 (3H, d J=6.3 Hz).

Example 50

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-piperidin-4-yl-urea

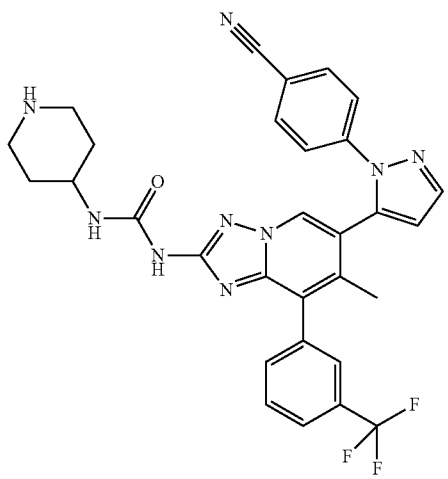 [SMILES: Cc1c(-c2ccnn2-c2ccc(C#N)cc2)cn2nc(NC(=O)NC3CCNCC3)nc2c1-c1cccc(C(F)(F)F)c1]

Step 1. 4-{3-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-ureido}-piperidine-1-carboxylic acid tert-butyl ester (Intermediate 32)

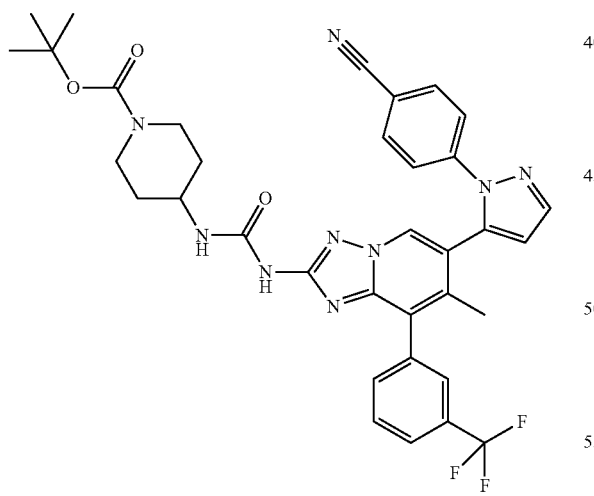

A solution of 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 460 mg, 1.0 mmol), N-BOC piperidine-4-isocyanate (680 mg, 3 mmol) and triethylamine (0.48 ml, 3.5 mmol) in DMF (5 mL) was stirred at RT for 18 hrs. The reaction mixture was poured into water and the product extracted into EtOAc. The organic phase was separated and washed with water, then brine and dried (Na$_2$SO$_4$), filtered and concentrated in vacuo. The resultant residue was subjected to C$_{18}$ HPLC, eluting with a gradient 30-100% MeCN in water (+0.1% formic acid) to give the title compound as a yellow solid (190 mg).

LC-MS (Method 3): Rt=5.56 min, m/z=686.2 [M+H]$^+$ $^1$H NMR (400 MHz, DMSO-d$_6$) δ 10.02 (1H, s), 8.97 (1H, s), 8.38 (1H, d J=1.8 Hz), 7.99 (1H, d J=1.8 Hz), 7.90-7.84 (2H, m), 7.80-7.65 (4H, m), 7.59-7.54 (2H, m), 6.81 (1H, d J=1.8 Hz), 3.78-3.69 (1H, m), 3.44-3.35 (2H, m), 3.07-2.94 (2H, m), 1.77 (3H, s), 1.74-1.65 (2H, m), 1.37 (9H, s), 1.17-1.061.07 (2H, m)

Step 2. 1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-piperidin-4-yl-urea (Example 50)

To a solution of 4-{3-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-ureido}-piperidine-1-carboxylic acid tert-butyl ester (Int. 32, 95 mg, 0.14 mmol) in DCM (2 mL) was added TFA (1 mL) and the solution was stirred at RT for 1 hr, then toluene (10 mL) was added and the reaction mixture concentrated in vacuo. The reaction mixture was partitioned between DCM (15 ml) and aqueous 2 M Na$_2$CO$_3$, and the organic extract was dried (Na$_2$SO$_4$), filtered and concentrated in vacuo to give the title compound as a white solid (61 mg).

LC-MS (Method 3): Rt=3.50 min, m/z=586.2 [M+H]$^+$ $^1$H NMR (400 MHz, DMSO-d$_6$) δ 9.92 (1H, s), 8.96 (1H, s), 8.21 (1H, d J=6.4 Hz), 7.99 (1H, d J=1.8 Hz), 7.90-7.80 (3H, m), 7.79-7.67 (3H, m), 7.60-7.54 (2H, m), 6.81 (1H, d J=1.7 Hz), 3.64-3.52 (1H, m), 2.77-2.67 (2H, m), 2.52-2.43 (2H, m), 1.76 (3H, s), 1.74-1.66 (2H, m), 1.18-1.05 (2H, m).

Example 51

(1-Methyl-4-piperidyl)[6-[2-(4-cyano-phenyl)-2H-pyrazol-3-yl]-7-methyl-8-(3-trifluoromethyl-phenyl)-[1,2,4]triazolo[1,5-a]pyridin-2-yl]-urea

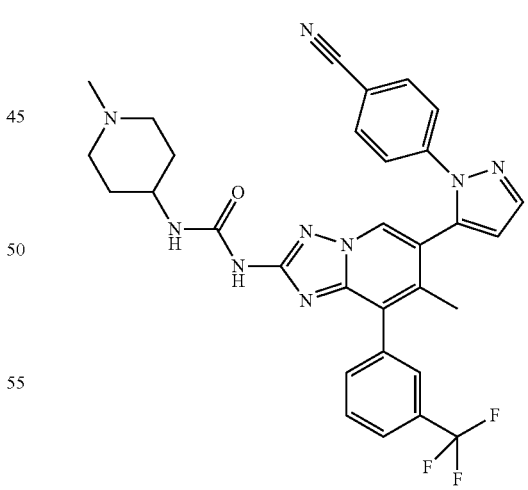

To a solution of 1-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-3-piperidin-4-yl-urea (Ex. 50, 53 mg, 0.09 mmol) in DCM (2 mL) was added 37% aqueous formaldehyde solution (75 µL.) and 2 drops of MeOH, followed by sodium triacetoxyborohydride (160 mg, 0.75 mmol), and the solution was stirred at RT for 18 hrs. The reaction mixture was partitioned between DCM (15 ml) and aqueous 2 M Na$_2$CO$_3$, and the organic extract was dried (Na$_2$SO$_4$), filtered and concentrated in vacuo to give the title compound as a white solid (19 mg).

LC-MS (Method 3): Rt=3.53 min, m/z=600.1 [M+H]$^+$ $^1$H NMR (400 MHz, DMSO-d$_6$) δ 9.91 (1H, s), 8.91 (1H, s), 8.21 (1H, d J=6.6 Hz), 7.94 (1H, d J=1.8 Hz), 7.86-7.77 (3H, m), 7.75-7.63 (3H, m), 7.57-7.52 (2H, m), 6.77 (1H, d J=1.8 Hz), 3.54-3.40 (1H, m), 2.27-2.14 (2H, m), 1.99-1.91 (3H, s), 1.91 (2H, m), 1.72 (3H, s), 1.70-1.62 (2H, m), 1.16-1.28 (2H, m).

Example 52

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-ethyl-urea

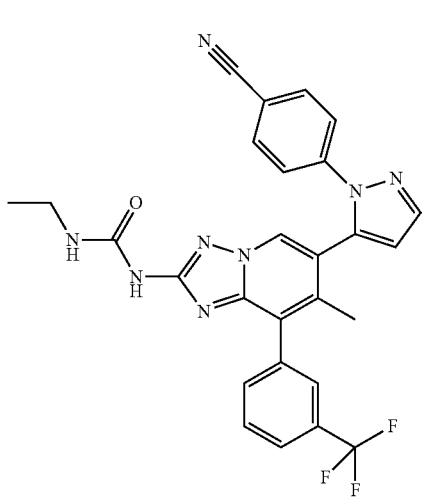 [SMILES: CCNC(=O)Nc1nc2c(-c3cccc(C(F)(F)F)c3)c(C)c(-c3ccnn3-c3ccc(C#N)cc3)cn2n1]

The title compound was prepared from 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 100 mg, 0.218 mmol) and ethyl isocyanate (90 μL, 1.089 mmol) using a similar method to that employed in Intermediate 21 (27 mg).

LC-MS (Method 3): Rt=5.04 mins, m/z=530.9 [M+1]$^+$ $^1$H NMR (400 MHz, DMSO-d$_6$) δ 9.88 (1H, s), 8.90 (1H, s), 7.94 (2H, m), 7.83 (2H, m), 7.80-7.61 (4H, m), 7.53 (2H, m), 6.76 (1H, d J=1.8 Hz), 3.08 (2H, m), 1.74 (3H, s), 0.94 (3H, t J=7.1 Hz).

Example 53

4-{5-[2-(3-Hydroxy-propylamino)-7-methyl-8-(3-trifluoromethyl-phenyl)-[1,2,4]triazolo[1,5-a]pyridin-6-yl]-pyrazol-1-yl}-benzonitrile

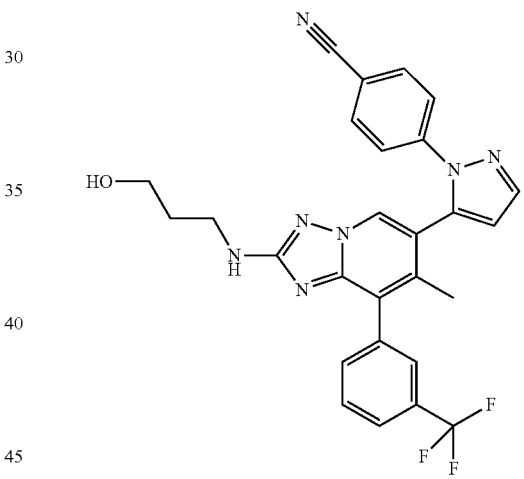

The title compound was prepared from 4-[5-[2-chloro-7-methyl-8-(3-trifluoromethyl-phenyl)-[1,2,4]triazolo[1,5-a]pyridin-6-yl]-pyrazol-1-yl]-benzonitrile (Int. 19, 60 mg, 0.126 mmol) and using a similar method to that employed in Example 48 (13 mg).

LC-MS (Method 3): Rt=4.64 min, m/z=518.2 [M+H]$^+$ $^1$H NMR (400 MHz, DMSO) δ 8.68 (1H, s), 7.91 (1H, d J=1.8 Hz), 7.86 (2H, m), 7.76-7.56 (4H, m), 7.53 (2H, m), 6.71 (1H, d J=1.8 Hz), 6.64 (1H, t J=5.7 Hz), 4.35 (1H, t J=5.3 Hz), 3.40 (2H, q J=6.2 Hz), 3.16 (2H, q J=6.7 Hz), 1.64 (3H, s), 1.62 (2H, m).

Example 54

4-{5-[2-(4-Hydroxy-butylamino)-7-methyl-8-(3-trifluoromethyl-phenyl)-[1,2,4]triazolo[1,5-a]pyridin-6-yl]-pyrazol-1-yl}-benzonitrile

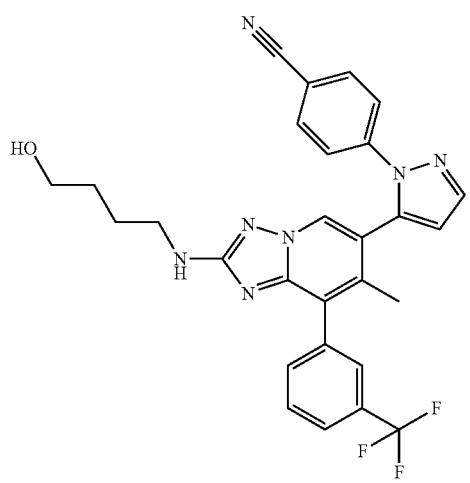 [SMILES: Cc1c(-c2ccnn2-c2ccc(C#N)cc2)cn2nc(NCCCCO)nc2c1-c1cccc(C(F)(F)F)c1]

The title compound was prepared from 4-{5-[2-chloro-7-methyl-8-(3-trifluoromethyl-phenyl)-[1,2,4]triazolo[1,5-a]pyridin-6-yl]-pyrazol-1-yl}-benzonitrile (Int. 19, 60 mg, 0.126 mmol) and 4-amino-butan-1-ol (1 mL) using a similar method to that employed in Example 48 (17 mg).

LC-MS (Method 3): Rt=4.72 min, m/z=532.1 [M+H]$^+$ $^1$H NMR (400 MHz, DMSO) δ 8.72 (1H, s), 7.95 (1H, d J=1.8 Hz), 7.92-7.87 (2H, m), 7.77 (1H, d J=8.0 Hz), 7.74-7.66 (2H, m), 7.63 (1H, d J=7.8 Hz), 7.60-7.55 (2H, m), 6.77-6.71 (2H, m), 4.35 (1H, t J=5.2 Hz), 3.38 (2H, q J=6.2 Hz), 3.15 (2H, q J=6.2 Hz), 1.69 (3H, s), 1.58-1.49 (2H, m), 1.48-1.39 (2H, m).

Example 55

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-succinamic acid

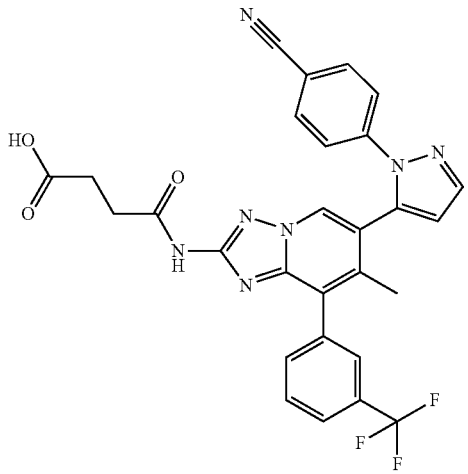 [SMILES: Cc1c(-c2ccnn2-c2ccc(C#N)cc2)cn2nc(NC(=O)CCC(=O)O)nc2c1-c1cccc(C(F)(F)F)c1]

A mixture of 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 230 mg, 0.50 mmol) and 4-methyl-morpholine (300 mg, 30.0 mmol) in THF (3 mL) was treated with dihydro-furan-2,5-dione (250 mg, 2.50 mmol) and heated at 120° C. under microwave irradiation for 4 hrs and then thermally at 60° C. for four days. The crude reaction mixture was purified by flash chromatography eluting with a gradient of 0-10% MeOH in DCM. The fractions containing product were concentrated in vacuo affording the title compound as a colorless glass which solidified in a white solid by standing (182 mg).

LC-MS (Method 3): Rt=4.44 min, m/z=560.1 [M+H]$^+$

1H NMR (400 MHz, DMSO) δ 10.94 (1H, bs), 8.99 (1H, s), 7.98 (1H, d J=1.9 Hz), 7.90-7.85 (2H, m), 7.83-7.65 (4H, m), 7.61-7.55 (2H, m), 6.81 (1H, d J=1.9 Hz), 2.59 (1H, bs), 2.2-2.44 (4H, m), 1.76 (3H, s).

Example 56

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-methylamino-butyramide

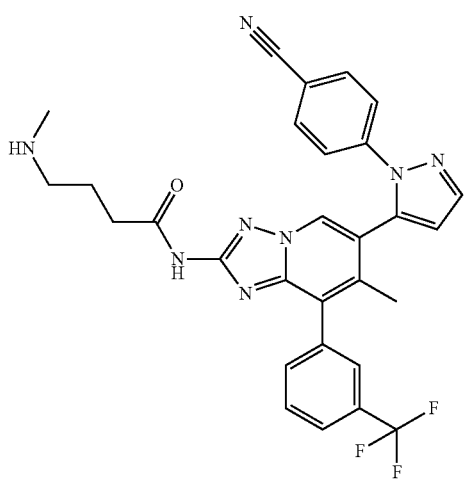 [SMILES: CNCCCC(=O)Nc1nc2c(-c3cccc(C(F)(F)F)c3)c(C)c(-c3ccnn3-c3ccc(C#N)cc3)cn2n1]

Step 1. {3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-propyl}-methyl-carbamic acid tert-butyl ester (Intermediate 33)

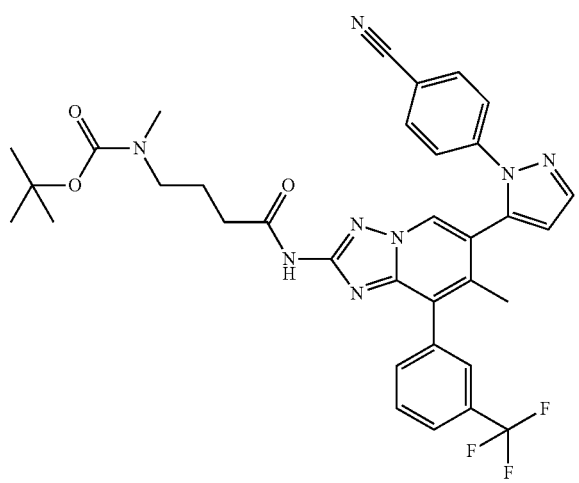 [SMILES: Cc1c(-c2ccnn2-c2ccc(C#N)cc2)cn2nc(NC(=O)CCCN(C)C(=O)OC(C)(C)C)nc2c1-c1cccc(C(F)(F)F)c1]

A solution of 4-(tert-butoxycarbonyl-methyl-amino)-butyric acid (109 mg, 0.50 mmol) in THF (5 mL) was treated with 4-methyl-morpholine (101 mg, 1.0 mmol) followed by isobutyl chloroformate (68 mg, 0.5 mmol) and cooled to −22° C. under argon. The reaction mixture was stirred for 20 mins while warming to −15° C. After re-cooling to −24° C., 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 230 mg, 0.50 mmol) was added and the resulting suspension was slowly warmed to RT and stirred for 16 hrs. The reaction mixture was treated with a fresh batch of 1-({[(4-{[(tert-butoxy)carbonyl] (methyl)-amino}butanoyl)oxy]carbonyl}oxy)-2-methylpropane prepared from a solution of 4-(tert-butoxycarbonyl-methyl-amino)-butyric acid (218 mg, 1.0 mmol) in THF (5 mL), 4-methyl-morpholine (101 mg, 1.0 mmol) and isobutyl chloroformate (137 mg, 1.0 mmol) at RT. The reaction mixture was stirred at RT for 24 hrs and then heated at 60° C. for 7 hrs. After standing at RT for 18 hrs, the volatiles were removed in vacuo and the resulting residue was purified by flash chromatography eluting with a gradient of 0-100% EtOAc in DCM. The product containing fractions were concentrated in vacuo and the resulting residue (456 mg, 0.5 mmol) in THF (5 mL) was treated with a fresh batch of 1-({[(4-{[(tert-butoxy)carbonyl] (methyl)amino}butanoyl)oxy]carbonyl}oxy)-2-methylpropane prepared from a solution of 4-(tert-butoxycarbonyl-methyl-amino)-butyric acid (1.09 g, 5.0 mmol) in THF (20 mL), 4-methyl-morpholine (760 mg, 7.55 mmol) and isobutyl chloroformate (680 mg, 5.01 mmol) at RT. The resulting mixture was heated at 50° C. for 65 hrs and then purified by flash chromatography eluting with a gradient of 0-100% EtOAc in DCM followed by 10% MeOH in DCM affording the title compound (241 mg).

LC-MS (Method 1): Rt=4.06 min, m/z=659.3 [M+H]$^+$

Step 2. N-[6-[2-(4-Cyano-phenyl)-2H-pyrazol-3-yl]-7-methyl-8-(3-trifluoromethyl-phenyl) [1,2,4]triazolo[1,5-a]pyridin-2-yl]-4-methylamino-butyramide (Example 56)

The title compound was prepared from {3-[6-[2-(4-cyano-phenyl)-2H-pyrazol-3-yl]-7-methyl-8-(3-trifluoromethyl-phenyl)-[1,2,4]triazolo[1,5-a]pyridin-2-ylcarbamoyl]-propyl}-methyl-carbamic acid tert-butyl ester (Int. 33, 164 mg, 0.249 mmol) using a similar method to that employed in Example 50, step 2 (52 mg).

LC-MS (Method 3): Rt=3.55 min, m/z=559.2 [M+H]$^+$

1H NMR (400 MHz, DMSO) δ 9.00 (1H, s), 8.33 (1H, s), 7.98 (1H, d J=1.9 Hz), 7.91-7.86 (2H, m), 7.81 (1H, d, J=7.9 Hz), 7.78-7.71 (2H, m), 7.67 (1H, d, J=7.9 Hz), 7.61-7.55 (2H, m), 6.81 (1H, d J=1.9 Hz), 2.69-2.62 (2H, m), 2.46-2.38 (2H, m), 2.38 (3H, s), 1.81-1.71 (5H, m).

Example 57

1-(1-Acetyl-piperidin-4-yl)-3-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-urea

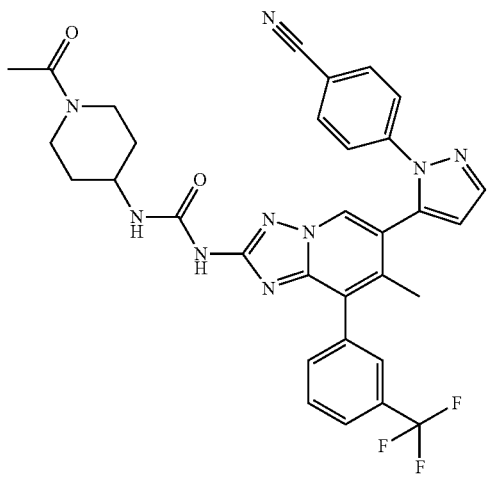 [SMILES: CC(=O)N1CCC(NC(=O)Nc2nc3c(-c4cccc(C(F)(F)F)c4)c(C)c(-c4ccnn4-c4ccc(C#N)cc4)cn3n2)CC1]

The title compound was prepared from 1-[6-[2-(4-cyanophenyl)-2H-pyrazol-3-yl]-7-methyl-8-(3-trifluoromethyl-phenyl)-[1,2,4]triazolo[1,5-a]pyridin-2-yl]-3-piperidin-4-yl-urea (Ex. 50, 50 mg, 0.085 mmol) and acetyl chloride (80 mg, 0.102 mmol) using a similar method to that employed for Intermediate 17 (30 mg).

LC-MS (Method 3): Rt=4.41 min, m/z=628.1 [M+H]$^+$ $^1$H NMR (400 MHz, DMSO) δ 10.02 (1H, s), 8.97 (1H, s), 8.38 (1H, d J=8.6), 7.98 (1H, d J=1.9 Hz), 7.89-7.85 (2H, m), 7.80 (1H, d J=7.5 Hz), 7.77-7.65 (3H, m), 7.60-7.54 (2H, m), 6.81 (1H, d J=1.7 Hz), 3.85-3.75 (1H, m), 3.63-3.53 (1H, m), 3.41-3.30 (1H, m), 3.22-3.13 (1H, m), 3.08-2.99 (1H, m), 1.97 (3H, s), 1.82-1.75 (4H, m), 1.73-1.65 (1H, m), 1.28-1.01 (2H, m).

Example 58

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(1-methanesulfonyl-piperidin-4-yl)-urea

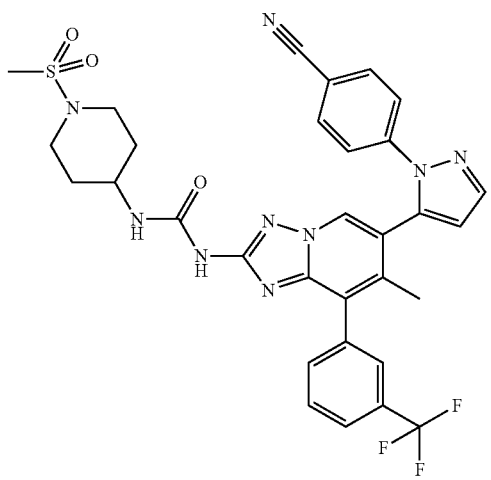 [SMILES: Cc1c(-c2ccnn2-c2ccc(C#N)cc2)cn2nc(NC(=O)NC3CCN(S(C)(=O)=O)CC3)nc2c1-c1cccc(C(F)(F)F)c1]

The title compound was prepared from 1-[6-[2-(4-cyanophenyl)-2H-pyrazol-3-yl]-7-methyl-8-(3-trifluoromethyl-phenyl)-[1,2,4]triazolo[1,5-a]pyridin-2-yl]-3-piperidin-4-yl-urea (Ex. 50, 50 mg, 0.085 mmol) and methanesulfonyl chloride (7.9 μL, 0.102 mmol) using a similar method to that employed for Example 27 (30 mg).

LC-MS (Method 3): Rt=4.75 min, m/z=664.0 [M+H]$^+$

1H NMR (400 MHz, DMSO) δ 10.02 (1H, s), 8.98 (1H, s), 8.22 (1H, d J=7.4), 7.99 (1H, d J=1.9 Hz), 7.90-7.81 (3H, m), 7.79-7.67 (3H, m), 7.60-7.54 (2H, m), 6.81 (1H, d J=1.7 Hz), 3.71-3.59 (1H, m), 3.30-3.20 (2H, m), 2.94-2.84 (2H, m), 2.80 (3H, s), 1.93-1.82 (2H, m), 1.78 (3H, s), 1.38-1.20 (2H, m).

Example 59

4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N-methyl-butyramide

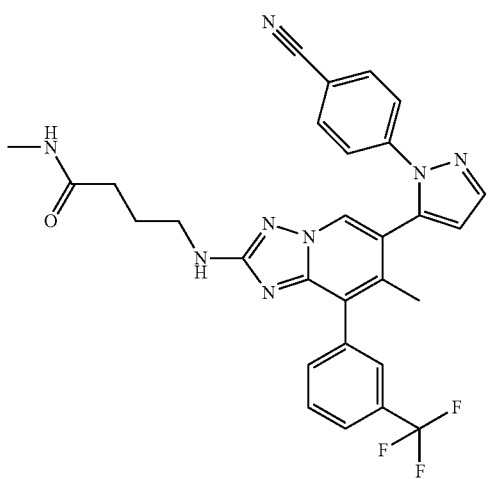 [SMILES: CNC(=O)CCCNc1nc2c(-c3cccc(C(F)(F)F)c3)c(C)c(-c3ccnn3-c3ccc(C#N)cc3)cn2n1]

Step 1. 4-Bromo-N-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-butyramide (Intermediate 34)

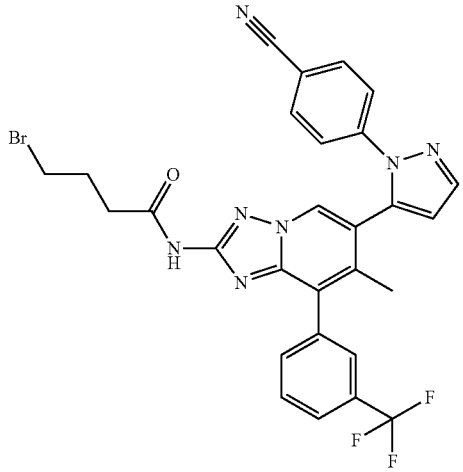 [SMILES: Cc1c(-c2ccnn2-c2ccc(C#N)cc2)cn2nc(NC(=O)CCCBr)nc2c1-c1cccc(C(F)(F)F)c1]

The title compound was prepared from 4-{5-[2-amino-7-methyl-8-(3-trifluoromethyl-phenyl)-[1,2,4]triazolo[1,5-a]pyridin-6-yl]-pyrazol-1-yl}-benzonitrile (Ex. 1, 400 mg, 1.0 mmol), 4-bromo-butyryl chloride (0.5 mL, 4.32 mmol) and triethylamine (0.84 mL, 6.02 mmol) instead of DIPEA using a similar method to that employed for Intermediate 17 (362 mg).

LC-MS (Method 5): Rt=3.82 min, m/z=608.2/610.1 [M+H]+

Step 2. 4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N-methyl-butyramide (Example 59)

4-Bromo-N-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-butyramide (Int. 34, 122 mg, 0.20 mmol) was dissolved in methylamine (33% wt in EtOH, 3 mL, 24.09 mmol) and the resulting mixture was heated at 120° C. under microwave irradiation for 30 mins. After cooling, volatiles were removed in vacuo and the resultant residue was purified by HPLC with a 20 min gradient eluting with 40-98% MeCN in water (+0.1% formic acid) to afford the title compound as a white solid (67 mg).

LC-MS (Method 3): Rt=4.53 min, m/z=559.1 [M+H]+

¹H NMR (400 MHz, DMSO) δ 8.73 (1H, s), 7.9 (1H, d J=1.9 Hz), 7.92-7.87 (2H, m), 7.77 (1H, d J=7.7), 7.74-7.0 (4H, m), 7.59-7.55 (2H, m), 6.78-6.73 (2H, m), 3.13 (2H, q J=7.2 Hz), 2.53 (3H, d J=4.5 Hz), 2.09 (2H, t 7.2 Hz), 1.78-1.67 (5H, m).

Example 60

4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N-(2-dimethylamino-ethyl)-N-methyl-butyramide formate salt

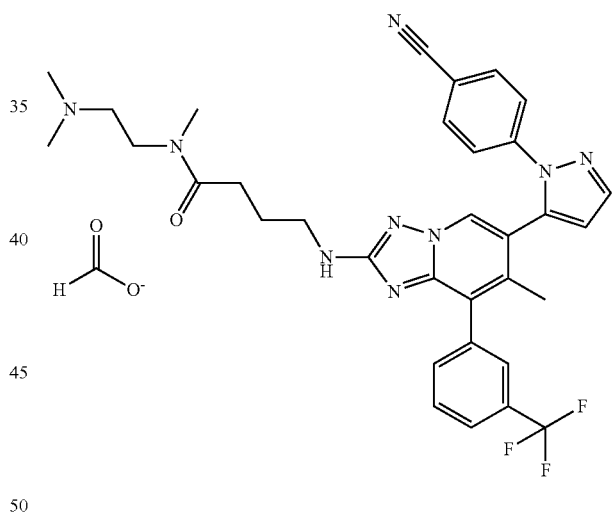

To a solution of 4-bromo-N-[6-[2-(4-cyano-phenyl)-2H-pyrazol-3-yl]-7-methyl-8-(3-trifluoromethyl-phenyl)- [1,2,4]-triazolo[1,5-a]pyridin-2-yl]-butyramide (Int. 34, 105 mg, 0.173 mmol) in IMS (2.0 mL) was added N,N,N'-trimethylethane-1,2-diamine (1.1 mL, 18.63 mmol) and the reaction mixture was heated at 130° C. under microwave irradiation for 3 hrs and 15 mins. The volatiles were removed in vacuo and a further amount of N,N,N'-trimethyl-ethane-1,2-diamine (2.5 mL, 19.67 mmol) was added. The resulting mixture was heated at 150° C. for 16 hrs and then left standing at RT for 48 hrs. The volatiles were removed in vacuo and the resulting residue was purified by chromatography on silica eluting with a gradient of 0-80% EtOAc in DCM, then with 10% MeOH in DCM followed by 2M NH₃ in MeOH. The product containing fractions were combined and concentrated in vacuo. The resulting residue was further purified by HPLC, X-select C18 column, eluting with a gradient 10-98%

MeCN in water (+0.1% formic acid) to afford the title compound as a white solid (14 mg).

LC-MS (Method 3): Rt=3.72 min, m/z=630.1 [M+H]⁺

¹H NMR (400 MHz, DMSO)S 8.72-8.69 (1H, m), 8.26 (0.4H, formate), 7.9 (1H, d J=1.8 Hz), 7.92-7.87 (2H, m), 7.77 (1H, d J=7.9 Hz), 7.74-7.60 (3H, m), 7.59-7.55 (2H, m), 6.79-6.74 (2H, m), 3.37-3.26 (2H, m), 3.17 (2H, q J=6.3 Hz), 2.91 (1.7H, s, rotamer), 2.78 (1.3H, s, rotamer), 2.38-2.25 (4H, m), 2.12 (3.7H, s, rotamer), 2.10 (2.3H, s, rotamer), 1.80-1.68 (5H, m).

Example 61

4-{3-Amino-5-[2-amino-7-methyl-8-(3-trifluoromethyl-phenyl)-[1,2,4]triazolo[1,5-a]pyridin-6-yl]-[1,2,4]triazol-1-yl}-benzonitrile

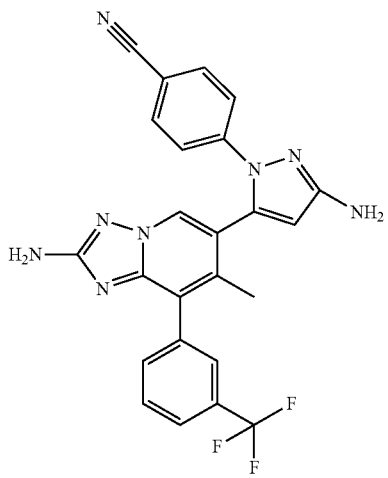 [SMILES: Cc1c(-c2cc(N)nn2-c2ccc(C#N)cc2)cn2nc(N)nc2c1-c1cccc(C(F)(F)F)c1]

Step 1. 2-Amino-7-methyl-8-(3-trifluoromethyl-phenyl)-[1,2,4]triazolo[1,5-a]pyridine-6-carboxylic acid methyl ester (Intermediate 35)

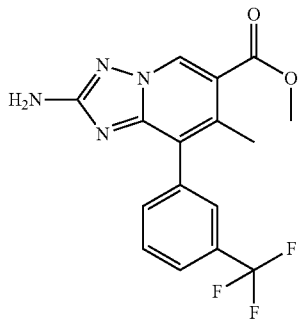 [SMILES: COC(=O)c1cn2nc(N)nc2c(-c2cccc(C(F)(F)F)c2)c1C]

A mixture of 6-bromo-7-methyl-8-(3-trifluoromethyl-phenyl)-[1,2,4]triazolo[1,5-a]pyridin-2-ylamine (1.0 g, 2.695 mmol), trans-bis(acetato)bis[o-(di-o-tolylphosphino)-benzyl]dipalladium(II) (253 mg, 0.27 mmol), tri-tert-butylphosphonium tetrafluoroborate, (156 mg, 0.539 mmol), 1,8-diazabicyclo[5.4.0]undec-7-ene (0.604 mL, 4.043 mmol), and molybdenum hexacarbonyl (713 mg, 2.70 mmol) in a mixture of MeCN and MeOH (1:1, mL) was heated at 150° C. for 30 mins under microwave irradiation. The resulting mixture was cooled and filtered through Celite®. The solvent was concentrated in vacuo and the residue purified by chromatography eluting with 0-80% EtOAc in cyclohexane to afford the title compound as an orange solid (445 mg).

LC-MS (Method 2): Rt=3.24 min, m/z=351 [M+H]⁺

Step 2. 2-Amino-7-methyl-8-(3-trifluoromethyl-phenyl)-[1,2,4]triazolo[1,5-a]pyridine-6-carboxylic acid (Intermediate 36)

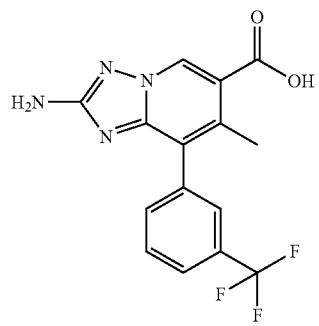 [SMILES: Cc1c(C(=O)O)cn2nc(N)nc2c1-c1cccc(C(F)(F)F)c1]

To a suspension of 2-amino-7-methyl-8-(3-trifluoromethyl-phenyl)-[1,2,4]triazolo[1,5-a]pyridine-6-carboxylic acid methyl ester (Int. 35, 1.0 g, 2.857 mmol) in THF (10 mL) and water (5 mL) was added lithium hydroxide (273 mg, 11.34 mmol) and the reaction mixture was stirred at 45° C. for 1.75 hrs. Cooled then acidified to pH 1. The resultant precipitate was collected by filtration, washing with water, to afford the title compound as a white solid (590 mg).

LC-MS (Method 1): Rt=2.88 min, m/z=337 [M+H]⁺

Step 3. 2-Amino-7-methyl-8-(3-trifluoromethyl-phenyl)-[1,2,4]triazolo[1,5-a]pyridine-6-carbonylimino-methylthiomethyl)-carbamic acid tert-butyl ester (Intermediate 37)

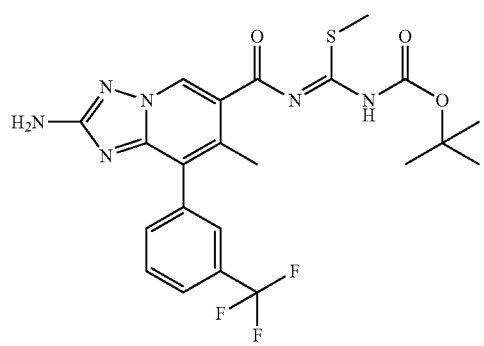 [SMILES: CS/C(=N\C(=O)c1cn2nc(N)nc2c(-c2cccc(C(F)(F)F)c2)c1C)NC(=O)OC(C)(C)C]

2-Amino-7-methyl-8-(3-trifluoromethyl-phenyl)-[1,2,4]triazolo[1,5-a]pyridine-6-carboxylic acid (Int. 36, 246 mg, 0.732 mmol) and N-(tert-butyloxycarbonyl)-S-methyl-isothiourea (139 mg, 0.732 mmol) in THF (5 mL) were treated with triethylamine (306 μL, 2.196 mmol) and HATU (384 mg, 1.098 mmol) and then the reaction mixture was heated at 80° C. for 1.5 hrs. The reaction mixture was treated with saturated aqueous NaHCO$_3$ solution (20 mL) and DCM (20 mL) and the organic phase was separated and concentrated in vacuo. The resulting material was purified by chromatography on silica eluting with a gradient of 0-10% MeOH in DCM to give the title compound as a white solid (348 mg).

LC-MS (Method 2): Rt=4.32 min, m/z=509 [M+H]$^+$

Step 4. [5-[2-Amino-7-methyl-8-(3-trifluoromethyl-phenyl)-[1,2,4]triazolo[1,5-a]pyridin-6-yl]-1-(4-cyano-phenyl)-1H-[1,2,4]triazol-3-yl]-carbamic acid tert-butyl ester (Intermediate 38)

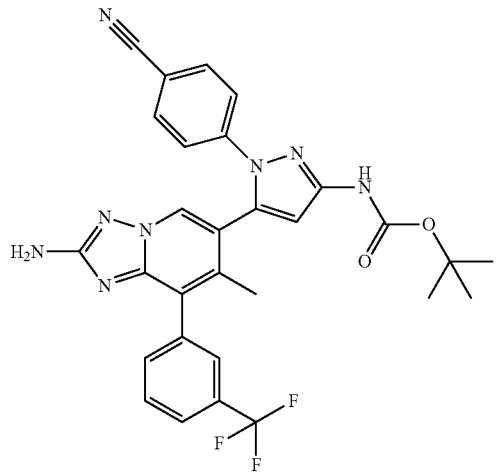 [SMILES: Cc1c(-c2cc(NC(=O)OC(C)(C)C)nn2-c2ccc(C#N)cc2)cn2nc(N)nc2c1-c1cccc(C(F)(F)F)c1]

2-Amino-7-methyl-8-(3-trifluoromethyl-phenyl)-[1,2,4]triazolo[1,5-a]pyridine-6-carbonylimino-methylthiomethyl)-carbamic acid tert-butyl ester (Int. 37, 400 mg, 0.79 mmol) and 4-cyanophenylhydrazine hydrochloride (160 mg, 0.945 mmol) were suspended in IMS (25 mL) and heated at 80° C. for 2 hrs. The reaction mixture was concentrated in vacuo then the material was purified by chromatography on silica eluting with a gradient of 0-5% (2N NH$_3$ in MeOH) in DCM to give the title compound as an orange solid (478 mg).

LC-MS (Method 2): Rt=3.57 min, m/z=576 [M+H]$^+$

Step 5. 4-{3-Amino-5-[2-amino-7-methyl-8-(3-trifluoromethyl-phenyl)-[1,2,4]triazolo[1,5-a]pyridin-6-yl]-[1,2,4]triazol-1-yl}-benzonitrile (Example 61)

Trifluoroacetic acid (1 mL) was added to a solution of [5-[2-amino-7-methyl-8-(3-trifluoromethyl-phenyl)-[1,2,4]triazolo[1,5-a]pyridin-6-yl]-1-(4-cyano-phenyl)-1H-[1,2,4]triazol-3-yl]-carbamic acid tert-butyl ester (Int. 38, 325 mg, 0.565 mmol) in DCM (5 mL) and the reaction mixture was stirred for 2.5 hrs. Saturated aqueous NaHCO$_3$ solution (10 mL) was added and the phases were separated then the organics were concentrated in vacuo. The resulting residue was purified by HPLC, C 18 column, eluting with a gradient 40-80% MeCN in water (+0.1% formic acid) to give the title compound as a white solid (6 mg).

LC-MS (Method 3): Rt=3.89 min, m/z=476 [M+H]$^+$

1H NMR (400 MHz, DMSO) δ 8.73 (1H, s), 7.91-7.84 (2H, m), 7.82-7.67 (4H, m), 7.52-7.47 (2H, m), 6.18 (2H, s), 5.92 (2H, s), 1.88 (3H, s).

$^1$H NMR and LCMS for examples 62-97 and the references to their methods of synthesis are reported in the following:

| Example No. | Structure | $^1$H NMR (400 MHz) | LCMS | Methods of synthesis |
|---|---|---|---|---|
| 62 | 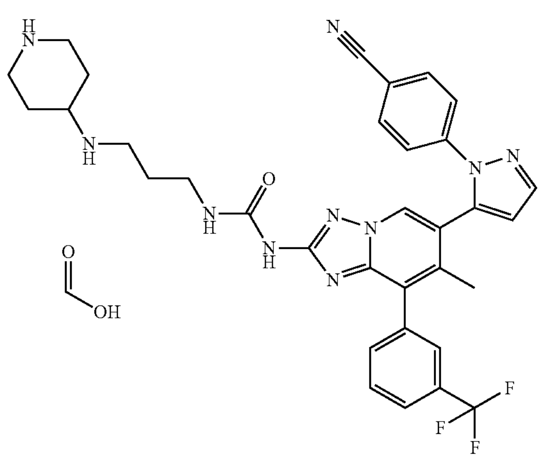 [SMILES: Cc1c(-c2ccnn2-c2ccc(C#N)cc2)cn2nc(NC(=O)NCCCNC3CCNCC3)nc2c1-c1cccc(C(F)(F)F)c1 ; O=CO] | $^1$H NMR (DMSO) δ 9.94 (1H, s), 8.95 (1H, s), 8.33 (1.7H, s), 8.03-7.95 (2H, m), 7.91-7.86 (2H, m), 7.82 (1H, d, J = 7.8 Hz), 7.80-7.73 (2H, m), 7.69 (1H, d, J = 7.8 Hz), 7.62-7.55 (2H, m), 6.81 (1H, d J = 1.7 Hz), 3.21-3.13 (2H, m), 3.13-3.04 (2H, m), 2.74-2.63 (2H, m), 2.58-2.43 (3H, obs., m), 1.81 (2H, m), 1.78 (3H, s), 1.57-1.46 (2H, m), 1.36-1.21 (2H, m). Aliphatic NH's not observed | LC-MS (Method 3): Rt = 3.10 mins, m/z = 643.3 | Scheme 1 (From Ex 1) |

1-[6-[2-(4-Cyano-phenyl)-2H-pyrazol-3-yl]-7-methyl-8-(3-trifluoromethyl-phenyl) [1,2,4]triazolo[1,5-a]pyridin-2-yl]-3-[3-(piperidin-4-ylamino)-propyl]-urea

| Example No. | Structure | ¹H NMR (400 MHz) | LCMS | Methods of synthesis |
|---|---|---|---|---|
| 63 | 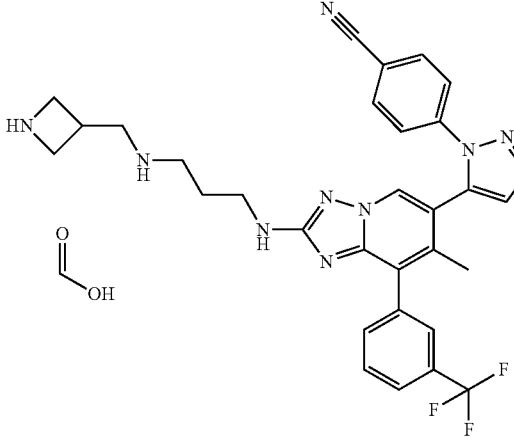<br>4-{5-[2-{3-[(Azetidin-3-ylmethyl)-amino]-propylamino}-7-methyl-8-(3-trifluoromethyl-phenyl)-[1,2,4]triazolo[1,5-a]pyridin-6-yl]-pyrazol-1-yl}-benzonitrile | ¹H NMR (DMSO) δ 8.70 (1H, s), 8.31 (2 H, br. s), 7.96 (1H, d, J = 1.8 Hz), 7.92-7.87 (2H, m), 7.78 (1H, d, J = 7.8 Hz), 7.72 (1H, t, J = 7.8 Hz), 7.68 (1H, br. s), 7.63 (1H, d, J = 7.6 Hz), 7.60-7.54 (2H, m), 6.80-6.72 (2H, m), 3.86 (2H, t J = 9.7 Hz), 3.65-3.54 (2H, m), 3.23-3.25 (2H, m), 2.85-2.73 (1H, m), 2.71-2.64 (2H, m), 2.58-2.49 (2H, obs., m), 1.71 (3H, s ), 1.69-1.59 (2H, m). Aliphatic NH's not observed. | LC-MS (Method 3): Rt = 3.11 mins, m/z = 586.3 | Scheme 1 (From Ex 1) |
| 64 | 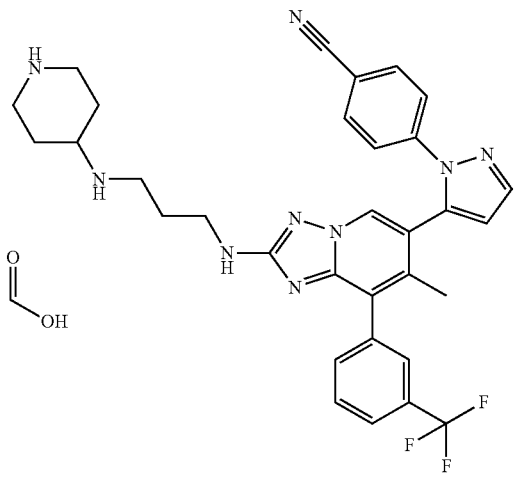 [SMILES: O=CO ; Cc1c(-c2ccnn2-c2ccc(C#N)cc2)cn2nc(NCCCNC3CCNCC3)nc2c1-c1cccc(C(F)(F)F)c1]<br>4-{5-[7-Methyl-2-[3-(piperidin-4-ylamino)-propylamino]-8-(3-trifluoromethyl-phenyl)-[1,2,4]triazolo[1,5-a]pyridin-6-yl]-pyrazol-1-yl}-benzonitrile | ¹H NMR (DMSO) δ 8.71 (1H, s), 8.36 (1.5H, br. s), 7.96 (1H, d J = 1.7 Hz), 7.92-7.87 (2H, m), 7.78 (1H, d, J = 7.8 Hz), 7.72 (1H, t, J = 7.8 Hz), 7.68 (1H, br. s), 7.63 (1H, d, J = 7.6 Hz), 7.59-7.54 (2H, m), 6.81-6.72 (2H, m), 3.25-3.15 (2H, m), 3.12-3.02 (2H, m), 2.72-2.55 (5H, m), 1.87-1.76 (2H, m), 1.71 (3H, s), 1.69-1.60 (2H, m), 1.38-1.21 (2H, m). Amino NH's not observed. | LC-MS (Method 3): Rt = 3.10 mins, m/z = 600.3 | Scheme 1 (From Ex 1) |

| Example No. | Structure | ¹H NMR (400 MHz) | LCMS | Methods of synthesis |
|---|---|---|---|---|
| 65 | 1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-{3-[(3-dimethylamino-propyl)-methyl-amino]-propyl}-urea | ¹H NMR (DMSO) δ 9.92 (1H, s), 8.94 (1H, s), 8.04 (1H, m), 7.99 (1H, d, J = 1.8 Hz), 7.90-7.85 (2H, m), 7.83 (1H, d, J = 7.8 Hz), 7.78 (1H, br. s), 7.75 (1H, t, J = 7.8 Hz), 7.72-7.67 (1H, m), 7.60-7.55 (2H, m), 6.81 (1H, d, J = 1.8 Hz), 3.18-3.08 (2H, m), 2.23-2.09 (6H, m), 2.03 (6H, s), 2.01 (3H, s), 1.80 (3H, s), 1.54-1.35 (4H, m). | LC-MS (Method 3): Rt = 3.06 mins, m/z = 659.4 | Scheme 1 (From Ex 1) |
| 66 | 4-{5-[2-{3-[(3-Dimethylamino-propyl)-methyl-amino]-propylamino}-7-methyl-8-(3-trifluoromethyl-phenyl)-[1,2,4]triazolo[1,5-a]pyridin-6-yl]-pyrazol-1-yl}-benzonitrile | ¹H NMR (DMSO) δ 8.70 (1H, s), 8.33 (0.7H, s), 7.95 (1H, d J = 1.8 Hz), 7.92-7.87 (2H, m), 7.78 (1H, d, J = 8.0 Hz), 7.71 (1H, t J = 7.7 Hz), 7.67 (1H, br. s), 7.63 (1H, d, J = 7.6 Hz), 7.60-7.54 (2H, m), 6.77-6.70 (2H, m), 3.21-3.12 (2H, m), 2.35-2.29 (2H, m), 2.26 (2H, t, J = 7.1 Hz), 2.17 (2H, t, J = 7.1 Hz), 2.10 (3H, s), 2.07 (6H, s), 1.70 (3H, s), 1.68-1.57 (2H, m), 1.53-1.42 (2H, m). | LC-MS (Method 3): Rt = 3.12 mins, m/z = 616.3 | Scheme 1 (From Ex 1) |
| 67 | 4-{5-[7-Methyl-2-[3-(4-methylamino-piperidin-1-yl)-propylamino]-8-(3-trifluoromethyl-phenyl)-[1,2,4]triazolo[1,5-a]pyridin-6-yl]-pyrazol-1-yl}-benzonitrile | ¹H NMR (DMSO) δ 8.71 (1H, s), 8.26 (1H, br. s), 7.96 (1H, d J = 1.8 Hz), 7.92-7.83 (2H, m), 7.78 (1H, d, J = 7.8 Hz), 7.72 (1H, t, J = 7.8 Hz), 7.68 (1H, br. s), 7.63 (1H, d, J = 7.6 Hz), 7.60-7.55 (2H, m), 6.78-6.69 (2H, m), 3.20-3.11 (2H, m), 2.85 (2H, m), 2.75-2.62 (1H, m), 2.44 (3H, s), 2.31 (2H, t, J = 7.2 Hz), 1.93-1.78 (4H, m), 1.70 (3H, s), 1.66 (2H, m), 1.44-1.29 (2H, m). Aliphatic NH not observed. | LC-MS (Method 3): Rt = 3.09 mins, m/z = 614.3 | Scheme 1 (From Ex 1) |

| Example No. | Structure | ¹H NMR (400 MHz) | LCMS | Methods of synthesis |
|---|---|---|---|---|
| 68 | 1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-[2-(4-methylamino-piperidin-1-yl)-ethyl]-urea | ¹H NMR (DMSO) δ 9.94 (1H, s), 8.94 (1H, s), 8.29 (2H, br. s), 7.98 (1H, d, J = 1.8 Hz), 7.95 (1H, m), 7.91-7.86 (2H, m), 7.83 (1H, d, J = 7.5 Hz), 7.78-7.72 (2H, m), 7.68 (1H, d, J = 7.8 Hz), 7.61-7.56 (2H, m), 6.81 (1H, d, J = 1.8 Hz), 3.26-3.15 (2H, m), 2.88-2.69 (3H, m), 2.38 (3H, s), 2.35-2.28 (2H, m), 1.99-1.85 (2H, m), 1.84-1.77 (2H, obs., m), 1.77 (3H, s), 1.42-1.19 (2H, m). Aliphatic NH not observed. | LC-MS (Method 3): Rt = 3.05 min, m/z = 643.3 [M + H]⁺ | Scheme 1 (From Ex 1) |
| 69 | N-[6-[4-(4-Cyano-phenyl)-5-oxo-4,5-dihydro-1H-[1,2,4]triazol-3-yl]-7-methyl-8-(3-trifluoromethyl-phenyl)-[1,2,4]triazolo[1,5-a]pyridin-2-yl]-acetamide | ¹H NMR (DMSO) δ 12.49 (1H, s), 10.90 (1H, s), 9.05 (1H, s), 7.94-7.89 (2H, m), 7.81 (1H, d, J = 7.8 Hz), 7.73 (1H, t, J = 7.6 Hz), 7.71 (1H, br. s), 7.64 (1H, d, J = 7.8 Hz), 7.57-7.53 (2H, m), 2.06 (3H, s), 1.95 (3H, s). | LC-MS (Method 3): Rt = 3.78 min, m/z = 519.1 [M + H]⁺ | Scheme 15 (It) |

| Example No. | Structure | $^1$H NMR (400 MHz) | LCMS | Methods of synthesis |
|---|---|---|---|---|
| 70 | 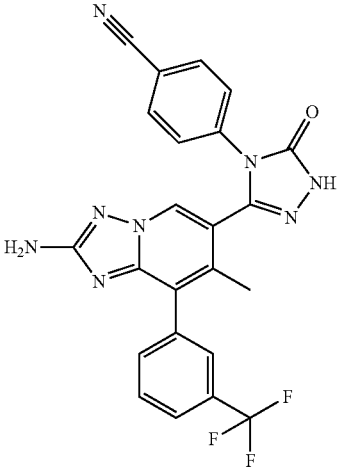 [SMILES: Cc1c(-c2n[nH]c(=O)n2-c2ccc(C#N)cc2)cn2nc(N)nc2c1-c1cccc(C(F)(F)F)c1]<br>4-{3-[2-Amino-7-methyl-8-(3-trifluoro-methyl-phenyl)-[1,2,4]triazolo[1,5-a]pyridin-6-yl]-5-oxo-1,5-dihydro-[1,2,4]triazol-4-yl}-benzonitrile | $^1$H NMR (DMSO) δ 12.42 (1H, s), 8.74 (1H, s), 7.95-7.90 (2H, m), 7.77 (1H, d, J = 8.0 Hz), 7.70 (1H, t, J = 8.0 Hz), 7.63 (1H, br. s), 7.59 (1H, d, J = 8.0 Hz), 7.50-7.55 (2H, m), 6.19 (2H, s), 1.87 (3H, s). | LC-MS (Method 3): Rt = 3.77 min, m/z = 477.0 [M + H]$^+$ | Scheme 15 (It) |
| 71 | 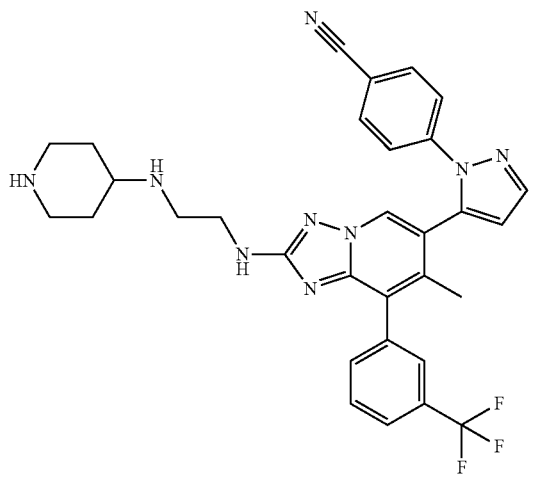 [SMILES: Cc1c(-c2ccnn2-c2ccc(C#N)cc2)cn2nc(NCCNC3CCNCC3)nc2c1-c1cccc(C(F)(F)F)c1]<br>4-{5-[7-Methyl-2-[2-(piperidin-4-yl amino)-ethylamino]-8-(3-trifluoromethyl-phenyl)-[1,2,4]triazolo[1,5-a]pyridin-6-yl]-pyrazol-1-yl}-benzonitrile | $^1$H NMR (CDCl$_3$) δ 8.31 (1H, s), 7.85 (1H, s), 7.71-7.55 (5H, m), 7.54-7.45 (3H, m), 6.56 (1H, d, J = 1.4 Hz), 5.15 (1H, br. s), 3.57-3.52 (2H, m), 3.22-3.06 (2H, m), 2.90 (2H, br. s), 2.76-2.51 (3H, m), 1.98-1.81 (2H, m), 1.41-1.21 (2H, m). Aliphatic NH not observed. | LC-MS (Method 3): Rt = 3.01 min, m/z = 586.2 [M + H]$^+$ | Scheme 1 (From Ex 1) |

| Example No. | Structure | ¹H NMR (400 MHz) | LCMS | Methods of synthesis |
|---|---|---|---|---|
| 72 | 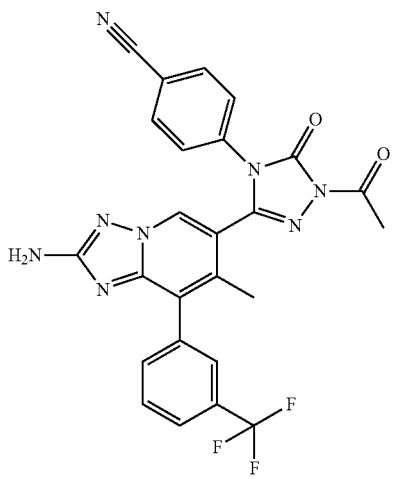 [SMILES: CC(=O)n1nc(-c2cn3nc(N)nc3c(-c3cccc(C(F)(F)F)c3)c2C)n(-c2ccc(C#N)cc2)c1=O]<br>4-{1-Acetyl-3-[2-amino-7-methyl-8-(3-trifluoro-methyl-phenyl)-[1,2,4]triazolo[1,5-a]pyridin-6-yl]-oxo-1,5-dihydro-[1,2,4]triazol-4-yl}-benzonitrile | ¹H NMR (DMSO) δ 8.72 (1H, s), 7.99-7.95 (2H, m), 7.78 (1H, d, J = 8.0 Hz), 7.71 (1H, t, J = 7.5 Hz), 7.64 (1H, br. s), 7.62-7.56 (3H, m), 6.26 (2H, s), 2.60 (3H, s), 1.94 (3H, s). | LC-MS (Method 3): Rt = 4.21 min, m/z = 519.1 [M + H]⁺ | Scheme 15 (It) |
| 73 | 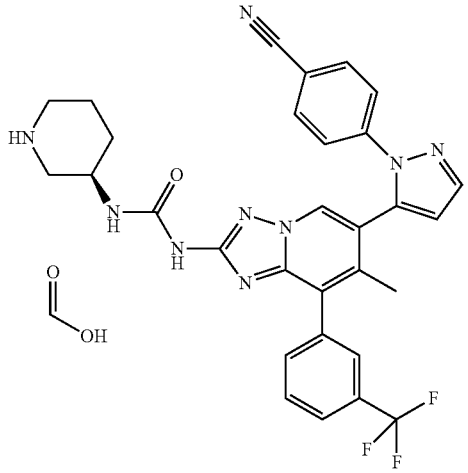 [SMILES: Cc1c(-c2ccnn2-c2ccc(C#N)cc2)cn2nc(NC(=O)N[C@@H]3CCCNC3)nc2c1-c1cccc(C(F)(F)F)c1 ; O=CO]<br>1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(R)-piperidin-3-yl-urea | ¹H NMR (DMSO) δ 9.99 (1H, s), 8.96 (1H, s), 8.27 (1H, s), 8.28-8.22 (1H, m), 7.99 (1H, d, J = 1.8 Hz), 7.90-7.86 (2H, m), 7.84 (1H, d, J = 8.0 Hz), 7.79-7.74 (2H, m), 7.70 (1H, d, J = 8.0 Hz), 7.60-7.56 (2H, m), 6.82 (1H, d, J = 1.8 Hz), 3.70-3.58 (1H, m), 3.02-2.92 (1H, m), 2.83-2.73 (1H, m), 2.51-2.42 (1H, m), 2.41-2.31 (1H, m), 1.78 (3H, s), 1.78-1.69 (1H, m), 1.51-1.31 (2H, m), 1.26-1.13 (1H, m). Aliphatic NH not observed. | LC-MS (Method 3): Rt = 3.61 min, m/z = 586.3 [M + H]⁺ | Scheme 1 (From Ex 1) |

| Example No. | Structure | ¹H NMR (400 MHz) | LCMS | Methods of synthesis |
|---|---|---|---|---|
| 74 | {3-[6-[2-(4-Cyano-phenyl)-5-methoxycarbonyl-2H-[1,2,4]triazol-3-yl]-7-methyl-8-(3-trifluoromethyl-phenyl)-[1,2,4]triazolo[1,5a]pyridin-2-ylcarbamoyl]-propyl}-trimethyl ammonium formate | ¹H NMR (DMSO) δ 10.93 (1H, br. s), 8.98-8.96 (1H, m), 8.43 (1H, br s), 7.99 (1H, d, J = 1.8 Hz), 7.91-7.86 (2H, m), 7.83 (1H, d, J = 8.0 Hz), 7.76 (1H, t, J = 7.8 Hz), 7.74 (1H, br. s), 7.68 (1H, d, J = 7.8 Hz), 7.60-7.55 (2H, m), 6.82 (1H, d, J = 1.7 Hz), 3.70 (2H, t, J = 6.8 Hz), 3.41 (2H, t, J = 6.8 Hz), 3.07 (9H, br. s), 3.04 (3H, s), 2.57-2.68 (4H, m), 1.79 (3H, s). | LC-MS (Method 3): Rt = 3.61 min, m/z = 658.3 [M]⁺ | Scheme 1 (From Ex 55) |
| 75 | (3-{2-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-ylcarbamoyl]-ethanesulfonyl}-propyl)-trimethyl-ammonium formate | ¹H NMR (DMSO) δ 11.28 (1H, s), 9.08 (1H, s), 8.52 (1H, s), 8.47 (1H, s), 7.99-7.94 (2H, m), 7.87-7.81 (2H, m), 7.79-7.75 (2H, m), 7.77-7.64 (2H, m), 3.35-3.53 (4H, m, obscured by water signal), 3.22 (2H, t, J = 7.5 Hz), 3.07 (9H, s), 2.94-2.78 (2H, m), 2.20-2.09 (2H, m), 1.99 (3H, s). | LC-MS (Method 3): Rt = 3.40 min, m/z = 680.3 [M]⁺ | Scheme 15 (Iu) |

| Example No. | Structure | ¹H NMR (400 MHz) | LCMS | Methods of synthesis |
|---|---|---|---|---|
| 76 | 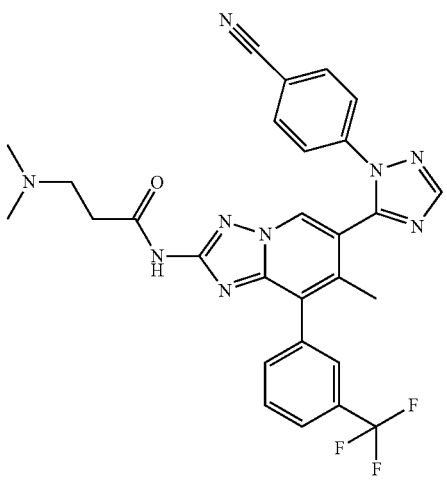 [SMILES: Cc1c(-c2ncnn2-c2ccc(C#N)cc2)cn2nc(NC(=O)CCN(C)C)nc2c1-c1cccc(C(F)(F)F)c1]<br>Carboxymethyl-(3-{3-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-ureido}-propyl)-dimethyl-ammonium formate | ¹H NMR (CDCl₃) δ 11.66 (1H, br. s), 8.50 (1H, s), 8.25 (1H, s), 7.77-7.69 (4H, m), 7.66 (1H, t, J = 7.7 Hz), 7.61 (1H, d, J = 7.4 Hz), 7.52-7.47 (2H, m), 2.68-2.74 (2H, m), 2.66-2.54 (2H, m), 2.37 (6H, s), 2.11 (3H, s). | LC-MS (Method 3): Rt = 3.34 min, m/z = 560.2 [M + H]⁺ | Scheme 15 (Iu) |
| 77 | 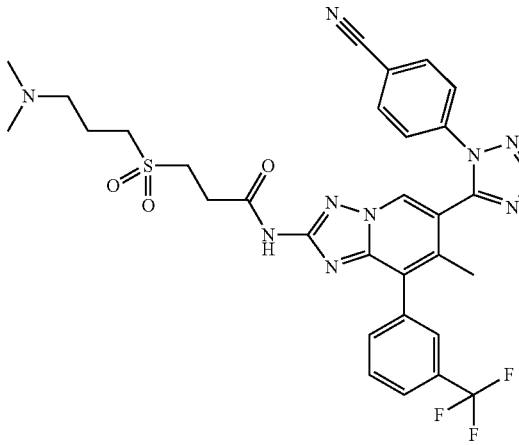<br>N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-3-dimethylamino-propionamide | ¹H NMR (CDCl₃) δ 9.34 (1H, br. s), 8.52 (1H, s), 8.27 (1H, s), 7.79-7.71 (3H, m), 7.70-7.62 (2H, m), 7.59 (1H, d, J = 7.8 Hz), 7.56-7.48 (2H, m), 3.42 (2H, t, J = 7.3 Hz), 3.19-3.09 (2H, m), 2.60 (2H, t, J = 6.9 Hz), 2.35 (6H, s), 2.14-2.09 (2H, m), 2.08 (3H, s), 2H obscured by solvent. | LC-MS (Method 3): Rt = 3.43 min, m/z = 666.3 [M + H]⁺ | Scheme 15 (Iu) |

| Example No. | Structure | ¹H NMR (400 MHz) | LCMS | Methods of synthesis |
|---|---|---|---|---|
| 78 | 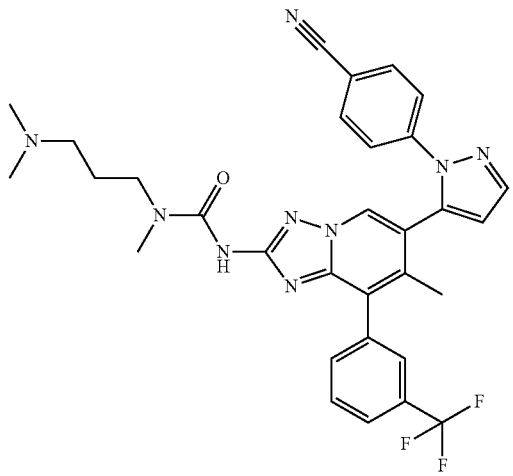 [SMILES: Cc1c(-c2ccnn2-c2ccc(C#N)cc2)cn2nc(NC(=O)N(C)CCCN(C)C)nc2c1-c1cccc(C(F)(F)F)c1]<br>3-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-1-(3-dimethylamino-propyl)-1-methyl-urea | ¹H NMR (CDCl₃) δ 8.52 (1H, s), 8.27 (1H, br. s), 7.89 (1H, d, J = 1.8 Hz), 7.73-7.67 (2H, m), 7.71(1 H, s), 7.67-7.62 (2H, m), 7.60 (1H, t, J = 7.6 Hz), 7.50-7.43 (2H, m), 6.59 (1H, d, J = 1.7 Hz), 3.46 (2H, t, J = 6.2 Hz), 3.0 (3H, s), 2.76-2.62 (2H, m), 2.46 (6H, br. s), 1.90 (2H, m), 1.86 (3H, s). | LC-MS (Method 3): Rt = 3.59 min, m/z = 602.3 [M + H]⁺ | Scheme 1 (From Ex 1) |
| 79 | 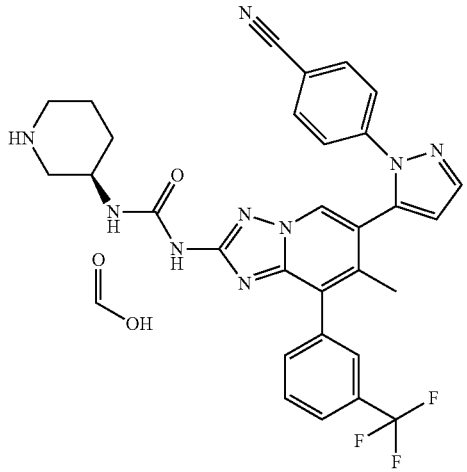<br>1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(S)-piperidin-3-yl-urea | ¹H NMR (DMSO) δ 10.0 (1H, s), 8.96 (1H, s), 8.26-8.22 (1H, obs. m), 8.24 (1H, s), 7.99 (1H, d, J = 1.8 Hz), 7.91-7.86 (2H, m), 7.83 (1H, d, J = 7.7 Hz), 7.80-7.73 (2H, m), 7.70 (1H, d, J = 7.6 Hz), 7.61-7.54 (2H, m), 6.77 (1H, d, J = 1.7 Hz), 3.70-3.59 (1H, m), 3.05-3.93 (1H, m), 2.86-2.75 (1H, m), 2.53-2.48 (1H, obs. m), 2.45-2.33 (1H, m), 1.71 (3H, s), 1.78-1.69 (1H, m), 1.53-1.33 (2H, m), 1.26-1.13 (1H, m). Aliphatic NH not observed. | LC-MS (Method 3): Rt = 3.60 min, m/z = 586.3 [M + H]⁺ | Scheme 1 (From Ex 1) |

| Example No. | Structure | ¹H NMR (400 MHz) | LCMS | Methods of synthesis |
|---|---|---|---|---|
| 80 | 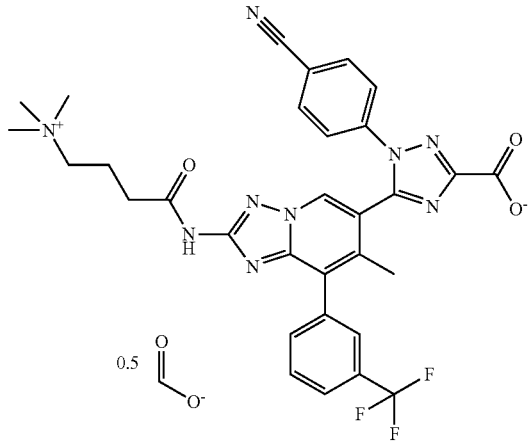<br>{3-[6-[5-Carboxy-2-(4-cyano-phenyl)-2H-[1,2,4]triazol-3-yl]-7-methyl-8-(3-trifluoromethyl-phenyl)-[1,2,4]triazolo[1,5-a]pyridin-2-ylcarbamoyl]-propyl}-trimethyl-ammonium formate | ¹H NMR (DMSO) δ 11.05 (1H, s), 9.04 (1H, s), 8.20 (0.5H, s), 7.97-7.91 (2H, m), 7.86-7.81 (2H, m). 7.86-7.81-7.73 (2H, m), 7.69-7.60 (2H, m), 3.26 (2H, m), 3.05 (9H, s), 2.50-2.39 (2H, m), 2.0 (3H, s), 2.0-1.89 (2H, m). | LC-MS (Method 3): Rt = 3.09 min, m/z = 632.3 [M + H]⁺ | Scheme 18 (Iz') |
| 81 | 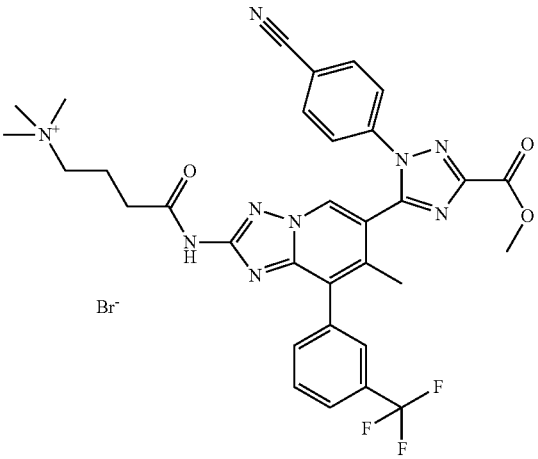 [SMILES: COC(=O)c1nc(-c2cn3nc(NC(=O)CCC[N+](C)(C)C)nc3c(-c3cccc(C(F)(F)F)c3)c2C)n(-c2ccc(C#N)cc2)n1 ; [Br-]]<br>{3-[6-[2-(4-Cyano-phenyl)-5-methoxycarbonyl-2H-[1,2,4]triazol-3-yl]-7-methyl-8-(3-trifluoromethyl-phenyl)-[1,2,4]triazolo[1,5-a]pyridin-2-ylcarbamoyl]-propyl}-trimethyl-ammonium bromide | ¹H NMR (CDCl₃) δ 8.55 (1H, s), 8.42 (1H, br. s), 7.79-7.74 (2H, m), 7.73-7.68 (1H, m), 7.67-7.54 (5H, m), 4.07 (3H, s), 3.78-3.64 (2H, m), 3.22 (9H, s), 2.87-2.65 (2H, m). 2.19-2.10 (2H, m), 2.09 (3H, s). | LC-MS (Method 3): Rt = 3.46 min, m/z = 646.4 [M + H]⁺ | Scheme 18 (Iz') |

| Example No. | Structure | ¹H NMR (400 MHz) | LCMS | Methods of synthesis |
| --- | --- | --- | --- | --- |
| 82 | Carboxymethyl-(3-{3-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-ureido}-propyl)-dimethyl-ammonium formate | ¹H NMR (DMSO) δ 10.00 (1H, s), 9.03 (1H, s), 7.99 (1H, d J = 1.8 Hz), 7.94 (1H, t J = 5.6 Hz), 7.92-7.86 (2H, m), 7.83 (1H, d, J = 7.8 Hz), 7.78 (1H, t, J = 7.6 Hz), 7.74 (1H, br. s), 7.72 (1H, d, J = 7.6 Hz), 7.62-7.57 (2H, m), 6.81 (1H, d J = 1.8 Hz), 3.55-3.48 (4H, m), 3.22-3.13 (2H, m), 3.08 (6H, s), 1.86-1.77 (2H, m), 1.78 (3H, s). | LC-MS (Method 3): Rt = 3.85 min, m/z = 646.2 [M + H]⁺ | Scheme 1 (From Ex 1) |
| 83 | 1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(3-methylamino-propyl)-urea | ¹H NMR (DMSO) δ 9.98 (1H, br. s), 8.95 (1H, s), 8.33 (1H, s), 8.03-7.96 (1H, obs. m), 7.99 (1H, d, J = 1.8 Hz), 7.91-7.86 (2H, m), 7.83 (1H, d, J = 8.0 Hz), 7.80-7.73 (2H, m), 7.70 (1H, d, 7.7 Hz), 7.61-7.55 (2H, m), 6.81 (1H, d J = 1.8 Hz), 3.23-3.13 (2H, m), 2.60 (2H, t, 7.2 Hz), 2.34 (3H, s), 1.78 (3H, s), 1.68-1.56 (2H, m). Aliphatic NH not observed. | LC-MS (Method 3): Rt = 3.59 min, m/z = 574.3 [M + H]⁺ | Scheme 1 (From Ex 1) |

| Example No. | Structure | ¹H NMR (400 MHz) | LCMS | Methods of synthesis |
|---|---|---|---|---|
| 84 | 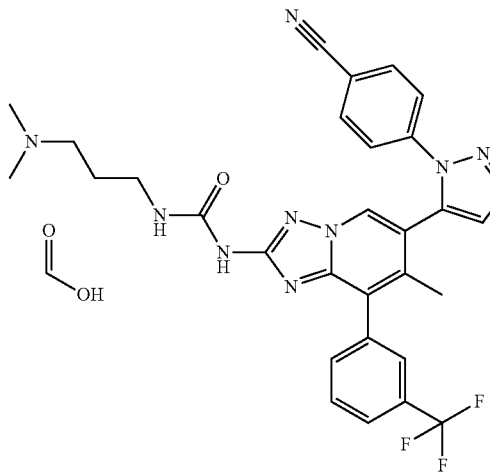

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(3-dimethylamino-propyl)-urea | ¹H NMR (DMSO) δ 9.93 (1H, s), 8.93 (1H, s), 8.20 (1H, s), 8.03 (1H, t, J = 5.1 Hz), 7.99 (1H, d, J = 1.8 Hz), 7.91-7.85 (2H, m), 7.83 (1H, d, J = 8.0 Hz), 7.79-7.73 (2H, m), 7.70 (1H, d, J = 8.0 Hz), 7.61-7.55 (2H, m), 6.81 (1H, d, J = 1.8 Hz), 3.17-3.08 (2H, m), 2.16 (2H, t, J = 7.0 Hz), 2.06 (6H, s), 1.79 (3H, s), 1.55-1.45 (2H, m). | LC-MS (Method 3): Rt = 3.61 min, m/z = 588.3 [M + H]⁺ | Scheme 1 (From Ex 1) |
| 85 | 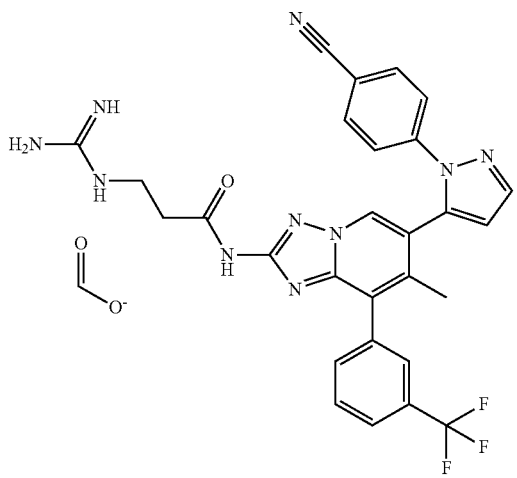

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-guanidino-propionamide | ¹H NMR (DMSO) δ 11.07 (1H, s), 9.00 (1H, s), 8.41 (1H, s), 8.20 (1H, s), 7.99 (1H, d, J = 1.8 Hz), 7.91-7.86 (2H, m), 7.82 (1H, d, J = 7.8 Hz), 7.76 (1H, t, J = 8.0 Hz),), 7.73 (1H, br. s), 7.68 (1H, d, J = 6.9 Hz), 7.61-7.65 (2H, m), 6.93 (1H, br. s), 6.82 (1H, d, J = 1.8 Hz), 2.70-2.55 (2H, m), 2.52 (2H, obs. m), 1.77 (3H, s). NB: amidine NH₂ obscured 7.79-7.55. | LC-MS (Method 3): Rt = 3.58 min, m/z = 573.2 [M + H]⁺ | Scheme 1 (From Ex 1) |

| Example No. | Structure | ¹H NMR (400 MHz) | LCMS | Methods of synthesis |
|---|---|---|---|---|
| 86 | {3-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-ylcarbamoyl]-propyl}-trimethyl-ammonium bromide | ¹H NMR (DMSO) δ 11.05 (1H, s), 9.05 (1H, s), 8.52 (1H, s), 8.00-7.94 (2H, m), 7.87-7.81 (2H, m), 7.79-7.74 (2H, m), 7.70-7.65 (2H, m), 3.30-3.24 (2H, m), 3.04 (9H, s), 2.48-2.41 (2H, m), 2.00 (3H, s), 1.99-1.91 (2H, m). | LC-MS (Method 3): Rt = 3.38 min, m/z = 588.3 [M]⁺ | Scheme 15 (Iu) |
| 87 | N-[6-[1-(4-Cyano-phenyl)-1H-imidazol-2-yl]-7-methyl-8-(3-trifluoromethyl-phenyl)-[1,2,4]triazolo[1,5-a]pyridin-2-yl]-acetamide | ¹H NMR (CDCl₃) δ 8.42 (1H, s), 7.89 (1H, br. s), 7.75-7.69 (3H, m), 7.67-7.61 (2H, m), 7.57-7.50 (1H, m), 7.40 (1H, m), 7.33 (1H, m), 7.32-7.28 (2H, m), 2.27 (3H, br. s), 2.07 (3H, s). | LC-MS (Method 3): Rt = 3.82 min, m/z = 502.2 [M + H]⁺ | Scheme 14 (Ip) |

| Example No. | Structure | ¹H NMR (400 MHz) | LCMS | Methods of synthesis |
|---|---|---|---|---|
| 88 | N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-hydroxy-butyramide | ¹H NMR (DMSO) δ 10.84 (1H, br. s), 9.00 (1H, s), 7.98 (1H, d, J = 1.8 Hz), 7.91-7.86 (2H, m), 7.81 (1H, d, J = 7.9 Hz), 7.75 (1H, t, J = 7.6 Hz), 7.73 (1H, br. s), 7.67 (1H, d, J = 7.6 Hz), 7.61-7.56 (2H, m), 6.81 (1H, d, J = 1.8 Hz), 4.44 (1H, t, J = 4.9 Hz), 3.43-3.35 (2H, m), 2.45-3.34 (2H, m), 1.76 (3H, s), 1.74-1.64 (2H, m). | LC-MS (Method 3): Rt = 4.38 min, m/z = 546.1 [M + H]⁺ | Scheme 1 (From Ex 1) |
| 89 | N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-4-dimethylamino-butyramide | ¹H NMR (CDCl₃) δ 11.23 (1H, br. s), 8.50 (1H, s), 8.31 (1H, br. s), 8.27 (1H, s), 7.77-7.70 (4H, m), 7.65 (1H, t, J = 7.7 Hz), 7.58 (1H, d, J = 7.7 Hz), 7.54-7.48 (2H, m), 2.79 (2H, t, J = 7.1 Hz), 2.68-2.57 (2H, m), 2.52 (6H, s), 2.10 (3H, s), 2.07-1.98 (2H, m). | LC-MS (Method 3): Rt = 3.38 min, m/z = 574.2 [M + H]⁺ | Scheme 15 (Iu) |

| Example No. | Structure | ¹H NMR (400 MHz) | LCMS | Methods of synthesis |
|---|---|---|---|---|
| 90 | 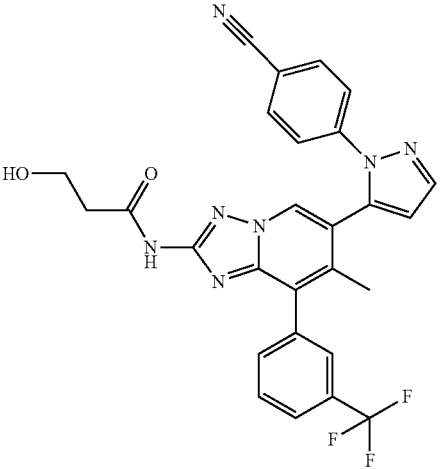 [SMILES: Cc1c(-c2ccnn2-c2ccc(C#N)cc2)cn2nc(NC(=O)CCO)nc2c1-c1cccc(C(F)(F)F)c1]<br>N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-hydroxy-propionamide | ¹H NMR (DMSO) δ 10.85 (1H, s), 9.00 (1H, s), 7.99 (1H, d, J = 1.8 Hz), 7.91-7.86 (2H, m), 7.82 (1H, d, J = 7.7 Hz), 7.75 (1H, t, J = 7.7 Hz), 7.73 (1H, br. s), 7.68 (1H, d, J = 7.7 Hz), 7.61-7.55 (2H, m), 6.81 (1H, d, J = 1.8 Hz), 4.61 (1H, t, J = 5.0 Hz), 3.70-3.63 (2H, m), 3.30-3.27 (2H, m), 1.77 (3H, s). | LC-MS (Method 3): Rt = 4.34 min, m/z = 532.1 [M + H]⁺ | Scheme 1 (From Ex 1) |
| 91 | 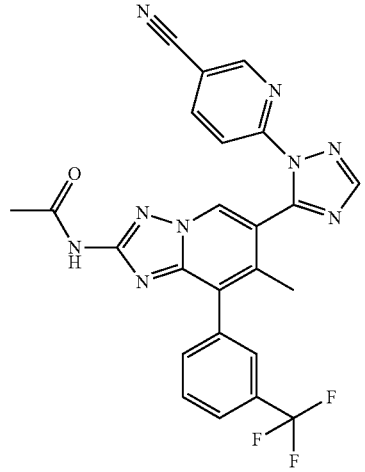 [SMILES: CC(=O)Nc1nc2c(-c3cccc(C(F)(F)F)c3)c(C)c(-c3ncnn3-c3ccc(C#N)cn3)cn2n1]<br>N-[6-[2-(5-Cyano-pyridin-2-yl)-2H-[1,2,4]triazol-3-yl]-7-methyl-8-(3-trifluoromethyl-phenyl)-[1,2,4]triazolo[1,5-a]pyridin-2-yl]-acetamide | ¹H NMR (DMSO) δ 10.89 (1H, br. s), 9.04 (1H, s), 8.80 (1H, dd, J = 1.0, 2.0 Hz), 8.57 (1H, s), 8.55 (1H, dd, J = 8.5, 2.0 Hz), 8.12 (1H, dd, J = 8.8, 0.7 Hz), 7.88 (1H, br. s), 7.86-7.75 (3H, m), 2.06 (3H, s), 1.93 (3H, s). | LC-MS (Method 3): Rt = 4.23 min, m/z = 504.1 [M + H]⁺ | Scheme 15 (Iu) |

| Example No. | Structure | ¹H NMR (400 MHz) | LCMS | Methods of synthesis |
|---|---|---|---|---|
| 92 | 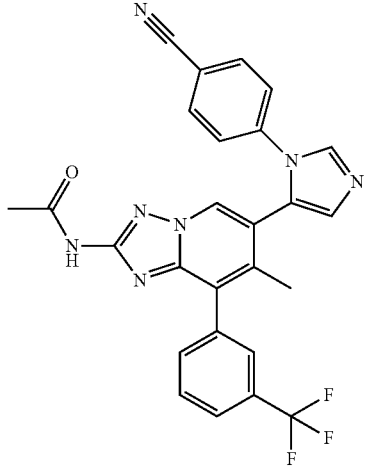 [SMILES: CC(=O)Nc1nc2c(-c3cccc(C(F)(F)F)c3)c(C)c(-c3cncn3-c3ccc(C#N)cc3)cn2n1]<br>N-[6-[3-(4-Cyano-phenyl)-3H-imidazol-4-yl]-7-methyl-8-(3-trifluoromethyl-phenyl)-[1,2,4]triazolo[1,5-a]pyridin-2-yl]-acetamide | ¹H NMR (CDCl₃) δ 8.54 (1H, s), 7.93-7.87 (2H, m), 7.75-7.69 (3H, m), 7.63 (1H, t, J = 7.9 Hz), 7.57 (1H, br. s), 7.46 (1H, d, J = 7.6 Hz), 7.34-7.28 (3H, m), 2.29 (3H, br, s), 1.87 (3H, s). | LC-MS (Method 3): Rt = 3.53 min, m/z = 502.1 [M + H]⁺ | Scheme 14 (Io) |
| 93 | 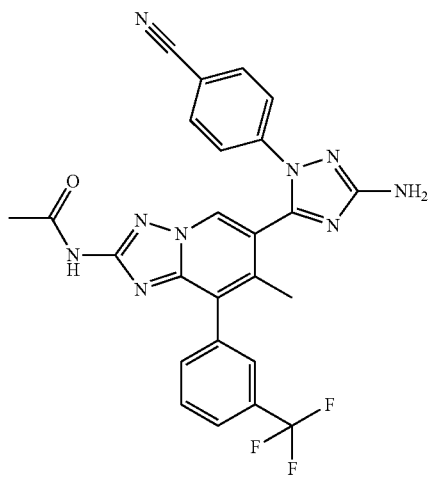 [SMILES: CC(=O)Nc1nc2c(-c3cccc(C(F)(F)F)c3)c(C)c(-c3nc(N)nn3-c3ccc(C#N)cc3)cn2n1]<br>N-[6-[5-Amino-2-(4-cyano-phenyl)-2H-[1,2,4]triazol-3-yl]-7-methyl-8-(3-trifluoromethyl-phenyl)-[1,2,4]triazolo[1,5-a]pyridin-2-yl]-acetamide | ¹H NMR (DMSO) δ 10.91 (1H, s), 9.07 (1H, s), 7.88-7.81 (4H, m), 7.79-7.73 (2H, m), 7.54-7.48 (2H, m), 5.97 (2H, s), 2.06 (3H, s), 1.96 (3H, s). | LC-MS (Method 3): Rt = 3.91 min, m/z = 518.2 [M + H]⁺ | Scheme 18 (Iz) (from Ex 61) |

| Example No. | Structure | ¹H NMR (400 MHz) | LCMS | Methods of synthesis |
|---|---|---|---|---|
| 94 | 5-[2-Acetylamino-7-methyl-8-(3-trifluoromethyl-phenyl)-[1,2,4]triazolo[1,5-a]pyridin-6-yl]-1-(4-cyano-phenyl)-1H-[1,2,4]triazole-3-carboxylic acid methyl ester | ¹H NMR (DMSO) δ 10.94 (1H, s), 9.06 (1H, s), 8.03-7.97 (2H, m), 7.86-7.81 (2H, m), 7.80-7.75 (2H, m), 7.75-7.70 (2H, m), 3.96 (3H, s), 2.05 (3H, s), 2.03 (3H, s). | LC-MS (Method 3): Rt = 4.33 min, m/z = 561.1 [M + H]⁺ | Scheme 18 (Iz') |
| 95 | N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-succinamide | ¹H NMR (DMSO) δ 10.88 (1H, s), 9.0 (1H, s), 7.99 (1H, d, J = 1.8 Hz), 7.91-7.86 (2H, m), 7.82 (1H, d, J = 8.0 Hz), 7.76 (1H, d, J = 7.6 Hz), 7.73 (1H, br. s), 7.67 (1H, d, J = 7.6 Hz), 7.60-7.55 (2H, m), 7.28 (1H, br. s), 6.81 (1H, d, J = 1.8 Hz), 6.73 (1H, br. s), 2.62-2.52 (2H, m), 2.35 (2H, t, J = 7.2 Hz), 1.76 (3H, s). | LC-MS (Method 3): Rt = 4.25 min, m/z = 559.2 [M + H]⁺ | Scheme 1 (from Ex 55) |

| Example No. | Structure | $^1$H NMR (400 MHz) | LCMS | Methods of synthesis |
|---|---|---|---|---|
| 96 | N-[6-[5-Acetylamino-2-(4-cyano-phenyl)-2H-[1,2,4]triazol-3-yl]-7-methyl-8-(3-trifluoromethyl-phenyl)-[1,2,4]triazolo[1,5-a]pyridin-2-yl]-acetamide | $^1$H NMR (DMSO) δ 10.93 (1H, s), 10.81 (1H, s), 9.10 (1H, s), 7.97-7.92 (2H, m), 7.86-7.80 (2H, m), 7.79-7.74 (2H, m), 7.65-7.60 (2H, m), 2.13 (3H, br. s), 2.05 (3H, s), 2.00 (3H, s). | LC-MS (Method 3): Rt = 3.81 min, m/z = 560.1 [M + H]$^+$ | Scheme 18 (lz) (from Ex 61) |
| 97 | N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-N'-(2-dimethylamino-ethyl)-N'-methylsuccinamide | $^1$H NMR (DMSO) δ 10.88 (1H, s), 8.99 (1H, d, J = 2.6 Hz), 8.2 (1H, s), 7.99 (1H, d, J = 1.8 Hz), 7.91-7.86 (2H, m), 7.82 (1H, d, J = 8.0 Hz), 7.76 (1H, d, J = 7.6 Hz), 7.73 (1H, br. s), 7.68 (1H, d, J = 7.6 Hz), 7.60-7.55 (2H, m), 6.81 (1H, d, J = 1.8 Hz), 3.40-3.30 (2H, m), 2.97 (3H, s), 2.65-2.52 (4H, m), 2.40 (1H, t, J = 7.0 Hz), 2.30 (1H, t, J = 7.0 Hz), 2.18 (3H, br. s), 2.14 (3H, s), 1.77 (3H, s). | LC-MS (Method 3): Rt = 3.57 min, m/z = 644.3 [M + H]$^+$ | Scheme 1 (from Ex 55) |

Biological Assay.

Compounds of the present invention were tested for potency in a human neutrophil elastase (HNE) enzyme activity assay.

HNE Enzyme Assay.

Assays were performed in 96-well plates in a total assay volume of 100 μl. The final concentration of elastase enzyme (human leukocyte elastase, Sigma E8140) was 0.0036 units/well or 0.00072 U/mL. The peptide substrate (MeOSuc-Ala-Ala-Pro-Val-AMC, Calbiochem #324740) was used at a final concentration of 100 μM. The final concentration of DMSO was 1% in the assay buffer (0.05M Tris.HCl, 0.1M NaCl, 0.1M CaCl$_2$, 0.0005% brij-35, pH 7.5). The enzymatic reaction was started by addition of the enzyme and incubated at 25° C. for 30 minutes. After incubation, the reaction was stopped by addition of soybean trypsin inhibitor (Sigma T9003) at a final concentration of 50 μg/well. Fluorescence was measured using a Molecular Devices fluorescence plate reader using 380 nm excitation and 460 nm emission wavelengths.

A dose response to each compound was performed and the effect of compound in each experiment was expressed as a percentage inhibition of the control enzyme fluorescence. Dose response curves were plotted and compound potency (IC$_{50}$) was determined. Compounds were tested in at least two separate experiments.

IC$_{50}$s for tested Examples, representative of the invention, are shown in the following table.

| Example | HNE inhibition |
|---|---|
| 56, 61, 54, 53, 55, 58, 57, 60, 51, 49, 48, 47, 50, 46, 45, 49, 41, 36, 52, 42, 39, 40, 43, 34, 19, 30, 37, 20, 21, 32, 33, 38, 35, 28, 24, 18, 22, 17, 16, 14, 7, 23, 26, 9, 3, | ++++ |

-continued

| Example | HNE inhibition |
|---|---|
| 44, 25, 29, 27, 15, 6, 1 | +++ |
| 13, 12, 31, 10, 8, 2 | ++ |
| 11, 5, 4 | + |

In the table above, HNE enzyme inhibition (IC$_{50}$ values) are indicated as follows: >500 nM '+'; 100-500 nM '++'; 20-100 nM '+++'; <20 nM '++++'.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound represented by formula (I):

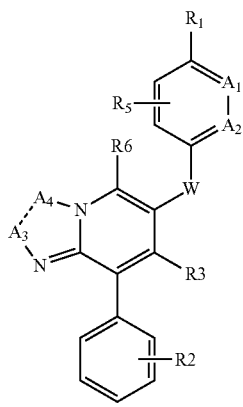

wherein
$R_1$ is halogen, —CN, —OH or $(C_1-C_4)$alkyl;
$R_2$ is halogen, $(C_1-C_4)$alkyl, $(C_1-C_4)$haloalkyl, —CN, $(C_1-C_4)$alkoxy, $(C_1-C_4)$haloalkoxy, nitro, or —OH;
W is a:
(i) a 5,6-membered heteroarylene ring optionally substituted by one or two groups independently selected from the group consisting of halogen, —OH, $(C_1-C_4)$alkyl, $(C_1-C_4)$haloalkyl, —CN, $(C_1-C_4)$alkoxy, nitro, a group —NHR$_{18}$, a group —COOR$_{28}$, a group —COR$_{29}$, and a group —CONHR$_{19}$;
(ii) a $(C_5-C_6)$heterocycloalkylene ring partially unsaturated and optionally substituted by one or two groups independently selected from the group consisting of halogen, $(C_1-C_4)$alkyl, $(C_1-C_4)$haloalkyl, —CN, —OH, $(C_1-C_4)$alkoxy, nitro, carbonyl, a group —NHR$_{18}$, and a group —CONHR$_{19}$; or
(iii) a phenylene group optionally substituted by one or two groups independently selected from the group consisting of halogen, $(C_1-C_4)$alkyl, $(C_1-C_4)$haloalkyl, —CN, nitro, a group —NHR$_{18}$, a group —CONHR$_{19}$, and a group —OR$_{20}$;

$R_{18}$ is hydrogen, $(C_1-C_4)$alkyl, —SO$_2$R$_{21}$ or $(C_1-C_4)$alkyl carbonyl;
$R_{21}$ is $(C_1-C_4)$alkyl;
$R_{19}$ is hydrogen or $(C_1-C_4)$alkyl;
$R_{20}$ is hydrogen, $(C_1-C_4)$alkyl or —$(C_1-C_4)$alkylene-OR$_{22}$;
$R_{22}$ is hydrogen or $(C_1-C_4)$alkyl;
$R_3$ is a group —CH$_2$—R$_{23}$;
$R_{23}$ is hydrogen, $(C_1-C_4)$alkyl, $(C_1-C_4)$haloalkyl, —CN, $(C_1-C_4)$alkoxy or halogen;
$R_5$ is a hydrogen, $(C_1-C_4)$alkyl, $(C_1-C_4)$haloalkyl, —CN, $(C_1-C_4)$alkoxy or halogen;
$R_6$ is hydrogen, halogen, $(C_1-C_4)$alkyl, or CN;
$A_1$ is a group —CR$_7$= or a group —N=;
$A_2$ is a group =CR$_8$— or a group =N—;
$R_7$ is hydrogen, halogen, $(C_1-C_4)$alkyl, $(C_1-C_4)$haloalkyl or $(C_1-C_4)$alkoxy;
$R_8$ is hydrogen, halogen, $(C_1-C_4)$alkyl, $(C_1-C_4)$haloalkyl, $(C_1-C_4)$alkoxy, a group —S$(C_1-C_4)$alkyl, or a group —SO$_2$$(C_1-C_4)$alkyl;
wherein $A_1$ and $A_2$ cannot both be a group —N=;
$A_3$-$A_4$ is a group —CR$_4$=N—, a group —CR$_4$=CR$_9$— or a group —NR$_{17}$—CO—;
$R_9$ is hydrogen or $(C_1-C_4)$alkyl;
$R_4$ is hydrogen, $(C_1-C_4)$alkyl, —NR$_{10}$R$_{11}$, —NHCOR$_{12}$, —NHCOO—R$_{13}$, —NHCONR$_{27}$—R$_{14}$, $(C_1-C_4)$alkoxy, —NH(CH$_2$)$_n$—SO$_2$$(C_1-C_4)$alkyl, —(NH)$_q$(CH$_2$)$_n$—(C$_6$H$_6$)—SO$_2$$(C_1-C_4)$alkyl, —NHSO$_2$$(C_1-C_4)$alkyl or —(NH)$_r$(CH$_2$)$_n$CONR$_{15}$R$_{16}$;
$R_{17}$ is hydrogen, $(C_1-C_4)$alkyl, —(CH$_2$)$_n$—(C$_6$H$_6$)—SO$_2$$(C_1-C_4)$alkyl, —(CH$_2$)$_n$—SO$_2$$(C_1-C_4)$alkyl or —(CH$_2$)$_n$CONR$_{15}$R$_{16}$;
n is zero or an integer ranging from 1 to 5;
q is zero or 1;
r is zero or 1;
$R_{10}$ is hydrogen, a group $(C_1-C_6)$alkyl, a group $(C_1-C_6)$hydroxyalkyl, a group $(C_1-C_4)$alkylene-NH—(C=NH)—NH$_2$, a group $(C_1-C_6)$alkyleneNR$_a$R$_b$, a group $(C_1-C_6)$alkyleneNR$_a$R$_d$, or a group $(C_1-C_6)$alkyleneN$^+$R$_a$R$_b$R$_c$;
$R_{11}$ is hydrogen, a group $(C_1-C_6)$alkyl, a group $(C_1-C_6)$hydroxyalkyl, a group $(C_1-C_4)$alkylene-NH—(C=NH)—NH$_2$, a group $(C_1-C_6)$alkyleneNR$_a$R$_b$ or a group $(C_1-C_6)$alkyleneN$^+$R$_a$R$_b$Rc;
or $R_{10}$ and $R_{11}$, together with the nitrogen atom to which they are bonded, form a $(C_5-C_7)$heterocycloalkyl;
$R_a$ and $R_b$ are at each occurrence independently hydrogen, $(C_1-C_4)$alkyl, which $(C_1-C_4)$alkyl may be optionally substituted by a group —COOR$_{30}$ or by a group $(C_5-C_7)$heterocycloalkyl, a group $(C_5-C_7)$heterocycloalkyl, a group $(C_1-C_6)$alkyleneNR$_e$R$_f$ or a group $(C_1-C_6)$alkyleneN$^+$R$_e$R$_f$R$_g$; alternatively, $R_a$ and $R_b$, together with the nitrogen atom to which they are bonded, form a $(C_5-C_7)$heterocycloalkyl ring system optionally substituted by one or more groups $C_1-C_6$ alkyl and which $(C_5-C_7)$heterocycloalkyl optionally contains a group —S(O)— or —S(O)$_2$— or a further heteroatom which is oxygen, sulfur or nitrogen, said nitrogen atom is optionally substituted by $(C_1-C_6)$alkyl;
or $R_a$ is as above defined and $R_b$ is linked to one carbon atom of the $(C_1-C_6)$alkylene portion of the group linked to the nitrogen to which they are bonded to form a saturated $(C_5-C_6)$heterocycloalkyl ring;
$R_a$, $R_b$ and $R_c$ if simultaneously present are at each occurrence independently $(C_1-C_4)$alkyl, which $(C_1-C_4)$alkyl may be optionally substituted by a group —COOR$_{30}$ or by a group $(C_5-C_7)$heterocycloalkyl, a group $(C_5-C_7)$ heterocycloalkyl, a group $(C_1-C_6)$alkyleneNR$_e$R$_f$ or a group $(C_1-C_6)$alkyleneN$^+$R$_e$R$_f$R$_g$; alternatively, R$_a$ and R$_b$ or R$_a$ and R$_c$, together with the nitrogen atom to which they are bonded, form a $(C_5-C_7)$heterocycloalkyl ring system optionally substituted by one or more groups $C_1-C_6$ alkyl or —NHR$_{24}$ and which $(C_5-C_7)$heterocycloalkyl ring optionally contains a group —S(O)— or —S(O)$_2$— or a further heteroatom which is oxygen, sulfur or nitrogen, said nitrogen atom optionally substituted by $(C_1-C_6)$ alkyl; or R$_a$ and R$_b$ are as above defined and R$_c$ is linked to one carbon atom of the $(C_1-C_6)$alkylene portion of the group linked to the nitrogen to which they are bonded to form a saturated $(C_5-C_6)$heterocycloalkyl ring;

R$_d$ is $(C_5-C_7)$heterocycloalkyl;

R$_e$ and R$_f$ are at each occurrence independently hydrogen or $(C_1-C_4)$alkyl;

or R$_e$, R$_f$ and R$_g$ if simultaneously present are at each occurrence independently $(C_1-C_4)$alkyl;

R$_{12}$ is selected from the group consisting of —(C$_6$H$_6$)—SO$_2$(C$_1$-C$_4$)alkyl, $(C_1-C_6)$alkyl, $(C_1-C_4)$haloalkyl, $(C_5-C_7)$heterocycloalkyl, a group —(CH$_2$)$_n$—S(O)$_t$(C$_1$-C$_4$) alkyl, a group —(CH$_2$)$_n$—S(O)$_t$(C$_1$-C$_4$)alkylNR$_a$R$_b$, a group —(CH$_2$)$_n$—S(O)$_t$(C$_1$-C$_4$)alkylN$^+$R$_a$R$_b$R$_c$, a group $(C_1-C_4)$alkylene-NH—(C=NH)—NH$_2$, a group $(C_1-C_4)$alkylene-CO$_2$H, a group —(C$_1$-C$_4$)alkylene-CO$_2$NR$_{25}$R$_{26}$, a group —(C$_1$-C$_4$)alkylene-CO$_2$NR$_{25}$(C$_1$-C$_6$)alkyleneNR$_a$R$_b$, a group —(C$_1$-C$_4$)alkylene-CO$_2$NR$_{25}$(C$_1$-C$_6$)alkyleneN$^+$R$_a$R$_b$R$_c$, a group —(C$_1$-C$_6$)alkyleneNR$_a$R$_b$, a group —(C$_1$-C$_6$)alkyleneN$^+$R$_a$R$_b$R$_c$, and $(C_1-C_4)$alkyl$(C_5-C_7)$heterocycloalkyl, wherein such groups may be optionally substituted by one or two substituents selected from the group consisting of $(C_1-C_4)$alkyl, hydroxy, halogen, —SO$_2$(C$_1$-C$_4$)alkyl, amino and $(C_1-C_4)$alkylamino;

t may be zero, 1 or 2;

R$_{13}$ is selected from the group consisting of —(C$_6$H$_6$)—SO$_2$alkyl, $(C_1-C_6)$alkyl, $(C_1-C_4)$haloalkyl, $(C_5-C_7)$heterocycloalkyl, a group $(C_1-C_4)$alkylene-NH—(C=NH)—NH$_2$, $(C_1-C_6)$alkyleneNR$_a$R$_b$, —(C$_1$-C$_6$)alkyleneN$^+$R$_a$R$_b$R$_c$ and $(C_1-C_4)$alkylene$(C_5-C_7)$heterocycloalkyl, wherein such groups may be optionally substituted by one or two substituents selected from the group consisting of $(C_1-C_4)$alkyl, $(C_1-C_4)$alkoxy, hydroxy, halogen, —SO$_2$(C$_1$-C$_4$)alkyl, amino and $(C_1-C_4)$alkylamino;

R$_{14}$ is selected from the group consisting of $(C_1-C_4)$alkyl, —(C$_6$H$_6$)—SO$_2$alkyl, $(C_1-C_4)$haloalkyl, $(C_5-C_7)$heterocycloalkyl, a group $(C_1-C_4)$alkylene-NH—(C=NH)—NH$_2$, $(C_1-C_6)$alkyleneNR$_a$R$_b$, —(C$_1$-C$_6$)alkyleneN$^+$R$_a$R$_b$R$_c$ and $(C_1-C_4)$alkyl$(C_5-C_7)$heterocycloalkyl, wherein such groups may be optionally substituted by one or two substituents selected from the group consisting of $(C_1-C_4)$alkyl, hydroxy, halogen, —SO$_2$(C$_1$-C$_4$)alkyl, amino, $(C_1-C_4)$alkylcarbonyl and $(C_1-C_4)$alkylamino;

R$_{15}$ is hydrogen, a group $(C_1-C_6)$alkyl, a group $(C_1-C_4)$alkylene-NH—(C=NH)—NH$_2$, a group $(C_1-C_6)$alkyleneNR$_a$R$_b$, or a group —(C$_1$-C$_6$)alkyleneN$^+$R$_a$R$_b$R$_c$;

R$_{16}$ is hydrogen, a group $(C_1-C_6)$alkyl, a group $(C_1-C_4)$alkylene-NH—(C=NH)—NH$_2$, a group $(C_1-C_6)$alkyleneNR$_a$R$_b$ or a group —(C$_1$-C$_6$)alkyleneN$^+$R$_a$R$_b$R$_c$;

or R$_{15}$ and R$_{16}$, together with the nitrogen atom to which they are bonded, form a $(C_5-C_7)$heterocycloalkyl;

R$_{24}$ is hydrogen or $(C_1-C_4)$alkyl;
R$_{25}$ is hydrogen or $(C_1-C_4)$alkyl;
R$_{26}$ is hydrogen or $(C_1-C_4)$alkyl;
R$_{27}$ is hydrogen or $(C_1-C_4)$alkyl;
R$_{28}$ is hydrogen or $(C_1-C_4)$alkyl;
R$_{29}$ is hydrogen or $(C_1-C_4)$alkyl;
R$_{30}$ is hydrogen or $(C_1-C_4)$alkyl;

wherein if one or more groups —(C$_1$-C$_6$)alkyleneN$^+$R$_a$R$_b$R$_c$ are present, they form a quaternary salt with a pharmaceutically acceptable counter ion;

and wherein groups R$_{18}$, R$_{19}$, R$_{20}$, R$_{21}$, R$_{22}$, R$_{24}$, R$_{25}$, R$_{26}$, R$_{27}$, R$_{28}$, R$_{29}$, R$_{30}$, R$_a$, R$_b$, R$_c$, R$_d$, R$_e$, R$_f$, R$_g$, and n may assume the same or different meanings at each occurrence, if present in more than one group;

or a pharmaceutically acceptable salt thereof.

2. A compound of formula (I) or salt thereof as claimed in claim 1, wherein R$_1$ is —CN.

3. A compound of formula (I) or salt thereof as claimed in claim 1, wherein R$_2$ is 3-trifluoromethyl.

4. A compound of formula (I) or salt thereof as claimed in claim 2, wherein R$_2$ is 3-trifluoromethyl.

5. A compound of formula (I) or salt thereof as claimed in claim 1, wherein W is a 5 or 6-membered heteroaryl ring which is optionally substituted.

6. A compound of formula (I) or salt thereof as claimed in claim 2, wherein W is a 5 or 6-membered heteroaryl ring which is optionally substituted.

7. A compound of formula (I) or salt thereof as claimed in claim 3, wherein W is a 5 or 6-membered heteroaryl ring which is optionally substituted.

8. A compound of formula (I) or salt thereof as claimed in claim 1, wherein R$_3$ is a group —CH$_2$—R$_{23}$ and R$_{23}$ is hydrogen.

9. A compound of formula (I) or salt thereof as claimed in claim 2, wherein R$_3$ is a group —CH$_2$—R$_{23}$ and R$_{23}$ is hydrogen.

10. A compound of formula (I) or salt thereof as claimed in claim 3, wherein R$_3$ is a group —CH$_2$—R$_{23}$ and R$_{23}$ is hydrogen.

11. A compound of formula (I) or salt thereof as claimed in claim 4, wherein R$_3$ is a group —CH$_2$—R$_{23}$ and R$_{23}$ is hydrogen.

12. A compound of formula (I) or salt thereof as claimed in claim 1, wherein A$_3$-A$_4$ is —CR$_4$=N—.

13. A compound of formula (I) or salt thereof as claimed in claim 1, wherein A$_1$ is a group —CR$_7$=, R$_7$ is hydrogen, A$_2$ is a group —CR$_8$=, and R$_8$ is hydrogen or group —SO$_2$(C$_1$-C$_4$)alkyl.

14. A compound of formula (I) or salt thereof as claimed in claim 1, wherein R$_5$ is hydrogen and R$_6$ is hydrogen.

15. A compound of formula (I) or salt thereof as claimed in claim 1, which is a compound selected from the group consisting of:

4-{5-[2-Amino-7-methyl-8-(3-trifluoromethyl-phenyl)-[1,2,4]triazolo[1,5-a]pyridin-6-yl]-pyrazol-1-yl}-benzonitrile;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2,2,2-trifluoro-acetamide;

4-{5-[7-Methyl-8-(3-trifluoromethyl-phenyl)-[1,2,4]triazolo[1,5-a]pyridin-6-yl]-pyrazol-1-yl}-benzonitrile;

4-{5-[2,7-Dimethyl-8-(3-trifluoromethyl-phenyl)-[1,2,4]triazolo[1,5-a]pyridin-6yl]-pyrazol-1-yl}-benzonitrile;

4-{5-[2,7-Dimethyl-8-(3-trifluoromethyl-phenyl)-imidazo[1,2-a]pyridin-6-yl]-pyrazol-1-yl}-benzonitrile;

4-{5-[7-Methyl-8-(3-trifluoromethyl-phenyl)-imidazo[1,2-a]pyridin-6-yl]-pyrazol-1-yl}-benzonitrile;

4-{5-[2-(4-Methanesulfonyl-phenylamino)-7-methyl-8-(3-trifluoromethyl-phenyl)-[1,2,4]triazolo[1,5-a]pyridin-6-yl]-pyrazol-1-yl}-benzonitrile;

4-{5-[2-(4-Methanesulfonyl-benzyl)-7-methyl-8-(3-trifluoromethyl-phenyl)-[1,2,4]triazolo[1,5-a]pyridin-6-yl]-pyrazol-1-yl}-benzonitrile;

4-{5-[7-Methyl-3-oxo-8-(3-trifluoromethyl-phenyl)-2,3-dihydro-[1,2,4]triazolo[4,3-a]pyridin-6-yl]-pyrazol-1-yl}-benzonitrile;

4-{5-[2-(4-Methanesulfonyl-benzyl)-7-methyl-3-oxo-8-(3-trifluoromethyl-phenyl)-2,3-dihydro-[1,2,4]triazolo[4,3-a]pyridin-6-yl]-pyrazol-1-yl}-benzonitrile;

2-[6-[2-(4-Cyano-phenyl)-2H-pyrazol-3-yl]-7-methyl-3-oxo-8-(3-trifluoromethyl-phenyl)-[1,2,4]triazolo[4,3-a]pyridin-2-yl]-N,N-dimethyl-acetamide;

2-[6-[2-(4-Cyano-phenyl)-2H-pyrazol-3-yl]-7-methyl-3-oxo-8-(3-trifluoromethyl-phenyl)-[1,2,4]triazolo[4,3-a]pyridin-2-yl]-N-methyl-acetamide;

4-{5-[2-(3-Methanesulfonyl-propyl)-7-methyl-3-oxo-8-(3-trifluoromethyl-phenyl)-2,3-dihydro-[1,2,4]triazolo[4,3-a]pyridin-6-yl]-pyrazol-1-yl}-benzonitrile;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-dimethylamino-acetamide;

{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-trimethyl-ammonium bromide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-dimethylamino-butyramide;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-propyl}-trimethyl-ammonium bromide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-(4-methyl-piperazin-1-yl)-acetamide;

4-{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-1,1-dimethyl-piperazin-1-ium iodide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-morpholin-4-yl-acetamide;

4-{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-1,1-dimethyl-piperazin-1-ium iodide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-2-morpholin-4-yl-acetamide;

N-[6-[1-(4-Cyano-phenyl)-1H-pyrazol-5-yl]-7-methyl-8-(3-trifluoromethyl-phenyl)-[1,2,4]triazolo[1,5-a]pyridin-2-yl]-2-(1,1-dioxothiomorpholin-4-yl)-acetamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-methanesulfonyl-benzamide;

4-{5-[2-(4-Methanesulfonyl-benzylamino)-7-methyl-8-(3-trifluoromethyl-phenyl)-[1,2,4]triazolo[1,5-a]pyridin-6-yl]-pyrazol-1-yl}-benzonitrile;

2-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N,N-dimethyl-acetamide;

1-{[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyl]-methyl}-1,4-dimethyl-piperazin-1-ium chloride;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-acetamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-methanesulfonamide;

4-{5-[2-(3-Dimethylamino-propylamino)-7-methyl-8-(3-trifluoromethyl-phenyl)-[1,2,4]triazolo[1,5-a]pyridin-6-yl]-pyrazol-1-yl}-benzonitrile;

4-{5-[2-(2-Dimethylamino-ethylamino)-7-methyl-8-(3-trifluoromethyl-phenyl)-[1,2,4]triazolo[1,5-a]pyridin-6-yl]-pyrazol-1-yl}-benzonitrile;

4-{5-[2-(4-Dimethylamino-butylamino)-7-methyl-8-(3-trifluoromethyl-phenyl)-[1,2,4]triazolo[1,5-a]pyridin-6-yl]-pyrazol-1-yl}-benzonitrile;

4-{5-[2-Methoxy-7-methyl-8-(3-trifluoromethyl-phenyl)-[1,2,4]triazolo[1,5-a]pyridin-6-yl]-pyrazol-1-yl}-benzonitrile;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-propyl}-trimethyl-ammonium benzenesulfonate;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-ethyl}-trimethyl-ammonium benzenesulfonate;

{4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-butyl}-trimethyl-ammonium formate;

[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-carbamic acid ethyl ester;

[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-carbamic acid 2-methoxyethyl ester;

{3-[6-[2-(4-Cyano-phenyl)-2H-pyrazol-3-yl]-7-methyl-8-(3-trifluoromethyl-phenyl)-[1,2,4]triazolo[1,5-a]pyridin-2-ylcarbamoyloxy]-propyl}-trimethyl-ammonium formate;

(3-{3-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-ureido}-propyl)-trimethyl-ammonium formate;

N-[6-[2-(4-Cyano-phenyl)-2H-[1,2,4]triazol-3-yl]-7-methyl-8-(3-trifluoromethyl-phenyl)-[1,2,4]triazolo[1,5-a]pyridin-2-yl]-acetamide;

4-{5-[2-Amino-7-methyl-8-(3-trifluoromethyl-phenyl)-[1,2,4]triazolo[1,5-a]pyridin-6-yl]-pyrazol-1-yl}-3-methanesulfonyl-benzonitrile;

N-[6-[2-(4-Cyano-2-fluoro-phenyl)-2H-pyrazol-3-yl]-7-methyl-8-(3-trifluoromethyl-phenyl)-[1,2,4]triazolo[1,5-a]pyridin-2-yl]-acetamide;

N-[6-[2-(4-Cyano-phenyl)-4-methyl-2H-pyrazol-3-yl]-7-methyl-8-(3-trifluoromethyl-phenyl)-[1,2,4]triazolo[1,5-a]pyridin-2-yl]-acetamide;

N-[6-(4'-Cyano-biphenyl-2-yl)-7-methyl-8-(3-trifluoromethyl-phenyl)-[1,2,4]triazolo[1,5-a]pyridin-2-yl]-acetamide;

N-[6-[2-(4-Cyano-phenyl)-2H-pyrazol-3-yl]-7-methyl-8-(3-trifluoromethoxy-phenyl)-[1,2,4]triazolo[1,5-a]pyridin-2-yl]-acetamide;

N-[6-[2-(4-Cyano-phenyl)-2H-pyrazol-3-yl]-7-methyl-8-(3-trifluoromethyl-phenyl)[1,2,4]triazolo[1,5-a]pyridin-2-yl]-3-methanesulfinyl-propionamide;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-methanesulfonyl-propionamide;

4-{5-[2-(3-Methanesulfonyl-propylamino)-7-methyl-8-(3-trifluoromethyl-phenyl)-[1,2,4]triazolo[1,5-a]pyridin-6-yl]-pyrazol-1-yl}-benzonitrile;

4-{5-[2-(2-Hydroxy-ethylamino)-7-methyl-8-(3-trifluoromethyl-phenyl)-[1,2,4]triazolo[1,5-a]pyridin-6-yl]-pyrazol-1-yl}-benzonitrile;

4-{5-[2-(2-Hydroxy-propylamino)-7-methyl-8-(3-trifluoromethyl-phenyl)-[1,2,4]triazolo[1,5-a]pyridin-6-yl]-pyrazol-1-yl}-benzonitrile;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-piperidin-4-yl-urea;

(1-methyl-4-piperidyl)[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-urea;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-ethyl-urea;

4-{5-[2-(3-Hydroxy-propylamino)-7-methyl-8-(3-trifluoromethyl-phenyl)-[1,2,4]triazolo[1,5-a]pyridin-6-yl]-pyrazol-1-yl}-benzonitrile;

4-{5-[2-(4-Hydroxy-butylamino)-7-methyl-8-(3-trifluoromethyl-phenyl)-[1,2,4]triazolo[1,5-a]pyridin-6-yl]-pyrazol-1-yl}-benzonitrile;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-succinamic acid;

N-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-4-methylamino-butyramide;

1-(1-Acetyl-piperidin-4-yl)-3-[6-[2-(4-cyano-phenyl)-2H-pyrazol-3-yl]-7-methyl-8-(3-trifluoromethyl-phenyl)-[1,2,4]triazolo[1,5-a]pyridin-2-yl]-urea;

1-[6-[2-(4-Cyano-phenyl)-2H-pyrazol-3-yl]-7-methyl-8-(3-trifluoromethyl-phenyl)-[1,2,4]triazolo[1,5-a]pyridin-2-yl]-3-(1-methanesulfonyl-piperidin-4-yl)-urea;

4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N-methyl-butyramide;

4-[6-[2-(4-Cyano-phenyl)-2H-pyrazol-3-yl]-7-methyl-8-(3-trifluoromethyl-phenyl)-[1,2,4]triazolo[1,5-a]pyridin-2-ylamino]-N-(2-dimethylamino-ethyl)-N-methyl-butyramide;

4-{3-Amino-5-[2-amino-7-methyl-8-(3-trifluoromethyl-phenyl)-[1,2,4]triazolo[1,5-a]pyridin-6-yl]-[1,2,4]triazol-1-yl}-benzonitrile;

or a pharmaceutically acceptable salt of said compound.

16. A pharmaceutical composition, comprising a compound of formula (I) or a salt thereof as claimed in claim 1 and a pharmaceutically acceptable carrier or excipient.

17. A pharmaceutical composition as claimed in claim 16, which is suitable for oral administration or administration by the pulmonary route.

* * * * *